US006986294B2

(12) United States Patent
Fromme et al.

(10) Patent No.: US 6,986,294 B2
(45) Date of Patent: Jan. 17, 2006

(54) BULK MATERIALS MANAGEMENT APPARATUS AND METHOD

(75) Inventors: Guy A. Fromme, Louisville, CO (US); Timothy O'Connor, Lafayette, CO (US); David A. Gutow, Boulder, CO (US); Dean A. Paschen, Lafayette, CO (US); Paul I. Kolesnikoff, II, Pinecliffe, CO (US); Vincent A. Hirsch, Boulder, CO (US); Gary Emerson, Golden, CO (US); Charles Bradford, Longmont, CO (US); Leon C. Webb, Naples, FL (US); Paul Hendershott, Boulder, CO (US)

(73) Assignee: Bintech LLLP, Louisville, CO (US)

( * ) Notice: Subject to any disclaimer, the term of this patent is extended or adjusted under 35 U.S.C. 154(b) by 166 days.

(21) Appl. No.: 10/223,339

(22) Filed: Aug. 19, 2002

(65) Prior Publication Data

US 2004/0031335 A1 Feb. 19, 2004

Related U.S. Application Data

(63) Continuation of application No. PCT/US01/05082, filed on Feb. 16, 2001.
(60) Provisional application No. 60/183,271, filed on Feb. 17, 2000.

(51) Int. Cl.
*G01M 19/00* (2006.01)

(52) U.S. Cl. .......................... 73/865.8; 73/866

(58) Field of Classification Search ............... 73/865.8, 73/866
See application file for complete search history.

(56) References Cited

U.S. PATENT DOCUMENTS

| 3,695,107 A | 10/1972 | Hertz et al. |
| 4,043,199 A | 8/1977 | Greer |
| 4,339,664 A | 7/1982 | Wiklund et al. |

(Continued)

FOREIGN PATENT DOCUMENTS

| EP | 0 159 187 | 10/1985 |
| EP | 0 244 163 | 11/1987 |
| EP | 0 310 564 | 4/1989 |
| EP | 0 938 837 A1 | 9/1999 |

OTHER PUBLICATIONS

PCT Notification of Transmittal of International Preliminary Examination Report.

*Primary Examiner*—Robert Raevis
(74) *Attorney, Agent, or Firm*—Rick Martin; Patent Law Offices of Rick Martin, P.C.

(57) ABSTRACT

Bulk material measurement packages are described including the preferred embodiment of an automated instrument package (AIP) suited to mount on the inside ceiling of a large silo. The gimbaled AIP vertical mounting bracket rotates in an approximate 360° azimuth. An instrument housing is mounted to the vertical mounting bracket, and it rotates approximately 190° in a vertical plane. The instrument housing has at least one range finding sensor such as a scanning laser to measure the top surface contours of the bulk material. The instrument housing can also contains other sensors such as air and quality instruments including temperature, humidity, spectral recognition sensor to detect grain/material type and/or flow rate, gas detectors for sniffing off-odors/spoilage/or safety problems, and live video. Optionally grain penetrating radar (GPR), time domain reflectometry (TDR), ultrasonics, and portable sensors are taught as well as alternate packaging.

20 Claims, 154 Drawing Sheets

U.S. PATENT DOCUMENTS

| | | |
|---|---|---|
| 4,495,807 A | 1/1985 | Field et al. |
| 4,807,471 A | 2/1989 | Cournane et al. |
| 4,920,799 A | 5/1990 | Low |
| 4,932,243 A | 6/1990 | Suh et al. |
| 4,992,998 A | 2/1991 | Woodward |
| 4,998,826 A | 3/1991 | Wood et al. |
| 5,067,817 A | 11/1991 | Glenn |
| 5,128,656 A | 7/1992 | Watanabe |
| 5,131,271 A | 7/1992 | Haynes et al. |
| 5,218,858 A | 6/1993 | Jen |
| 5,400,651 A | 3/1995 | Welch |
| 5,438,867 A | 8/1995 | van der Pol |
| 5,502,898 A | 4/1996 | Manore |
| 5,533,392 A | 7/1996 | Kira |
| 5,638,961 A | 6/1997 | Satake et al. |
| 5,751,421 A | 5/1998 | Wright et al. |
| 5,760,309 A | 6/1998 | Maltby et al. |
| 5,768,939 A | 6/1998 | Quayle et al. |
| 5,799,534 A | 9/1998 | van der Pol |
| 5,840,012 A | 11/1998 | Krauter et al. |
| 5,847,294 A | 12/1998 | Poole |
| 5,871,397 A | 2/1999 | Nelson et al. |
| 5,912,639 A | 6/1999 | Beckner |
| 5,957,773 A | 9/1999 | Olmsted et al. |
| 5,987,994 A | 11/1999 | Maltby et al. |
| 5,994,908 A | 11/1999 | McMahon |

| ITEM NO. | PART NO. | NOMENCLATURE |
|---|---|---|
| 1 | 200211-500 | HOUSING ASSY |
| 2 | 200212-500 | HOUSING WELD |
| 3 | 200213-001 | HOUSING COVER |
| 4 | 200214-001 | SUPPORT, IR |
| 5 | 200215-001 | SUPPORT, CAMERA |
| 6 | 200216-001 | RETAINER, WINDOW-IR |
| 7 | 200217-001 | RETAINER, WINDOW-CAMERA |
| 8 | 200218-001&-002 | GASKET, WINDOW-IR & CAMERA |
| 9 | 200219-001 | GASKET, HOUSING |
| 10 | 200220-500 | HAT, HOUSING, ASSY |
| 11 | 200221-500 | HAT, HOUSING-WELDMENT |
| 12 | 200222-001 | ANGLE, SUPPORT-HAT |
| 13 | 200223-001 | SEAL, DUST |
| 14 | 200224-500 | ARM ASSY |
| 15 | 200225-500 | ARM, WELDMENT |
| 16 | 200226-500 | COVER, ARM-WELDMENT |
| 17 | 200227-001 | GASKET, ARM |
| 18 | 200228-001 | SHAFT, HOLLOW-ARM |
| 19 | 200229-001 | SUPPORT, SENSOR |
| 20 | 200230-001 | SUPPORT, SHAFT-HOLLOW |

"ALTERNATE GSU PARTS LIST"

FIG. 9A

| ITEM NO. | PART NO. | NOMENCLATURE |
|---|---|---|
| 21 | 200231-001 | GEAR, MOD-HOLLOW SHAFT |
| 22 | 200232-001 | HOLDER, BEARING-ADJUST |
| 23 | 200233-001 | SUPPORT, BEARING-UPPER |
| 24 | 200234-001 | SUPPORT, MOTOR-UPPER |
| 25 | 200235-001 | SUPPORT, MOTOR-LOWER |
| 26 | 200236-001 | SUPPORT, ARM |
| 27 | 200237-001 | SUPPORT, ARM-ROOF |
| 28 | 200237-001&-002 | SHAFT, BEARING |
| 29 | 200238-001 | SPACER |
| 30 | 200239-001 | SHAFT |
| 31 | | |
| 32 | LA23ECK | MOTOR |
| 33 | 31GBF-5FT | DRIVE BELT 1/10" PITCH (BERG) |
| 34 | GP31A28-24 | 24 TEETH PULLEY |
| 35 | GP31A28-64 | 64 TEETH PULLEY |
| 36 | GP31A28-88 | 88 TEETH PULLEY |
| 37 | B13-8 | BEARING, SHIELDED-GREASE, 1/4" |
| 38 | B13-11 | BEARING, SHIELDED-GREASE, 3/8" |
| 39 | B11-15 | BEARING, RUBBER SHIELDED, 1/2" |
| 40 | B1-19 | BEARING, SHIELDED-GREASE, 3/4" |

"ALTERNATE GSU PARTS LIST"

FIG. 9B

| ITEM NO. | PART NO. | NOMENCLATURE |
|---|---|---|
| 41 | MS3186C39 | NUT, CONNECTOR 3/4-20 X 1/8 |
| 42 | MS320-6 | NUT, CASTELLATED 3/8-24 X 1/4 |
| 43 | MS9358-14 | NUT, CASTELLATED 1/2-20 X .56 |
| 44 | 9290-A194 | SPACER 5/16OD X .194 I.D. X .75 |
| 45 | | COTTER PIN 1/16 X 1" |
| 46 | | BOLT 1/2" DIR X 3 1/4 |
| 47 | | WASHER STD. 3/8 ID X 5/8 OD X 1/32 |
| 48 | | WASHER STD. 3/4 ID X 1 5/16 OD X 1/16 |
| 49 | | WASHER .755 ID X 1.000 OD X .060 |
| 50 | | WASHER .257 ID X .375 OD X .030 |
| 51 | 1/8 x 1/8 x 12" | KEY 1/8 X 1/8 X 12" LG STEEL |
| 52 | | WINDOW, LARGE 1/8 X 3.00" DIA |
| 53 | | WINDOW, SMALL 1/8 X 29.3 MM DIA |
| 54 | | SCREW 10-32 X 1 3/4" |
| 55 | | IR UNIT |
| 56 | | CAMERA |
| 57 | | SENSOR |
| 58 | ,2727-1-25 | RETAINING RING |

"ALTERNATE GSU PARTS LIST"

FIG. 9C

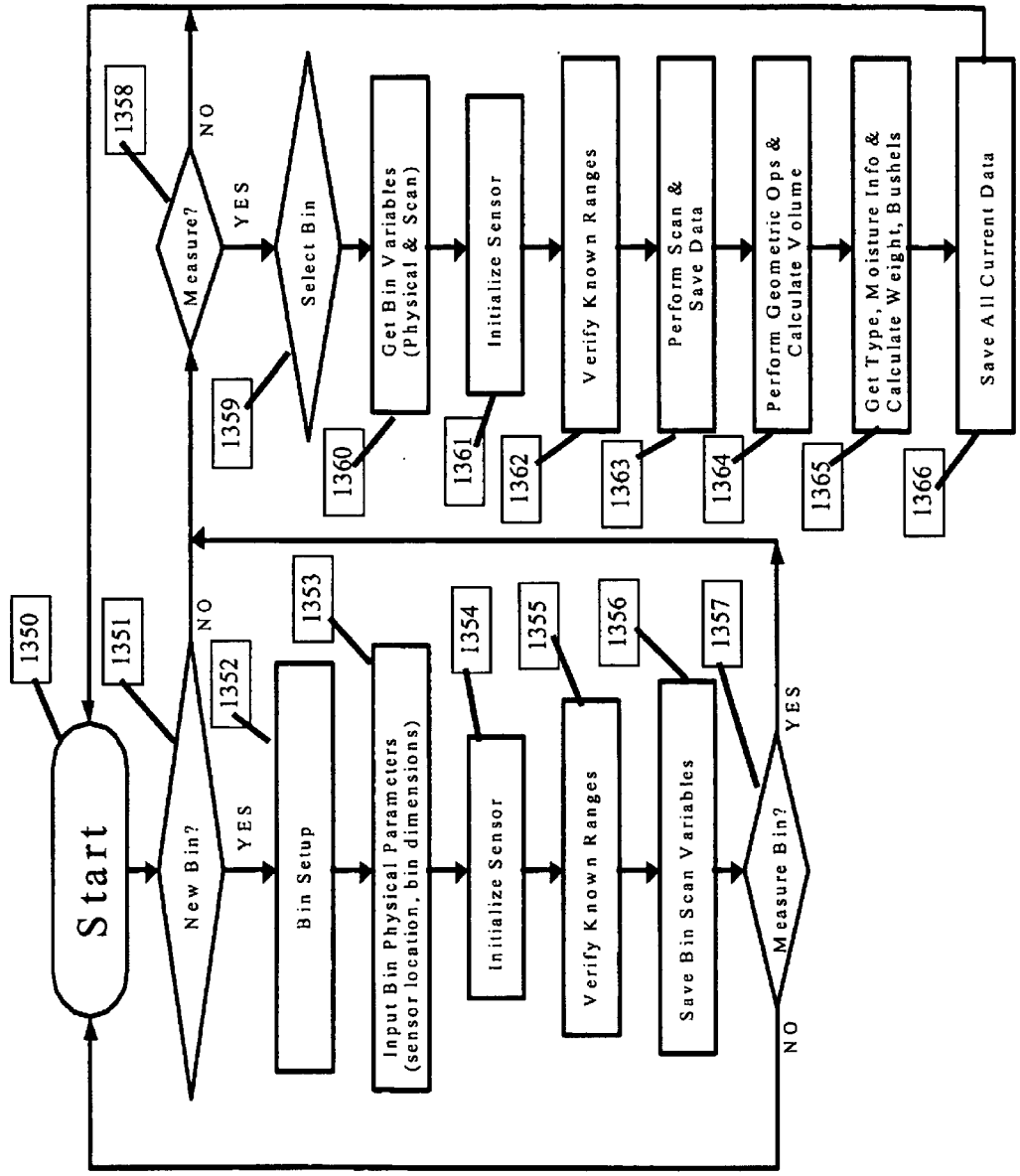
FIG. 13B Volume Measurement Flow

"TYPICAL BEAM FORMING CONFIGURATION"

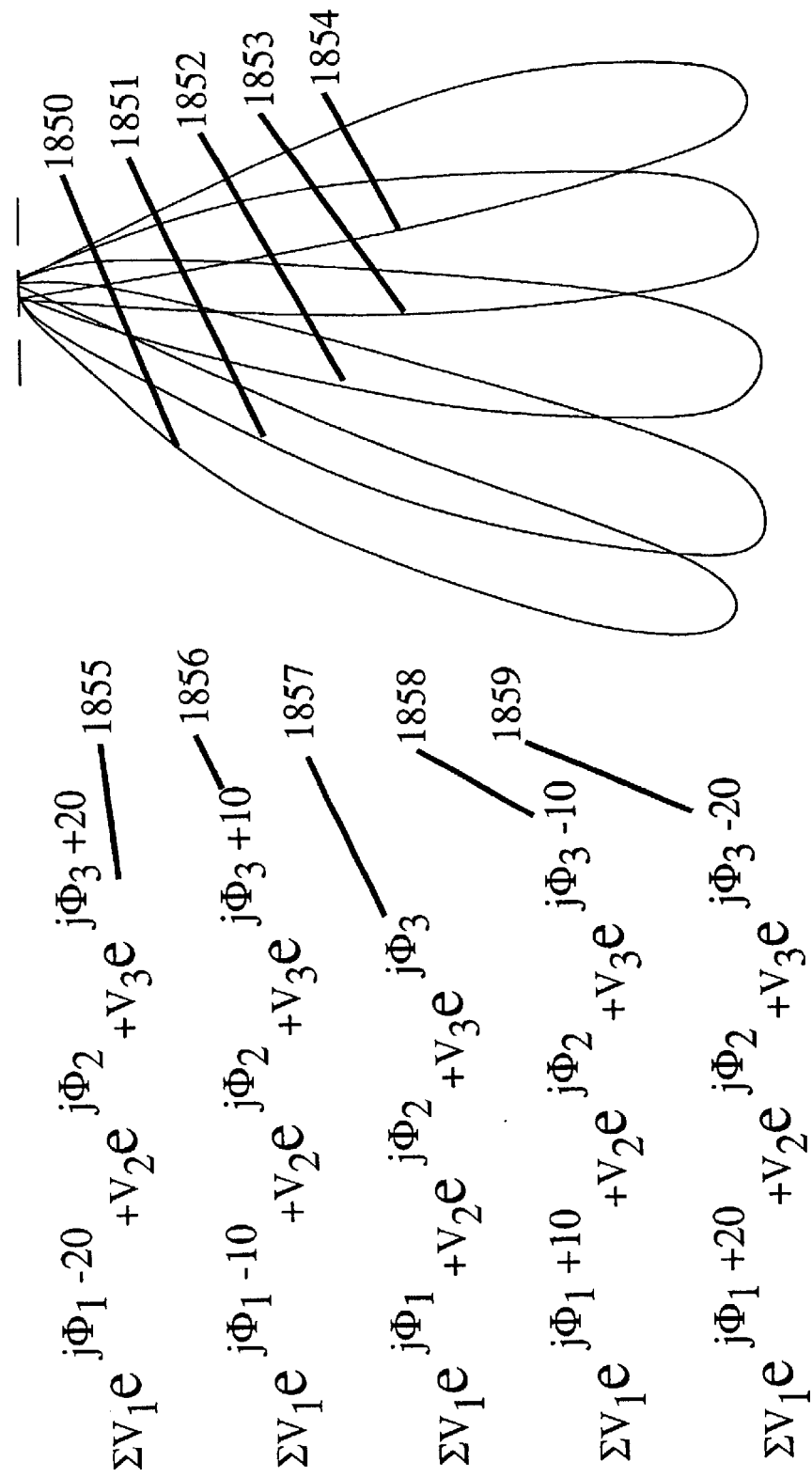
FIG. 18H "BEAM STEERING"

"RETURN SIGNAL CONVOLUTION"

"BEAM DECONVOLUTION ARRAY"

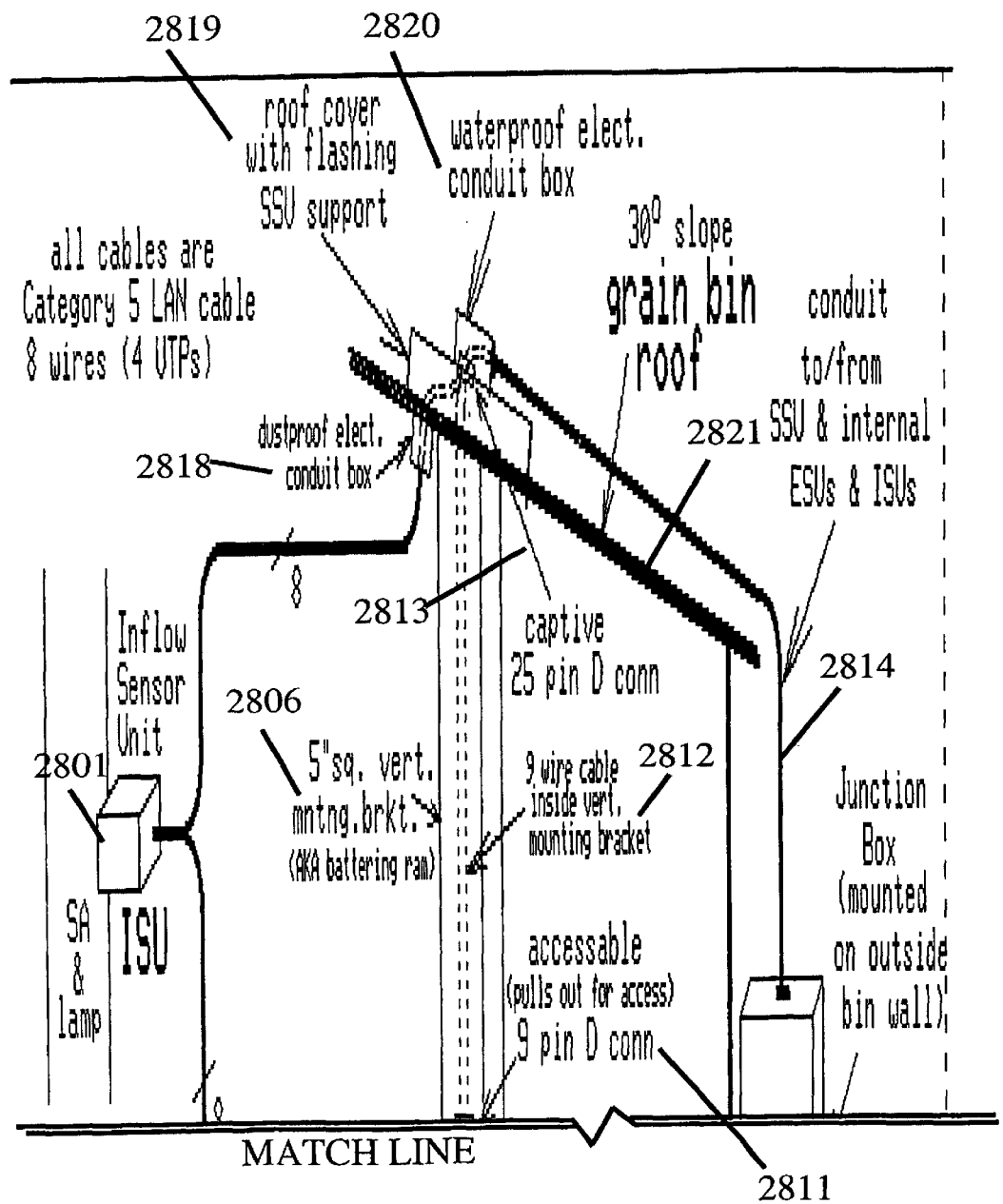
FIG. 28AA.1

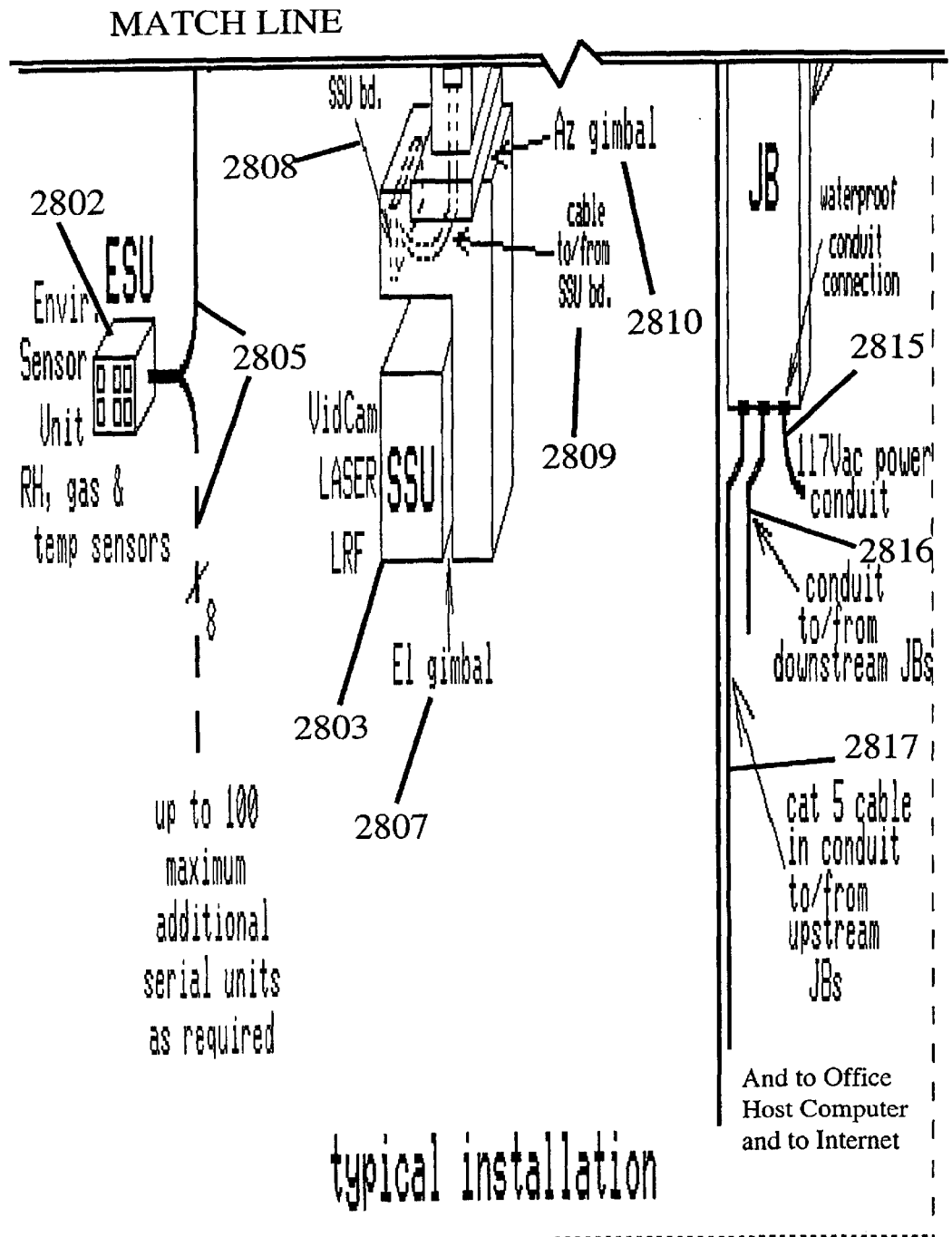
FIG. 28AA.2

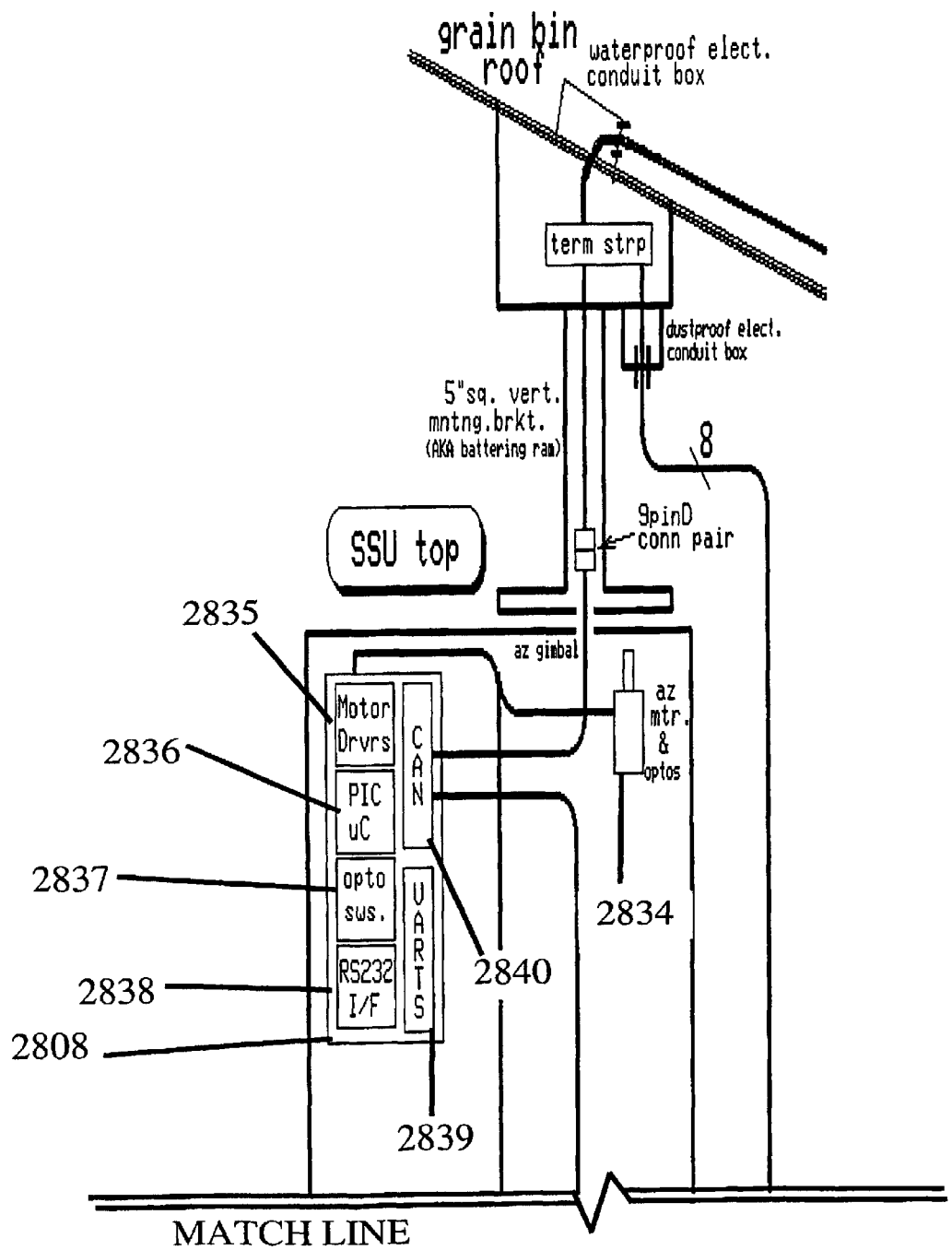
FIG. 28AB.1

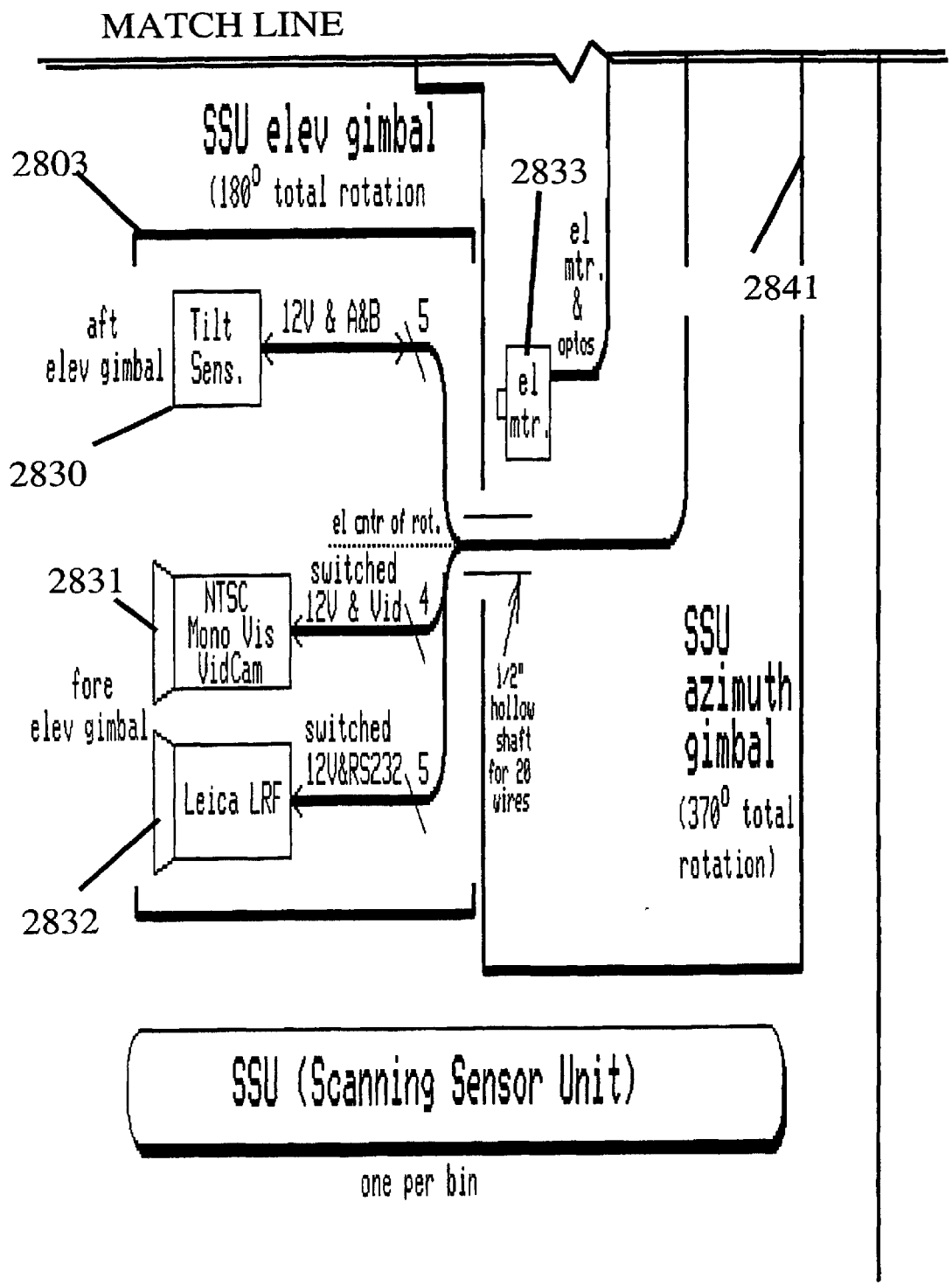
FIG. 28AB.2

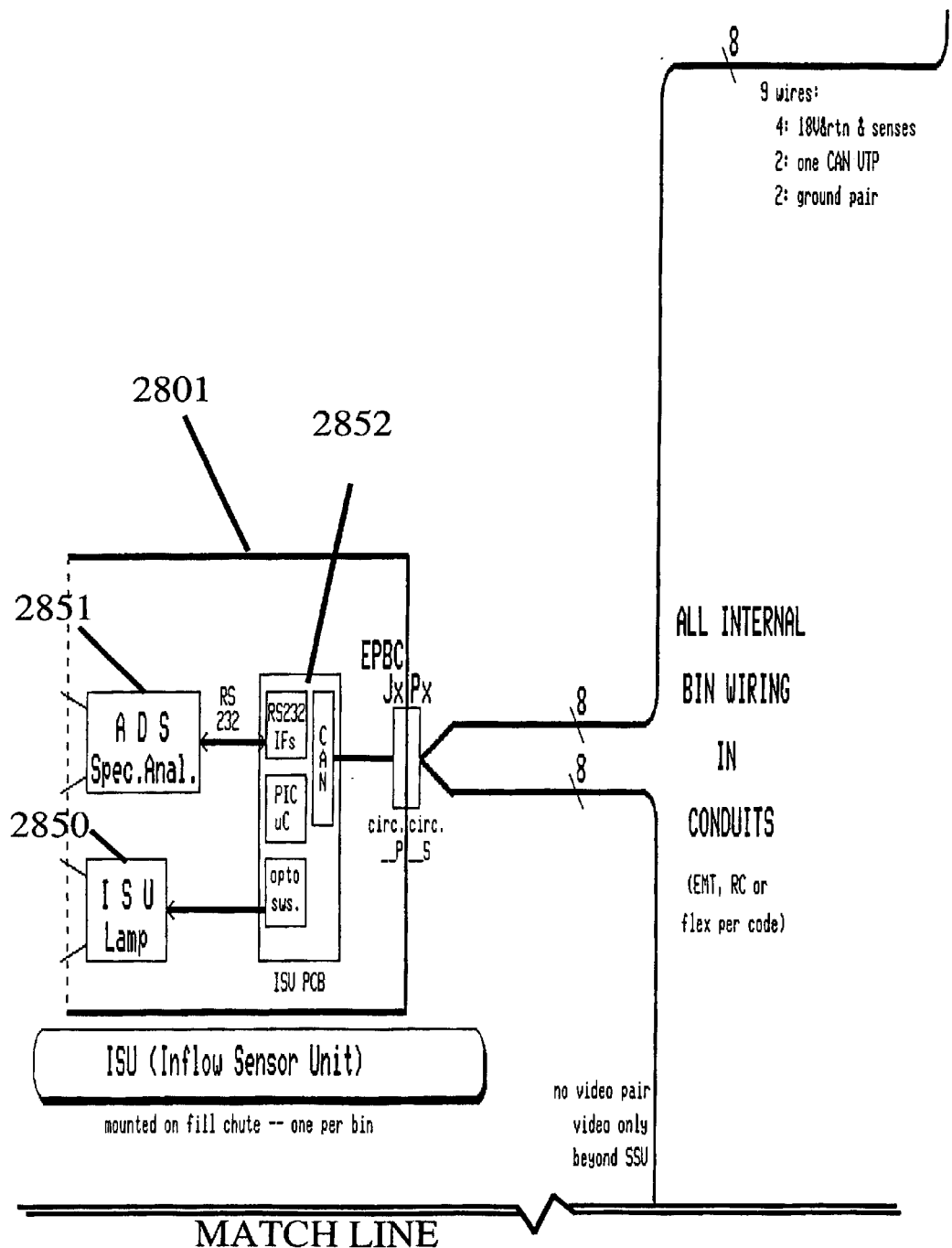
FIG. 28B.1

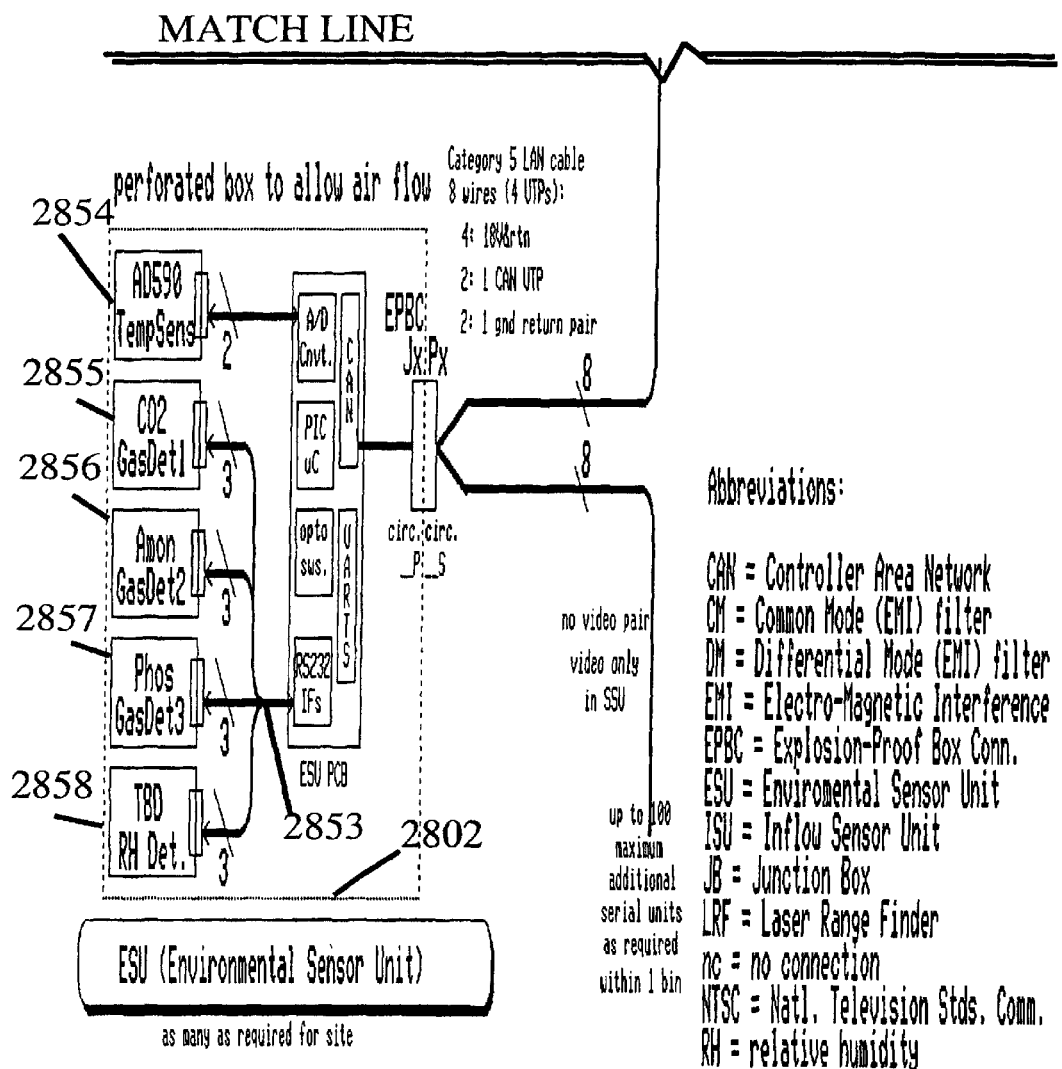
FIG. 28B.2

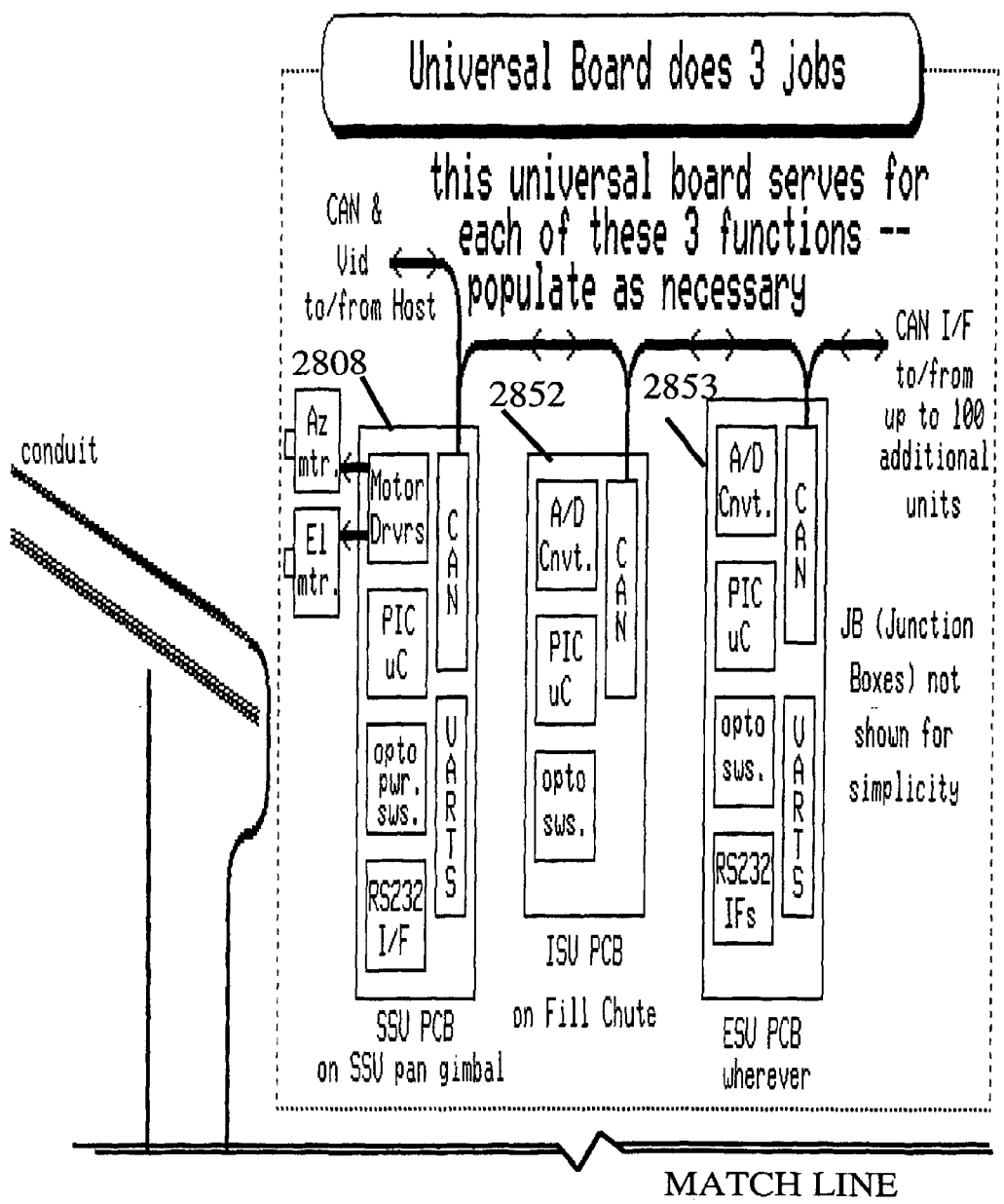
FIG. 28C.1

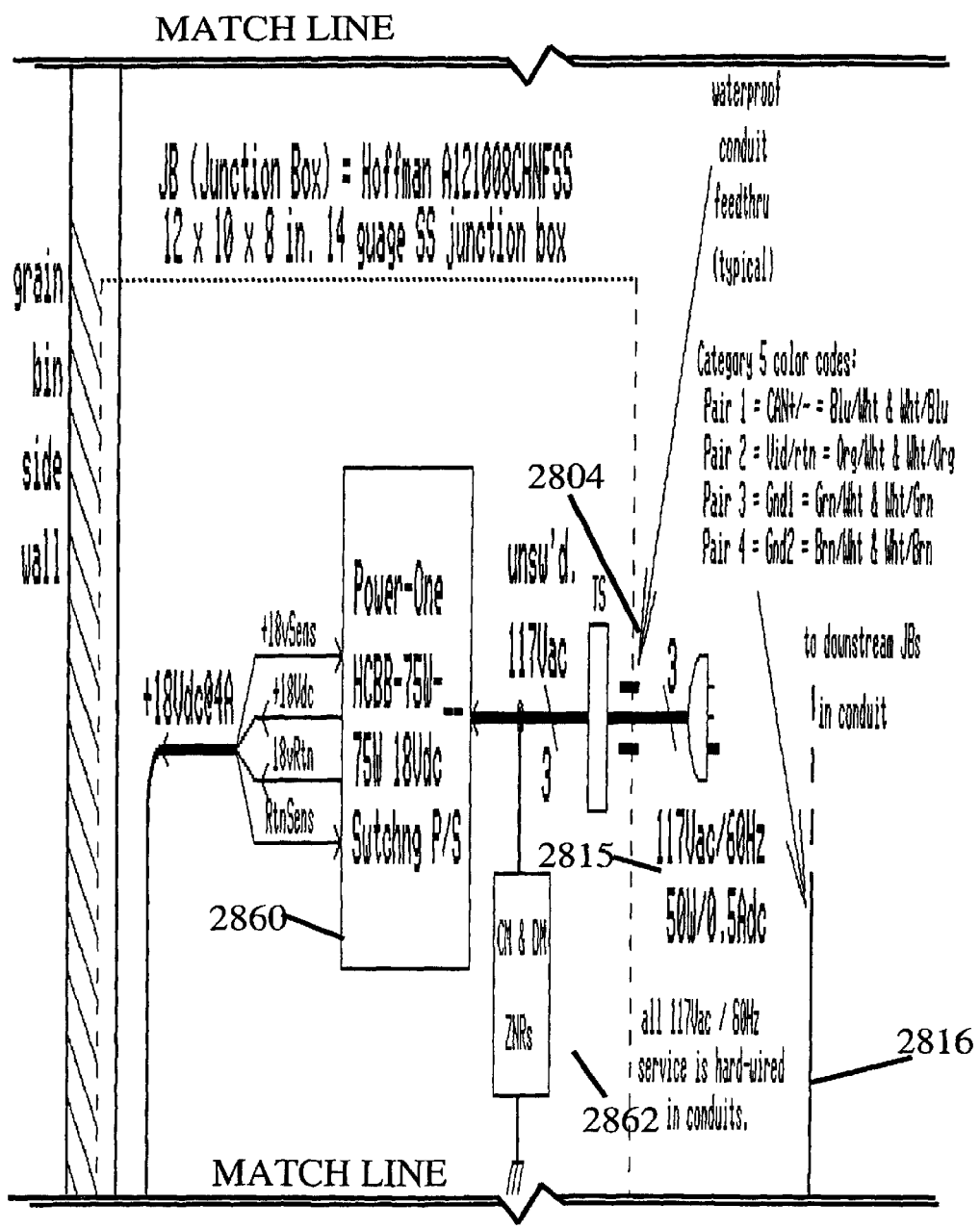
FIG. 28C.2

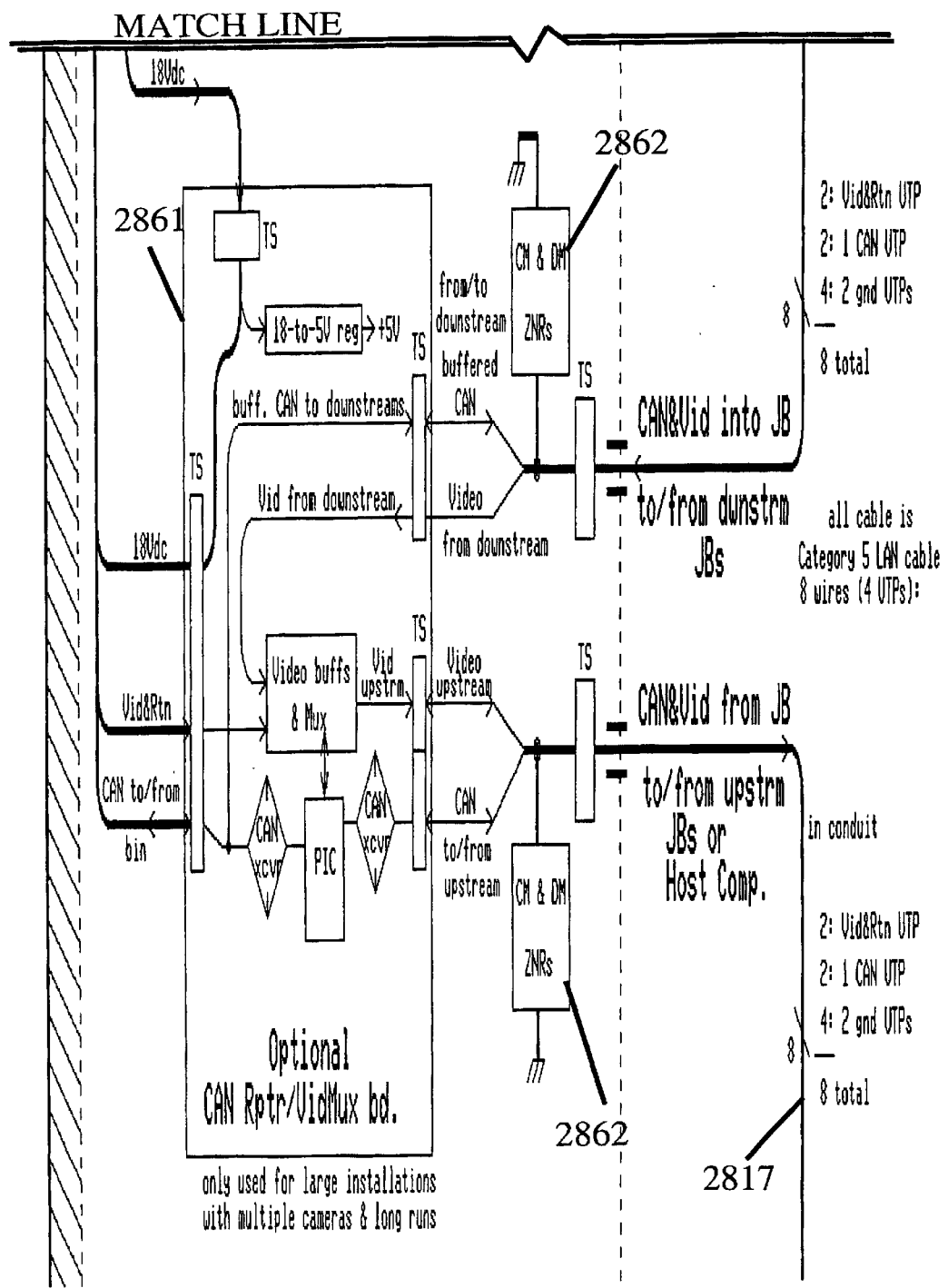
FIG. 28C.3

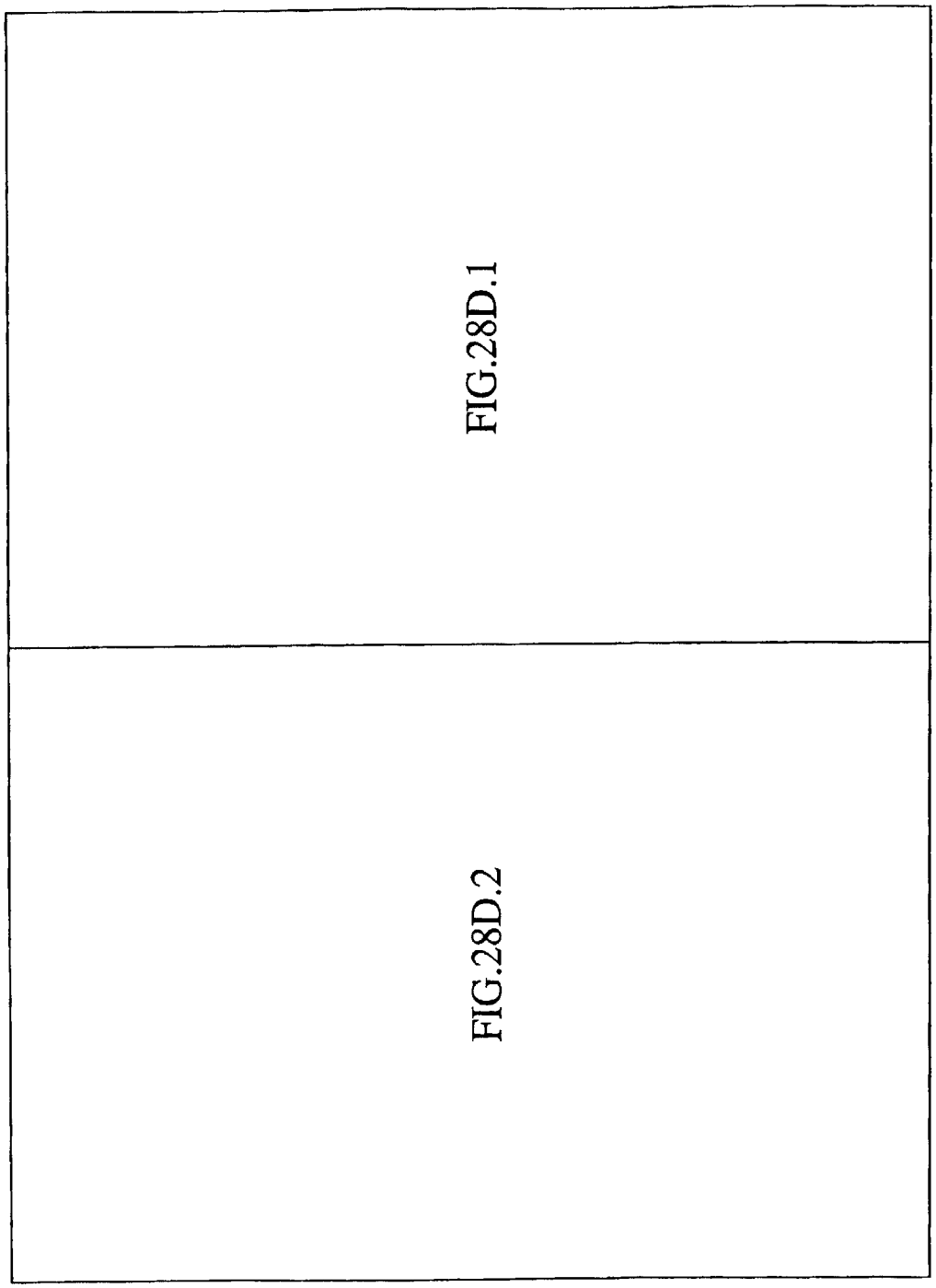

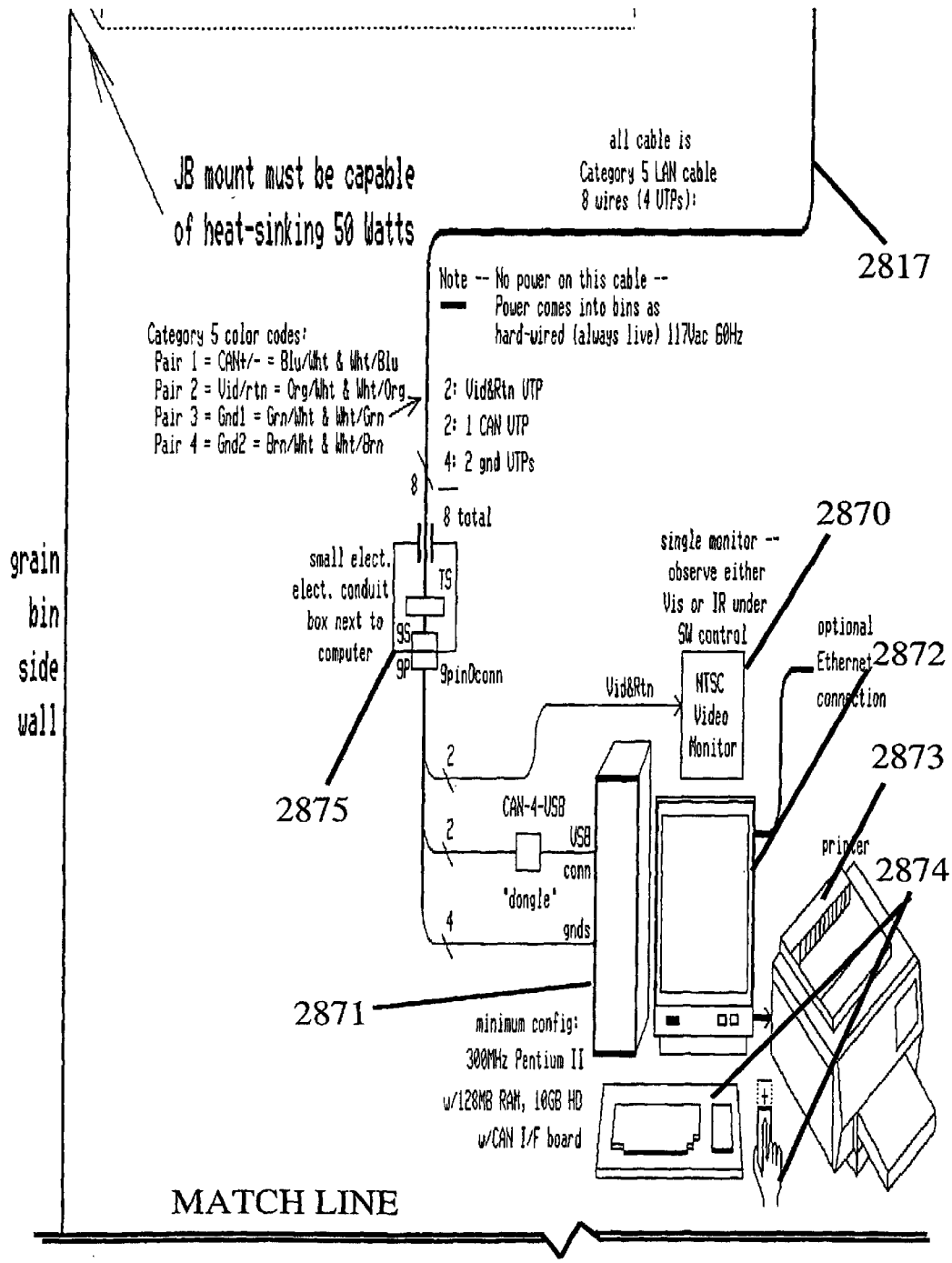
FIG. 28D.1

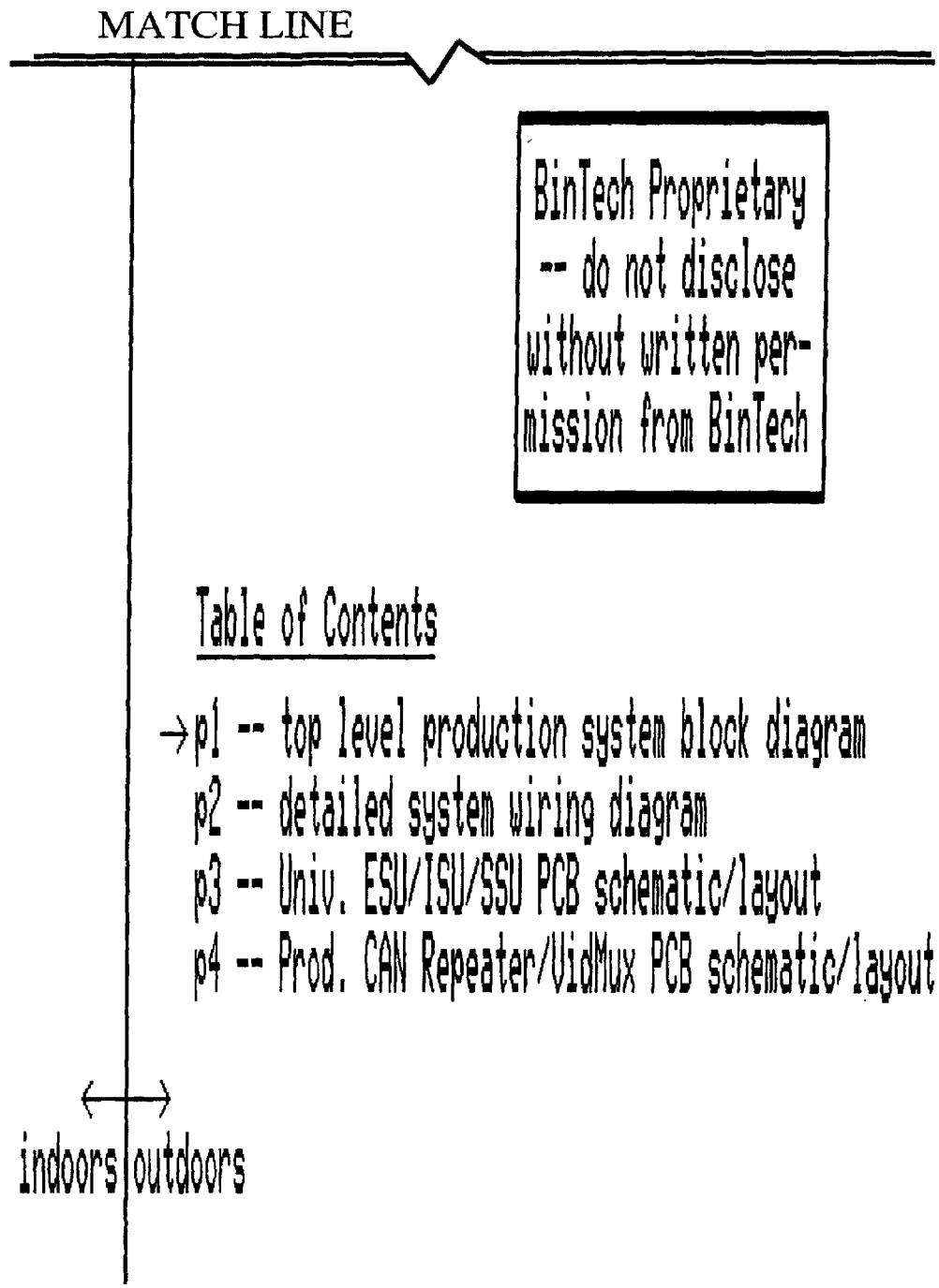
FIG. 28D.2

|         |         |         |         |
|---------|---------|---------|---------|
| FIG.29A<br>29A.1 \| 29A.2<br>29A.3 \| 29A.4 | FIG.29C<br>29C.1 \| 29C.2<br>29C.3 \| 29C.4 |
| FIG.29B<br>29B.1 \| 29B.2<br>29B.3 \| 29B.4 | FIG.29D<br>29D.1<br>29D.2 |

FIG. 29

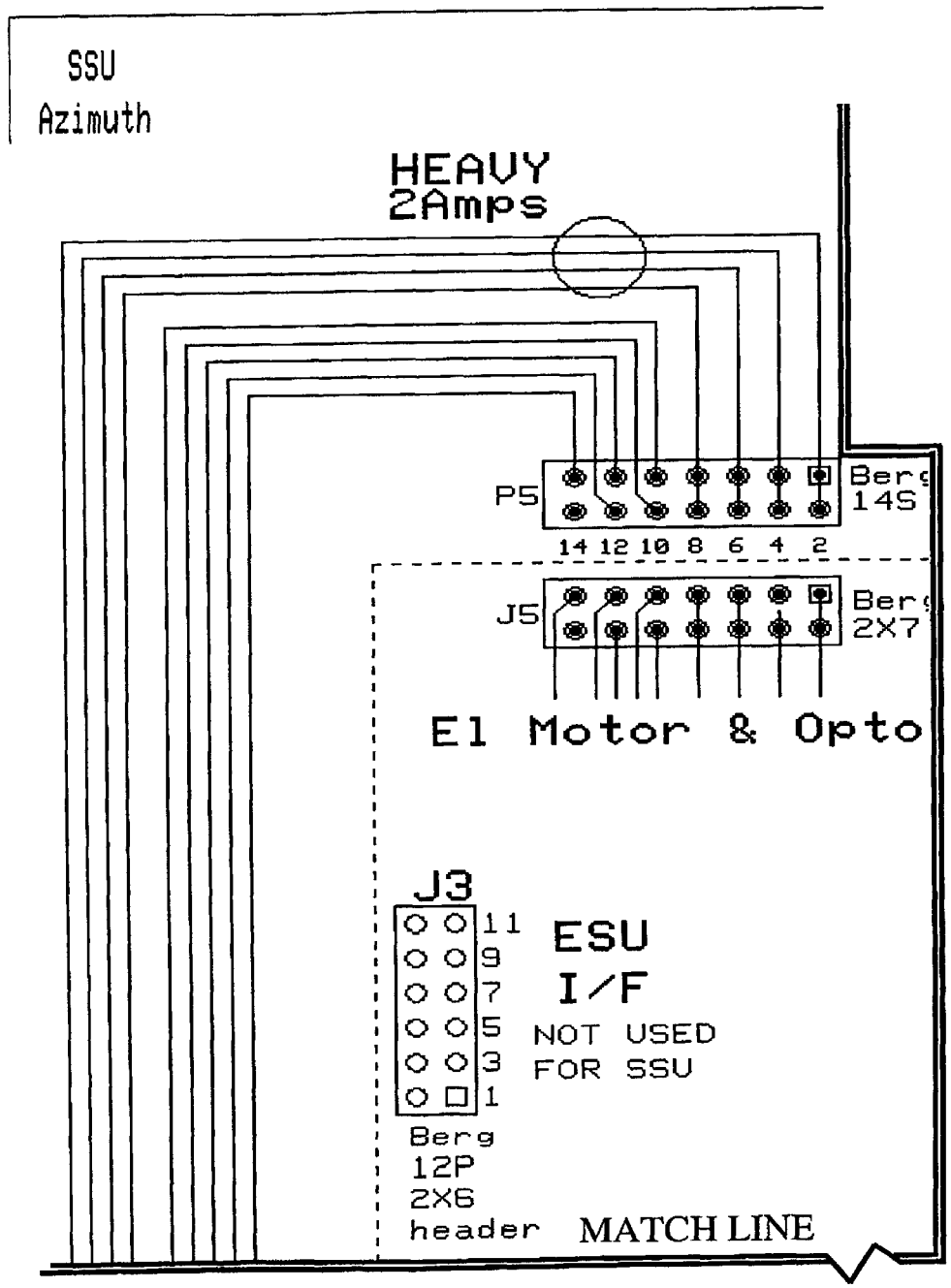
FIG. 29A.1

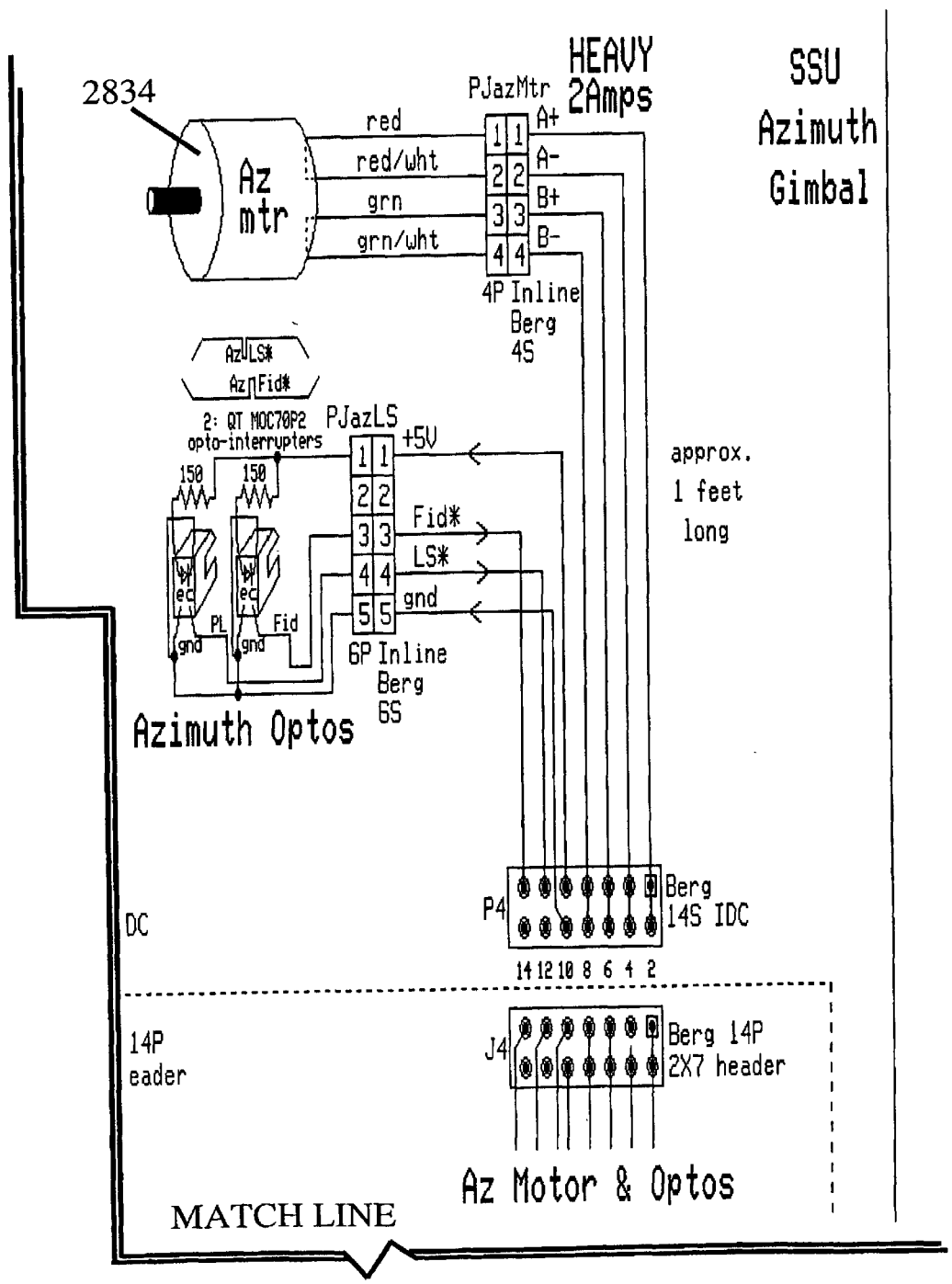
FIG. 29A.2

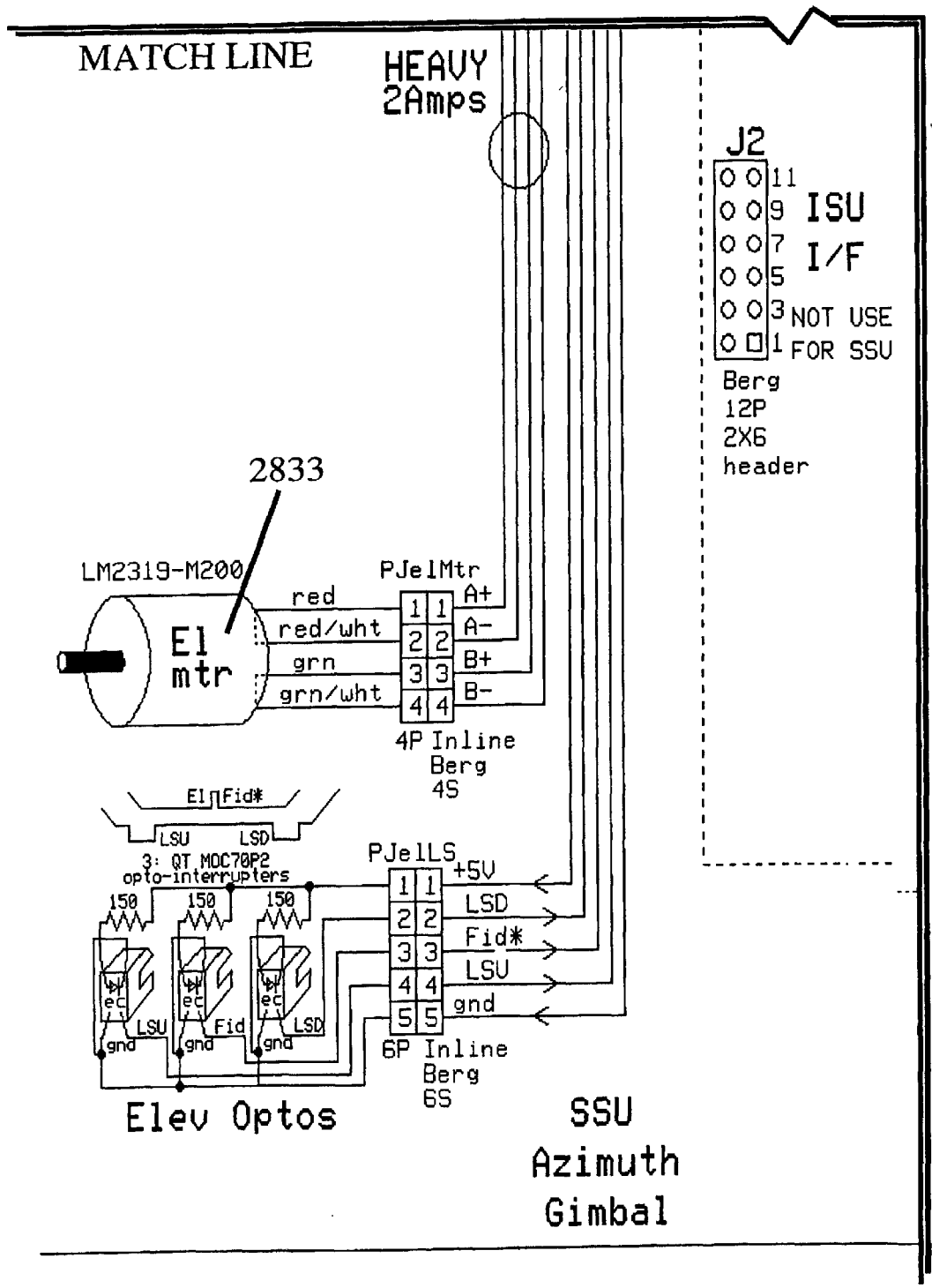
FIG. 29A.3

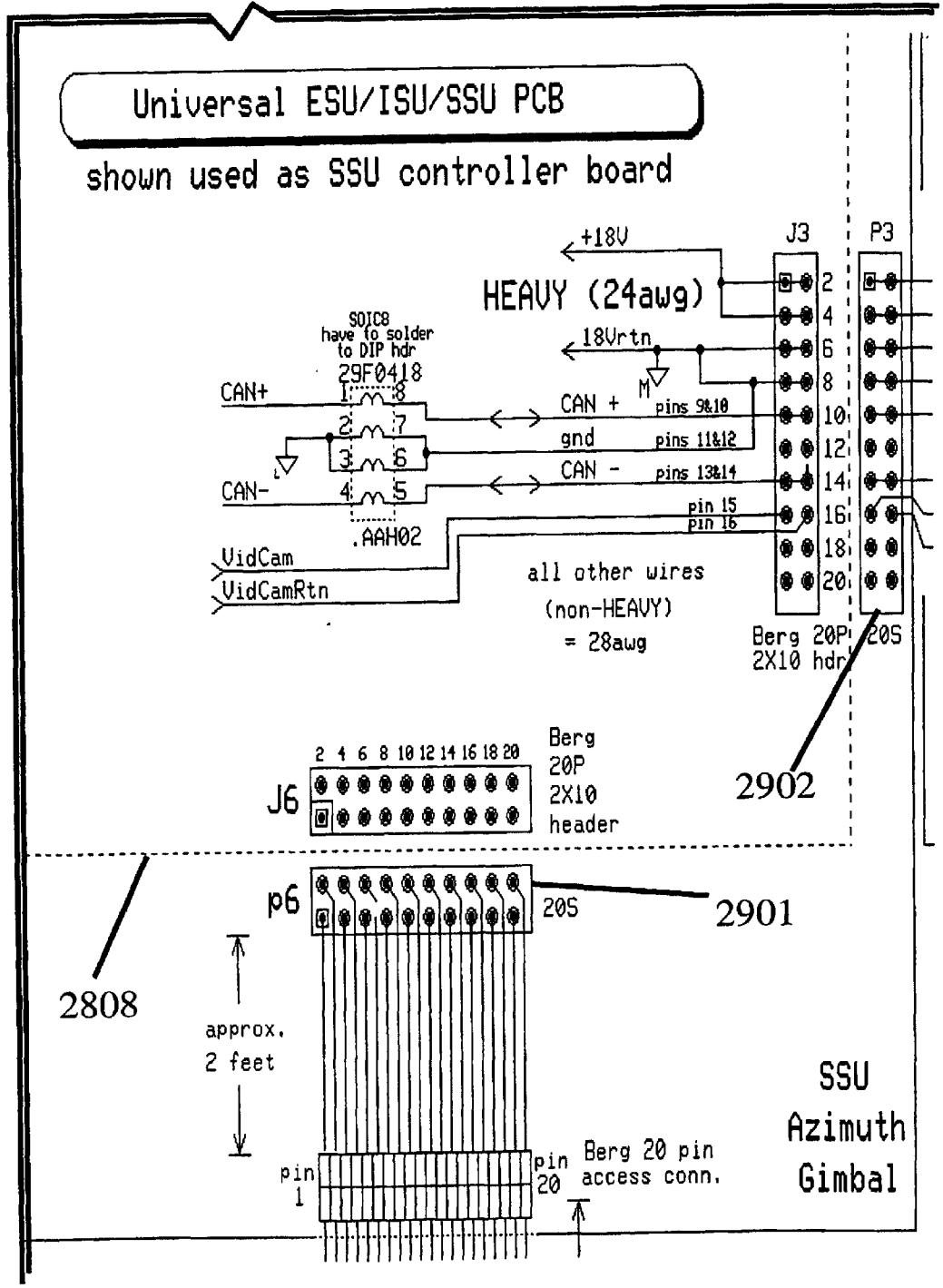
FIG. 29A.4

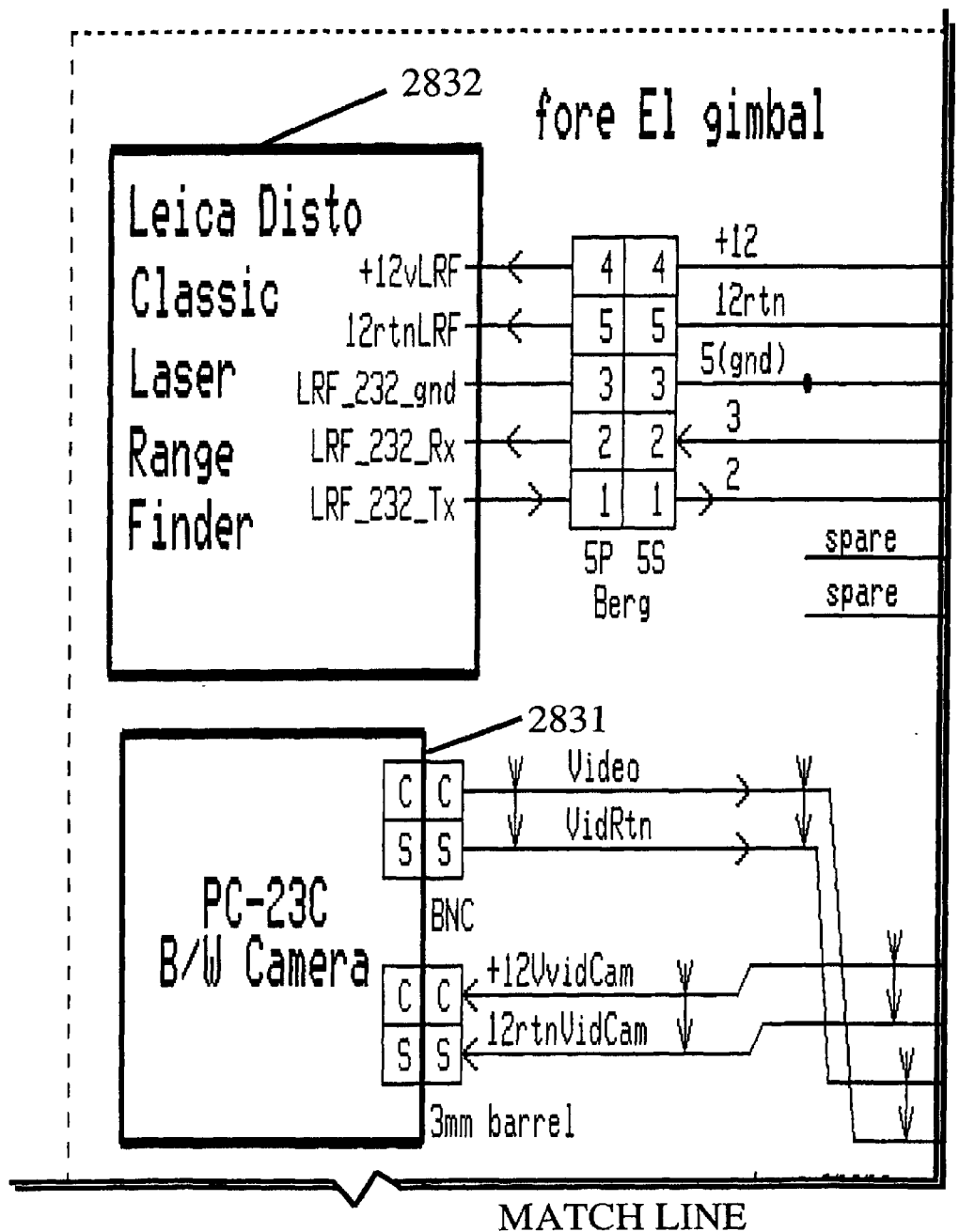
FIG. 29B.1

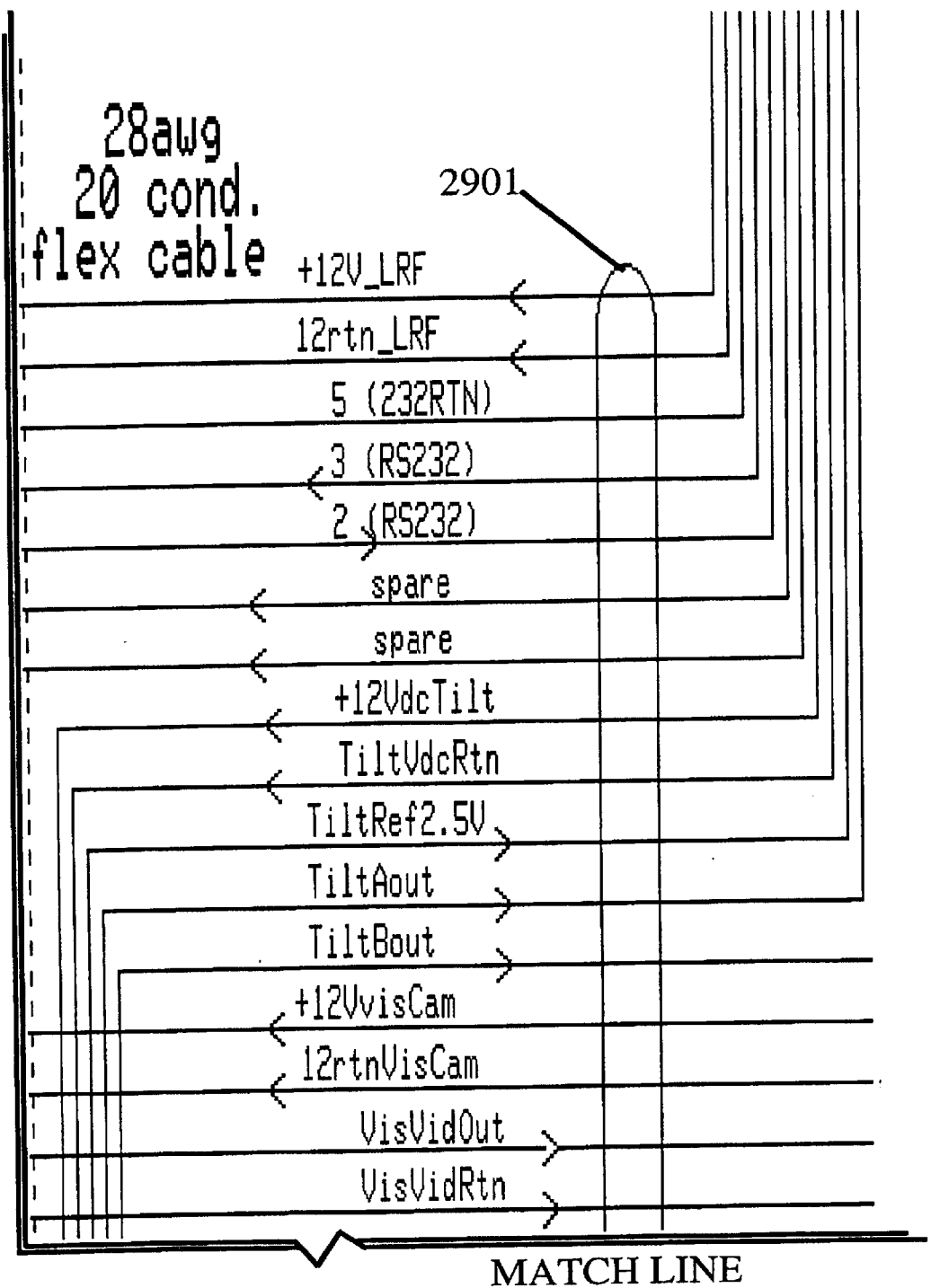
FIG. 29B.2

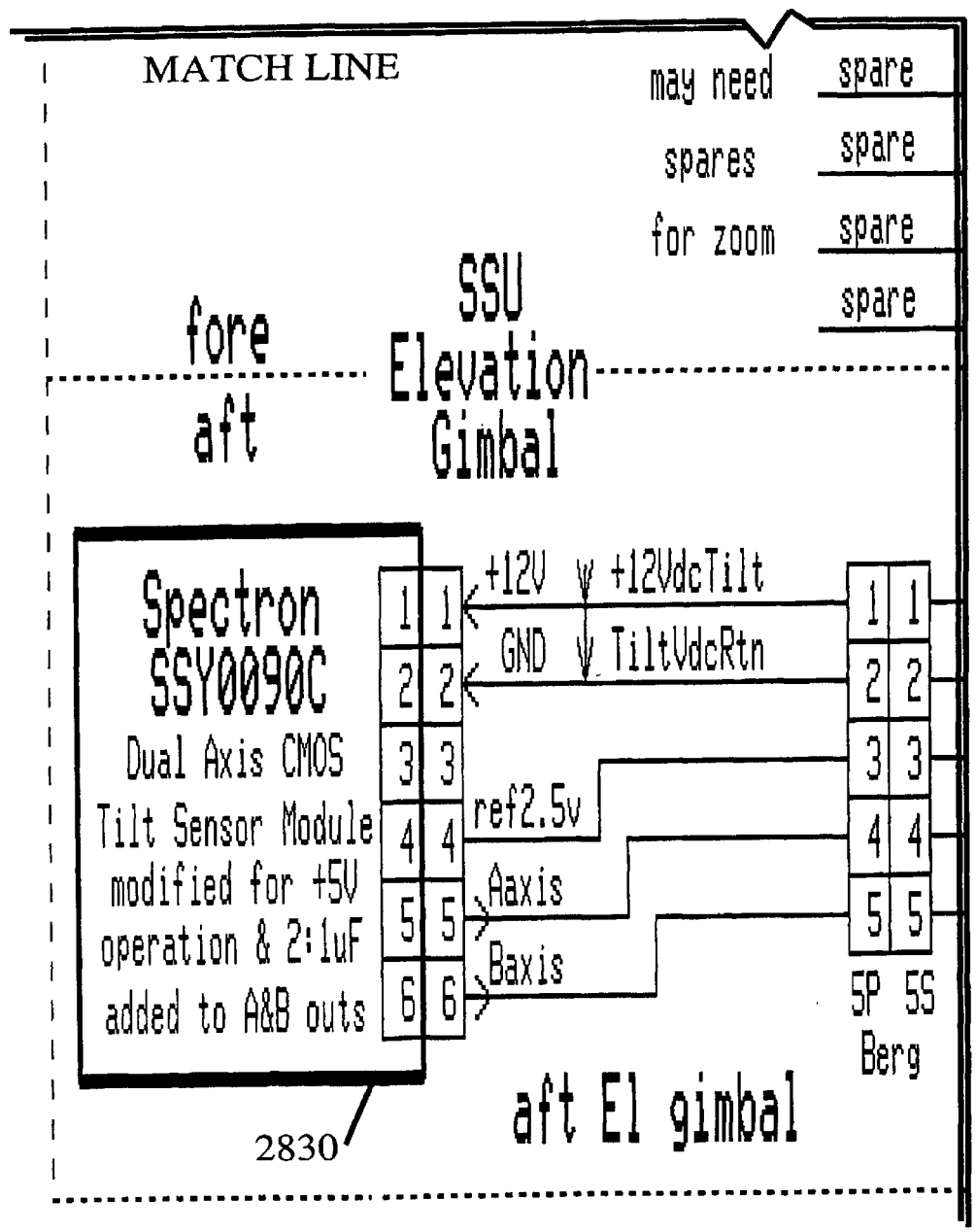
FIG. 29B.3

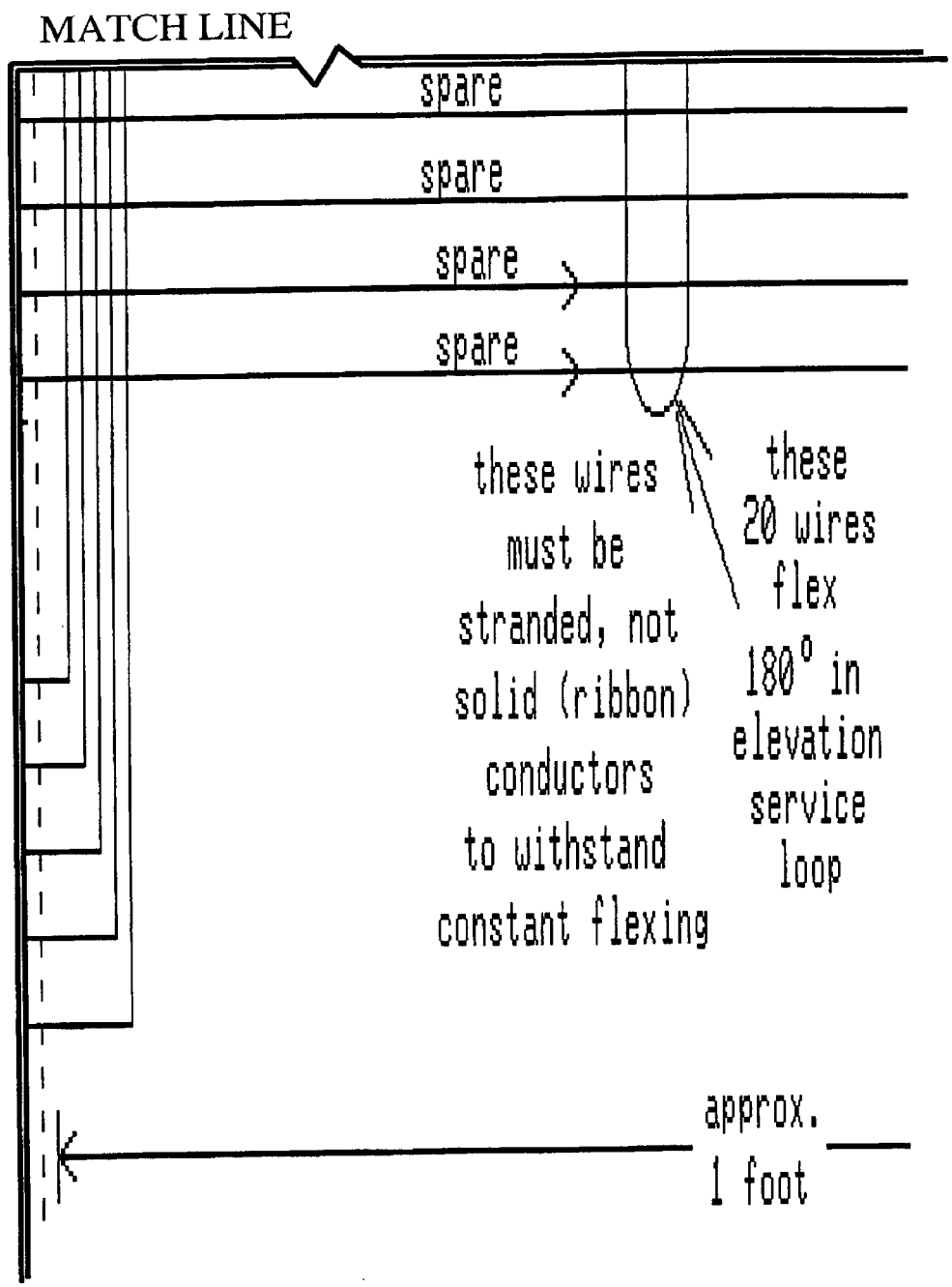
FIG. 29B.4

| FIG.29C.1 | FIG.29C.2 |
|---|---|
| FIG.29C.3 | FIG.29C.4 |

FIG. 29C

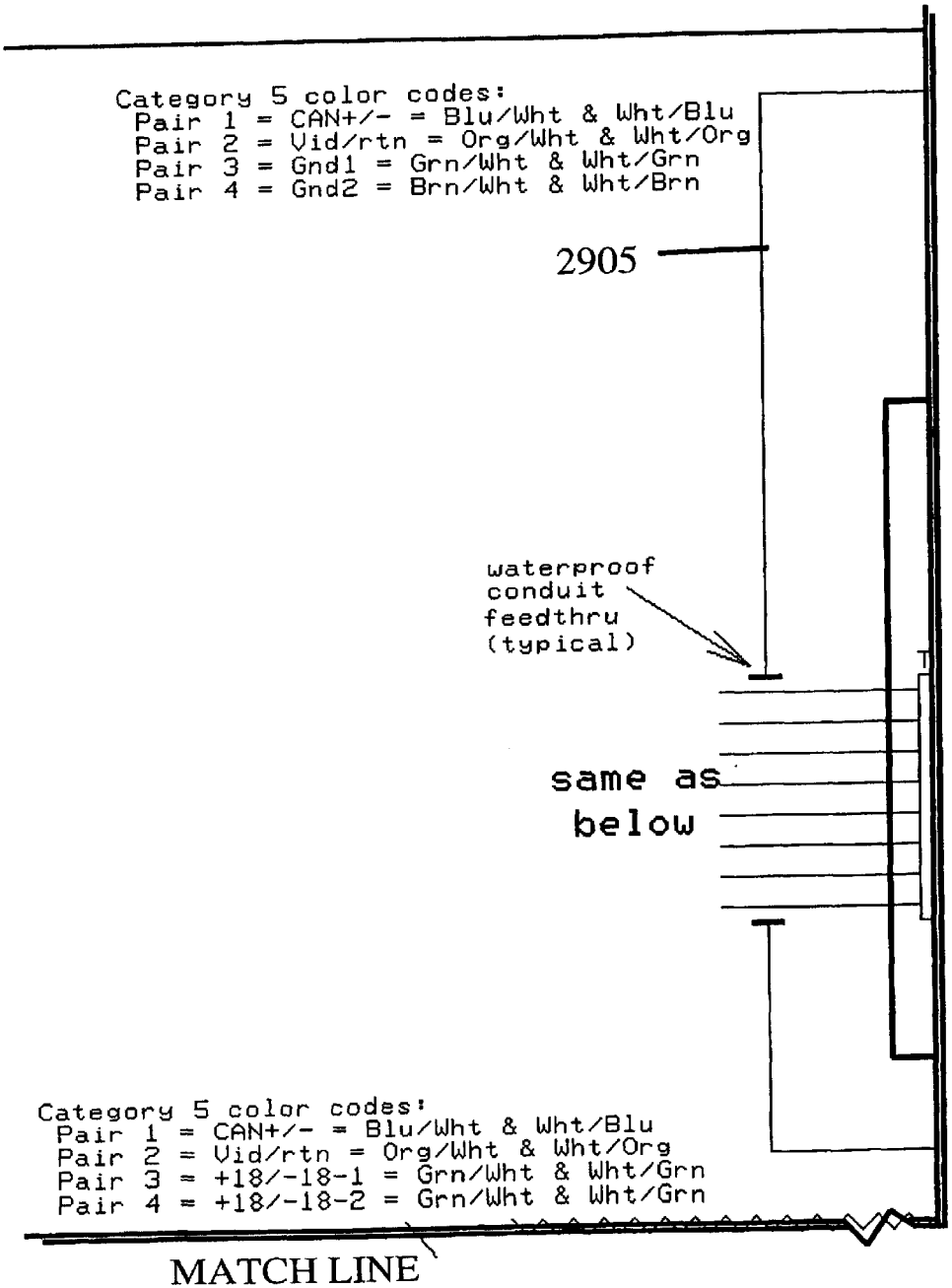
FIG. 29C.1

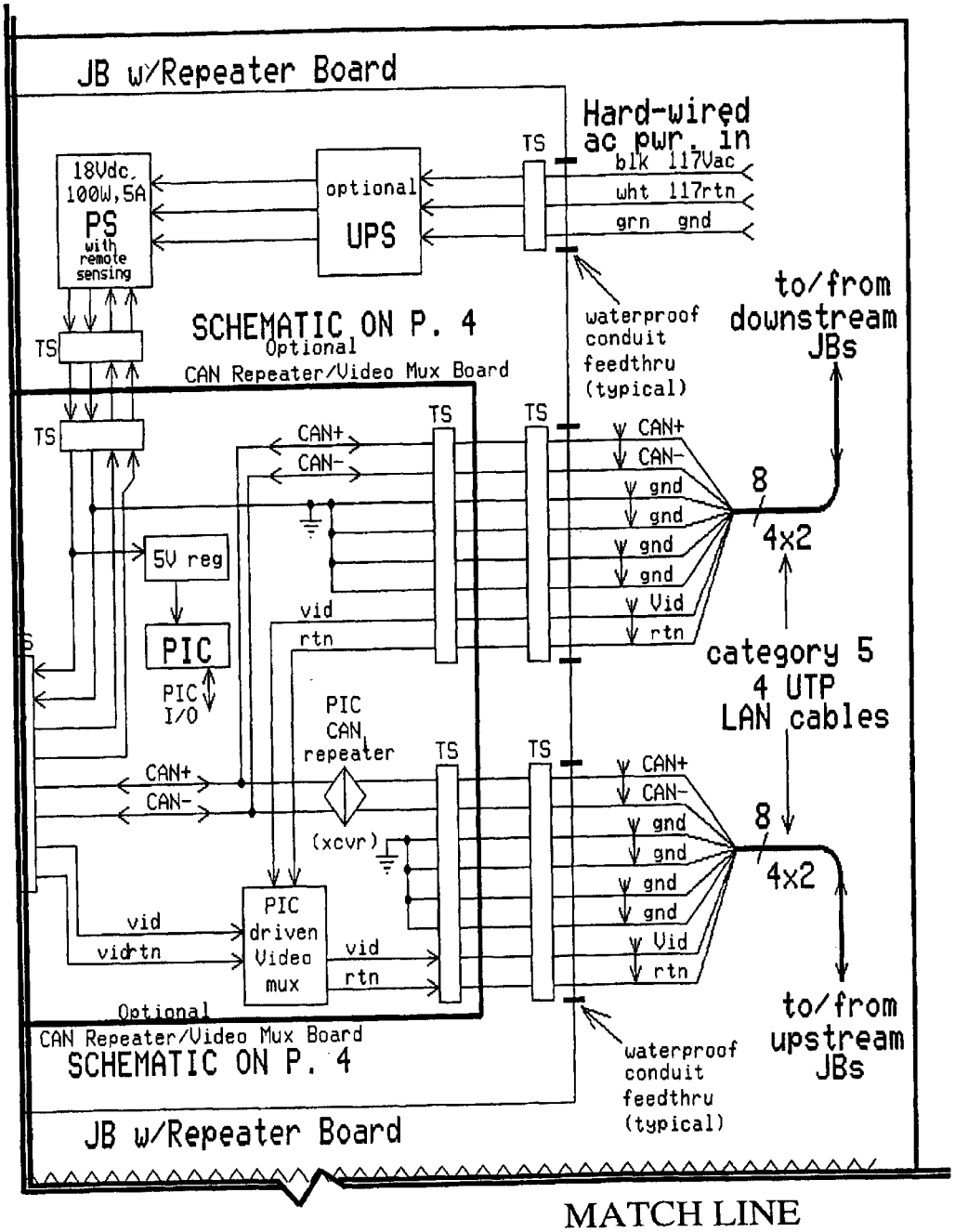
FIG. 29C.2

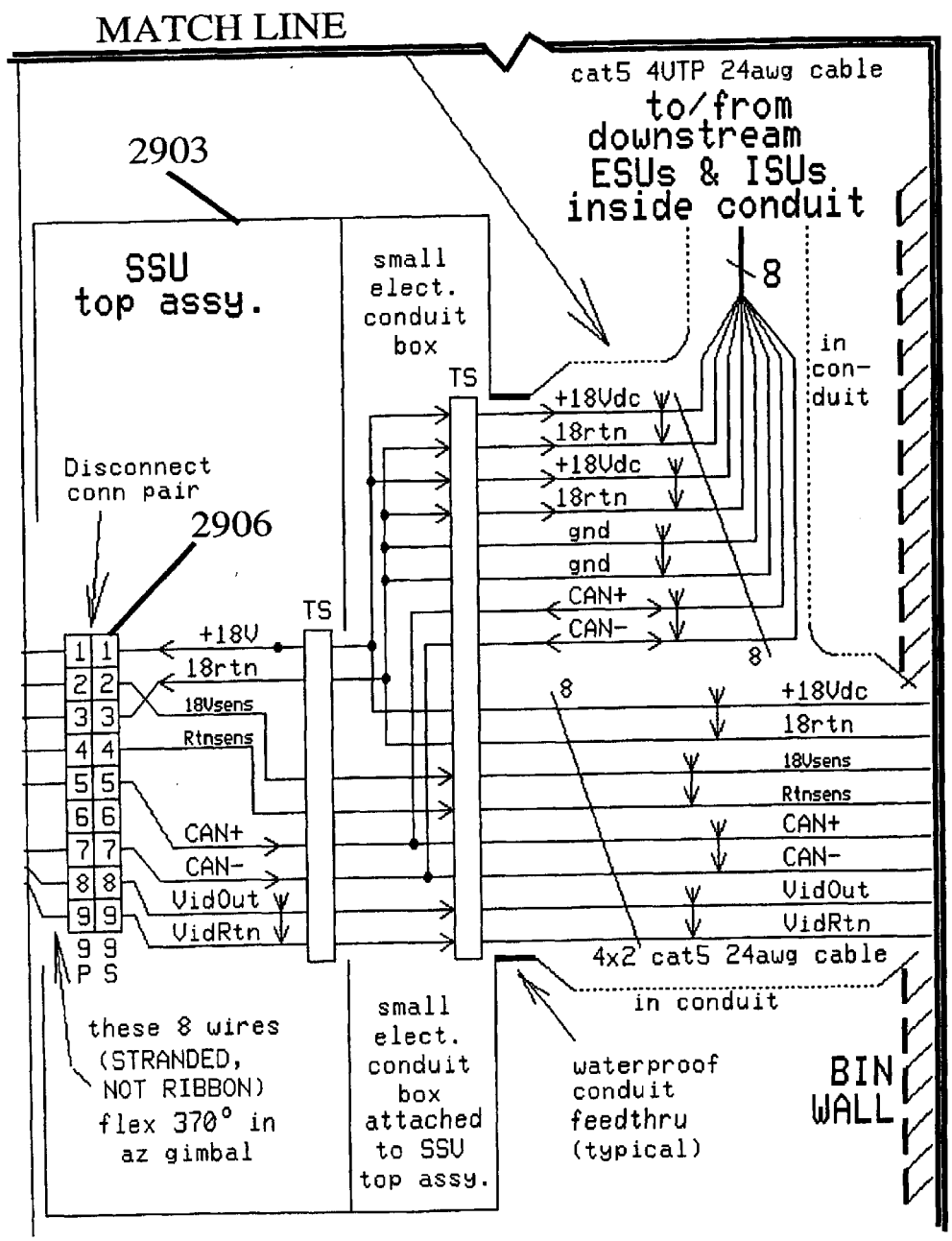
FIG. 29C.3

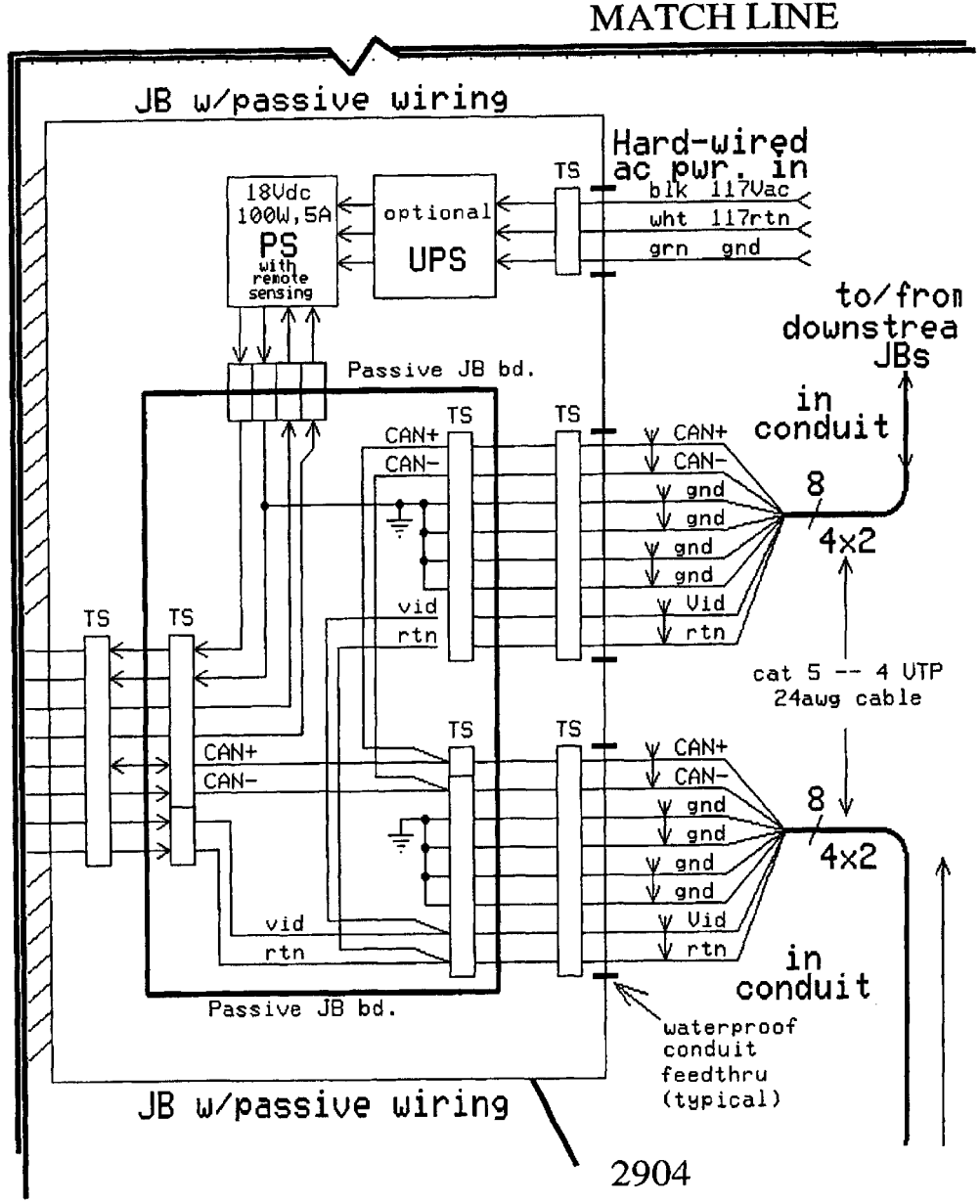
FIG. 29C.4

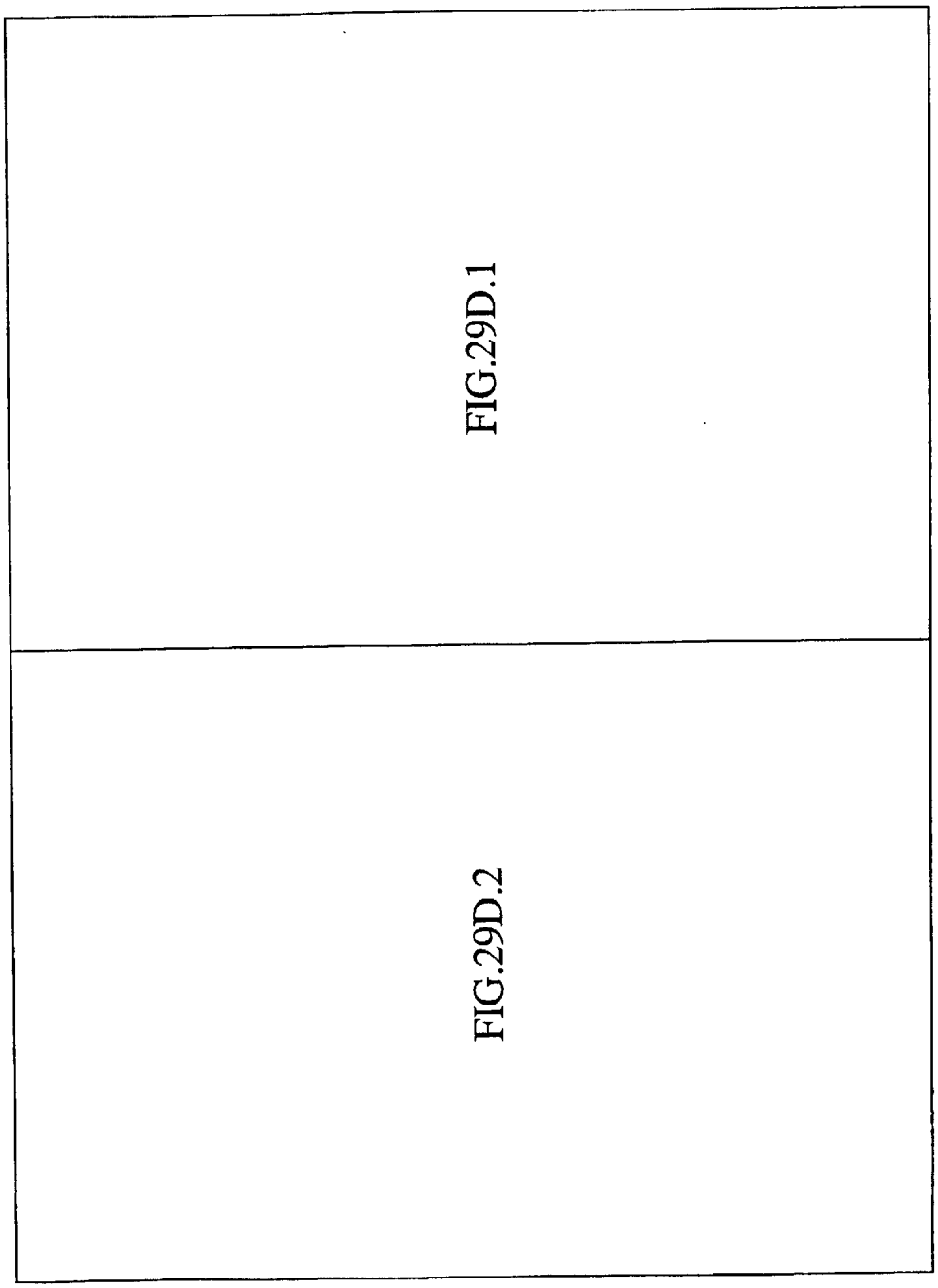

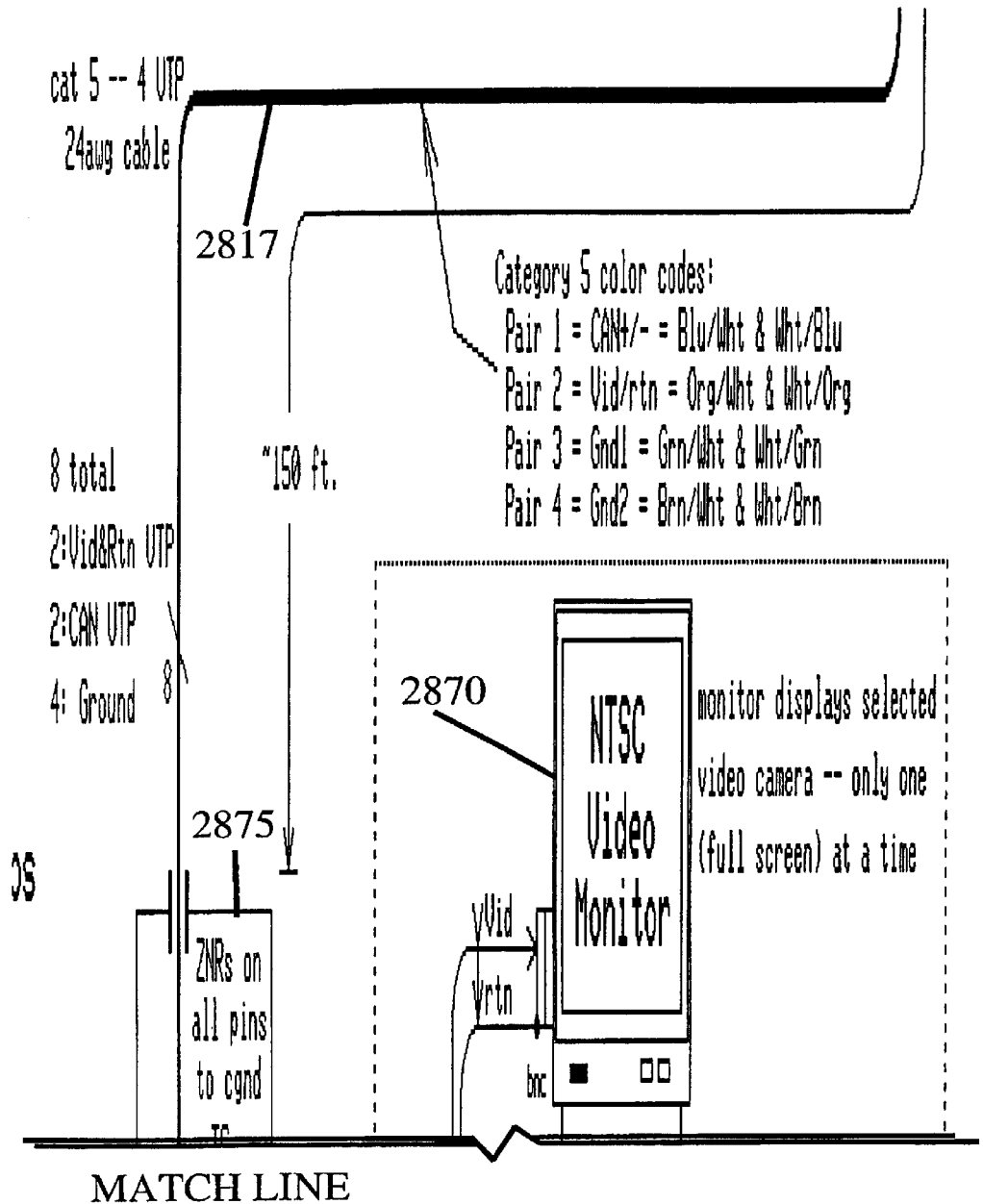
FIG. 29D.1

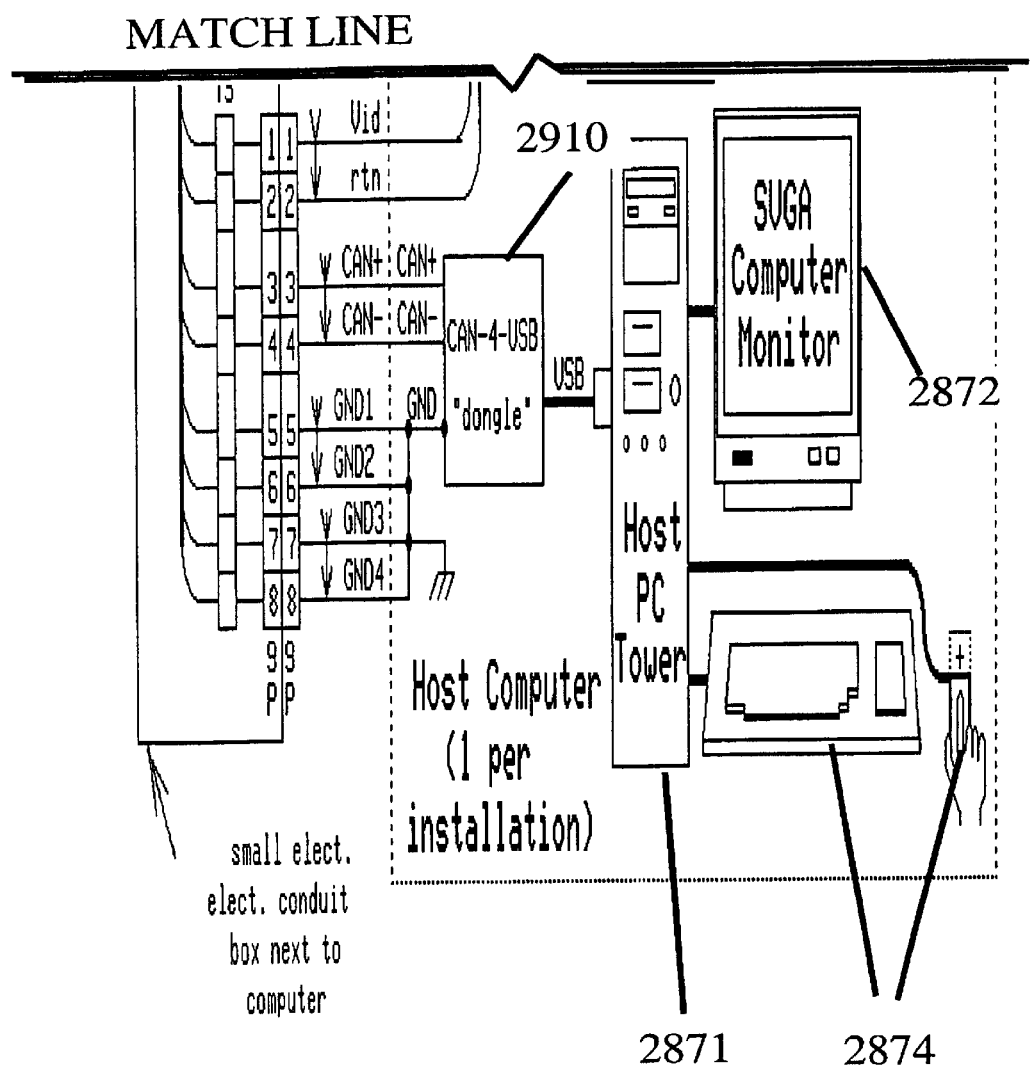
FIG. 29D.2

| FIG.30A | | FIG.30D | |
|---|---|---|---|
| 30A.1 | 30A.3 | 30D.1 | 30D.3 |
| 30A.2 | 30A.4 | 30D.2 | 30D.4 |

| FIG.30B | | FIG.30C | |
|---|---|---|---|
| 30B.1 | 30B.3 | 30C.1 | 30C.3 |
| 30B.2 | 30B.4 | 30C.2 | |

FIG. 30

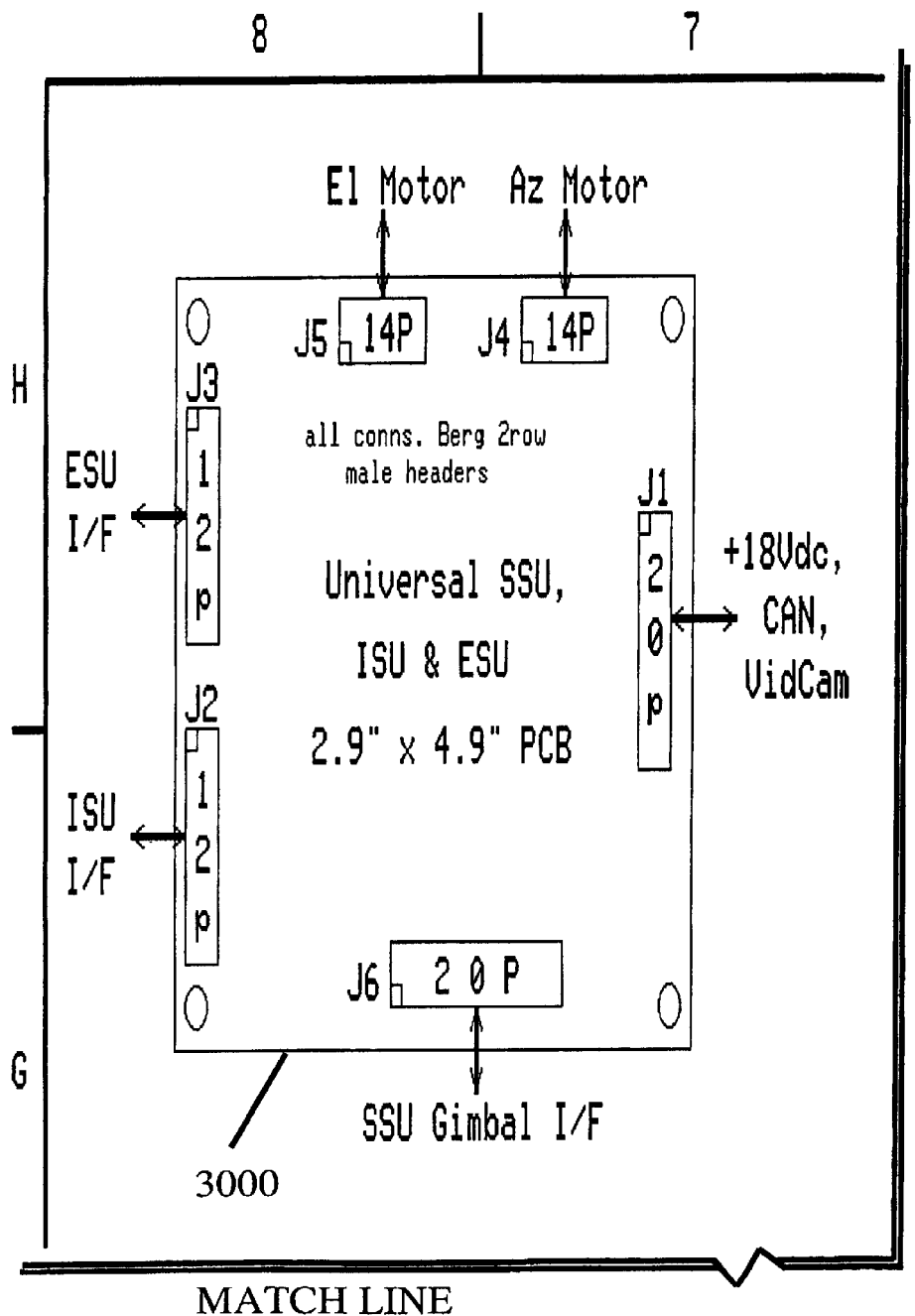
FIG. 30A.1

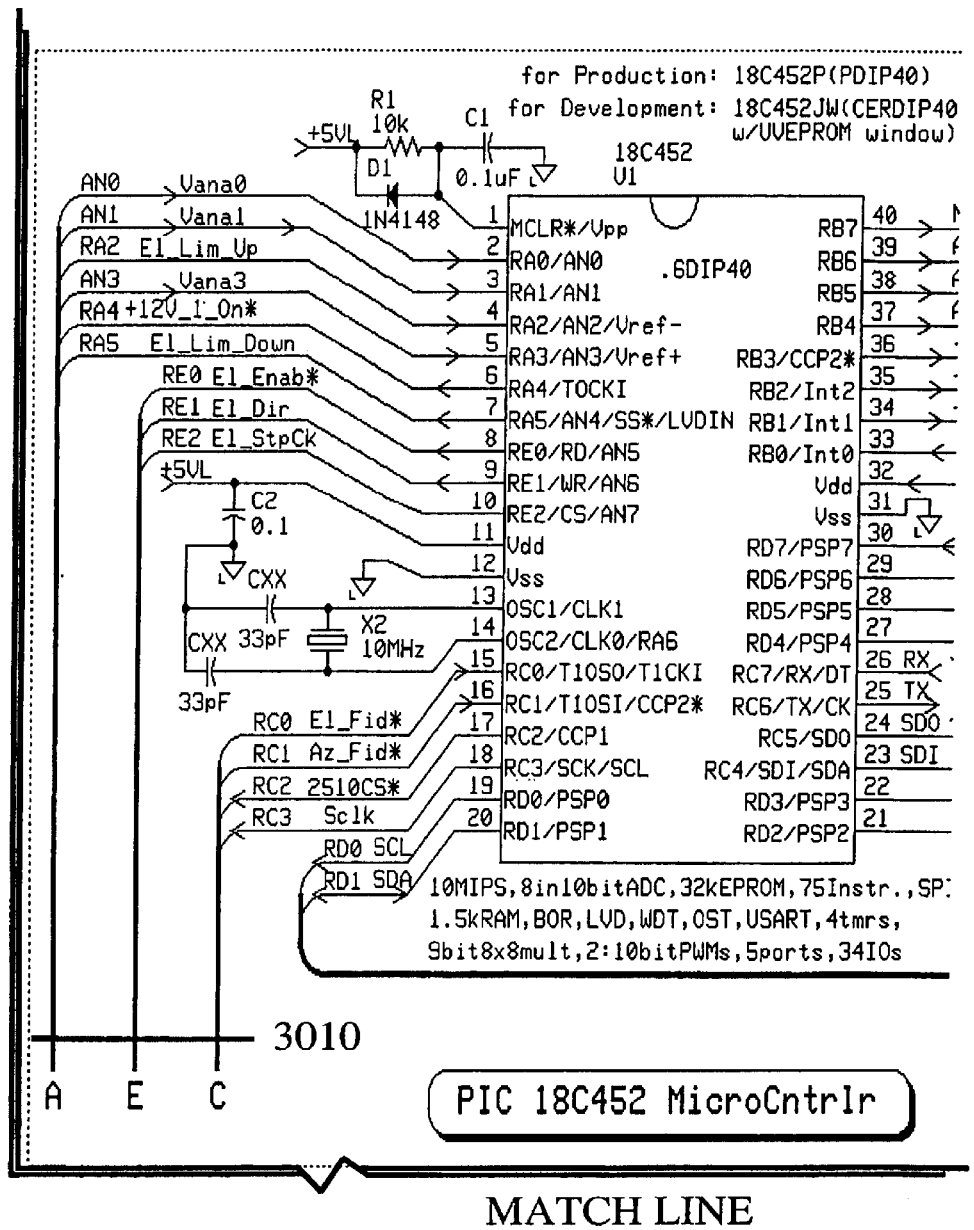
FIG. 30A.2

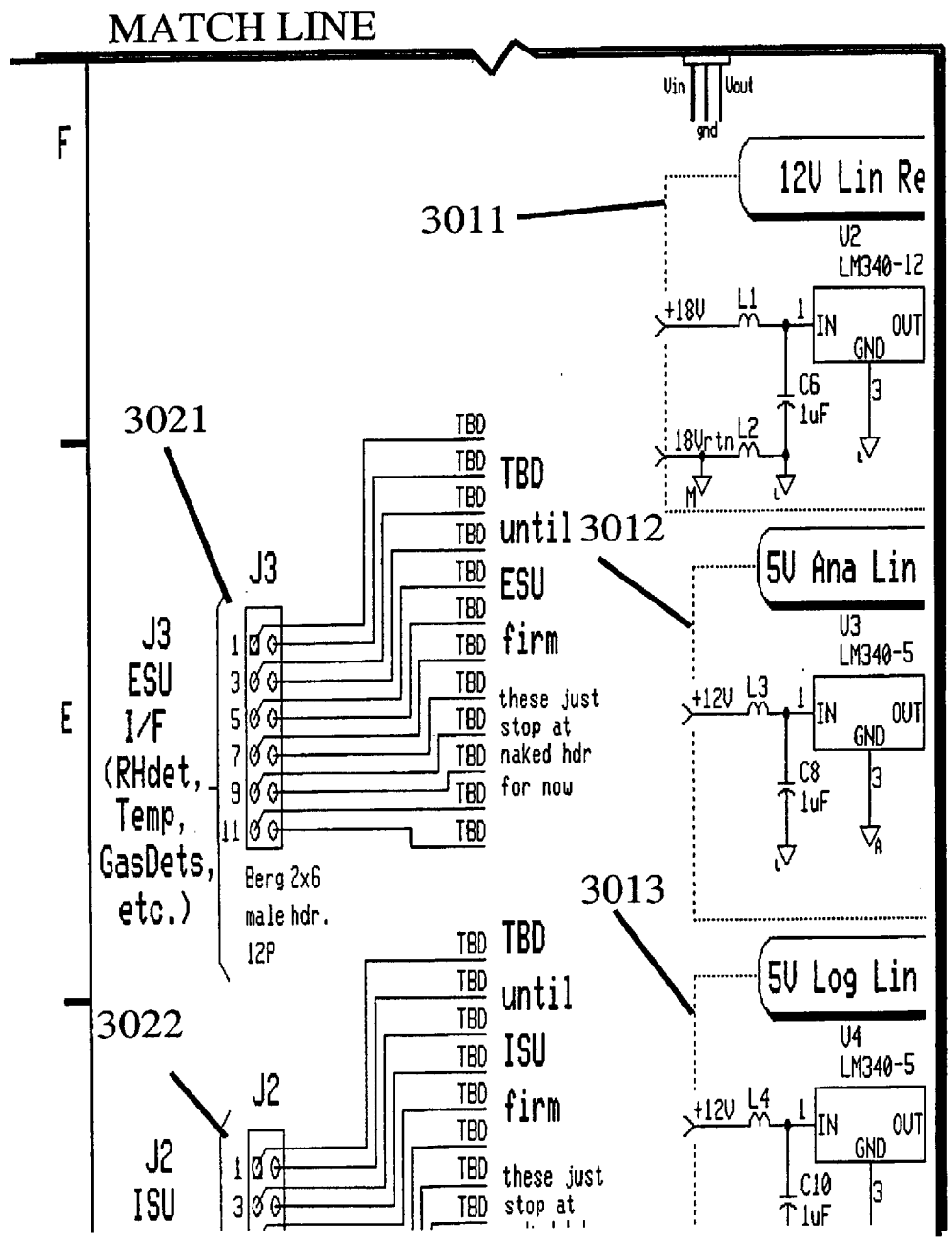
FIG. 30A.3

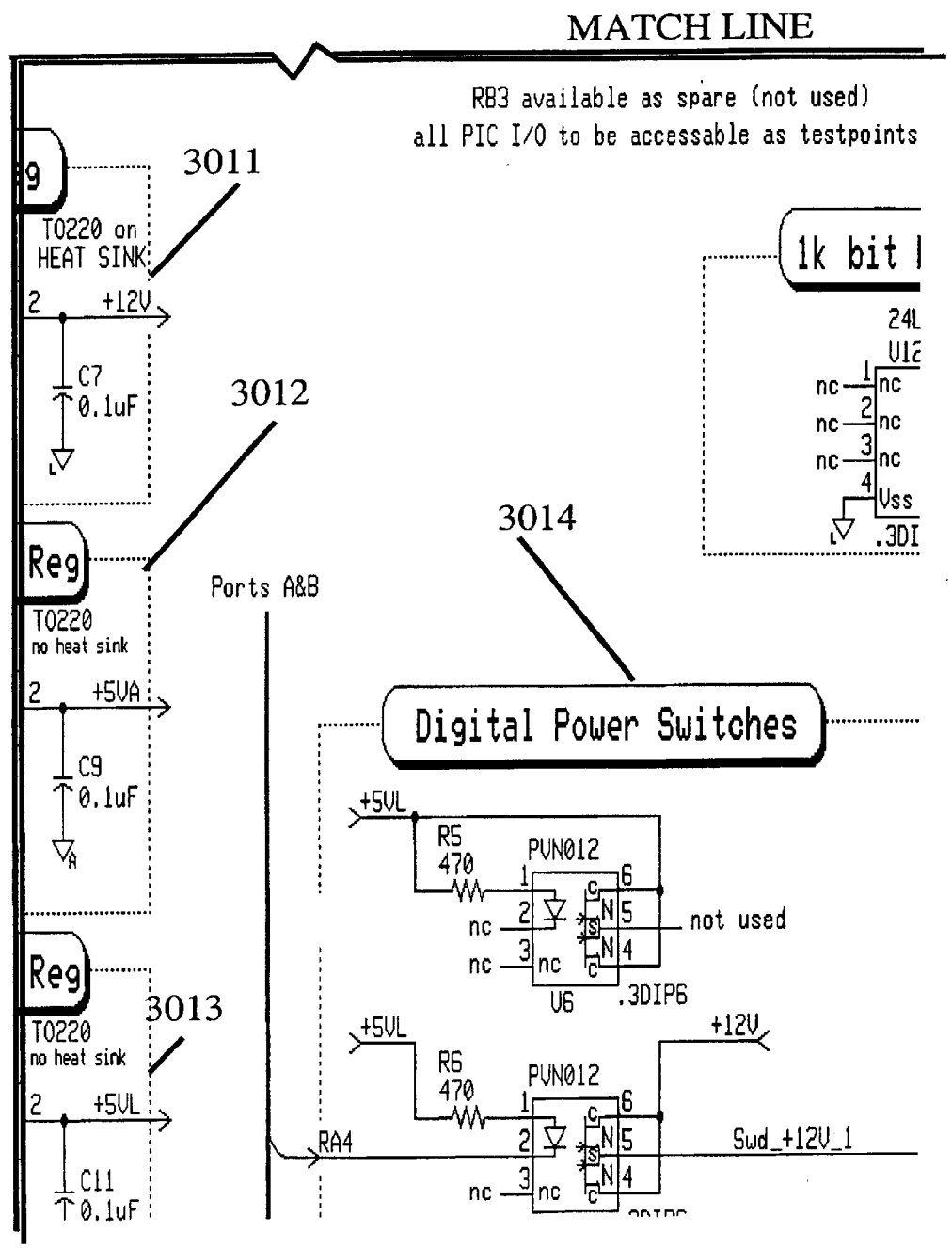
FIG. 30A.4

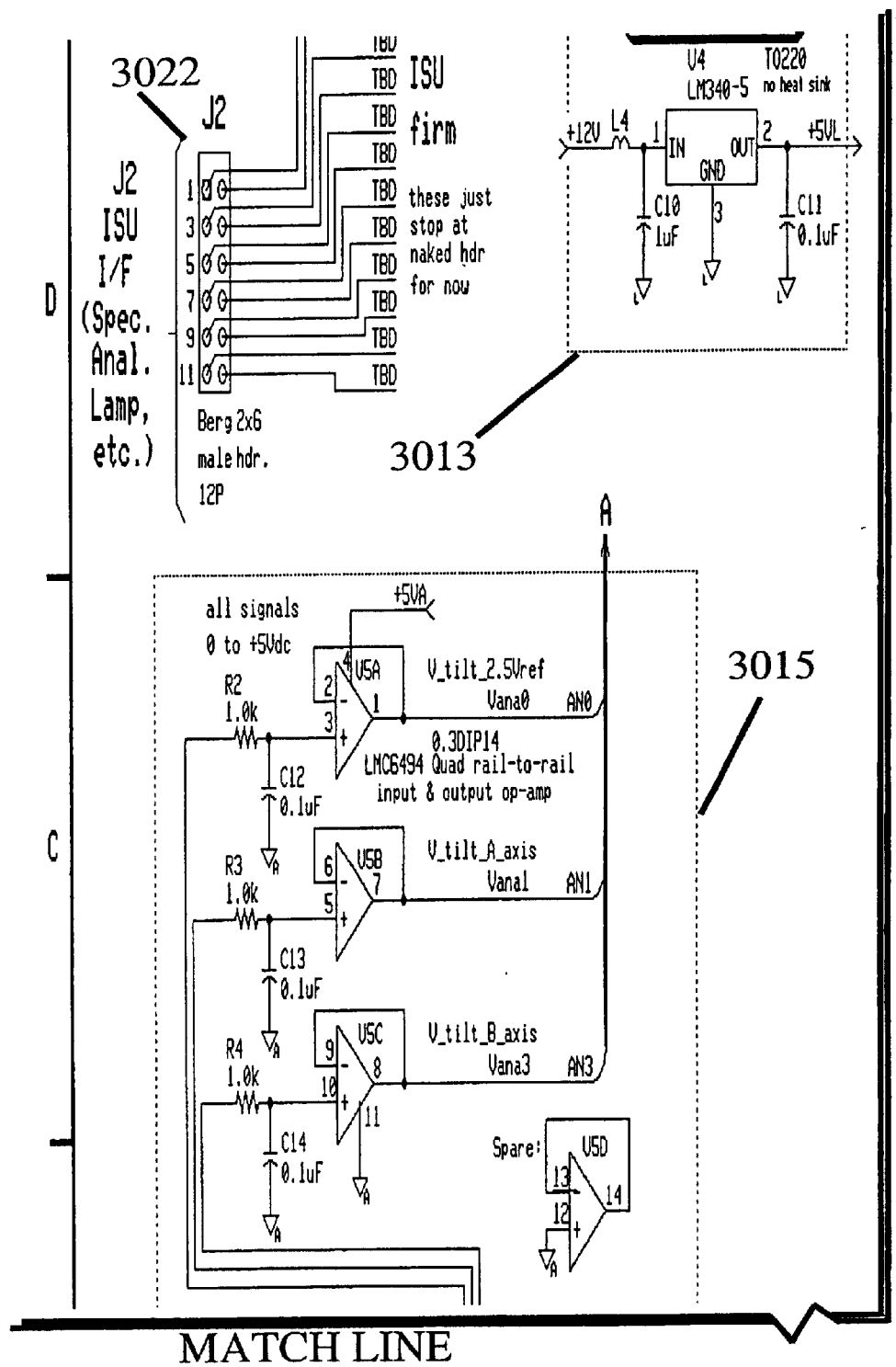
FIG. 30B.1

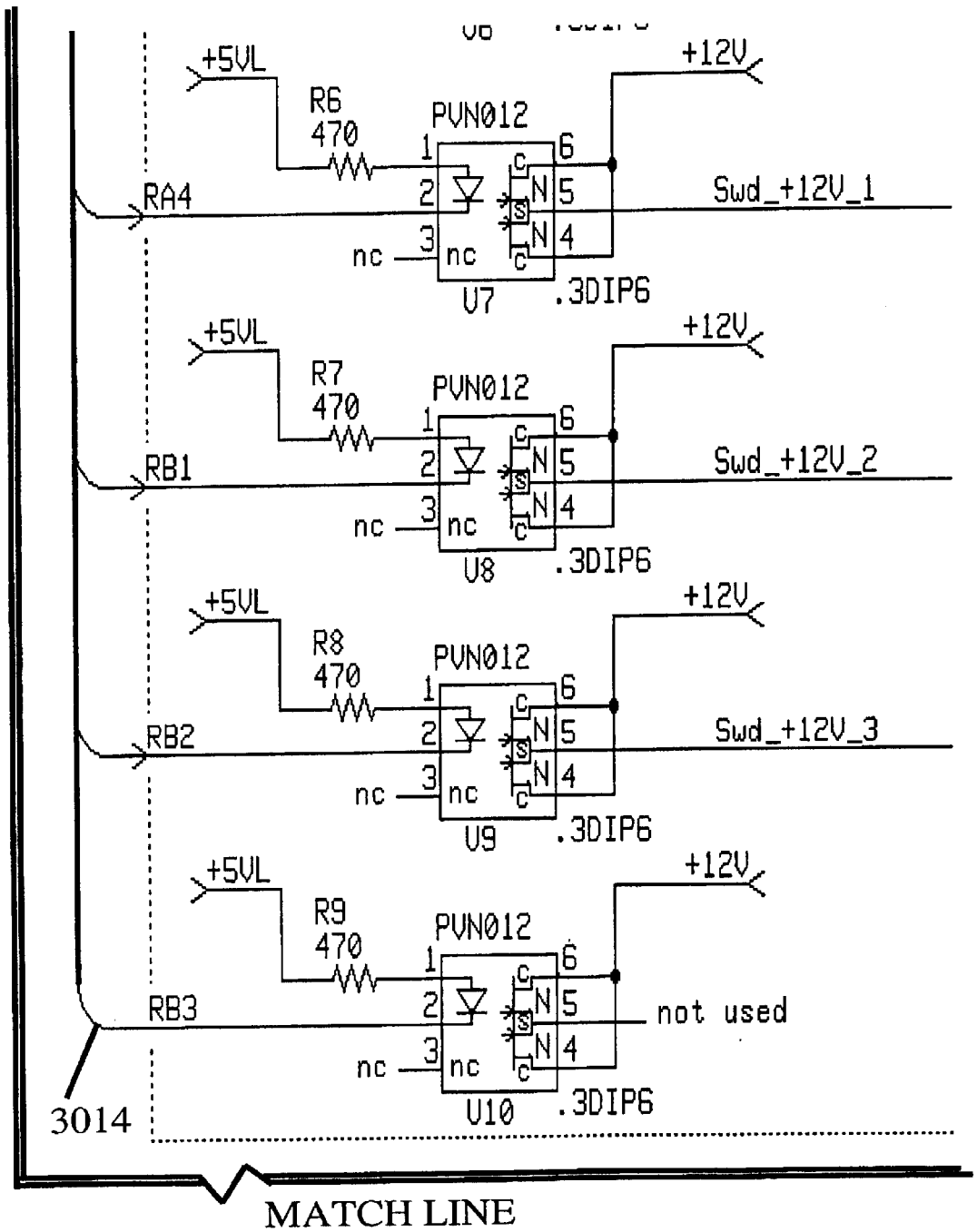
FIG. 30B.2

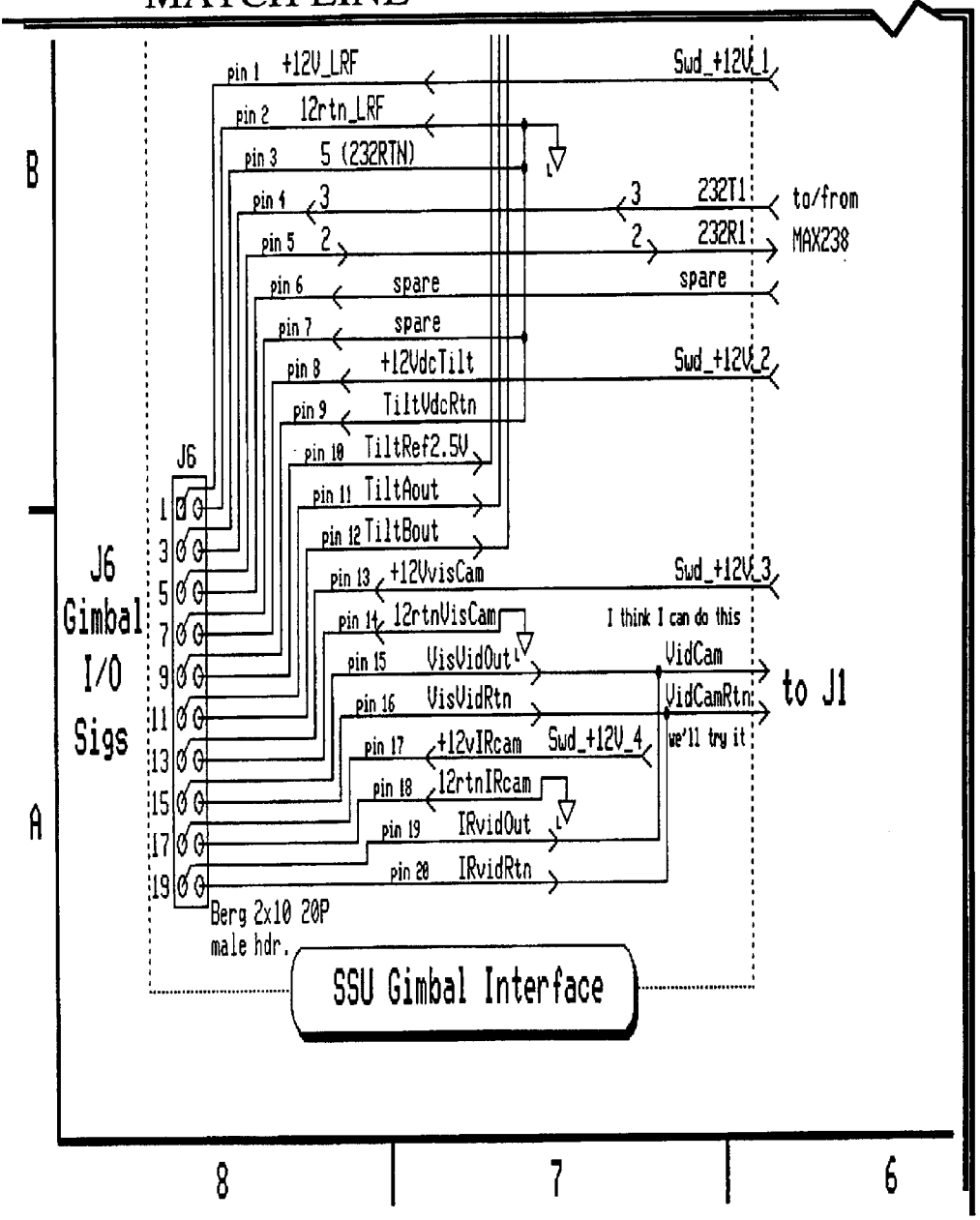
FIG. 30B.3

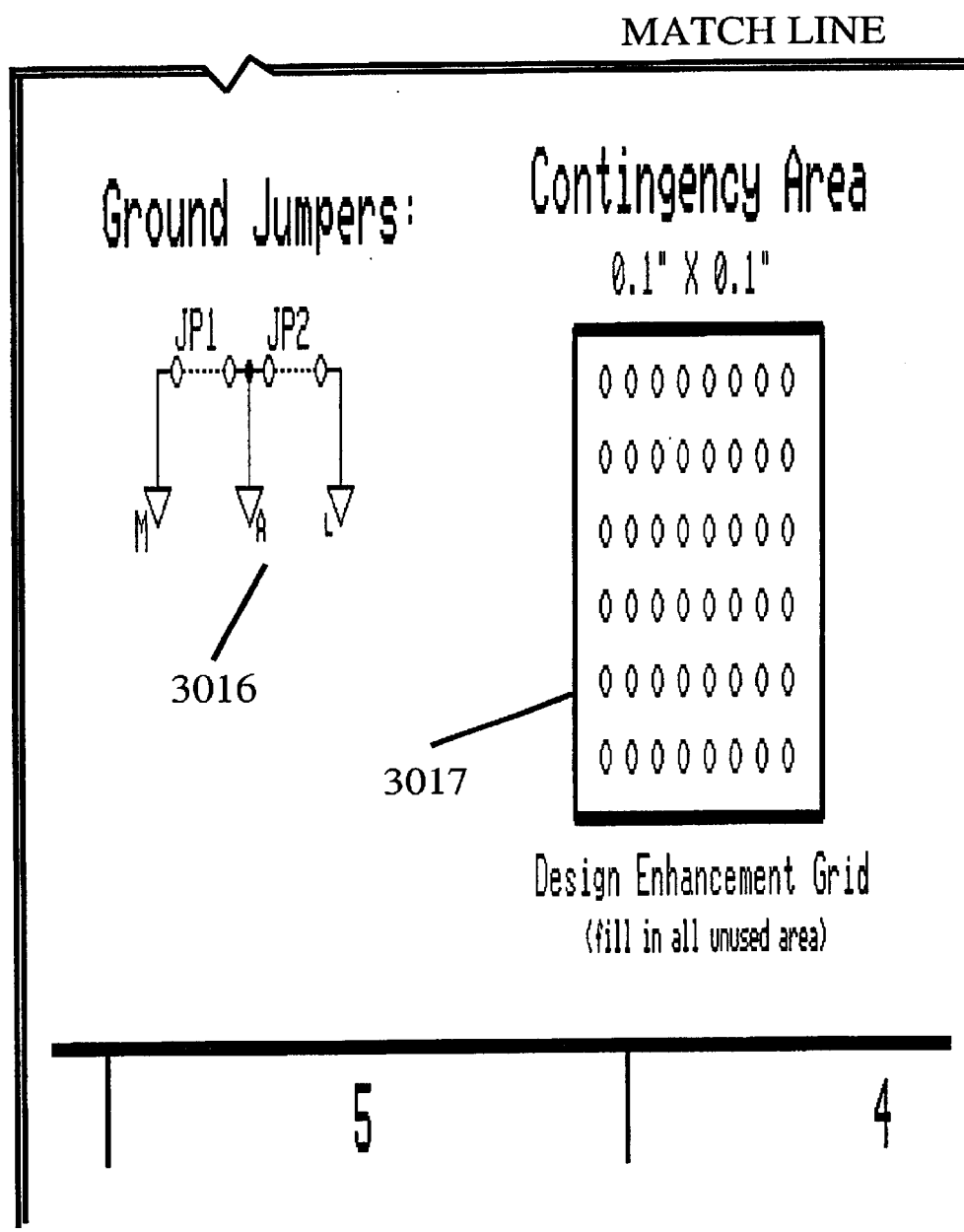
FIG. 30B.4

| FIG.30C.1 | FIG.30C.2 |
|---|---|
| FIG.30C.3 | |

FIG. 30C

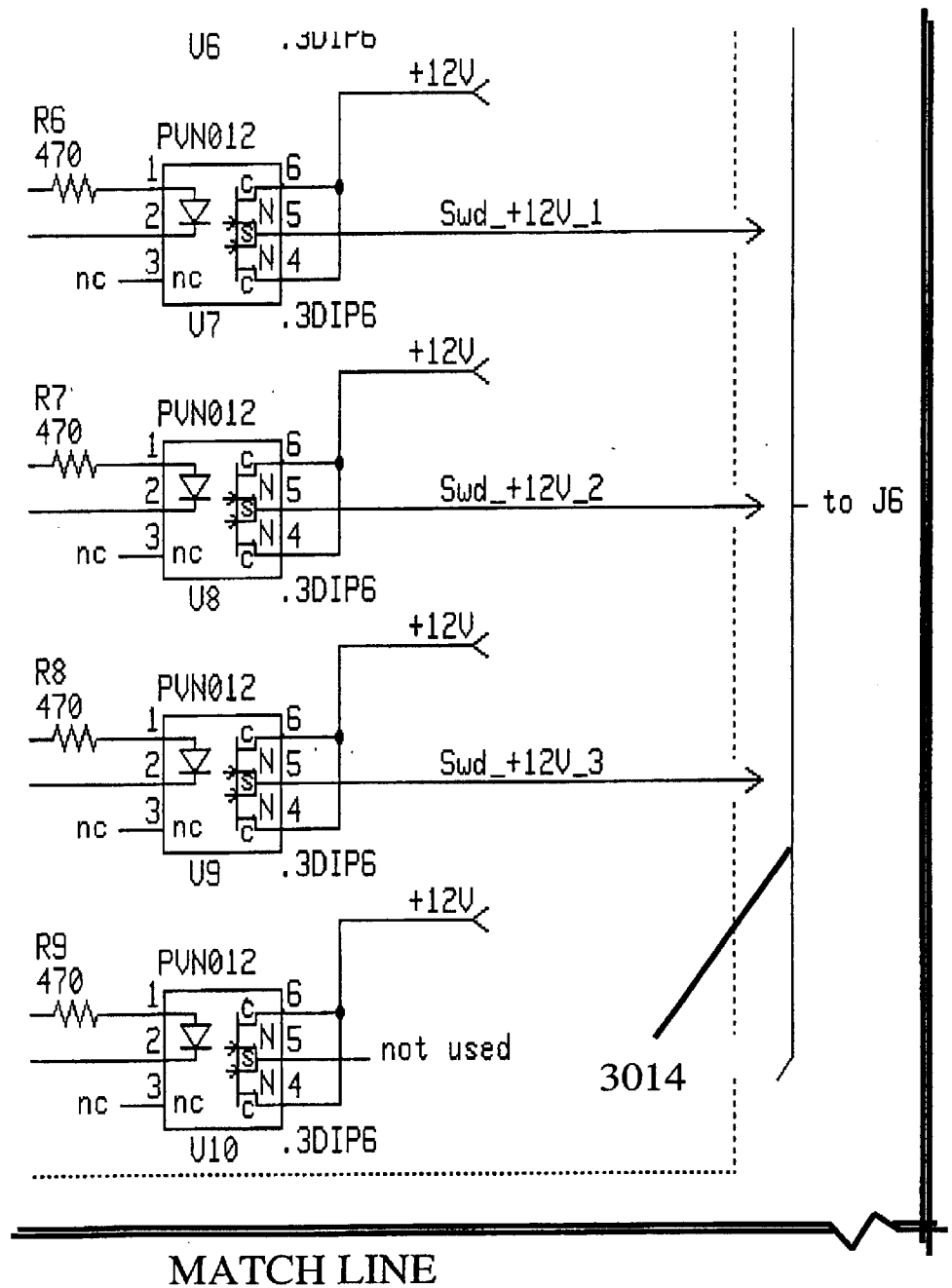
FIG. 30C.1

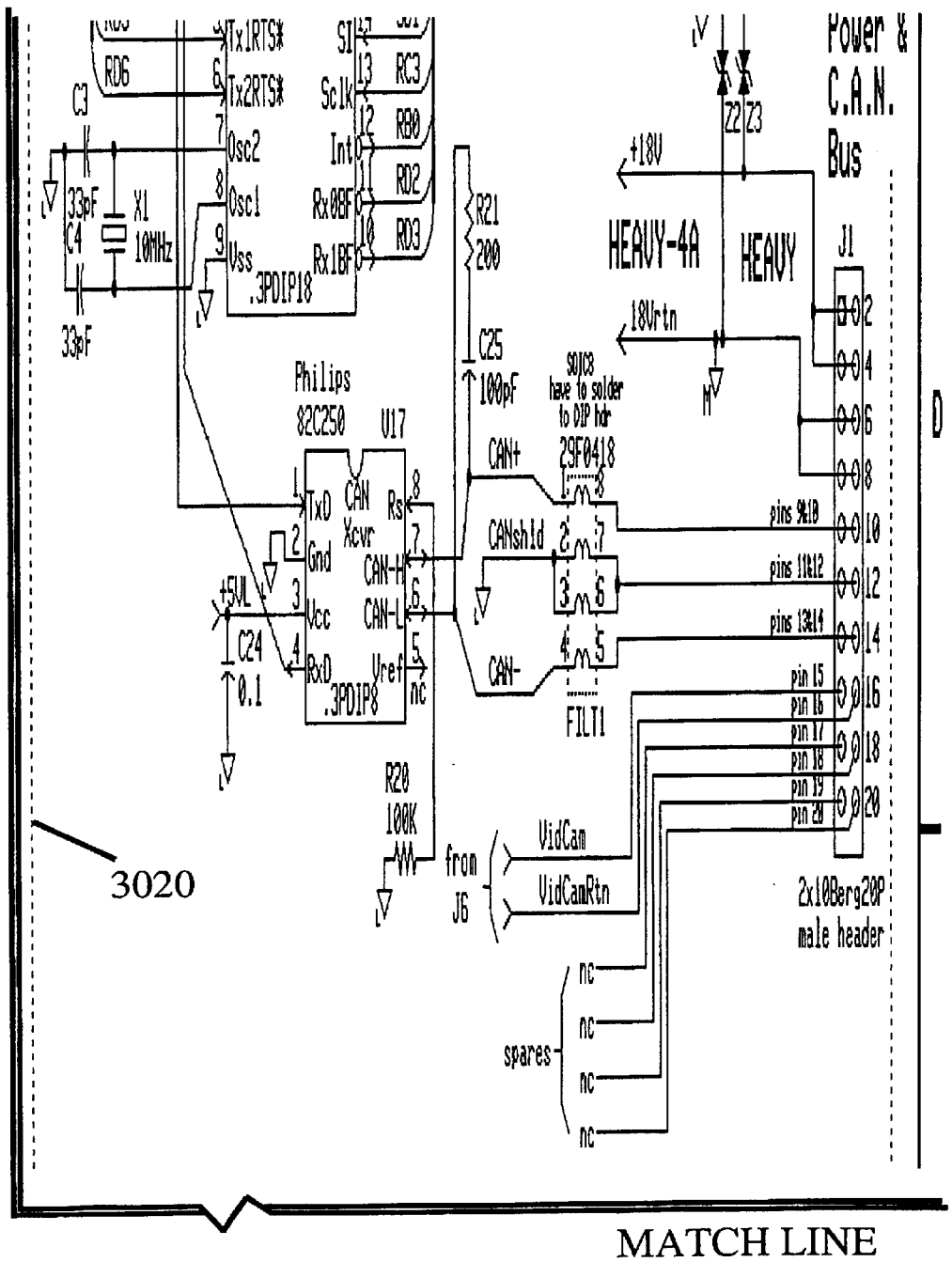
FIG. 30C.2

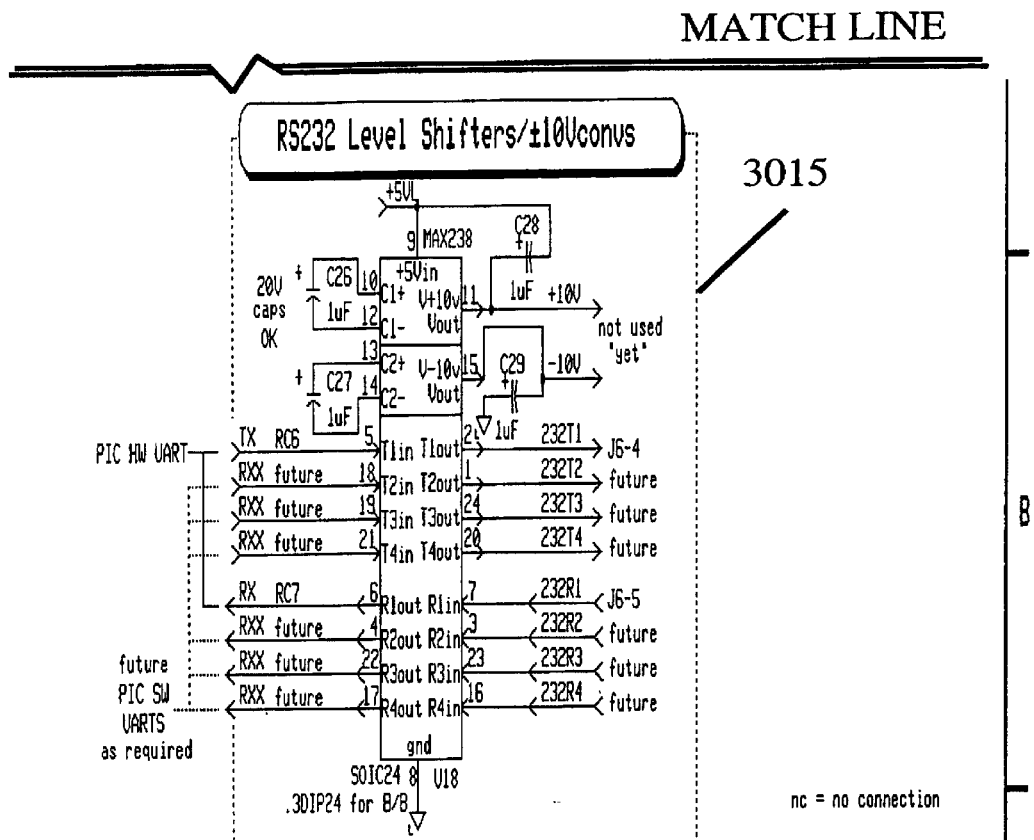
FIG. 30C.3

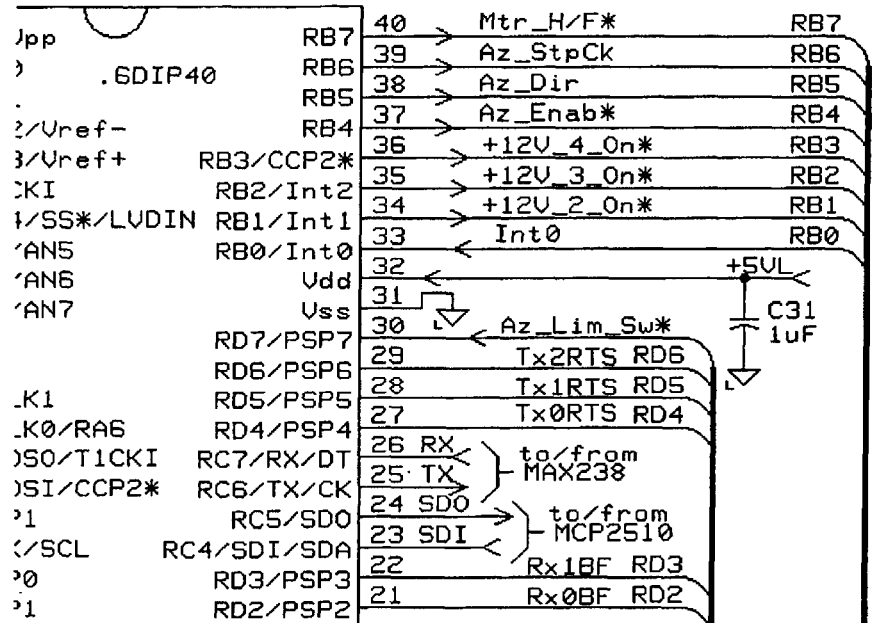
FIG. 30D.1

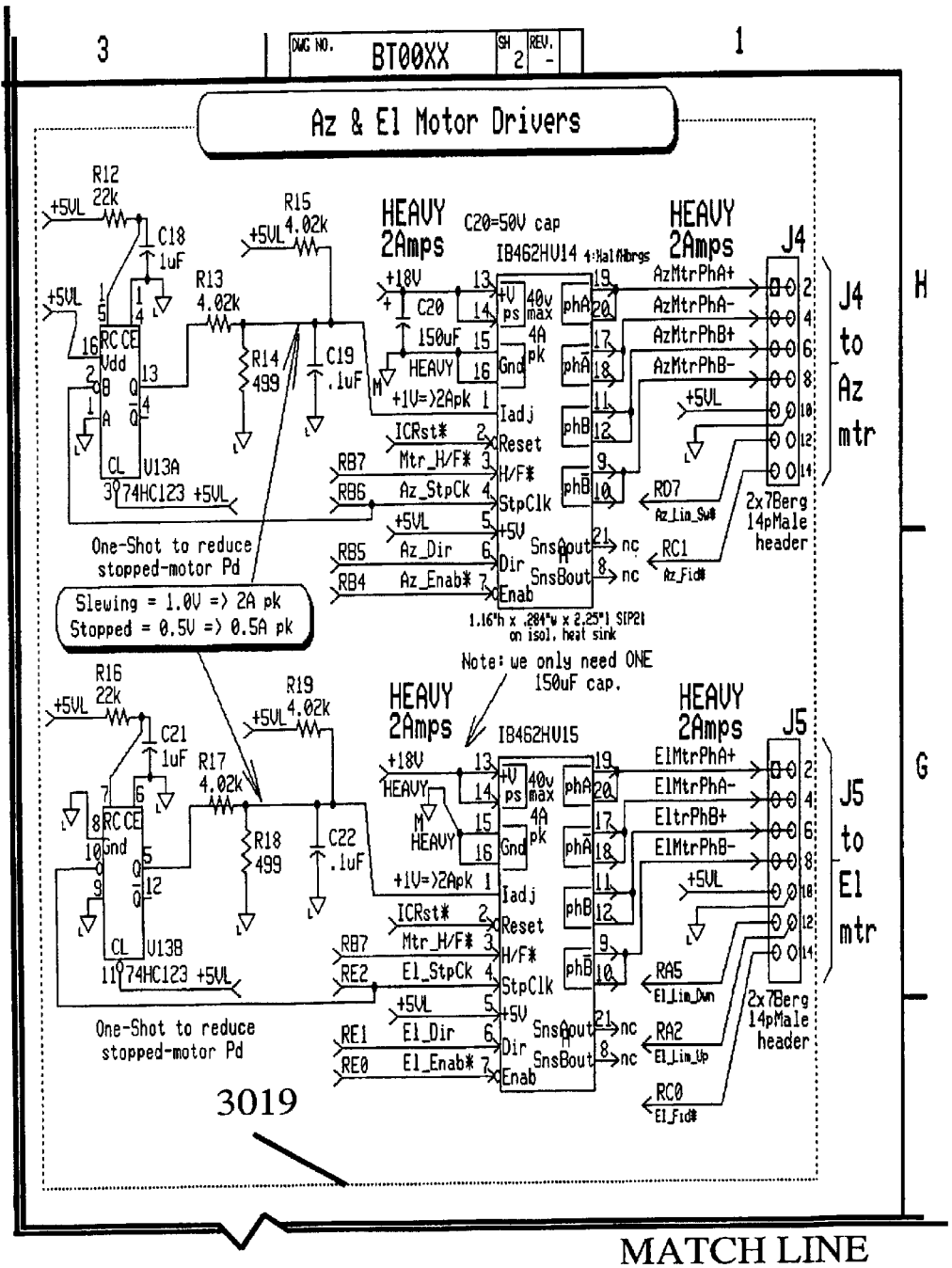
FIG. 30D.2

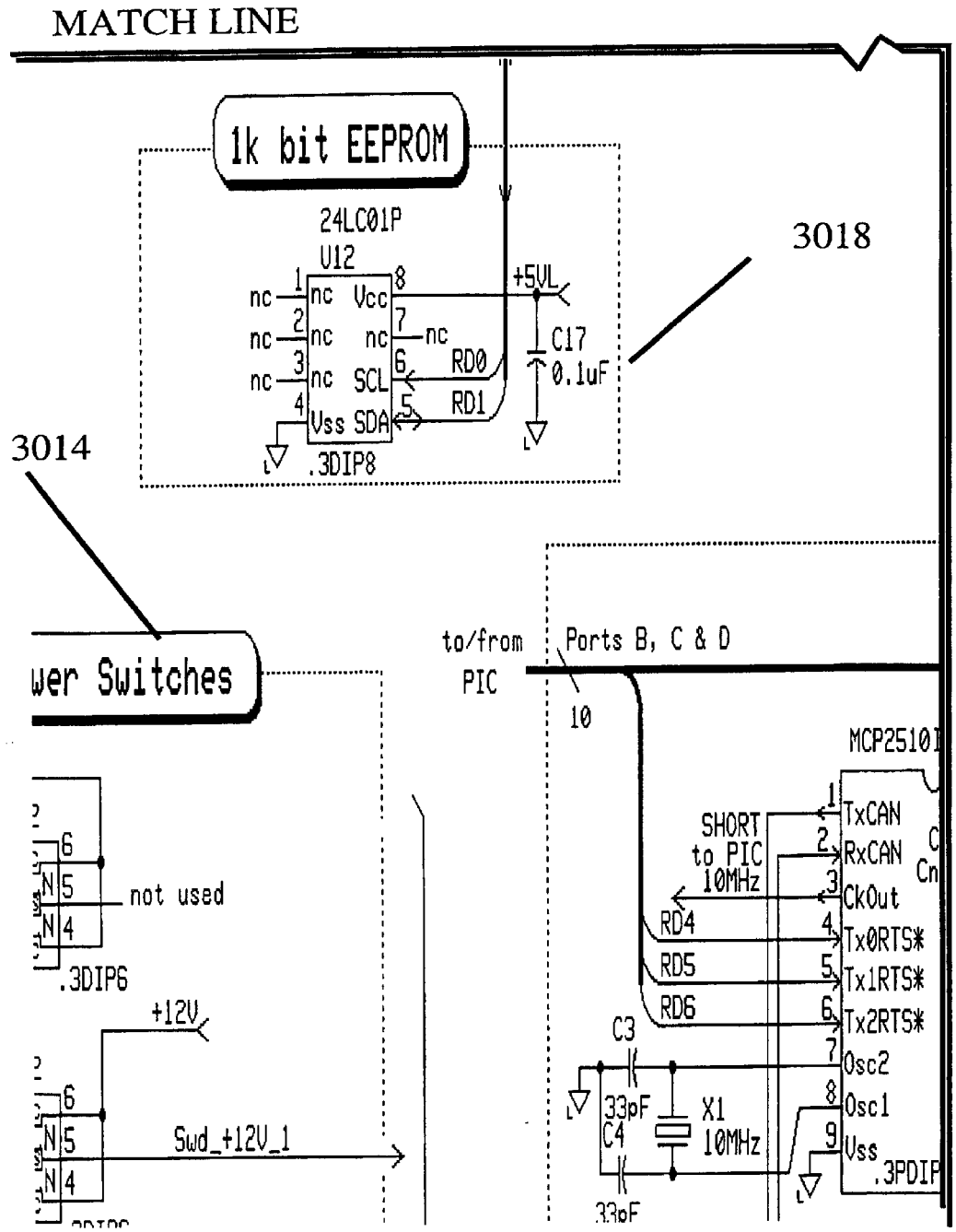
FIG. 30D.3

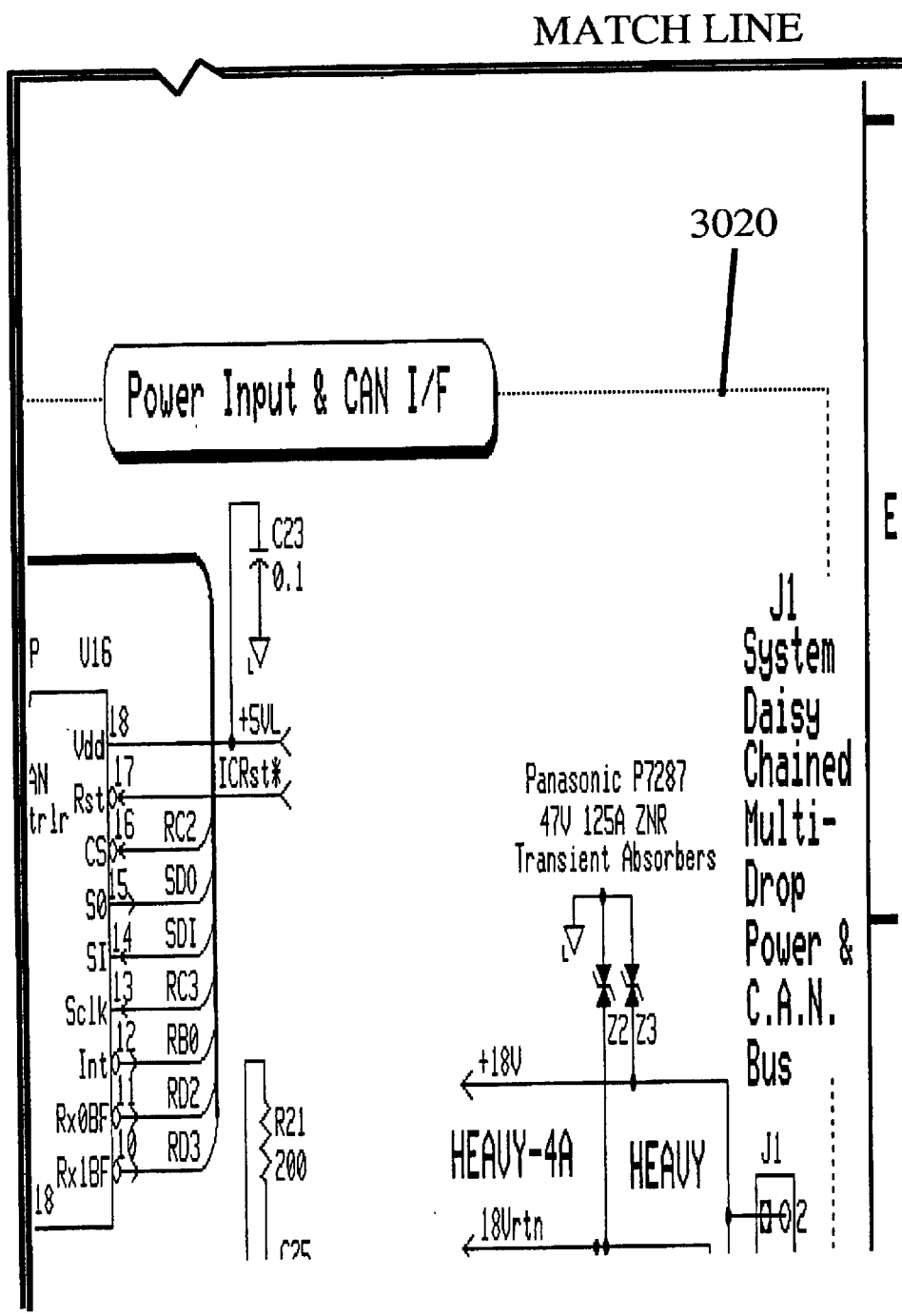
FIG. 30D.4

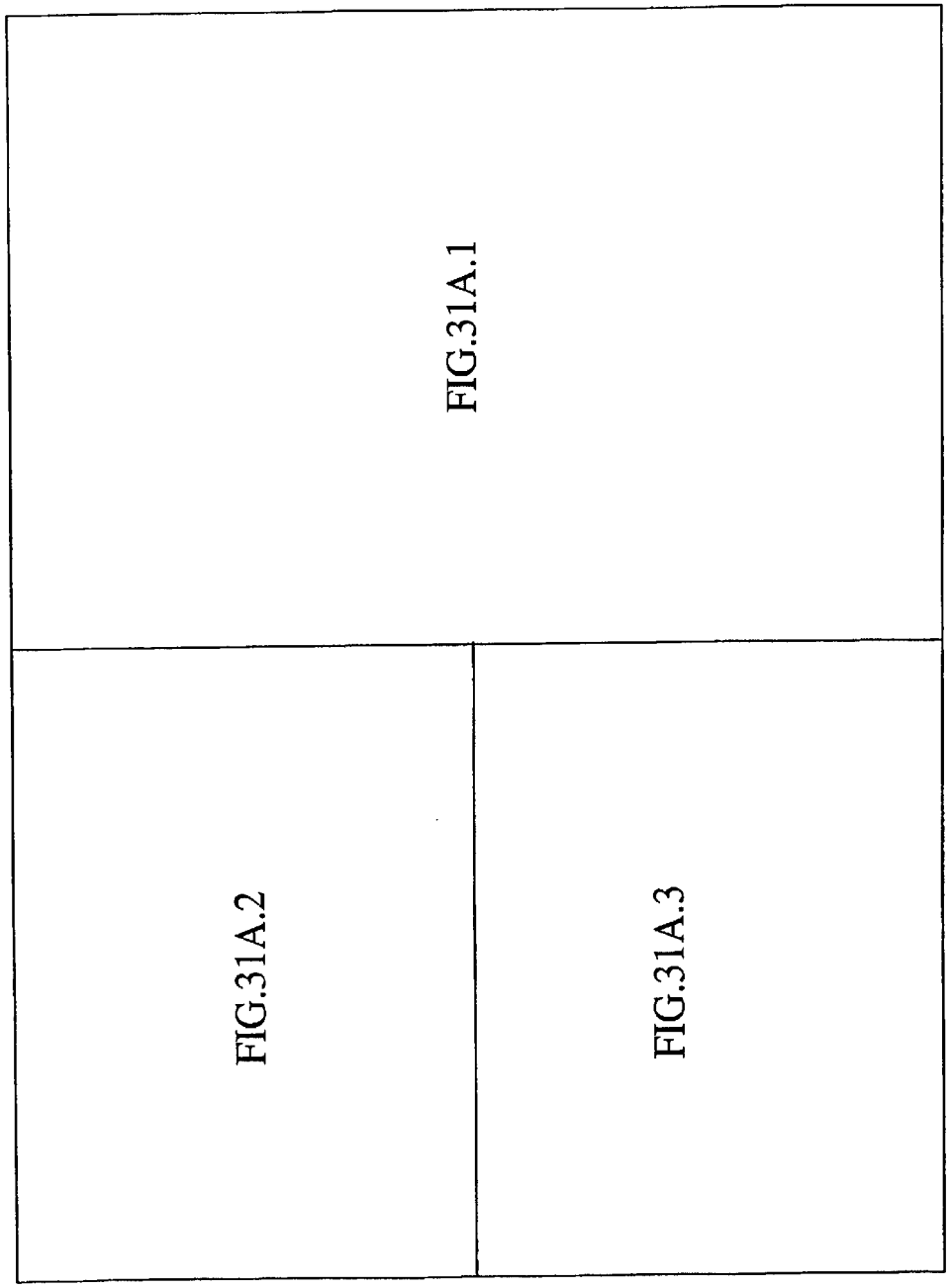

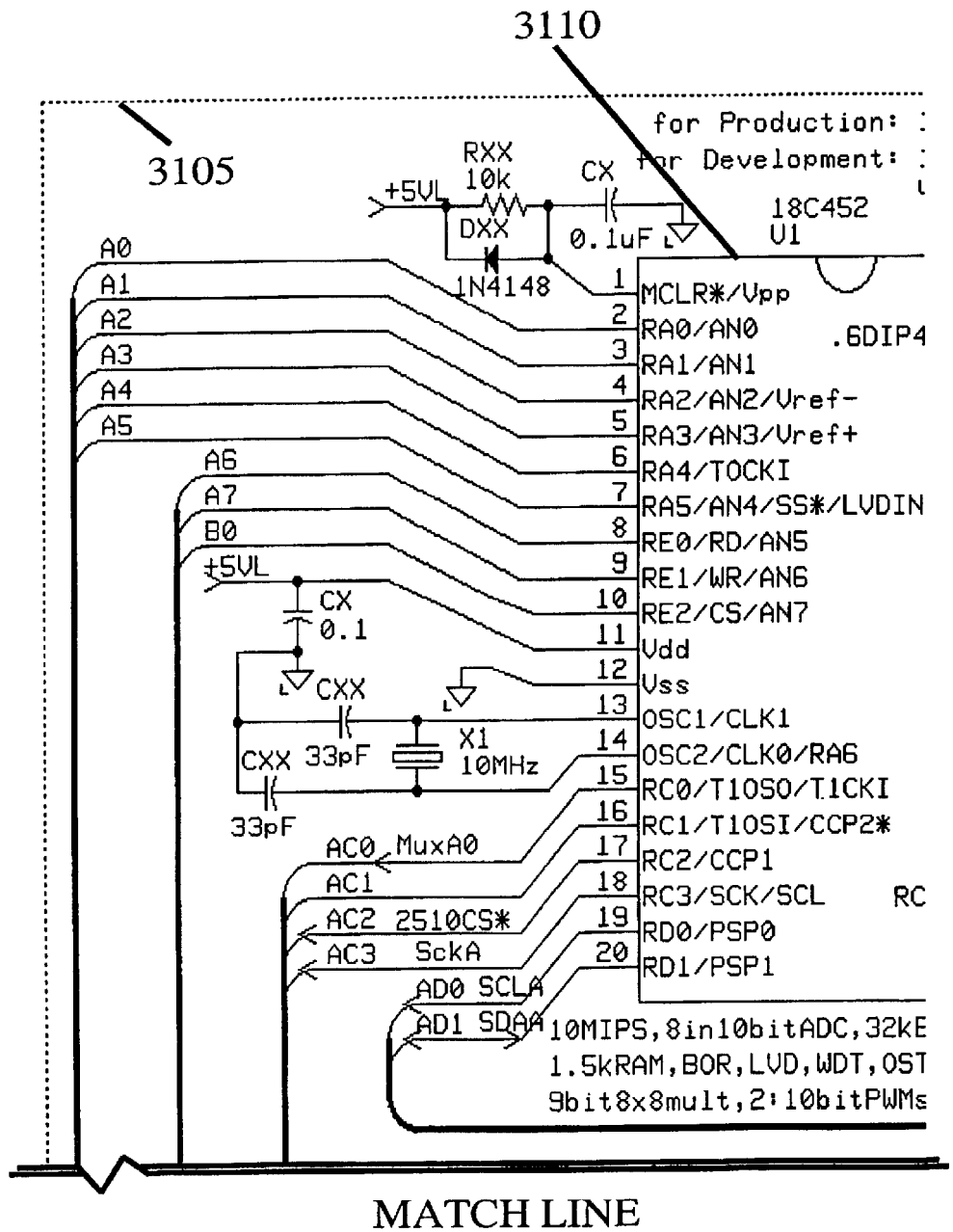
FIG. 31A.1

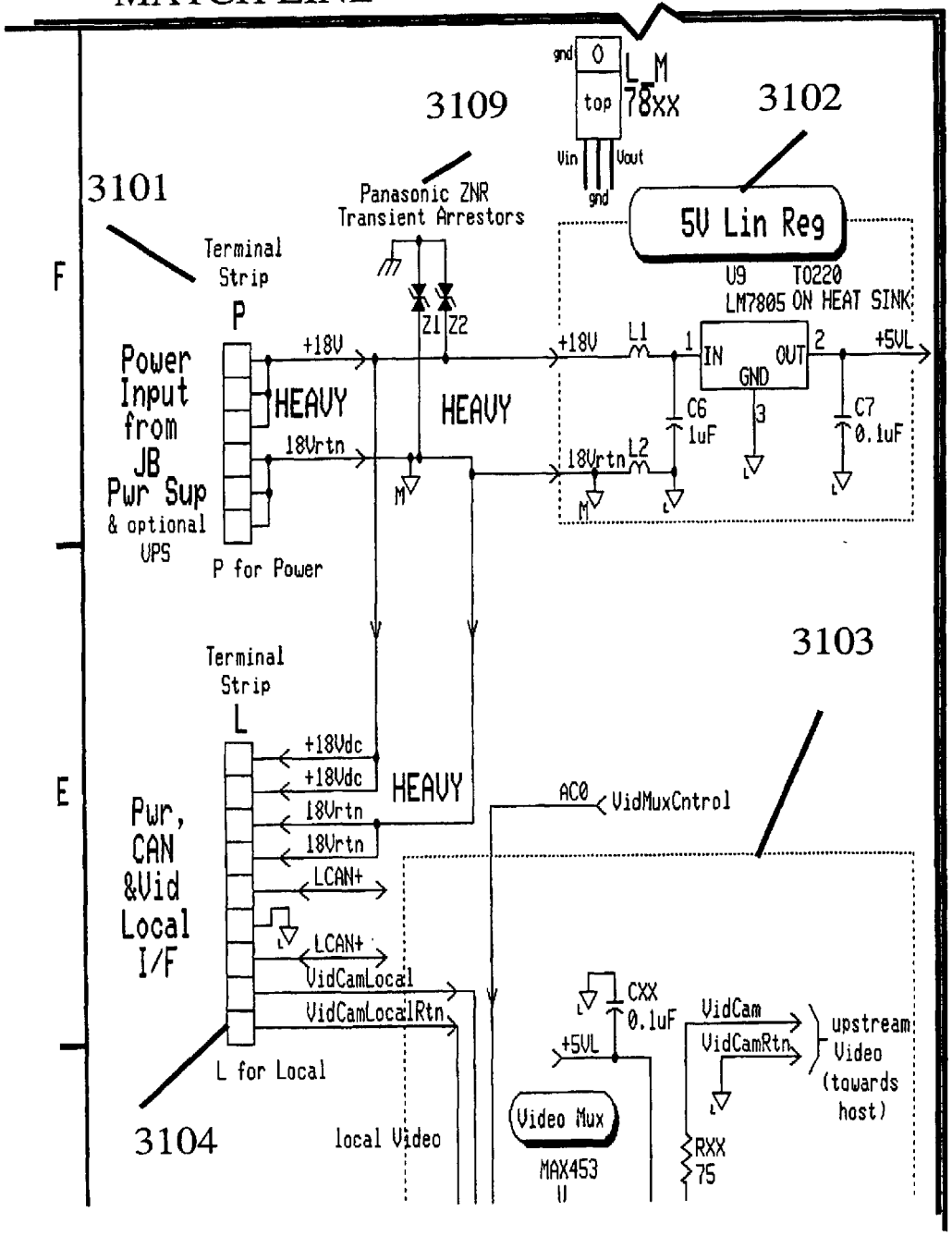
FIG. 31A.2

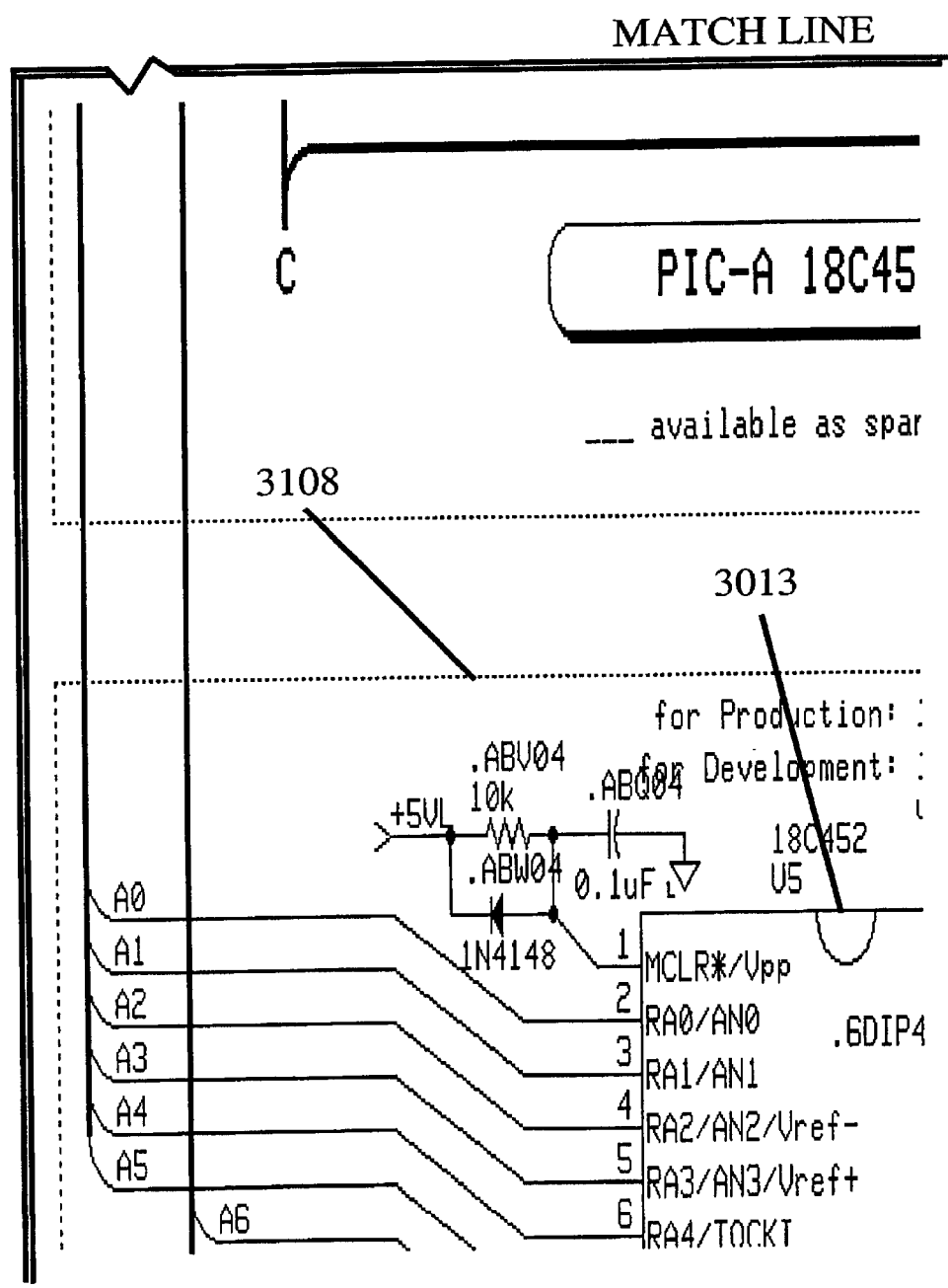
FIG. 31A.3

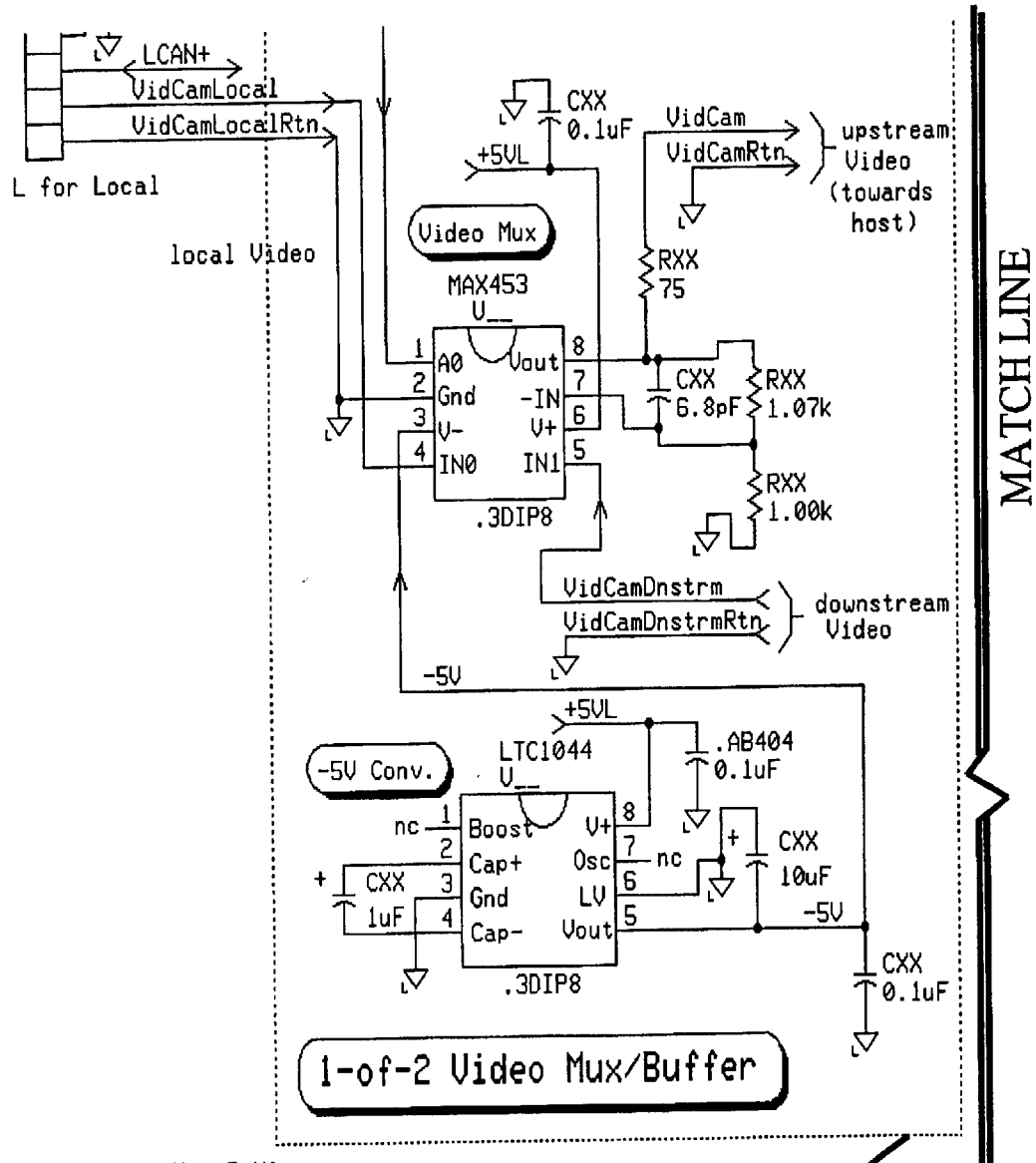
FIG. 31B.1

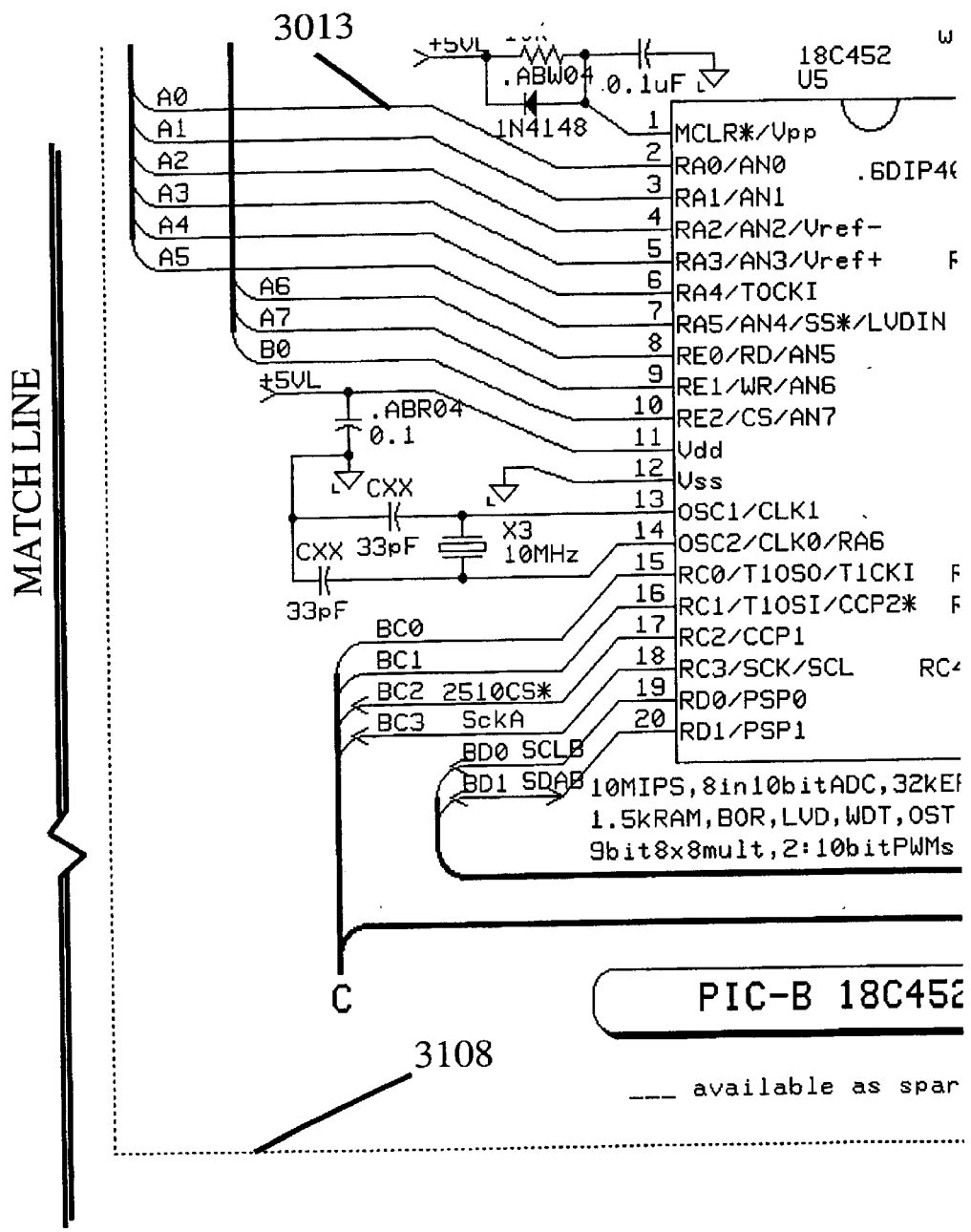
FIG. 31B.2

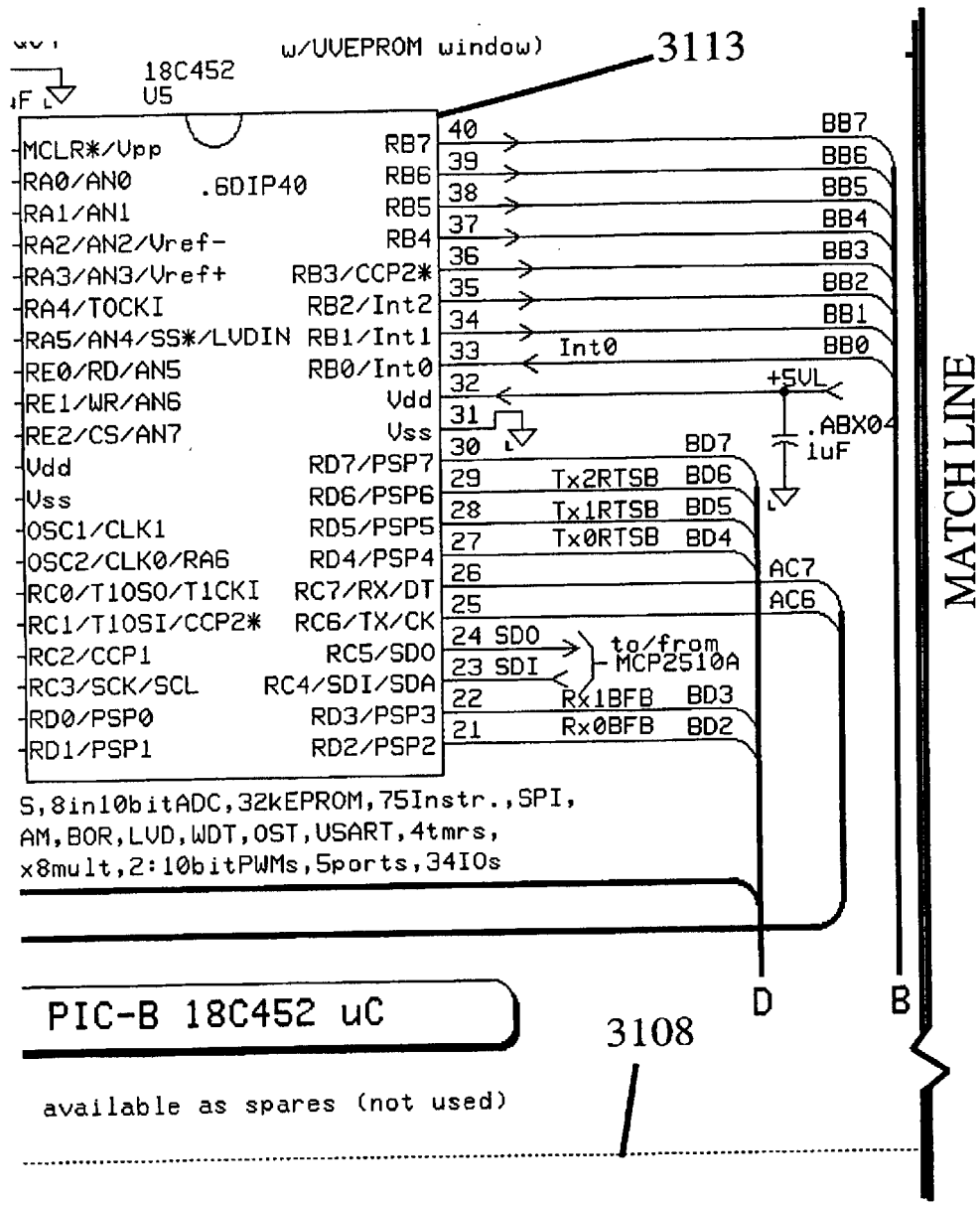
FIG. 31C.1

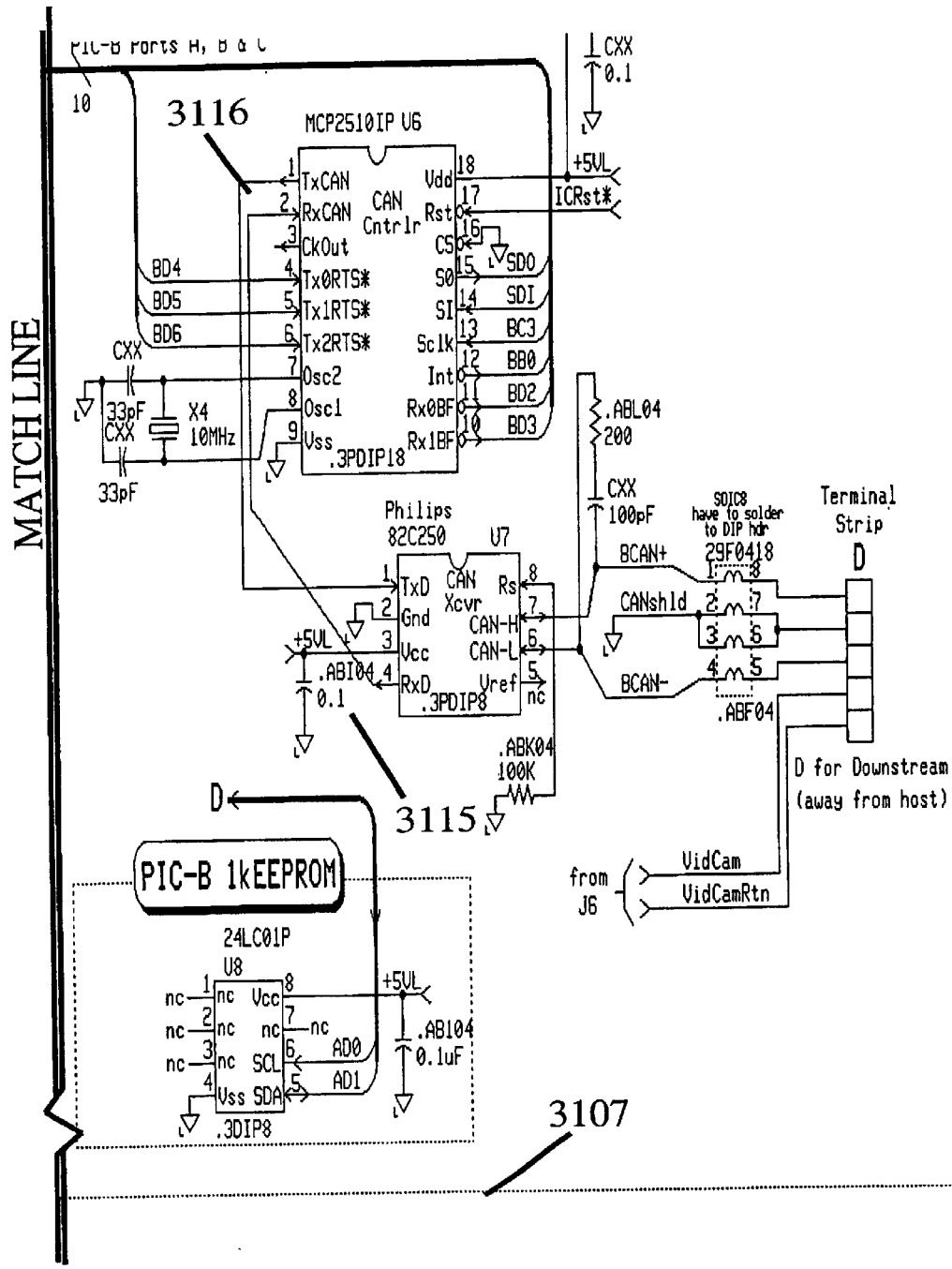
FIG. 31C.2

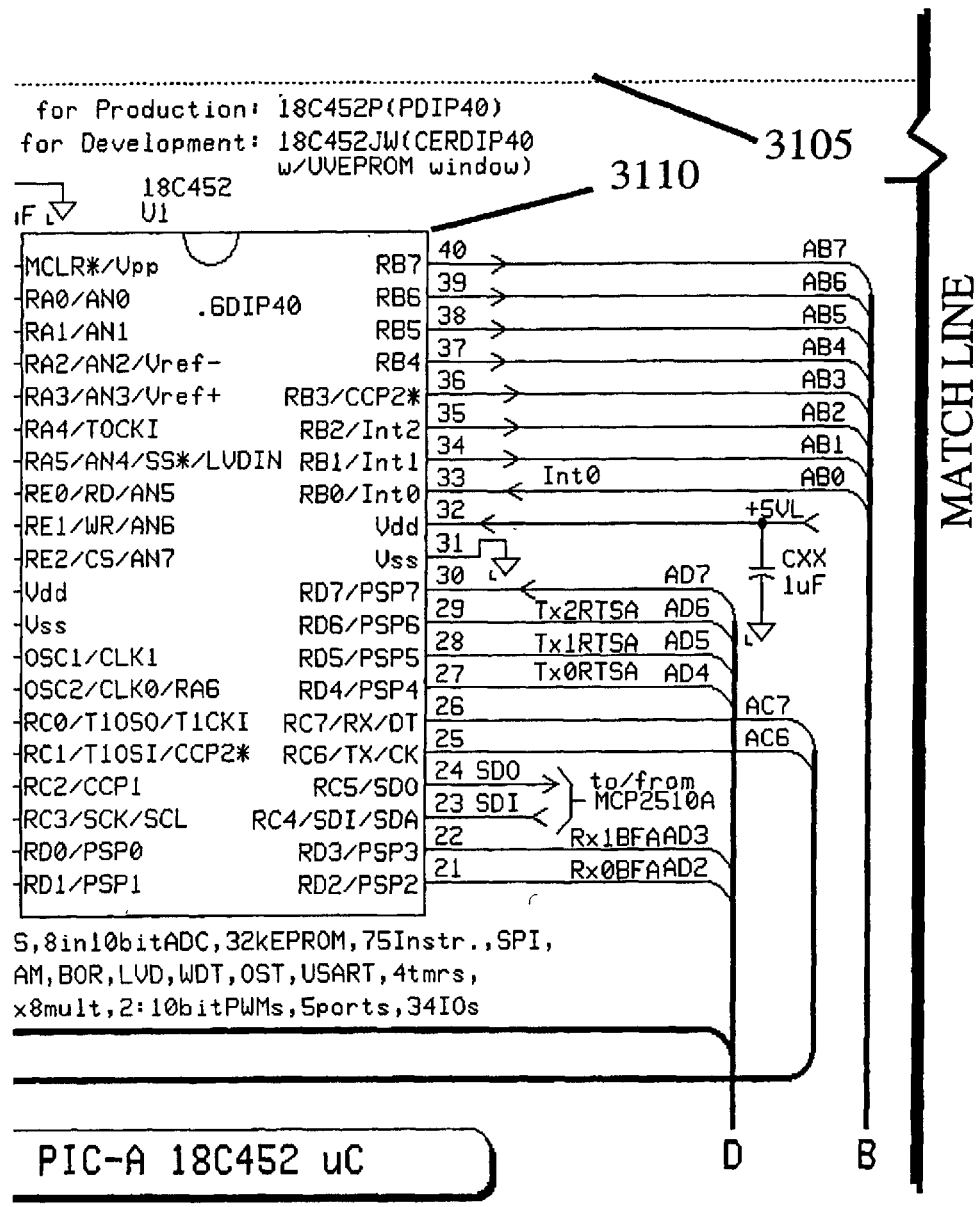
FIG. 31D.1

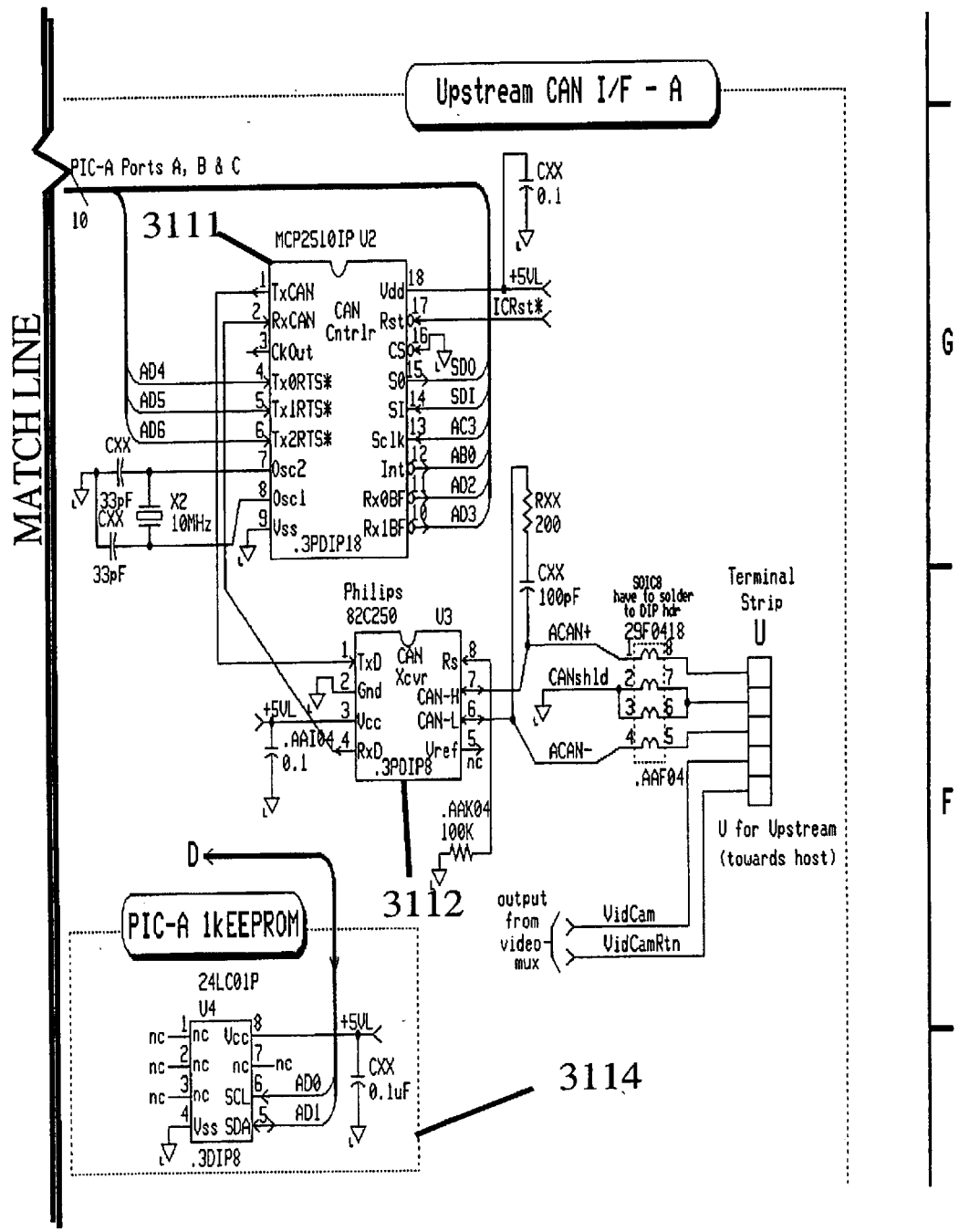
FIG. 31D.2

| 1. CU Material Items | | |
|---|---|---|
| 1.) | Enclosure: | |
| | | NEMA Watertight housing |
| | | Special connector holes |
| 2.) | OEM Sensors: | |
| | | Thermostat |
| | | Humidistat |
| | | Barometric pressure sensor |
| | | Kill switch |
| | | Mounting brackets |
| 3.) | Electronics: | |
| | | 1 Custom I/O PC/104 PCB |
| | | 1 MSM CPU PC/104 board |
| | | 10 Filter Capacitors |
| | | 7 Connectors |
| | | 1 MAX1481 RS485 Drvr/Rcvr IC |
| | | 2 quad Op amps |
| | | 30 resistors/R-packs |
| | | 6 ZNR Transient Suppressors |
| | | 3 Diodes |
| | | Board & PC/104 Assembly |
| | | Board & PC/104 Test |
| | | CU P/S (117Vac>48Vdc/50W) |
| | | CU cabling |
| | | CU misc. hardware |
| | | Wire connectors to enclosure |
| | | Mounting bracket |
| | | Enclosure penetrations Sealtight |
| 4.) | Misc: | |
| | | Screws |
| | | Class II labeling |

FIG. 32A

| 2. GSU Material Items | | | |
|---|---|---|---|
| 1.) | Mechanical parts for Sensor Housing, Pan-Tilt Arm, & Dust Sheild: | | |
| | | See pats list covered under Figure 5C | |
| 2.) | OEM Sensors: | | |
| | | Laser Rangefinder - 1 LRF (like Leica/Disto Classic) | |
| | | Acoustical Rangfinder - 1 transducer (like Bindicator ) | |
| | | Video Camera - 1 VidCam (like Panasonic GP-CX161) | |
| | | Visible laser diode for pointing - 1 Laser diode (like CalPac 1mW) | |
| 3.) | Electronics: | | |
| | | 2 EAD type 23 Stepper Motors | |
| | | 1 GSU PCB  (gimbal & PMSA-2) | |
| | | 6 LT1007 OpAmp Ics | |
| | | 1 REF-01 Vref IC | |
| | | 6 10turn 100k pots | |
| | | 1 PIC uCntrl IC | |
| | | 2 IMS IB462 StprMtr Driver Module | |
| | | 2 74AC241 CMOS Buff. Ics | |
| | | 1 Burr-Brown ADS8320 ADC IC | |
| | | 2 CD4051 Analog Mux Ics | |
| | | 1 AD590 temp sensor IC | |
| | | 1 NPC-103 press.sens.IC *opt* | |
| | | 1 MAS232 RS232 Tx/Rx IC *opt* | |
| | | 1 Xtal oscillator | |

FIG. 32B

| 2. GSU Material Items | | | |
|---|---|---|---|
| | | | 10 Filter Capacitors |
| | | | 4 PVN012 IsoPwrSw Ics |
| | | | 4 Connectors |
| | | | 2 MAX1481 RS485 Drvr/Rcvr Ics |
| | | | 4 quad Op amps |
| | | | 50 resistors/R-packs |
| | | | 6 ZNR Transient Suppressors |
| | | | 15 Diodes |
| | | | GSU enclosure |
| | | | misc. GSU cabling |
| | | | misc. GSU hardware |
| | | | Wire connectors to enclosure |
| | | | Mounting brackets |
| | | | Enclosure penetrations Sealtight |
| | 4.) | Misc: | |
| | | | Screws |
| | | | Class II labeling |

FIG. 32C

| 3. ISU Material Items | | |
|---|---|---|
| 1.) | Enclosure | |
| | | Nema box |
| | | Glass window |
| | | Chute mounting bracket |
| | | Window gasket |
| | | Door gasket |
| 2.) | Light Source: | |
| | | 2 GE 40W projector Lamps w/ reflectors or 100+ multispectral LEDs |
| | | Lamp Sockets |
| | | Mounting brackets |
| | | Light Baffles |
| | | Wiring |
| 3.) | Photometer: | |
| | | 3 or more optical filters |
| | | 3 or more J53-357 Photodiodes |
| | | Optical mounting barrel material |
| | | Mounting bracket |
| 4.) | Electronics: | |
| | | 1 ISU PCB |
| | | 1 200 LED PCB |
| | | 6 LT1007 OpAmp Ics |
| | | 6 precision resistors |
| | | 1 REF-01 Vref IC |
| | | 6 10turn 100k pots |
| | | 1 PIC uCntrl IC |

FIG. 32D

| 3. ISU Material Items | | | | |
|---|---|---|---|---|
| | | 1 Burr-Brown ADS8320 ADC IC | | |
| | | 4 CD4051 Analog Mux Ics | | |
| | | 1 AD590 temp sensor IC | | |
| | | 1 NPC-103 press.sens.IC *opt* | | |
| | | 1 MAX232 RS232 Tx/Rx IC *opt* | | |
| | | 1 Xtal oscillator | | |
| | | 10 Filter Capacitors | | |
| | | 4 PVN012 IsoPwrSw Ics | | |
| | | 4 Connectors | | |
| | | 2 MAX1481 RS485 Drvr/Rcvr Ics | | |
| | | 4 quad Op amps | | |
| | | 50 resistors/R-packs | | |
| | | 6 ZNR Transient Suppressors | | |
| | | 5 Diodes | | |
| | | misc. ISU hardware | | |
| | | ISU cabling | | |
| | | ISU misc. hardware | | |
| | | Wire connectors to enclosure | | |
| | | Enclosure penetrations Sealtight | | |
| | | Mounting bracket | | |
| 5.) | Misc: | | | |
| | | Screws | | |
| | | Class II labeling | | |

FIG. 32E

| 4. ESU Material Items | | | |
|---|---|---|---|
| | 1.) | Enclosure | |
| | | | Perferated box |
| | | | Mounting bracket |
| | 2.) | OEM Components: | |
| | | | Thermostat |
| | | | Humidistat |
| | | | Mounting brackets |
| | 3.) | OEM Enose Sensors: | |
| | | | CO-2 |
| | | | Future VOC detectors |
| | | | Mounting bracket |
| | 4.) | Electronics: | |
| | | | 1 ESU PCB |
| | | | 1 PIC uCntrl IC |
| | | | 2 74AC241 CMOS Buff. Ics |
| | | | 1 Burr-Brown ADS8320 ADC IC |
| | | | 2 CD4051 Analog Mux Ics |
| | | | 1 AD590 temp sensor IC |
| | | | 1 NPC-103 press.sens.IC *opt* |
| | | | 1 MAX232 RS232 Tx/Rx IC *opt* |
| | | | 1 Xtal oscillator |
| | | | 10 Filter Capacitors |
| | | | 4 PVN012 IsoPwrSw Ics |
| | | | 4 Connectors |
| | | | 2 MAX1481 RS485 Drvr/Rcvr Ics |
| | | | 4 quad Op amps |
| | | | 50 resistors/R-packs |
| | | | 6 ZNR Transient Suppressors |
| | | | 15 Diodes |
| | | | misc. ESU cabling |
| | | | misc. ESU hardware |
| | | | Wire connectors to enclosure |
| | | | Mounting bracket |

FIG. 32F

| A. | General Purpose Embedded Microcomputer | |
|---|---|---|
| | Similar to Advanced Digital Logic Microspace PC/104 | |
| | CPU: | Intel Pentium MMX or better |
| | Clock Speed: | 166MHz or higher |
| | DRAM: | 32MB or more |
| | Bus Type: | PC/104 and PCI |
| | Video Resolution: | 512 x 720 |
| | LAN-Ethernet: | Ethernet 91C96 or equivalent |
| | Hard Disk Controll | E-IDE |
| | Floppy Disk Contr | 3.5" microfloppy |
| | Serial Controller: | V24, RS232C, FIFO |
| | Parallel Controller: | Bi-directional (LPT1) |
| | Keyboard/Mouse: | PS/2 |
| | Electrical Power: | 5V @ 2.0A |
| | Operating Temp: | -25oC – 60oC |
| | Storage Temp: | -65oC – 125oC |
| | Dimensions: | PC/104 format (4.0" x 3.6" x 0.75") |
| B. | RS-232 Serial Protocol Module | |
| | Similar to PCM-3640 PC/104 4-Port Module | |
| | Number of ports: | 4 |
| | Selectable address | COM1 – COM4 minimum |
| | Interrupt selection: | jumper set |
| | Bus: | PC/104 |
| | Baud rate: | at least 115,200 bps |
| | Character length: | 5, 6, 7, and 8 bits (selectable) |
| | Parity: | even, odd, or none (selectable) |
| | Stop bits: | up to 2 (selectable) |
| | Interrupt levels: | IRQ 3,4,5,6,7, or 9 (selectable) |
| | Electrical power: | 5V @ 250mA |

FIG. 32G

| C. | Multiple Output DC Power Supply | |
|---|---|---|
| | Similar to Power-One Model HCBB-75W-A Triple Output Supply | |
| | AC Input: | 120VAC, +/-10%, 47-63Hz |
| | Output Voltages: | 5V |
| | | 12V |
| | | -12V |
| | Current Ratings: | 6.0A (5V) |
| | | 1.7A (12V) |
| | | 1.7A (-12V) |
| | Line Regulation: | +/- 0.05% on a 10% line change |
| | Load Regulation: | +/- 0.05% on a 50% load change |
| | Output Ripple: | 5mV peak to peak maximum |
| | Operating Temp: | 0oC – 50oC |
| | Efficiency: | 45% – 55% (typical) |
| D. | Stepper Motor Drive | |
| | Similar to Intelligent Motion Systems IB462 Bipolar Motor Drive | |
| | Input voltage: | 12V- 40VDC |
| | Drive current: | 0A – 2A (per phase) |
| | Logic input current | 7mA (typical) |
| | Step frequency: | 40kHz (maximum) |
| | Operating temp: | 0oC – 50oC |

FIG. 32H

| C. | Multiple Output DC Power Supply | |
|---|---|---|
| | Similar to Power-One Model HCBB-75W-A Triple Output Supply | |
| | AC Input: | 120VAC, +/-10%, 47-63Hz |
| | Output Voltages: | 5V |
| | | 12V |
| | | -12V |
| | Current Ratings: | 6.0A (5V) |
| | | 1.7A (12V) |
| | | 1.7A (-12V) |
| | Line Regulation: | +/- 0.05% on a 10% line change |
| | Load Regulation: | +/- 0.05% on a 50% load change |
| | Output Ripple: | 5mV peak to peak maximum |
| | Operating Temp: | 0oC – 50oC |
| | Efficiency: | 45% – 55% (typical) |
| D. | Stepper Motor Drive | |
| | Similar to Intelligent Motion Systems IB462 Bipolar Motor Drive | |
| | Input voltage: | 12V- 40VDC |
| | Drive current: | 0A – 2A (per phase) |
| | Logic input current | 7mA (typical) |
| | Step frequency: | 40kHz (maximum) |
| | Operating temp: | 0oC – 50oC |

FIG. 32I

| | | | | | | |
|---|---|---|---|---|---|---|
| E. | Embedded Microcontroller (alternative to embedded microcomputer) | | | | | |
| | | | | | | |
| | Similar to Microchip PIC16F8X Flash/EEPROM 8-Bit Microcontroller | | | | | |
| | | | | | | |
| | Power-on reset | | | | | |
| | Power-up timer | | | | | |
| | Oscillator startup timer | | | | | |
| | Watchdog timer | | | | | |
| | Supply voltage: | | | | | 2V – 6V |
| | Power dissipation: | | | | | <2mA @ 5V & 4MHz |
| | Instruction width: | | | | | 14 bits |
| | Data width: | | | | | 8 bits |
| | Interrupt sources: | | | | | external RB0/INT |
| | | | | | | TMR0 timer overflow |
| | | | | | | PORTB,7:4> interrupt on change |
| | | | | | | Data EEPROM write complete |
| | Program memory: | | | | | 1000 words FLASH EEPROM |
| | Data EEPROM: | | | | | 64 bytes |
| | Data RAM: | | | | | 68 bytes |
| | Maximum frequency | | | | | 10MHz |
| | Instruction cycle: | | | | | 400ns |
| | I/O pins: | | | | | 13 |
| | Instruction set: | | | | | 35 word RISC |

FIG. 32J

| F. | On-Board Analog to Digital Converters | |
|---|---|---|
| | Similar to Burr-Brown ADS8320 | |
| | Resolution: | 16 bits |
| | Power supply: | 2.7V – 5.25V |
| | Power dissipation: | 8.5mW |
| | Conversion time: | 16 clock cycles |
| | Acquisition time: | 4.5 clock cycles |
| | Sampling rate: | 100kHz |
| | Max clock frequen | 2.9MHz |
| | Operating temp: | -40oC – 85oC |
| G. | On-Board Serial Interface | |
| | Similar to Maxim MAX148X Series of RS-485/RS-422 Transceivers | |
| | Mode: | half or full duplex (SW selectable) |
| | Data rate: | up to 12Mbps |
| | Supply voltage: | up to 7V |
| | Operating temp: | -40oC – 85oC |

FIG. 32K

Laser Rangefinder Specification

PHYSICAL

| | |
|---|---|
| Maximum Dimensions: | 6"(h) x 3.5"(w) x 8"(l) |
| Maximum Weight: | 2.0 lbs |
| Chassis: | Minimum material to maintain performance & alignment with base plate for mounting inside of Ball's existing multi. sensor housing. Would accept an "open-construction" sub-assembly since we enclose the LRF in our own sealed enclosure. |

ELECTRICAL

| | |
|---|---|
| Power: | 5V to 24V DC at less than 500mA (2.5W/5V to 12W/24V maximum) & return (one pair of flying wires). Enable/Laser Pulse/Distance Readout Pulse/Level: one TTL (or CMOS) & return (second pair of flying wires) |
| Data Interface: | serial or parallel digital (or analog input/output) interface & return (third pair of flying wires) |

LASER

| | |
|---|---|
| Wavelength: | 600nm - 1500nm |
| Class: | IIIA or less |
| Beam Divergence: | ≤ 5 milliradians |
| Operation Mode: | Pulsed or CW |

FIG. 32L

PERFORMANCE

* Maximum Range: ≥ 200 feet (over entire temperature range)
* Minimum Range: ≤1.5 foot (over entire temperature range)
* Absolute Accuracy: ± 1 inch @ 200 feet (over entire distance & temperature range)

Resolution: ≤+/−1 inch (over entire distance & temperature range)

** Measurement Jitter: ± 0.25 inch (one sigma) (over entire distance & temperature range)

Drift at 72°F (22°C): ≤+/−0.5 inch per hour (over entire distance & temperature range)

Temperature Range: -20°F (-28°C) to +160°F (+71°C)

Humidity: All North American regions. Thus 10-100% RH

Vibration: Installation environment subject to periodic minor vibrations. LRF to be sufficiently ruggedized for long-term performance.

FIG. 32M

QUALITY

Components shall maintain above specs for 3 year targeted maintenance free operation.

QUANTITIES & COST

This LRF is an OEM component part of a sensor suite. As a new business, ramp-up to stable volumes is expected to take a few years. Due to the world wide commodity application involved, and due to $1^{st}$ of its kind available, and due system patent protection, volume expected to build to 1,000 units annually.

Design to cost pricing required under $300/unit. Provide price/unit in (or near to) the following delivered quantities:

5      25      50      100

\* *Diffuse reflecting, gray target (non-cooperative)*
\*\* *LRF attached to or resting on a stable platform*

FIG. 32N

BULK MATERIALS MANAGEMENT APPARATUS AND METHOD

CROSS REFERENCE TO RELATED APPLICATION

This application is a continuation of PCT application No. PCT/US01/05082 filed on Feb. 16, 2001 and claiming priority from the U.S. provisional application No. 60/183,271 filed Feb. 17, 2000.

FIELD OF THE INVENTION

The present invention relates to volume measurement, component identification, condition monitoring and safety systems for bulk materials such as grains stored in silos, other large containers and/or on the ground. Unique features of this invention also include multiple other fields of use.

BACKGROUND OF THE INVENTION

Cereal grains, processed grains, sand, minerals, and other bulk materials are stored within and moved among large bins, silos, tanks, buildings, ship holds, other large containers and on the ground. Dangers to humans handling these materials include asphyxiation due to avalanche, dust inhalation and explosions. Losses by the inaccurate shipping of the wrong quantities or components, and/or theft, and spoilage run into the billions of dollars worldwide. United States of America standard now call for +/−3% facility-wide accounting accuracy for volume measurement in commercial bulk storage bins. However, present methods of measurement can generally only accomplish +/−10% accuracy. OSHA (Occupational Safety and Health Administration) defined a grain silo as a confined space requiring detailed safety procedures, yet deaths still occur due to inaccurate or unavailable measurements of height and density of grain stockpiles.

The most common present day volume/height measurements generally use single point, manually measured plumb bob/tape measure methods and guesses as to surface contours or ultrasonic single point measurements. Occasional multi-point ultrasonic measurements of various heights are done, but the prohibitive costs of installing multi-thousand dollar sensors and their limited accuracy throughout a one hundred foot wide storage bin impede wide use of this known technology.

Cost effective, timely, and accurate material management is crucial to the economic viability of storage and transfer facilities. A method for eliminating the waste and inaccuracy inherent in current labor-intensive methods of measuring bulk material quantity is needed. The present invention is a state-of-the art improvement due to its ability to profile an entire surface/volume in three dimensions instead of just at a point. Furthermore, the same invention can be used to not only measure a static volume but also a dynamic volume (one that is changing). Finally, the present invention can be packaged for use in hazardous (explosive) locations, non-hazardous locations, damp or wet locations, and other exposures.

For grain, good management is crucial to preserve grain quality. To maintain grain in good quality, its condition must be constantly monitored for numerous reasons including preventing the grain from going bad and to prevent an isolated condition problem from spreading throughout the grain volume. For grain, moisture content (MC) management is also crucial. MC is a major factor in deciding when to move grain out to market or how to blend several grain loads to achieve a marketable, homogeneous commodity. MC is also used to determine whether or not-the grain needs artificial drying. Moisture content knowledge is also used to automate interlocked control of other plant equipment such as aeration fans, etc. Insect infestation, mold, bacteria, moisture, improper temperature control, rain and/or condensation all contribute to spoilage if not properly managed. This invention provides early detection and warning to storage facility operators.

In the handling and storage of bulk grains and other bulk materials, the substance(s) may be misidentified or misdirected to an incorrect storage facility. Usually this is a result of human error. Accidental mixing results in a significant expense to the grain or material handler, either in the cost of sorting the grain/material (if possible), or in the loss of value of the mixed product. Similarly, during audits of such facilities the grain or bulk material must be properly identified so that proper value may be assigned to each grain/material stored.

Quantity (volume) has been previously calculated via a manual process. A person typically travels to the material container and makes a single point measurement of distance from the container inspection port to the material surface. This is done by use of a tape measure and plumb bob, an ultrasonic transducer, or a handheld laser rangefinder. A visual estimate is then made of the shape at other points along the surface. Finally volume is calculated using a shape estimate and the single distance measurement.

Currently, personnel manually identify incoming bulk grain or other material and route the grain to a storage facility based on that identification. Correctness of the proper routing is based on their memory of where material is stored. There are no machine vision recognition systems to verify or cross check the human decisions. Also, some types of grain/material look very similar to others, such as different varieties of the same type of grain. These may thus be easily misidentified, adding to the human error potential. Another related source of error is the manual entry of material information into computer databases to track material location and movements. Errors in data entry often lead to the misdirection of material within a handling facility.

There are currently no real-time in-flow sampling systems on the market for constituent evaluation and quality grading. Grain recognition and condition monitoring are typically performed by entering a storage bin and using human vision, smell, and tactile feedback from "walking the grain".

Linear arrays of temperature sensors (temperature cables) have proliferated throughout the grain storage industry to assist in condition monitoring. Heat generated in the grain fermentation process builds up in the grain pile and is eventually detected via a temperature cable passing near or through the region of spoilage. The excellent thermal-insulating properties of bulk grain severely constrain the effective spoilage detection of a single temperature cable. As a result, condition monitoring of 100% of a container's grain volume via temperature cables is cost prohibitive, as it requires an enormous number of closely spaced cables. As well, a cable generated alarm is usually too late for spoilage prevention and only allows the user to prevent further excessive spoilage.

It is also common practice to use database accounting to track some of the above characteristics (volume and material type). No processes use machine vision systems that are sufficiently sophisticated and accurate enough to generate or validate the data because the enabling technology has not been available.

There currently is no manual or technological method for monitoring the moisture content or density of bulk stored grains or other bulk commodities.

For grain and some other bulk materials, a given volume is not homogeneous. Therefore, sampling and sorting are required to characterize the bulk content for value (possible discounting) and segregation. This quality sampling/management function is widely known and utilized on small samples. The small samples are taken as a statistical representation of the total bulk load. Statistical sampling is used because no continuous flow analysis (thus total bulk load) enabling technology exists.

Managing bulk contents (measuring it, verifying what type it is, checking its condition, etc.) or doing maintenance on the storage container can be dangerous. It is dangerous because personnel are often required to enter the storage tank to perform those management functions. Bin entry exposes personnel to dangers of asphyxiation, poisoning, as well as accidental burial in the bulk material due to unstable subsurface conditions and/or conditions due to loading or unloading the tank. Workers "walk the grain" and can be buried in the grain due to inaccurate depth estimates. Each year, numerous people are killed or injured in this manner. Consequently, personnel entry into nearly all bulk storage containers is regulated by OSHA under confined space rules.

Accurate quantity determination and safe personnel contact with the commodity are also dependent on knowing the density of the bulk. This includes both knowing the stratification of density and localized density irregularities. The present invention teaches many instrument types and methods to gather the density information.

The following is a summary of the deficiencies of the current art:

1. Volume Measurement

The chief deficiency in current methods of measuring quantity (volume) of stored powders and bulk materials is the failure to gather enough data for fine resolution of the stored pile's surface shape. Surface shape translates into volume. Thus, the more inaccurate the surface measurements the more inaccurate the calculated volume.

As material is loaded into or withdrawn from a storage container, the surface shape of the stored mass will change significantly. Since accurate volume knowledge is important to a storage facility's business goals of inventory accounting and regulatory compliance, common practice is to measure volume frequently. Most volume measurements are carried out using, as a basis for the calculation, the vertical distance from a reference point near the roof of a storage container to a single point on the material surface. An estimate is then made of the surface shape using human visual judgment or knowledge of the bin's recent fill/discharge history or a combination of both, and volume is calculated. Depending on the ratio of material volume to available container volume as well as on the container's aspect ratio (height to diameter or width), errors in surface shape assumptions can lead to volume miscalculations in excess of 10%. Error is minimal for tall, narrow bins since small bin diameter keeps all possible surface shape dependent volume variations small relative to the actual volume of the container's contents. Errors due to lack of material surface knowledge are largest for bins with aspect ratios nearer to unity. Error magnitude also has a strong dependence on the surface single-point location. A measurement made at the bin periphery will lack information about the height (load-in) or depth (discharge) of the central area which may be a conical shape. In contrast, a measurement made near the center of the pile surface may generally provide accurate knowledge of the cone height/depth, but it cannot provide an adequate picture of the complex surface profiles from center to perimeter that often result from repeated cycles of partial load-in and partial discharge. From a life-cycle cost standpoint, manual methods are very labor intensive, pose a potential safety risk to personnel trying to obtain the manual measurements, and can lead to large errors. For automated state-of-the-art systems like ultrasonic transducers suspended from the ceiling, the cost can be fairly expensive without significant accuracy improvement over a manual system. For instance a currently available ultrasonic system with 10 transducers measures only 10 points of information for a material cost ranging between 10–15 thousand dollars.

2. Volume Discharge, Structural Monitoring, & Live Video

There are no known bulk level detection systems that can also accurately determine tank discharge rates, monitor the structural integrity of the bulk tank, and provide live video all in one instrument.

3. Recognition

The primary deficiency in current bulk material type recognition and tracking techniques is the reliance on human operator input for critical inventory management information on type identification during load-in and retrieval operations. Human errors in identification, logging, and record management of material type, incoming inventory destinations, and existing inventory storage locations lead to costly, inadvertent material mixing incidents. When inadvertent mixing occurs in the grain handling industry, the remedy choice is to either sell the mixture as feed at 50% or less of market value or to separate it with separation equipment. Separators cost many thousands of dollars and require significant labor.

4. Condition Monitoring

The major deficiencies in the area of bulk material condition monitoring and tracking, especially organic materials such as cereal grains, is the reliance on relatively insensitive temperature cable technology and inspection via human olfactory and tactile sensing. Linear arrays of thermal sensors are arranged within long cables that are typically hung vertically from the roof of a storage bin such that, when material is loaded in, the cables pierce the pile at regularly spaced grid points across the surface. Since most bulk materials, including cereal grains, possess excellent thermal insulating properties, this method of condition monitoring detects only high rate exothermic condition loss reactions (e.g., fermentation during spoilage). The reaction heat is detectable only inasmuch as the zone of reaction is within the region of influence of a nearby temperature sensing cable. This often leads to situations where condition loss is well underway and has propagated through an economically significant portion of the stored material pile before detection by temperature cables is possible.

Human inspection is frequently employed to detect or verify condition loss problems, but this method requires a visit to the bin in question and, at a minimum, opening an inspection port for a sniffing test by the inspector to determine the presence of any telltale off-odors. Once detected, either by temperature cables or by human sniffing, the extent and recoverability of the condition loss problem is usually assessed via personnel "walking the grain" for tactile, visual and further olfactory information on the problem.

A typical temperature cable system cost is between 3–10 thousand dollars per bin depending on the number of cables employed.

5. Safety Hazards Awareness

The chief deficiencies in the area of safety hazards awareness are a lack of automation in routine inventory management tasks and a lack of up-to-the-minute information on important storage bin variables related to personnel safety. Manual verification of bin contents, manual inspection of bin content condition, and manual volume measurements all require storage facility personnel to perform potentially hazardous actions related to accessing the stored material, namely bin climbing and bin entry. If bin entry is required for troubleshooting, no current information is available to the entering personnel on vital factors such as material depth across the entire surface and environmental factors such as interior temperature and atmospheric constituents.

What is needed is an automated and integrated system of instrumentation for:

1.) accurately determining and tracking material volume by fully scanning a surface,
2.) recognizing material contents,
3.) monitoring material conditions,
4.) monitoring material physical properties,
5.) sampling and evaluating material constituents and quality during flow
6.) monitoring storage environmental conditions and
7.) providing safety data and awareness related to bulk materials storage within large bins, buildings, or other large containers.
8.) providing live in-bin video.

The present invention provides the above mentioned needs.

The present invention provides whole-surface measurement accuracy by providing +/−one inch accuracy over the entire surface of a pile of stored grain instead of measuring just one point, on a real time basis as the volume is changing during loading and unloading of the storage container. On-the-fly sampling of loading materials can measure and provide data such as moisture content, oil content, type of grain, contamination, and dust hazards. Cross checking of total grain flow during loading against a measured stored volume is achievable for the first time.

The present invention provides, automated, on-demand measurement of bulk material volume, recognition of material (e.g., grain species and variety), sampling measurement of flowing bulk material for other quality parameters (e.g. grain shapes for cross validation and count of whole versus damaged grains, foreign material, insect damage/presence, mold or heat damage, and constituent content such as moisture, protein, oil, starch, etc. The present invention will allow for total tank/silo monitoring and total bulk sampling/measuring of the flow into or from the storage tank/silo. It also monitors levels of condition degradation via sampling of by-product gases. It also improves life safety awareness. All of the above are implemented in the grain flow to, from, or within large storage and holding containers and on large ground piles.

The present invention is continuously operable as dust levels allow, but not during container load-in for optical instruments. This is also true for all other non-optical, non-contact instruments such as ultrasonic or radar-based instruments. Alternate embodiments teach instruments in a portable form having semi-continuous operation.

Since existing art in volume measurement employs single point distance measurements and visual estimation of material surface shape, volume errors can be large due to weakness in the accuracy of the surface shape estimate. The present invention increases volume measurement accuracy by using a surface profiling technique. Actual surface shape and height are thereby obtained, eliminating reliance on visual estimates. Human presence at the container is not required.

The present invention monitoring system is fully automatic, allowing a user to remotely monitor conditions within a storage bin. It is much more convenient and safe than traditional methods that require people to enter the storage bin. It provides a more accurate measurement of volume and can be used more frequently than traditional methods. It also can provide earlier detection of content degradation. The present invention also helps prevent inadvertent mixing of different types of bulk materials. Finally, the present invention provides critical safety related data to storage facility personnel when entering the storage bin is deemed necessary.

A Feature Summary Includes:

The present invention provides automation that eliminates the labor-intensive practice of visiting each storage container each time volume of contents must be measured or suspicious grain conditions must be investigated.

The present invention provides generation of a surface height profile that markedly increases accuracy of volume measurement over the current dominant method involving a single-point distance measurement and estimate of the pile's surface shape.

The present invention provides continuous whole-volume monitoring of moisture content and density variations that provide much earlier warning of deteriorating grain condition and provide a never-before-available ability to locate dangerous voids that may develop in the grain pile.

The present invention provides quick-response detection that is not dependent on large heat output from an exothermic reaction or other heat generating degradation sources. This detection is independent of grain insulating properties, which currently hamper detection via a temperature cable system. As well, it will replace the necessity of air monitoring for human presence in a confined space.

The present invention can be used for produce (vegetables) storage inland and/or during shipping, and also for coal/fossil fuel storage and shipping, wherein fuels are subject to state changes during storage. It can also apply to inorganic materials inventory accounting for high value products such as grit for architectural tiles and the like.

The present invention will give total surface measurement (as many points as desired) for less cost than the above stated ultrasonic system. Consequently, the single point systems, due to their inability to catch volume problems (i.e. theft), cost the user significant amounts of money where the present invention will prevent any problems of this nature from going undetected.

The present invention will render tank discharge rates along with tank structural monitoring and live video. Furthermore, these features are included in the base system cost.

The cost of the present invention system is significantly less than separators, which are required due to inadvertent mixing and will prevent these accidents.

The present invention will give earlier detection than temperature cables by monitoring any out-gassing while costing significantly less.

SUMMARY OF THE INVENTION

A main aspect of the present invention is to provide an automated inventory measurement and safety monitoring system (integrated hardware and software) with unique accuracy. The system provides remote monitoring of accurate height measurement data. The present invention also provides other safety awareness features which reduce the need for workers to enter a silo or other storage facility. If entry to a silo or other facility is deemed necessary, the system provides critical safety-related data to reduce the risk of entry.

Another aspect of the present invention is to provide a unique packaging solution of sensors for bulk and other potential applications. The packaging provides environmental protection from hazards such as explosions, dust, climate etc. It also provides for a self-cleaning viewing porthole apparatus to ensure an unobstructed window for the sensors.

Another aspect of the present invention is to provide accurate volume measurements for a flowing and/or stored bulk material.

Another aspect of the present invention is to provide a materials component (i.e. grain type, moisture content, protein content, starch, etc.) identification system for flowing and/or stored bulk material.

Another aspect of the present invention is to provide a quality monitoring system for bulk materials, especially to detect grain degradation (fermentation/rotting), bin headspace moisture content etc.

Another aspect of the present invention is to provide a stationary, rotating, dust ignition proof instrument housing suitable to scan various sensors across the top surface of a stored bulk material.

Another aspect of the present invention is to provide a multi-instrument quality monitoring package.

Another aspect of the present invention is to provide a spectrometer package for real-time analysis of flowing materials.

Another aspect of the present invention is to provide a ground penetrating radar (GPR) system for a storage bin.

Another aspect of the present invention is to provide a time domain reflectometry (TDR) package for a storage bin.

Another aspect of the present invention is to provide an accurate weight estimate for shipping loads and other purposes.

Another aspect of the present invention is to provide a computer based integrated measurement system using some or all of the above noted aspects.

Other aspects of this invention will appear from the following description and appended claims, reference being made to the accompanying drawings forming a part of this specification wherein like reference characters designate corresponding parts in the several views.

It should be noted that the following description of the present invention is not limited to the titles or selections discussed.

In general the present invention describes an automated and integrated system of instrumentation for:

1.) determining and tracking material quantity (volume) by fully scanning a surface, inclusive of structural monitoring of the storage vessel,
2.) recognizing material contents,
3.) monitoring material conditions,
4.) monitoring material physical properties,
5.) sampling and evaluating material constituents and quality during flow,
6.) monitoring storage environment conditions,
7.) providing on-board live video,
8.) providing safety awareness related to bulk materials storage within large bins, buildings, or other large containers,
9.) providing a unique sensor sealing and cleaning apparatus for the instrument package, and;
10.) providing a uniquely rugged envelope compliant to Class II Div I NEC ratings, as well as more rigorous ratings such as Class I Div I or lesser ratings, all of which ensure adaptability for other Fields of Use applications for the basic unique invention.

The total system integrates use of various sensor packages to solve bulk material storage problems with fixed or portable installations that convert observable phenomena into useful electronic data. This data collection can be accomplished remotely, automatically, semi-continuously, continuously (or on demand), safely, inexpensively, and with excellent repeatability. The data collected by sensors can then be transmitted over short or long distances to users who will view and manipulate the data with unique computer interfaces.

The total system is also part of the enabling technology because components of the entire system are what allow it to replace the manual effort. Converting a volume calculation to weight can be done by taking a volume measurement and multiplying the volume by a density. The density is dependent on many things such as the type of material, the moisture content of the material, what level of compaction is imparted to the material when it enters the storage tank, etc. Weight is an important aspect regarding shipping limitations etc. The present invention will allow for standard data factors but will also surpass prior art by having the system automatically collect all data factors. Spectral recognition technology will determine the material type that is useful for non-volume calculations but is also key to and will be used in converting the volume to bulk quantity such as bushels.

The present invention system sensor integrated package teaches various unique combinations never applied in this field of use, within this unique packaged and operable configuration, nor with this suite of sensors, all combining to solve related problems. Several sensors are packaged in one multipurpose instrument. This two-axis operable single instrument package can automatically monitor and provide all the necessary data for monitoring pertinent information of a given bulk solids storage container.

The volume (static or in-flow discharge rate) of bulk solids is measured using a scanning laser range finder or other scanning technology such as stereo cameras, structured light or acoustical beam-forming.

An acoustical single point ranger is used to prevent overfilling because ultrasonic technology can partially penetrate dust during a filling operation.

A photometric sensor or the rangefinder itself is used to determine the dust concentration entrained in the air to determine if measurements are possible.

The above sensors are mounted in a "Gimbaled (Scanning) Sensor Unit" (GSU) to monitor overfill, volume, dust concentration, container wall shape, provide live video, etc. Note: all references herein to the SSU-Scanning Sensor Unit-are equal to the GSU.

The type of bulk solid in the storage container is identified using photometric sensors (diodes or focal plane arrays like CCDs), lenses, and spectral filters, or spectrometers. The same sensor design is used for sampling the bulk for moisture content and specific chemistry of interest such as protein, starch, or oil content etc. The same sensor design is also used for foreign material sampling, shape recognition, and other quality sampling issues. The spectral sensors, lenses, etc. are mounted in an "In-Flow Sensor Unit" (ISU) in order to determine material type recognition.

The air quality within the storage container is monitored with a humidistat, a pressure transducer, a temperature sensor, and several gas detection sensors. These sensors will indicate:

Whether or not it is safe for humans to enter the confined space of the storage container.

Whether the headspace temperature and humidity psychrometric curves are approaching the dew point in which case dripping is ready to occur from the top structure onto the bulk material pile.

Whether a buildup or out-gassing is being detected due to the start of grain decomposition. The cause of the "off-odor" generation could be due to many causes such as insect infestation, bacterial or mold growth coupled with the accelerated conditions that foster their growth such as optimum temperature, moisture, or lack of air flow. The bulk material's condition is also monitored by photometric sensors and spectral filters detecting the gases of degradation. The combination of sensors will also monitor and set alarms for infestations and other human safety concerns.

The "Environmental Sensor Unit" (ESU) contains all necessary sensors for monitoring of outgassing, humidity, temperature, etc.

The present invention package(s) provides a unique instrument chassis housed within a dust-ignition proof enclosure. The package is "Explosion Proof" meaning it will not cause an explosion in an explosive sensitive area. It can also be designed for more demanding environmental conditions such as such as moisture, corrosives, etc. The laser rangefinder, photometric sensors, spectral filters, humidistat, temperature sensor, pressure sensor, gas detection sensors, (and other sensors), light source, onboard processing, and motion controls are all mounted in an instrument chassis. A video camera is also an optional component as well as a $2^{nd}$ visible laser for spot projection. Some components can be mounted in separate housings regarding non-gimbaled applications for installation in other specific spots of the tank or facility. To enhance window cleanliness for visual observation, a stepper motor may be used to rotate a window at one end of the enclosure. As the window rotates, an externally mounted wiper blade removes dust and debris. Alternatively, a pass-by brush system and/or a high velocity current of air can be used for cleaning the lens. The two-axis gimbaled setup for motion control of the instrument package(s) may be implemented with additional stepper motors or other motion control mechanisms to rotate the chassis/enclosure with respect to a supporting yoke. The yoke is a structural dust-ignition proof enclosure that mounts to a support base via a rotary stage. An additional stepper motor or other motion control mechanism may be used at the support base and is used to rotate the yoke through 360°. The yoke houses the bearings and seals of the two rotary stages as well as the on-board electronics and wire harnesses.

Grain penetrating radar (GPR) is another equally unique sensor head for gathering the same observable data such as volume, density, moisture content etc. This is accomplished via a mobile penetrating radar assembly. In this embodiment the electronic data is converted into useful graphical and other user friendly information at a user terminal after being transmitted from short or long distances. GPR is considered a unique embodiment of the present invention because this technology will provide nearly all of the same solutions as the integrated package but here with a single sensor.

Time domain reflectometry (TDR) is again another equally unique sensor for gathering the same observable data such as volume, density, moisture content etc. via use of a time domain reflectometer technique employing transmission line pairs located within the material to be measured. In this instance the electronic data is converted into useful graphical and other user friendly information at a user terminal after being transmitted from short or long distances. TDR is also considered a unique embodiment of the present invention because this technology will provide nearly all of the same solutions as the package but here with a single sensor.

In summary, a menu of various measurement package combinations are taught herein. Custom combinations of components provide cost effective, selectable, labor saving and redundant solutions for safety, quality and volume control issues related to bulk storage materials. The present invention can employ various technology packaging means to accomplish measurements. End user selection is a function of design requirements etc.

Systems Level or General Description of Inventions:

Total System:

The embodiment of the present invention provides a total system for using various sensor packages to solve bulk material storage problems with fixed or portable installations. The installation system converts observable phenomena into useful electronic data. This data collection can be done remotely, automatically, semi-continuously or continuously, or on demand. The data collection is performed safely, inexpensively, and with excellent repeatability. Data gathered by sensors can be transmitted over short or long distances via communication wires or wirelessly to users who can view and manipulate the data using the present invention computer software.

The system of the present invention is the enabling technology because the components of the system are what allow it to replace the manual effort. For instance, a volume to weight conversion can be done by taking a volume measurement and multiplying the volume by a density. The density is dependent on many things such as the type of material, the moisture content of the material, what level of compaction is imparted to the material when it enters the storage tank, etc.

This system will allow for standard factors but will also surpass prior art by having the system automatically gather those data factors. For instance, spectral recognition technology can determine the material type. Material type is useful for non-volume purposes and is also key to converting the volume to bulk measurements common in the trade, such as bushels.

System Sensors for the Automated Instrument Package (AIP):

Various sensor packages teach unique combinations of sensors never having been applied in this field of use. The present invention employs a unique packaged and operable configuration, with a unique suite of sensors, solving the particular problems aforementioned. Several sensors can be packaged in one multipurpose instrument. This two-axis operable single instrument package can automatically provide all of the data for status monitoring of a given bulk solids storage container.

The preferred embodiment of the present invention contains features that include:

A. Volume Measurement Solution:

The volume (static or in-flow discharge rate) of bulk solids is measured using a scanning laser range finder or other scanning technology such as stereo cameras and structured light or acoustical beam-forming. Height accuracy is typically measurable to less than 5 mm across the entire surface resulting in volume accuracy of greater than 99.5%. Volumetric changes (compaction, loading, unloading, pilfering etc.) can be measured within 0.5% change. The accuracy of the total volume of a storage site can be measured to within a 0.5% accuracy.

The preferred embodiment of the present invention utilizes a laser rangefinder (time-of-flight or phased-based design—both are existing art) which sends out pulses of infrared or visible light to obtain reflections off a desired surface. An acoustical single point ranger is used to prevent overfilling because ultrasonic technology can penetrate dust during a filling operation. A photometric sensor or the rangefinder itself is used to determine the dust concentration entrained in the air to determine if measurements are possible.

With a time-of-flight laser rangefinder, the time between emission of a pulse and detection of a reflection off the target surface is used to determine the distance from target to instrument. A phase-based laser rangefinder uses the measured phase difference between an outgoing train of pulses and the returning series of reflections to determine the distance from target to instrument.

By successively aiming the rangefinder at different points across the surface of the bulk material being measured, a collection of ranges is accumulated that characterizes the surface profile. Each measurement is a surface profile "element". Using knowledge of the instrument location within the container (or above the storage area), the pointing angle of the laser rangefinder, and the dimensions of the bulk material container or area, each surface element is converted to a volume element. When the accumulated surface elements are numerous enough to account for the entire bulk material surface or suitable interpolations between fewer measured points have been performed, the sum of their corresponding volume elements is equal to the volume of the entire mass being measured. A final conversion to standard volume measures may be necessary in order to account for higher at-depth packing densities typical in the storage of granular bulk commodities.

Information gathered by the rangefinder at each pointing location can be processed at the instrument itself to provide a volume and surface profile to an outside user. Alternatively, the data can be sent in raw form to an external computer for processing into the required volume and surface display data. The transfer of electronic data from the instrument installed at a particular container to an outside user at a computer station can be accomplished via conventional serial or parallel cable data communications, radio-frequency transmission/reception, infrared transmission/reception, or point-to-point laser transmission/reception. The remote user will capture the data sent by the volume measurement instrument in order to record and/or display the volume status of a particular bulk material storage container or area. Large containers may require multiple instruments to ensure full characterization of the bulk material surface. In lieu of multiple instruments, a single instrument can be fitted to a permanently installed rail near the top of the container's interior. For ground piled bulk materials, the methods are the same; the floor plane and edge retaining walls become the boundary basis.

Similar advantages over current practice in volume measurement of contained bulk materials can be realized using the following alternative embodiments such as:

1. Surface profiling via use of a stereoscopic camera pair and a source of structured light (a fixed pattern of light extending across material surface or a steered beam spot) to measure distances to a succession of different points across the material surface.
2. Surface profiling via use of a single scanning ultrasonic transducer articulated to successively measure distance to all points across the material surface.
3. Surface profiling via use of a widely dispersed assemblage of ultrasonic transducers which constitute a multiplicity of independent single point distance measurements.
4. Surface profiling via use of an assemblage of ultrasonic transducers operated as a phased array to progressively measure distance to points across the material surface through resultant ultrasonic wave-front and beam-steering.
5. Surface profiling via use of a single radar transceiver articulated to sense the discontinuity between the air and the bulk material at a succession of different points across the material surface.
6. Surface profiling via use of a widely dispersed assemblage of radar transceivers which constitute a multiplicity of independent single point distance measurements.
7. Surface profiling via use of an assemblage of radar transceivers which can be operated as a phased array to progressively measure points across the material surface through resultant radar wave-front and beam-steering.
8. Surface profiling via use of penetrating radar (steered or translated) located within the material to be measured which senses the discontinuity between the bulk material and the air above at a multiplicity of points across that surface.
9. Surface profiling via use of a mobile penetrating radar array combined with synthetic aperture imaging located within the material to be measured which senses the discontinuity between the bulk material and the air above at a multiplicity of points across that surface.
10. Surface profiling via use of time domain reflectometry techniques, over widely dispersed twin-conductor wire pairs hanging vertically throughout the contained material, to measure distance to the discontinuity between air and the material surface.

B. Type Recognition and Classification

The type of bulk solid(s) in the storage container is identified using photometric sensors (diodes or focal plane arrays such as CCDs), lenses, and spectral filters. The same sensor design is used for sampling the bulk for moisture content and specific chemistry of interest such as protein, starch, or oil content. The same sensor design is also used for foreign material sampling, shape recognition, and other quality sampling issues.

The recognition and classification of bulk grain/material may be performed by an automated recognition system. This recognition system consists of a multitude of optical photometric sensors, such as photocells, each coupled to an optical bandpass filter. A light source provides a known spectral illuminance across the bulk grain/material to be classified. The source can be in the visible and/or the near infrared region.

The optical system may be realized in several alternate forms; the multitude of photometers may be replaced with a single photometric sensor with multiple optical filters, each filter moved in front of the photometric sensor in turn. Another alternative is use of a focal plane array, such as CCD or CMOS image or line scan sensors which may also be used as the photometric sensor. These may be configured with individual optical filters located across the focal plane or as separate filters moved across the focal plane. A spectrometer arrangement may also be used in place of the multiple detectors and filters.

The photometric sensors are coupled to a computing apparatus which is able to input successive signal samples from each photometer (i.e.—the intensity of light falling on each sensor) into a pattern search, pattern matching, or similar type algorithm. The algorithm learns the characteristic spectral pattern for each grain/material type through training with known samples. Thus, with unknown samples, the automated recognition system uses prior knowledge of the spectral characteristics of each different type of grain/material, as well as the spectral characteristics of the illumination source. The measured intensity of each optical wavelength of interest is normalized to the illumination intensity at that wavelength and then compared with the known spectrum of light from each possible type of grain or bulk material. The closest match to the list of spectral characteristics yields the type of grain/material. Pattern matching algorithms may include table lookup, state space search, statistical and multi-dimensional pattern recognition, fuzzy logic, neural networks, or any other type of pattern matching scheme. This technique can be generalized to search for anticipated absorption and emission spectra that are indicative of important grain/material grading constituents such as moisture content, protein content, starch, and oil content.

Grain/material loads are currently graded on the basis of a few small samples. With appropriate optical narrow-band filter selection and training of the algorithm with known constituent compositions, the automated recognition system can be used to provide a continuous scorecard of important grading factors during any loading, unloading, or transfer procedure.

The computing apparatus for recognition systems may be implemented either with a digital computer, special purpose electronic computing equipment, or analog type computing circuitry.

The apparatus for the automatic recognition and classification of bulk grain/material may be used in several areas in the operation of a typical grain or material bulk storage facility. Incoming material into the facility comes from a transportation system such as trucks, railroad cars, barges, or ships, etc. Either a hand held version of the apparatus or some type of stationary or mobile recognition apparatus may be used to identify the material while it is still in its transportation container. The grain/material type identified at this stage is then inputted either manually or automatically into a system to determine the disposition of the material. This information is then used to configure the facility material handling system to route the grain/material to the correct storage bin.

Once unloading of the material is started, a second classification apparatus attached to the material handling system itself may be used to guarantee that the material handling system is routing the material correctly to the proper bin. Finally, each material storage bin may be equipped with a fixed classification apparatus to insure the grain/material type expected in each bin is actually correct. Upon shipping the material out, the same set of sensors may be used to insure that the proper grain or bulk material is actually shipped. Grain kernel shape, insect presence, kernel condition, and foreign material data usage will be configured similarly in the cycle of operation.

C. Condition Monitoring

The air quality within the storage container is monitored with a humidistat, a pressure transducer, a temperature sensor, and several gas detection sensors. These sensors indicate the following:

a) Whether or not it is safe for humans to enter the confined space of the storage container b) Whether the headspace temperature and humidity psychrometric curves are approaching dew point where dripping is ready to occur from the roof of the structure onto the bulk material pile.

c) Whether a gas buildup or out-gassing is being detected due to initial grain degradation. Potential causes of "off-odor" generation are possible insect infestation, bacterial or mold growth. Accelerators to these conditions are such factors as optimum temperature, moisture, and/or lack of airflow. The bulk material's condition is also monitored by photometric sensors and spectral filters detecting the gases evolved during degradation processes. These sensors will also monitor and activate alarms regarding human safety concerns.

Maintaining good grain quality today relies on manual methods and temperature monitoring. When grain begins to go bad, it ferments. The fermentation process in bulk stored grains gives off heat. When the problem gets bad enough and is close enough to a temperature sensor such as a thermocouple employed in a grain temperature cable, the operators can respond to an alarm. Temperature cables are at a disadvantage because grain is an excellent insulator, which often delays detection until the condition problem gets very bad and has propagated for some distance through the grain mass. Consequently thermocouple alarm detection often occurs very late in the condition loss cycle. The use of gas detectors for condition monitoring provides an early warning tool that, with appropriate sensitivity and background filtering, can help facility operators arrest the condition degradation process very early. Also, irrespective of condition concerns, grain bins have been ruled by OSHA regulations as "confined spaces". This requires management practices of air testing for human safe entry. Consequently, the automated instrument package and ESU gas detectors will be able to provide that information to operators.

Grain has a distinct odor of "good quality" when conditions are normal. As well, grain has distinct odors of "poor quality" when conditions are degrading. The odor constituents can be different depending on the grain type, any existing insect infestation, contributing molds, humidity levels, type of storage container, etc. There are many gaseous constituents responsible for the "musty-fermenting" smells that can be detected with appropriate gas detectors. Gas detection (electronic sniffing) sensors will be employed as part of the ESU to detect abnormal odors. There are two general classes of sensors available for the detection of gas concentrations, remote sensors and in situ sensors. Both classes of sensors will be incorporated into the ESU as appropriate. Finally, some fermentation by-products ($CO_2$) and gases important to human safe entry (CO, $CO_2$ and $O_2$) are odorless and abnormal quantities can be detected by the AIP sensors and alarmed to the operators. The present invention will apply the appropriate gas detector suite for the application.

Advanced and evolving in situ sensors based on surface acoustic wave technology and gas chromatography will be incorporated into the AIP as appropriate. These new sensor technologies are highly specific and highly sensitive and should be well suited to the detection of unique fermentation and degradation molecules (i.e. odors). These in situ sensors will operate by passing air samples over the sensor surface.

The detectors included in the ESU can be individual components or part of the total AIP package. Also they can be fixed installations or part of a portable instrument.

The gas detectors (E-nose) will sample the free air space above the grain pile (periodically or continuously) within the container or the interstitial air within the bulk stored grain in the container. This also applies to the combination humidistat and thermostat. Sampling and detection are accomplished by either relying on diffusion of target gases through the air mass above the grain pile to the sensor, or by actively passing air samples into or over appropriate sensor surfaces. The detected gas concentrations will be recorded by the system. Other data including time, grain type, changes in stored volume and other ambient factors (temperature, humidity, etc.) will be automatically logged. The AIP system's central processing unit (CPU) will analyze and filter the data. This may be accomplished via an onboard and/or remote processor. From this, the CPU will determine if significant changes or potential developing problems warrant an operational alarm. If the CPU posts an alarm, the operators will respond by entering the bin to search for the problem needing mitigation. The above also applies to the combination humidistat and thermostat process but these sensor readings are also compared to outside air temperature and humidity for user notification of an alarm condition.

If the AIP detectors are installed in a bin along with GPR or TDR products (see alternatives below), the system CPU will pinpoint the developing problem in the grain pile via three-dimensional dielectric analysis and the operators will know specifically where to mitigate. Once mitigation is complete, the operator will reset the alarms.

The transfer of electronic data from the instrument installed at a particular container to an outside user at a computer station can be accomplished via conventional serial or parallel cable-borne data communications, radio frequency transmission/reception, infrared transmission/reception, or point-to-point laser transmission/reception. The outside user will capture the data sent by the gas detectors in order to record and/or graphically display the full condition of a particular bulk material storage container.

The detectors and system for safe human entry will perform in the same way except data recording will be an "on demand" command from the operator.

Large containers may require multiple instruments to ensure full characterization of the bulk material. In lieu of multiple instruments, a single instrument as part of the AIP can be fitted to a permanently installed rail near the top of the container's interior.

Packaging:

The AIP contains an instrument chassis housed within a dust-ignition proof enclosure. The AIP can also be design hardened for ruggedness in more extreme conditions such as moisture, corrosives, etc. The laser range finder, photometric sensors, spectral filters, humidistat, temperature sensor, pressure sensor, gas detection sensors, light source, on-board processing, motion controls, electromechanical tilt sensor, and other sensors are all mounted to the instrument chassis. A video camera is also an optional component as well as a second visible laser for spot projection or a tuned laser for "gas" detection through light absorption/emission. Most components except the laser range finder may be mounted in separate housings for non-gimbaled applications for installation in other specific locations of a tank or facility. For window cleanliness and observability, a stepper motor may be used to rotate a window at one end of the enclosure. As the window rotates; an externally mounted wiper blade removes dust and debris. Alternatively, a pass-by brush system and/or a high velocity current of air can be used to clear dust off the lens. The two-axis gimbal mount for motion control of the instrument package may be accomplished via additional stepper motors or other motion control mechanisms to rotate the chassis/enclosure with respect to a supporting yoke. The yoke is an L or I shaped structural dust-ignition proof enclosure that mounts to a support base via a rotary stage. An additional stepper motor or other motion control mechanism may be used at the support base for controlled rotation of the yoke through 360°. The yoke houses the bearings and seals of the two rotary stages as well as the on-board electronics and wire harnesses.

An alternate lens cleaning method is available for ultrasonic or radar transducers. Ultrasonic or radar transducers are available with a shock mode in which case the transducer produces large amplitude pulses that shock any dust buildup loose thus keeping the transducer clear.

Alternate Solutions:

Alternate embodiments of the present invention that can be implemented are as follows:

A. Ground or Grain Penetrating Radar (GPR) Sensors:

GPR is another equally unique sensor head for gathering the same observable data such as volume, density, moisture content etc. This is accomplished via a mobile penetrating radar assembly. With GPR the electronic data is converted into useful graphical and other user-friendly information at a user terminal. Data for GPR can be transmitted there over short or long distances. GPR is an alternate embodiment of the present invention because this technology will provide nearly all of the same solutions as the standard package AIP, but with a single instrument. The volume, moisture content, condition (quality), density, commodity type, insect infestation and personnel risks of a commercially significant amount of bulk material (sand, grain, minerals, etc.) stored within a container may be accurately determined. GPR consists chiefly of a mobile radar transceiver employing synthetic aperture radar imaging techniques. The instrument is installed within an enclosed, but electromagnetically transparent raceway which is horizontally oriented along the floor or vertically oriented along the wall of the bulk material container. Grain Penetrating Radar (GPR) combined with synthetic aperture radar imaging (SARI) will see through the entire grain pile, allowing three-dimensional pinpointing of developing grain condition problems. The system will send RF or other high frequency signals through the grain pile and log the dielectric constant and/or dielectric gradient of the grain mass with graphical interfaces for the entire volume. When the grain begins to develop a degrading condition the local dielectric property of the grain will change whereby the GPR with SARI will highlight the location and alarm the operator of the problem and display the location. Like gas detection the CPU will log and filter out ambient background conditions to eliminate false alarms.

The mobile transceiver emits an electromagnetic pulse (a radar signal) into the bulk material volume. The pulse has the appropriate frequency content and power to penetrate the bulk material and provide sufficient amplitude for energy reflected from the container boundaries and the top surface of the material mass. The transceiver receives the reflected energy signals, which are then amplified, digitized, and stored by a signal processor. The transceiver is translated a small distance along the raceway and the process is repeated. By performing this procedure at a number of increments along the raceway and saving the resulting reflection signals, a synthetic aperture is assembled and the aggregate reflections can be processed to reveal characteristics of the bulk material volume. Most important are the locations of the container boundaries, the profile of the entire air/material boundary, any density gradients or discontinuities, variations in dielectric constant, and any other constituent signature changes such as due to insect infestation. Collected data yield precise information on the height and volume of the bulk material mass, the presence of any voids within the mass, the moisture content throughout the mass, the condition of the mass, and the identity of the material.

In a grain storage bin, the penetrating radar signature provides:

Measurement of height at many points across the air/grain interface allowing a highly accurate calculation of volume.

Monitoring of relative moisture content throughout the grain volume as well as changes over time.

Measurement of density gradients and location of density discontinuities throughout the grain volume.

Monitoring and pinpointing of changes in grain condition as revealed by changes in dielectric constant throughout the grain volume.

Identification of unwanted infestation.

Identification of grain type via dielectric constant classification

B. Time Domain Reflectometry (TDR) Sensors:

TDR is another equally unique sensor head for gathering the same observable data such as volume, density, moisture content etc. TDR uses a time domain reflectometry technique employing transmission line pairs located within the material to be measured. With TDR electronic data is converted into useful graphical and other user-friendly information at a user terminal. A TDR (Time Domain Reflectometry) instrument consists chiefly of a network of conductor pairs (coaxial cable shields or twisted pairs or shields of existing cables) hanging from the container roof with their roof-end connections terminated at a junction/switch box and their floor-ends swinging freely above or anchored to the container floor. TDR, like GPR, uses RF signals. With TDR the shielding or support wires of existing temperature cables and/or separate twin lead wires or separate coaxial cables are used to carry the RF signals. The signal processor captures and logs the time and gradient signal return changes based on amplitude and impedance to determine the dielectric constant as well as moisture content and changes thereof. Since TDR also provides imaging of the entire three-dimensional volume, it will give the operator precisely located condition detection via dielectric changes as well as full height moisture content. Data for TDR can be transmitted over short or long distances. TDR is also considered an alternate embodiment of the present invention, as this technology will provide nearly all of the same solutions as the standard package AIP but with a single instrument.

The volume, moisture content, condition (quality), density, commodity type, insect infestation and personnel risks of a commercially significant amount of bulk material (sand, grain, minerals, etc.) stored within a container may be accurately determined by employing a new instrument. This instrument consists chiefly of a network of conductor pairs (coaxial cable shields or twisted pairs or shields of existing cables) hanging from the container roof with their roof-end connections terminated at a junction/switch box and their floor-ends swinging freely above or anchored to the container floor. As well, this instrument can identify and monitor parameters of containerized liquid commodities.

The TDR instrument operates by exciting pairs of conductors as transmission line pairs. This excitation can be between the two leads of a twisted pair (self-excitation), the shields of two separate coax cables (crossed-excitation), or between any other pair of suitable conductors within the container, such as the shields of existing installed cables (crossed-excitation).

The TDR signature provides information on:

The height of the air/grain interface above the end of the transmission line as well as at the end of the transmission line.

Relative moisture content along the transmission path (via changes in the transmission medium's dielectric constant).

Relative density along the transmission path.

Condition state (quality) changes along the transmission path (via changes in the transmission medium's dielectric constant). Also, by detecting changes due to harmful items such as molds, insects, etc. Commodity type recognition along the transmission path (via the medium's dielectric constant).

Potential personnel safety risks such as voids, bridging, and cross sectional height.

Looking from above the grain pile, each hanging cable pierces the air/grain boundary creating an array of points along the surface. Successive self-excitation of installed twin-lead pairs provides an accurate measurement of the air/grain boundary height at each "pierce point" as well as a record of the combined effect of moisture, density and condition changes along the cable to its end. Cross-excitation yields the average air/grain boundary height between the two excited conductors as well as the average combined effects of moisture, density, and condition variations between the two conductors. With a sufficient number of cables, a combination of point and average measurements can be accumulated to accurately calculate the volume of grain present in the container. In addition, the moisture content, density, and condition variations can be characterized throughout the volume. By tracking moisture content and condition changes over time, potential degrading trouble-spots (quality reduction) can be detected far in advance of what is possible with current temperature cable technology. Likewise, by tracking density changes over time, voids can be detected and pinpointed to avoid potential life safety hazards to personnel who must enter the container.

C. Spectral Reflection or Absorption Spectroscopy:

Spectral reflection or absorption spectroscopy will be used to detect both the off-gassing by-products of degrading or fermenting grain and for monitoring safe air levels for human entry into the container. This spectroscopic gas monitoring and detection is accomplished via either the laser (already being used for distance ranging) and/or the focal plane detector camera (already being used for grain type spectral recognition) or an entirely separate spectroscopic sensor (i.e. infrared) more suitable for detecting the absorption and/or emission lines of the subject gases.

D. Silicon Enose "Sensors on a Chip":

Silicon Enose "sensors on a chip" that are under development elsewhere can, once commercially feasible, be incorporated into the AIP and integrated into the control and data-logging system. These silicon sensors will be tuned for specific organic molecules known to be associated with grain condition problems but which have been prohibitively expensive to analyze in the typical grain/feed elevator setting.

E. Volume Measurement Via Separate Transmit/Receive Penetrating Instruments:

Volume measurement via use of a separate transmit and receiver penetrating radar instruments (steered or translated) located within the material to be measured, which senses the discontinuity between the bulk material and the air above at a multiplicity of points across that surface. Reception of the radar transmissions provides information on average moisture content, and thereby condition, through changes in dielectric constant along the transmission path. Voids can be detected and located by sensing the discontinuity between the grain and air at the void boundaries.

F. Combined Mobile Radar Array:

Combined mobile radar array with all same features mentioned above and with synthetic aperture radar imaging for targeting specific areas of bulk requiring attention.

G. Bundle the Wire Transceivers:

An alternative sensor arrangement, instead of the mobile transceiver, will be a bundle of wire transceivers. Each wire will have a strategically placed fixed transceiver (transmitter and receiver) node along the bundle. In this bundle fashion, there will be a linear transceiver array due to the multitude of wires with multiple terminations at a single signal generator housing. The signal generator will sequentially pulse individual wires and antennae nodes. In this fashion a pulsed wave can be created in a similar fashion as the mobile transceiver array but with the advantage of no moving parts.

The three different types of instrument package (AIP, TDR, GPR) are alternative stand-alone solutions, representing different technology solution methods for the same problem set. The individual components (Laser rangefinder for volume, spectrometer for material type, etc.) of a system solution are unique in how they work together. For example, in the AIP for the grain "type" tracking system to work in the automatic mode it needs to integrate with the laser rangefinder (LRF) volume tracking solution. This is because the ISU (when mounted on the chute versus mounted on the GSU) will only tell the last material it detected going into the bin. The system then relies on the LRF to track and report that the bin was emptied to zero the system out. The integration is required or else the user interface can look as if dissimilar material (Corn vs. Wheat i.e.) was dumped on top of the last recognized material. Another example is the "Enose" detectors where, since different bulk materials emit different degradation byproduct gases, the ESU relies on the material recognition detectors in the ISU to first sort to the relevant byproduct database of that species.

In summary the embodiments present a menu of measurement package combinations that are taught herein. Custom combinations of components provide cost effective, selectable, labor saving and redundant solutions for safety, quality and volume control issues.

Other aspects of this invention will appear from the following description and appended claims, reference being made to the accompanying drawings forming a part of this specification wherein like reference characters designate corresponding parts in the several views.

BRIEF DESCRIPTION OF THE DRAWINGS

FIGS. 9A, 9B, 9C is a GSU parts listing for the alternate embodiment of the present invention.

FIG. 13B is a volume measurement flow diagram.

FIG. 18H is a schematic representation of narrow beam steering across the material surface.

FIG. 28C is a schematic of the internal electronics and power for the junction box.

FIG. 28D is a schematic of the host computer and interface to the junction box.

FIG. 29 is a schematic of the universal AIP instrument board.

FIG. 29B is an electrical schematic of the SSU elevation/tilt section wiring.

FIG. 29C is an electrical schematic of the main power and data junction box wiring.

FIG. 29D is an electrical schematic of the host computer connection.

FIG. 30 is a schematic layout of the "Universal" ESU/ISU/SSU printed circuit board I/O connectors.

FIGS. 30A, 30B, 30C, 30D are schematic component layouts of each quadrant of the "Universal" ESU/ISU/SSU circuit board.

FIGS. 31A, 31B, 31C, 31D, are schematic component layouts of each quadrant of the CAN repeater and video multiplexer circuit board.

FIGS. 32A, 32B, 32C, 32D, 32E, 32F, 32G, 32H, 32I, 32J, 32K are parts listings for an AIP for an alternate embodiment of the present invention.

FIG. 32L, 32M, 32N are a minimum performance specification for the laser rangefinder in an alternate embodiment of the present invention.

Before explaining the disclosed embodiment of the present invention in detail, it is to be understood that the invention is not limited in its application to the details of the particular arrangement shown, since the invention is capable of other embodiments. Also, the terminology used herein is for the purpose of description and not of limitation.

DETAILED DESCRIPTION OF DRAWINGS

The following figures represent various detail drawings and flow charts of the present invention.

Figure 1:
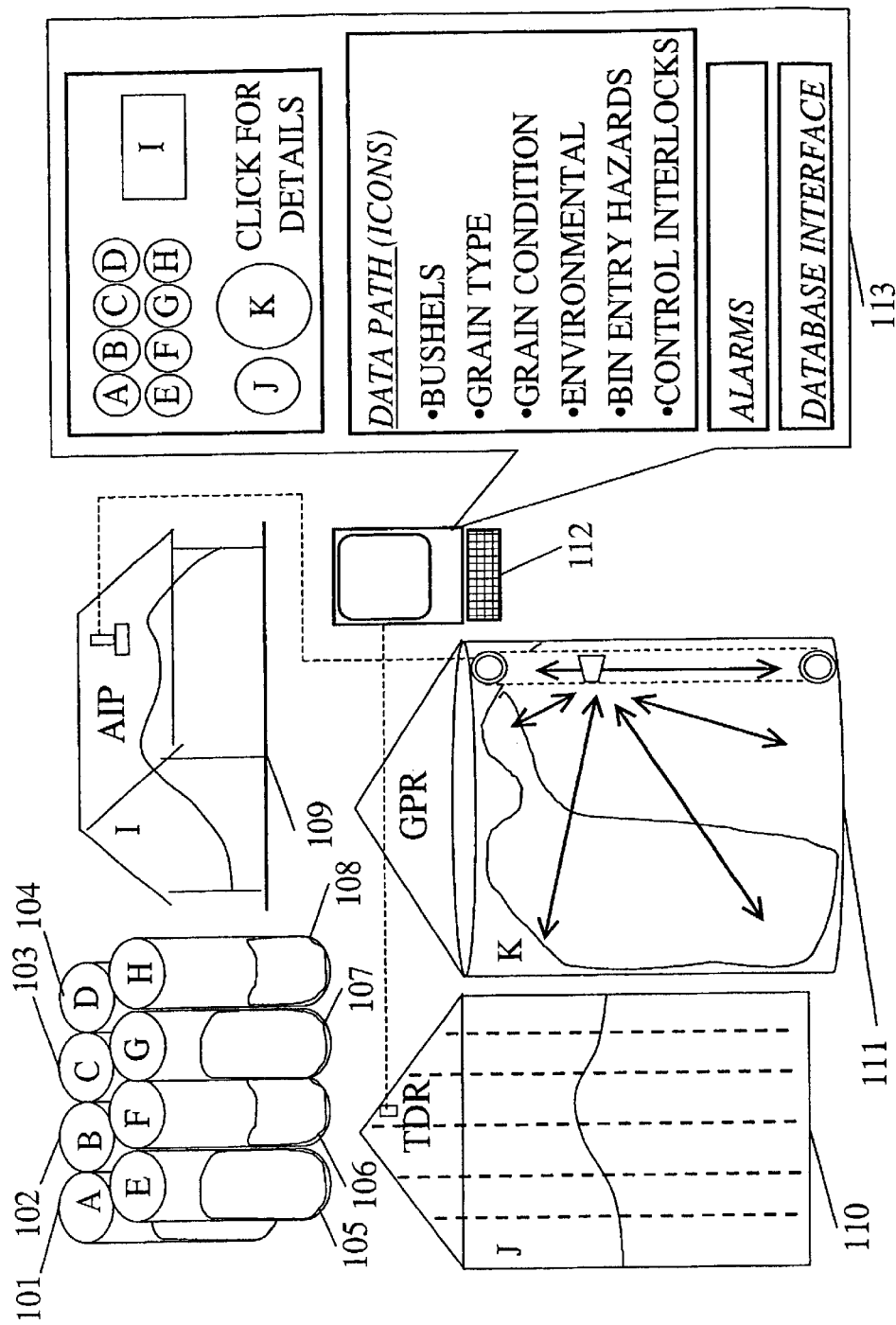
FIG. 1 is a schematic overview of an entire measurement system.

FIG. 1 is a schematic overview of the total system at a fixed installation. Various types of storage installations are depicted. Silo storage bins A–H (101–108) to hold a material are shown. Also shown are the various type of instrument packages mounted in other building types I, J, K (109, 110, 111) for alternative stand-alone solutions. Each package represents a different technology solution for the same problems. The Automated Instrument Package (AIP) 109, Time domain Reflectometry package (TDR) 110 and the Ground Penetrating Radar (GPR) package 111 are shown as various stand-alone solutions. Also shown in FIG. 1 is a depiction of the computer 112, and the computer screen (block 113) which allows the user to select a particular bin (Graphics Path) or to interrogate data (Data Path) for volume, weight, material type, material condition, environmental data, personnel hazards, control interlocks etc. The screen would also show alarms, and have a path to bookkeeping and accounting information. FIG. 1 depicts fixed installations versus stand-alone or portable versions which are also supported with the present invention.

Figure 2:
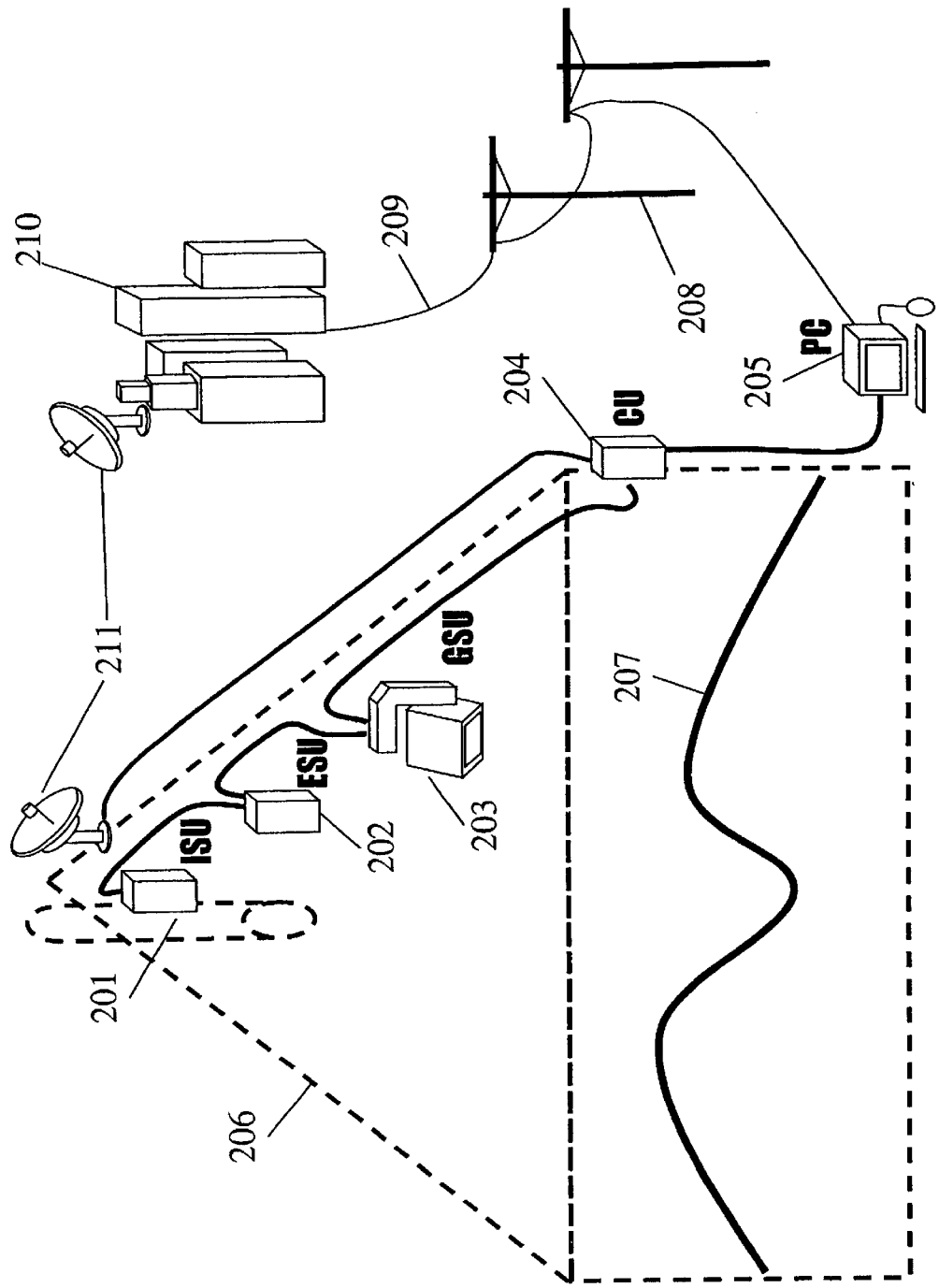
FIG. 2 is a cross sectional view of a silo showing a ceiling mounted automated instrument package (AIP) and the various components (ISU, ESU, GSU) and the various data communication methods.

FIG. 2 represents the AIP functional components. Instruments can be gimbaled and suspended. However, individual components designed for flow sampling like the spectrometer can be installed separately and in a fixed housing on the incoming chute or at the discharge chute or at the loading chute, etc. A storage facility 206 would contain the In-Flow Sensor Unit (ISU) 201, the Environmental Sensor Unit (ESU) 202, the Gimbaled (Scanning) Sensor Unit (GSU) 203, the Control Unit (CU) 204, and the central processing computer (PC) 205 which is located on the same site as the storage facility. Bulk material 207 is shown as stored in the building 206.

The ISU 201 is shown housed in an enclosure compliant to NEMA (National Electronic Manufacturers Association) AND NEC (National Electric Code) and UL (Underwriters Lab Inc.) equivalent standards for hazardous, non-hazardous, indoor and outdoor locations. The ISU 201 is shown mounted at an input loading chute. It provides universal mounting clamps and a scratchproof spectrally favorable window such as clear glass, sapphire or diamond vapor deposition glass. The multi-spectral photometer or spectrometer head is stored within along with a controlled light source such as 40-watt halogen lamps or multiple arrayed light emitting diodes (L.E.D.s). It also has onboard control electronics. The ISU 201 monitors material type.

The ESU 202 is shown housed in an enclosure compliant to the NEMA, NEC, and UL equivalent standards. It has onboard electronics and also contains an electronic thermostat, humidistat, barometric pressure sensor, and gas molecule detectors characterized as "Enosell sensors. These detect various gases such as:

1. $CO_2$
2. 3-octanone, 1-octanone, 3-octanol, 1-octen-3-ol, 3-Geosmin, 3-methyl-1-butanol
3. acetoin, diacetyo, butanediol
4. pheromones, 2-pentanol
5. methoxybenzene, nitromethane, acetic acid, metabolites The GSU is shown packaged in a universal mounting plate.

The GSU 203 contains a motorized arm with appropriate bearings and gears per individual accuracy requirements giving azimuth and elevation scanning. It contains a housing for sensors. The arm and housing comprise an enclosure compliant to the NEMA, NEC, and UL equivalent standards. It also contains a laser rangefinder and/or acoustical rangefinder, a video camera, a spectrometer (VIS, NIR, or MIR), and on-board electronics. The volume of a commercially significant amount of dry bulk material (sand, grain, minerals, etc.) stored within a container and/or piled on the ground may be accurately determined by employing the GSU instrument. The GSU can be mounted above the bulk material to be measured. This can be inside a bin, tank, silo, other bulk container or in open topographic applications such as over a pit or open storage area.

The CU 204 is shown housed in an enclosure compliant to the NEMA, NEC, and UL equivalent standards. It contains the "Central Processing Unit" for sensor control, sensor data acquisition, and communication back to the host computer. The CU has a manual override toggle or push-button switch, as well as a thermostat and humidistat for measuring outdoor conditions for comparison to the in-the-bin conditions. The CU is designed in a daisy chain feed to the bin shown 206 as well as to many other bins housed in the same general location. Thus the CU will support instrumentation in multiple bins. The host computer "PC" 205 is also shown. The PC contains all software necessary for user interface, report generation, etc. The AIP system of sensors is designed for the on-site user as well as the needs of other parties remotely located from the storage site 210 such as a corporate headquarters, governmental entities, or the facility's lending institution. Such remote communication access to the sensor-derived data can be delivered over phone line connections 208 through a dial-up modem or through the internet/intranet 209 or through wireless communication technology 211.

Figure 3:
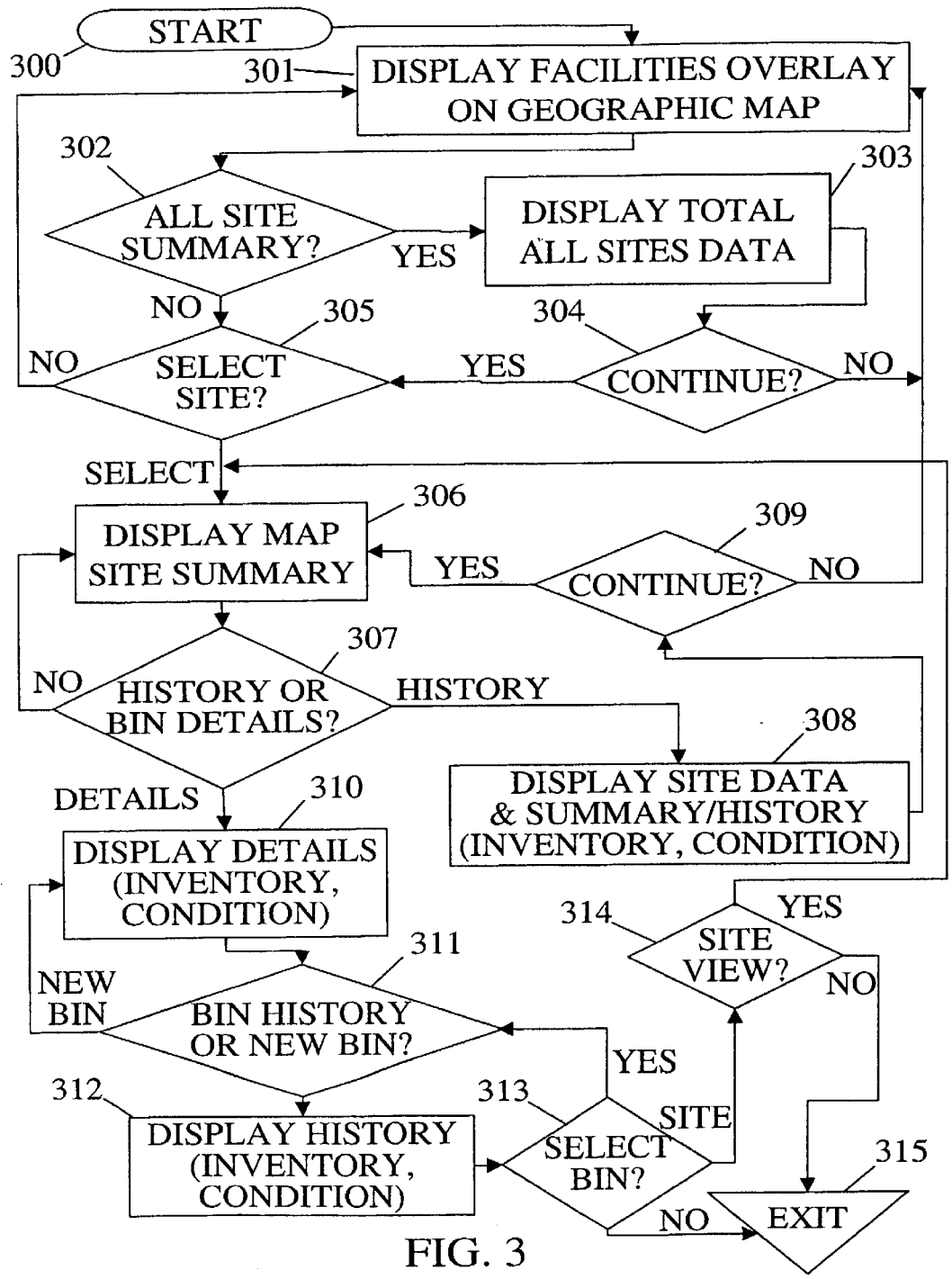
FIG. 3 is a flow diagram of a user interface flow.

FIG. 3 is a depiction of the user interface flow. At the start (block 300), the user will see a graphical display geographic locator map of all facilities in the database (block 301). If the user elects to see a summary of all facilities (block 302), a display will show the aggregate data on all facilities within the database (block 303), and the user will be prompted to continue (block 304). If the user does not elect to continue, the base display screen (block 301) will be displayed. If continue is elected or if the user did not elect to see all facilities (block 302), then the user can elect to select a particular facility (block 305). If a particular facility is elected, a display of the specific facility map is displayed (block 306). The user can select to see bin details or facility history (block 307). If history is selected a display of facility history charts and aggregate data is displayed (block 308) which shows volume, type, condition flagging etc. If "details" is selected, a display of specific bin details is presented (block 310) showing current volume, type, and condition. From here the user can select a new bin or bin history (block 311). If a new bin is selected the user is returned to specific bin details (block 310). If bin history is selected, a display with the selected bin history charts is presented (block 312). From this point the user can select a new bin or see the facility (block 313). If new bin is selected the user is returned to a display of specific bin details (block 310). If a new bin is not selected, the user is exited (block 315). If facility is selected, the user is asked if the facility is to be viewed (block 314). If the user opts to view another facility the user is returned to select the appropriate facility (block 305). If the user does not want to view another facility, the user is exited (block 315).

FIGS. 4A, 4B, 4C, 4D, 4E, and 4F represent user interface screens.

Figure 4A:
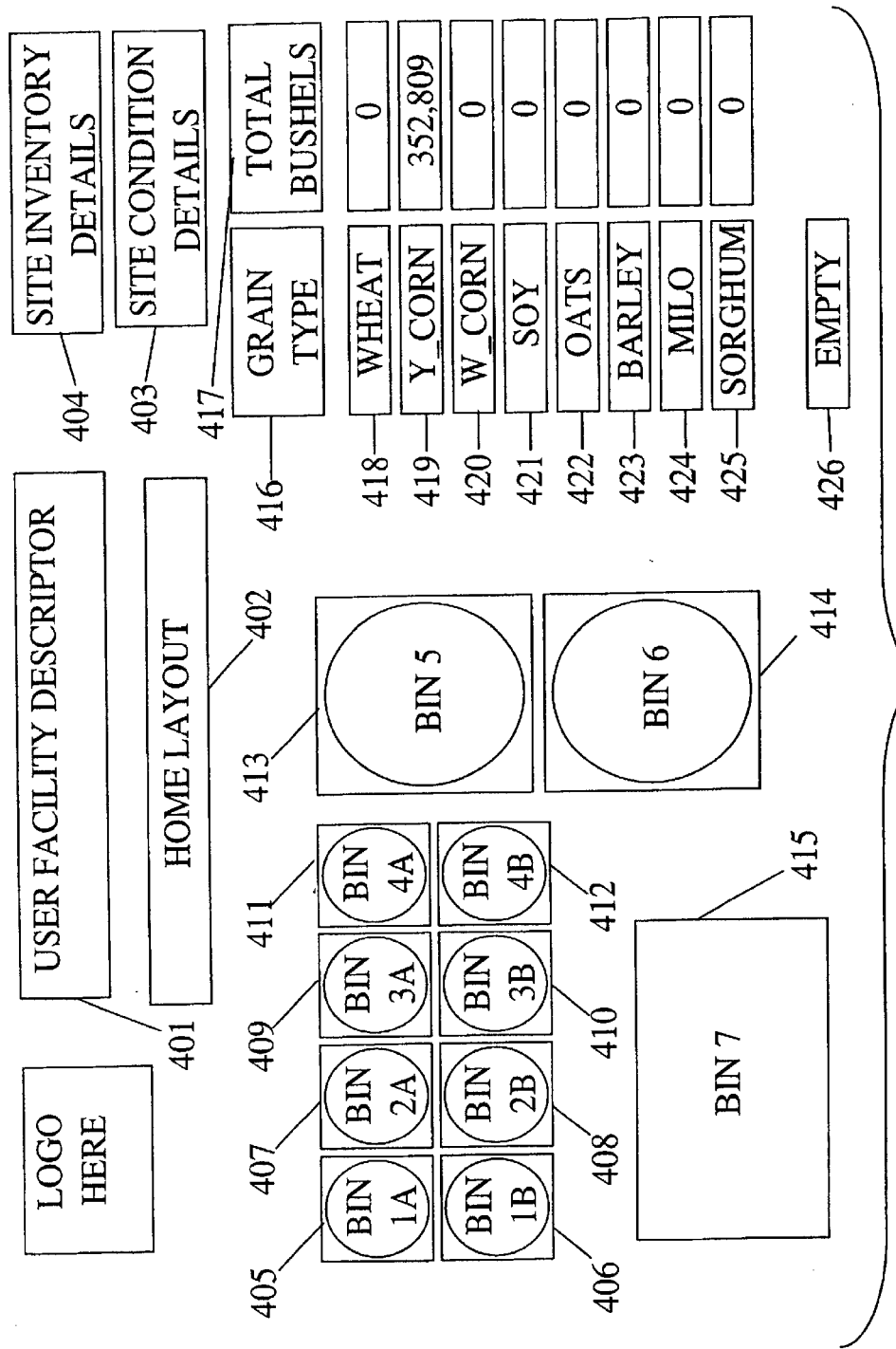
FIGS. 4A, 4B, 4C, 4D, 4E, 4F represent various graphical user interface (GUI) screens.

FIG. 4A depicts and is the home screen titled user site "Home Layout" (block 402) with eleven bins. The site location (block 401) depicts the company name and location. From this screen the user can elect to see site condition details (block 403) or site inventory details (block 404) or select a particular bin (via double clicking) for bin details. Bins are labeled 001A through 0007 (blocks 405–415). Grain type (block 416) and total bushel inventory (block 417) are shown. Each row (block 418–425) depicts the material type and volume. For example, wheat (block row 418) shows a zero volume whereas yellow corn (block 419) shows a volume of 179,675 bushels. Contents of each bin are color-coded (colors not shown) to match the grain type (column block 416). If a bin is empty (block 426) an "empty" color is displayed.

Figure 4B:
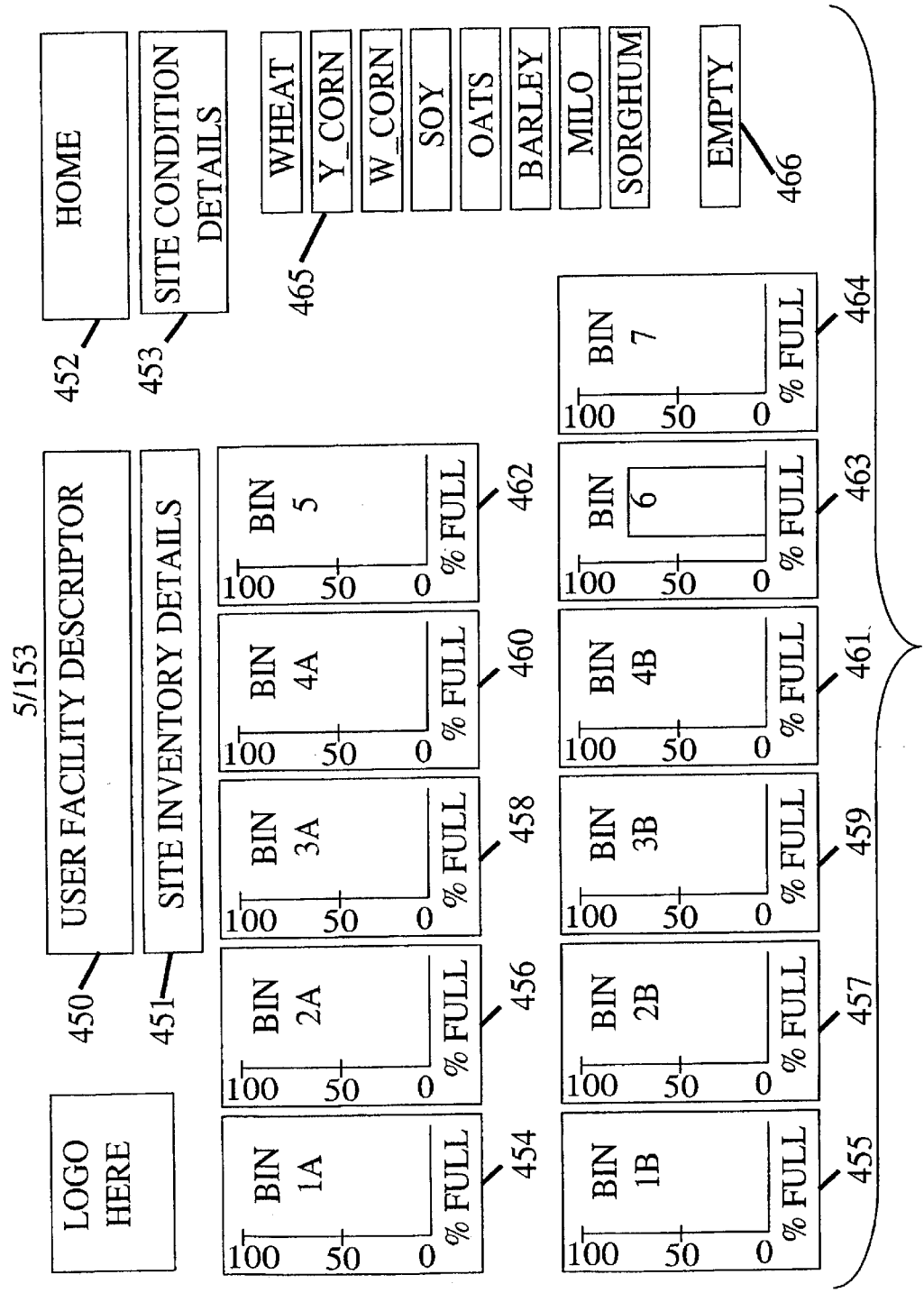

If the user selected site inventory details (block 404 of FIG. 4A), the display screen of FIG. 4B with site inventory details (block 451) is displayed with the company name and location (block 450). Graphical representations of each bin 001A through 0007 (blocks 454–464) are displayed. Bins are again color-coded (colors not shown) to match the material type (column block 465). An empty bin is also color-coded (block 466). From this screen the user can return to home (block 452), go to site condition details (block 453) or double click on a bin to display bin details. In the example of FIG. 4B, it can be seen that bin 0006 (block 463) is approximately 70% full. Color matching of bin 006 (block 463) and material type (column block 465) would show the user that the material type is yellow corn.

Figure 4C:
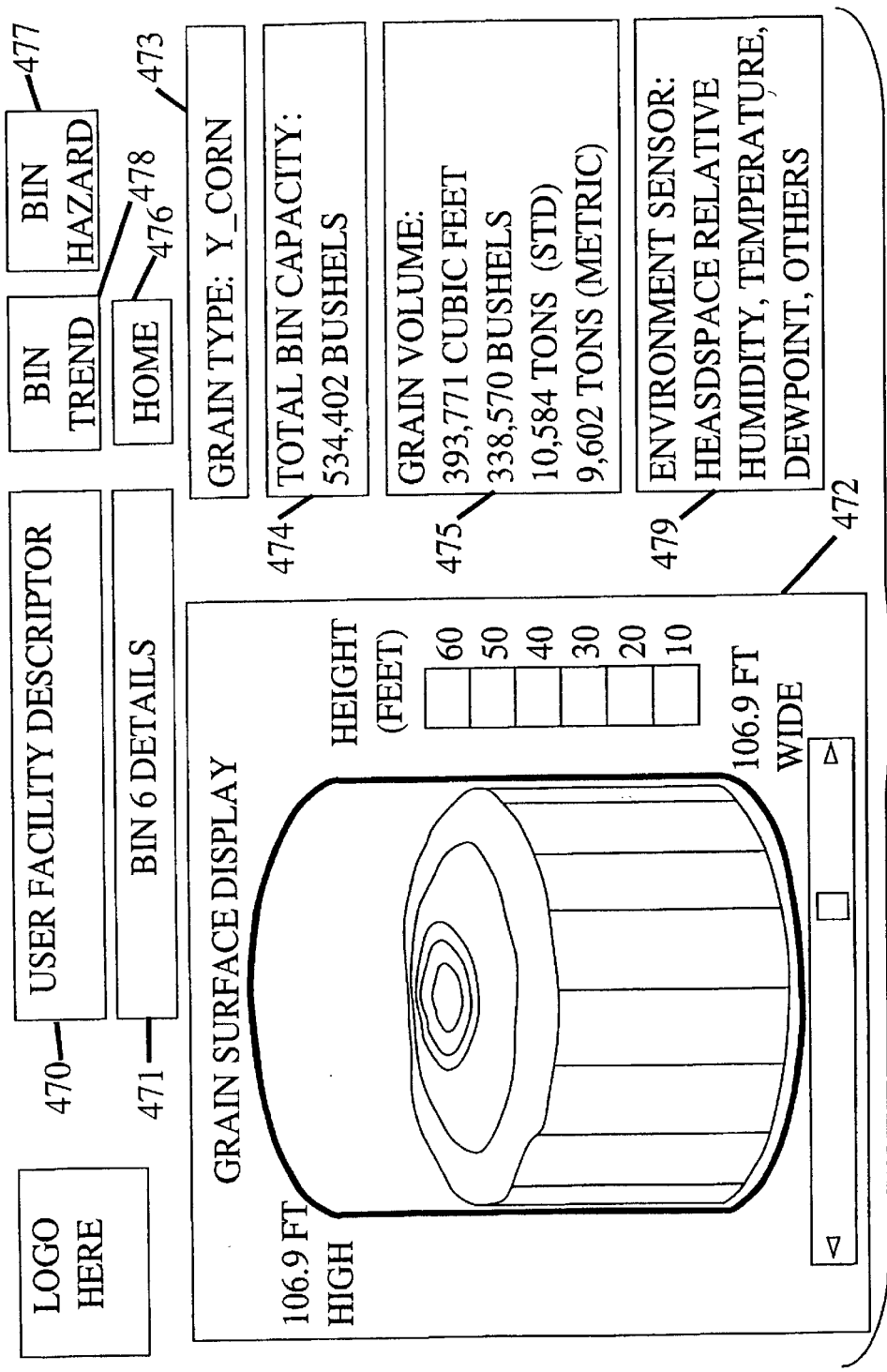

FIG. 4C depicts bin details title (block 471) for bin 0006. It shows the company name and locale (block 470). The user can get to this display screen by double clicking on a particular bin as previously described in FIGS. 4A, 4B. A detailed graphical display (block 472) depicts the bin height (block 472A) at 106.9 feet, the bin width (block 472D) of 89 feet and the bin height profile (block 472B). The profile is color-coded (colors not shown) (block 472C). Also shown are the grain type (block 473) of yellow corn, total bin capacity (block 474) of 534,402 bushels and grain volume (block 475) converted to cubic feet, bushels, tons and metric tons. From this display the user can select to return to home (block 476), go to display the screen for bin hazard (block 477) or go to the display screen for bin trend (block 478). The output of the environmental sensors (block 479) are displayed such as headspace relative humidity, headspace temperature, outside temperature and humidity and headspace dew point.

Figure 4D:
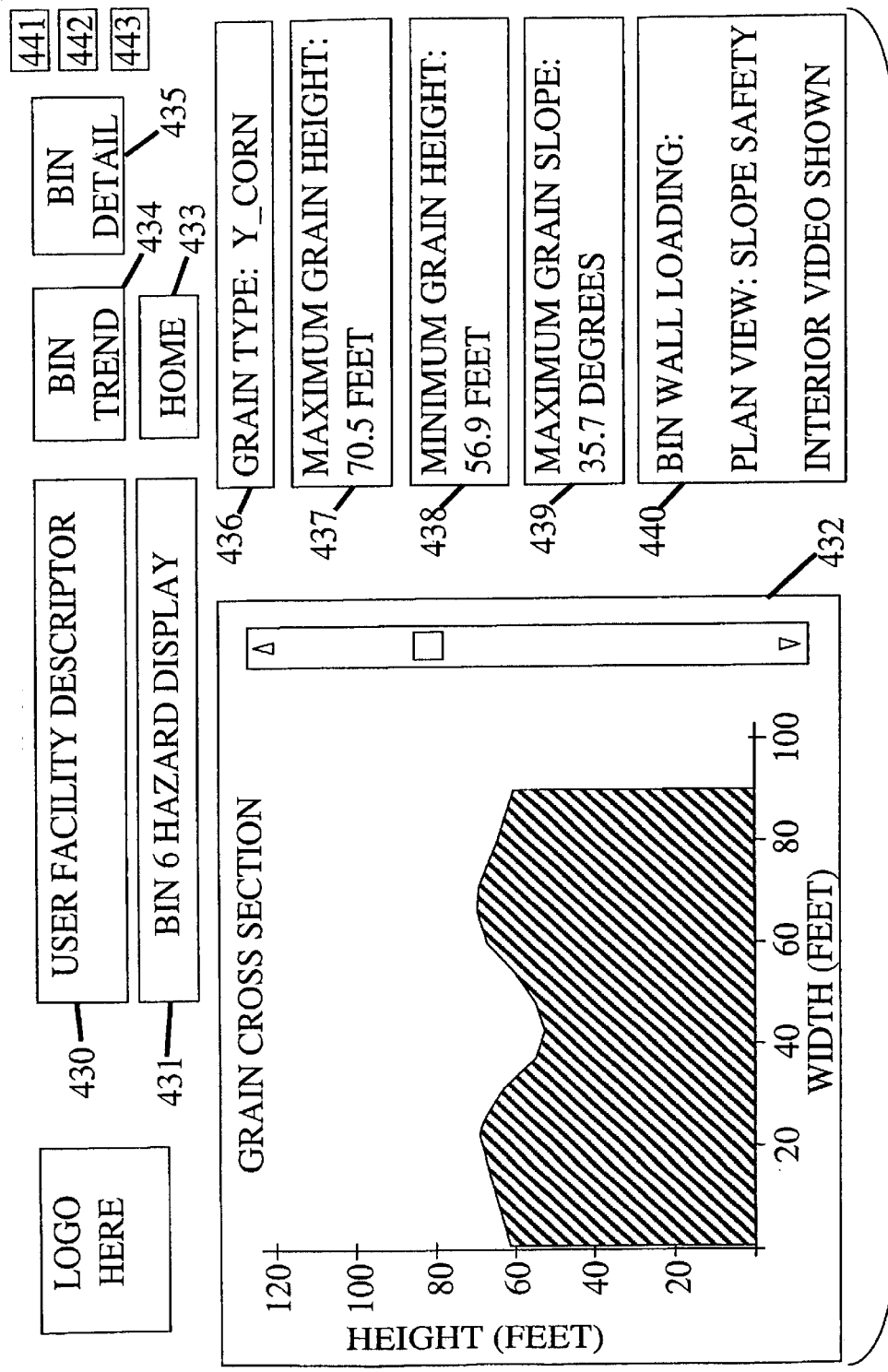

FIG. 4D depicts a display screen with a "bin 0006 hazard display" title (block 431). As in other screens described previously, it shows company name and locale (block 430). A "Grain Center Slice Profile" is shown graphically (block 432). The profile across a center slice of the bin width is shown graphically. The grain type (block 437) shows yellow corn in this example. Also shown are details of maximum grain height of 54.4 feet (block 438), minimum grain height of 41.3 feet (block 438), maximum grain slope of 30.1 degrees (block 439), and bin wall loading (no figures shown) (block 440). From this screen the user can elect to return to home (block 433), display the bin trend (block 434) or display the bin detail (block 435).

Figure 4E:
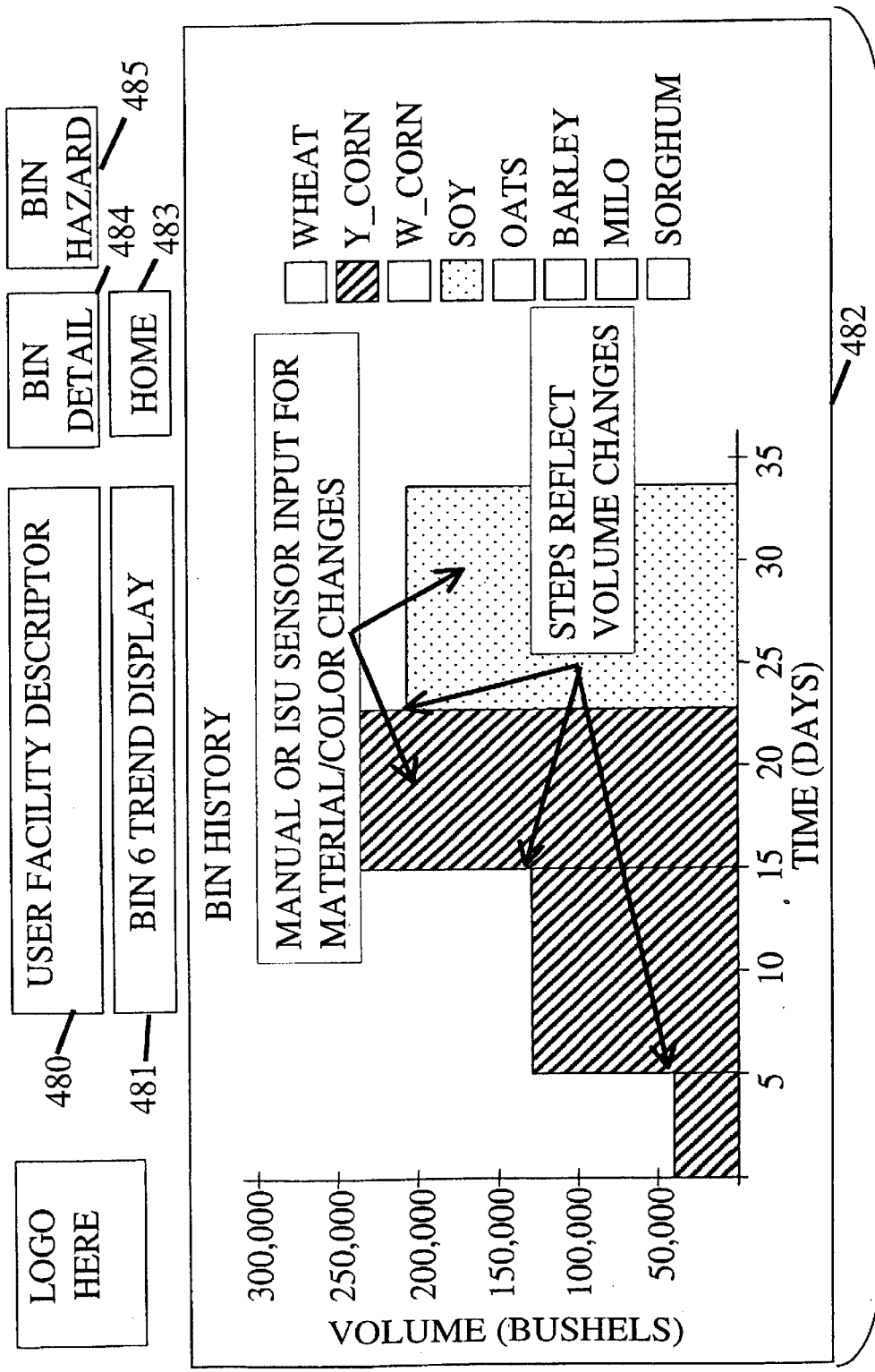

FIG. 4E depicts a display screen with a "bin 0006 trend display" title (block 481). As in other screens described previously, it shows company name and locale (block 480). The trend history is shown graphically (block 482) to reflect the fact that wheat was previously stored.

Figure 4F:
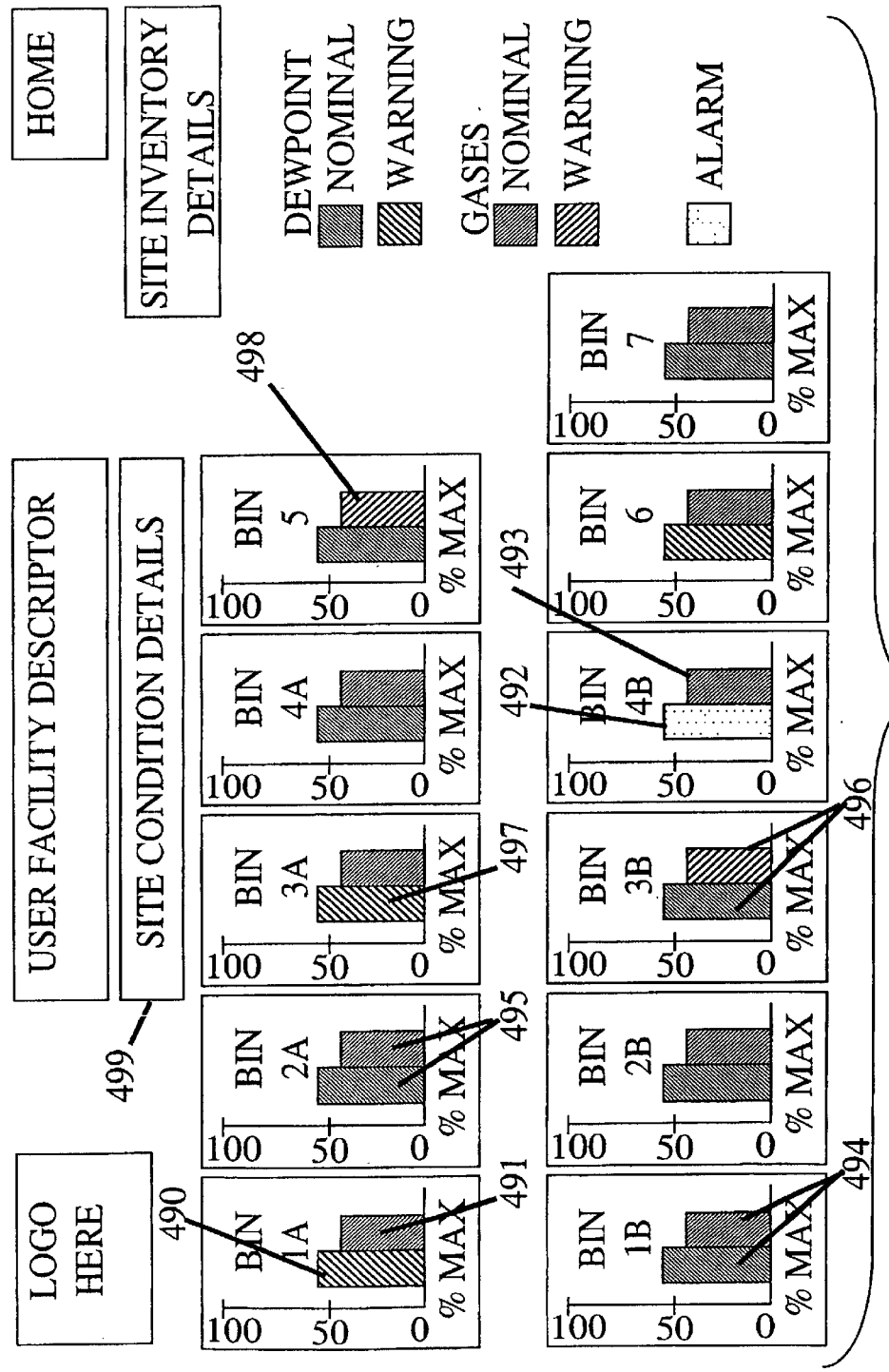

FIG. 4F depicts a site condition detail 499 display as reported from the ESU. The display set up similar to that described above in FIG. 4B but with bin dew point and gas detection being displayed instead of inventory. All bin dew points and gas levels are displayed with color coding (color not shown). The bar display(s) of each bin reflect an alarm (red), caution warning (yellow) or no problem (green) feedback. Gas that is being sniffed or optically detected and dew point warning(s) of pending condensation drips can thus be mitigated by turning on an exhaust fan(s) or taking other action as required. If a display bar is green (e.g., gas bar 491 of bin 001A) there is no problem. If a display bar is yellow (e.g., dew point bar 490 of bin 001), it indicates a caution warning to the user. If a display is red (e.g., dew point bar 492 of bin 004B), it indicates a problem alarm to the user. As various type gasses can be detected, only the highest level warning or alarm is shown. An operator can view other gasses by double clicking on an individual bar in the "gas" column (e.g., 493 of bin 004B). In the display represented, bin 001B displays 494, and bin 002A displays 495, show no problems (green), whereas bin 001A dew point display 490, and bin 003A dew point display 497, show dew point warnings (yellow). Bin 003B gas display 496 and bin 005A gas display 498 e.g. show a gas warning (yellow) whereas bin 004B gas display 492 shows a serious alarm condition (red).

Figure 5:
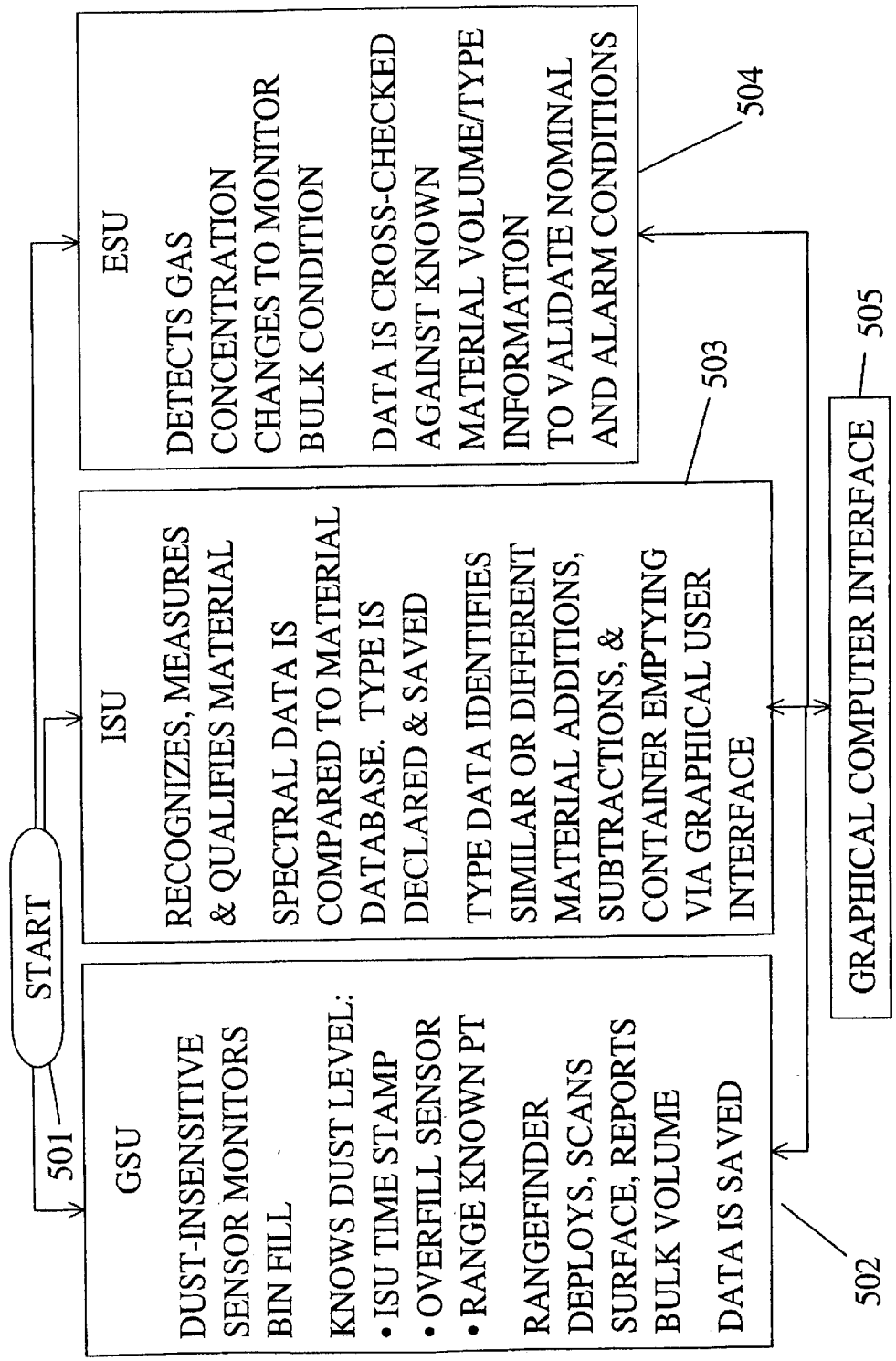
FIG. 5 is a representative AIP flow diagram to depict the interactions between the GSU, ISU, ESU, and Host Computer software.

FIG. 5 is a representative AIP flow to depict the interactions between the GSU, ISU, ESU, and Host Computer software. When the system is powered on to start (block 501), all units are activated. A common bus architecture is employed to communicate to the host (block 505). The GSU (block 502) will monitor overfill, volume, dust. It measures volume when dust settles out and it receives a signal from the ISU sensors (via the host) that input flow has ceased. The ISU (block 503) will determine the material type. The ESU (block 504) will monitor the material condition for changing gas and ambient levels etc. and set alarms as required to the host computer. The graphical interface at the host computer (block 505) will display all conditions. The software of the host computer will communicate with each individual unit. For example, the ESU (block 504) would require material type and volume prior to sending alarms to the host. For the ISU grain type recognition (block 503) tracking system to work in the automatic mode to give the user complete timeline trending data it needs to integrate with the GSU volume/quantity tracking solution (block 502). This integration is required because the ISU (when mounted on the chute vs. mounted on the GSU) will only tell the last material it detected going into the bin. The system then relies on the volume system to track and report that the bin was emptied and then to zero the system out. Otherwise the user's interface would look like dissimilar material (Corn vs. Wheat) was dumped on top of the last recognized material. Another example is the Enose detectors in the ESU (block 504) will rely on the material recognition detectors in the ISU (block 503) to first sort to the relevant database of that species because different bulk materials outgas unique spoilage/degradation by-product gases.

Figure 6:
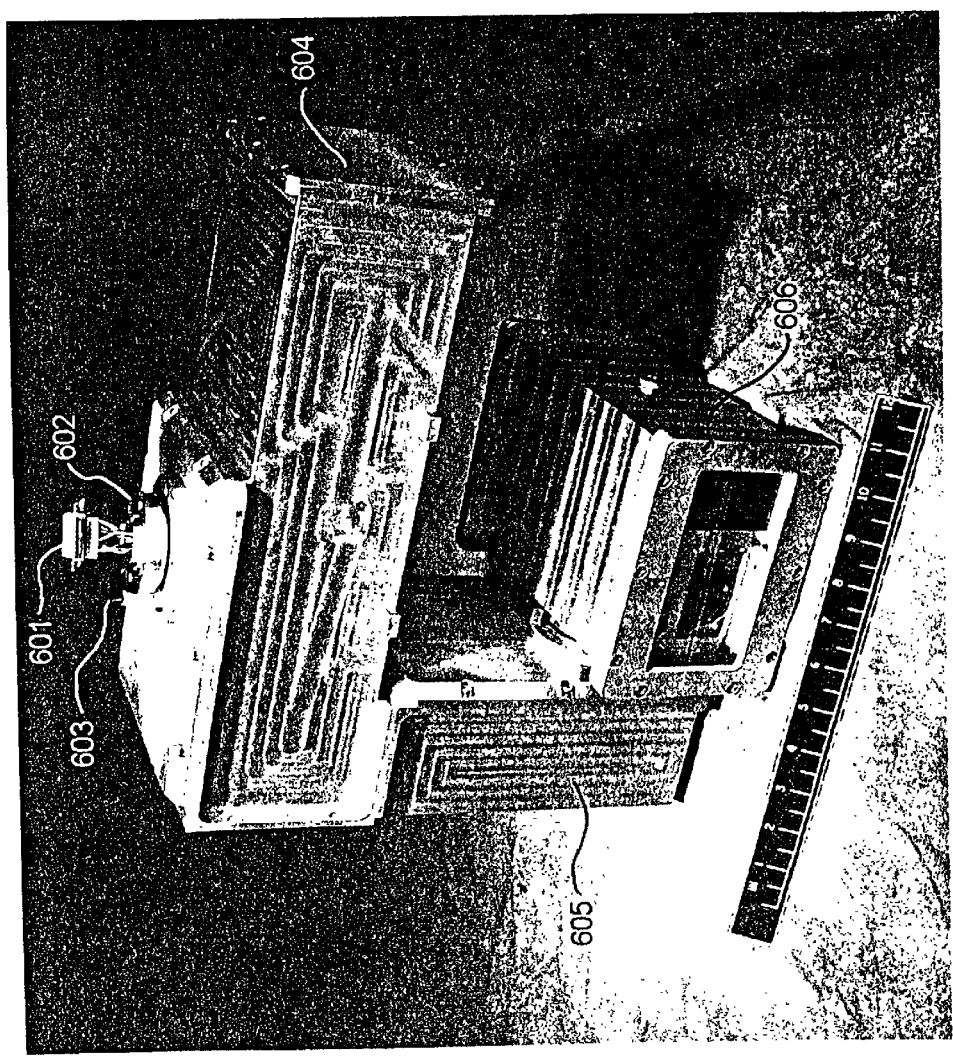
FIG. 6 is a digitized photo perspective view of the GSU (Gimbaled (Scanning) Sensor Unit).

FIG. 6 is a perspective digital image of a GSU unit showing detailed layout of scanning Class II Division I Group G dust-ignition proof design, the preferred embodiment. FIG. 6 shows the various components of the GSU. The power and data communication input/output port 601 is shown exiting from the mounting plate 602. The GSU can rotate about a 360 degree azimuth with respect to the mounting plate 602 and the azimuth drive assembly 604. A hard stop 603 is provided to insure a single rotation without damage to the device and/or exiting cables. The elevation tilt drive assembly 605 contains mechanisms to rotate the sensor housing assembly 606. The sensor housing 606 can rotate approximately 100 degrees in the downward direction and approximately 90 degrees in the upward direction. The combined rotation of the azimuth drive assembly 604 and the sensor housing assembly 606 are sufficient for surface profiling and thus volumetric data collection. When the sensor housing assembly 606 is in the upright position (90 degrees from the FIG. 6 location), the sensor lens is cleaned and protected from the environment. The instrument pictured can be embodied in numerous other configurations. Generally, this enabled unit can direct its on-board sensors by panning about its azimuth axis and tilting about its elevation axis. This design is required for the fixed "permanent" on-board laser rangefinder (LRF). It is designed for explosive, raining, dusty, dirty, etc. applications. In the picture of FIG. 6, the self-cleaning glass wiper is not pictured. Only the elevation element is required if the on-board sensor is an LRF directed by the on-board fast steering mirror.

FIGS. 7A, 7B, 7C, 7D, 7E, 7F, 7G, 7H, 7I, 7J represent drawings of various views of a GSU (gimbaled sensor unit).

Figure 7A:
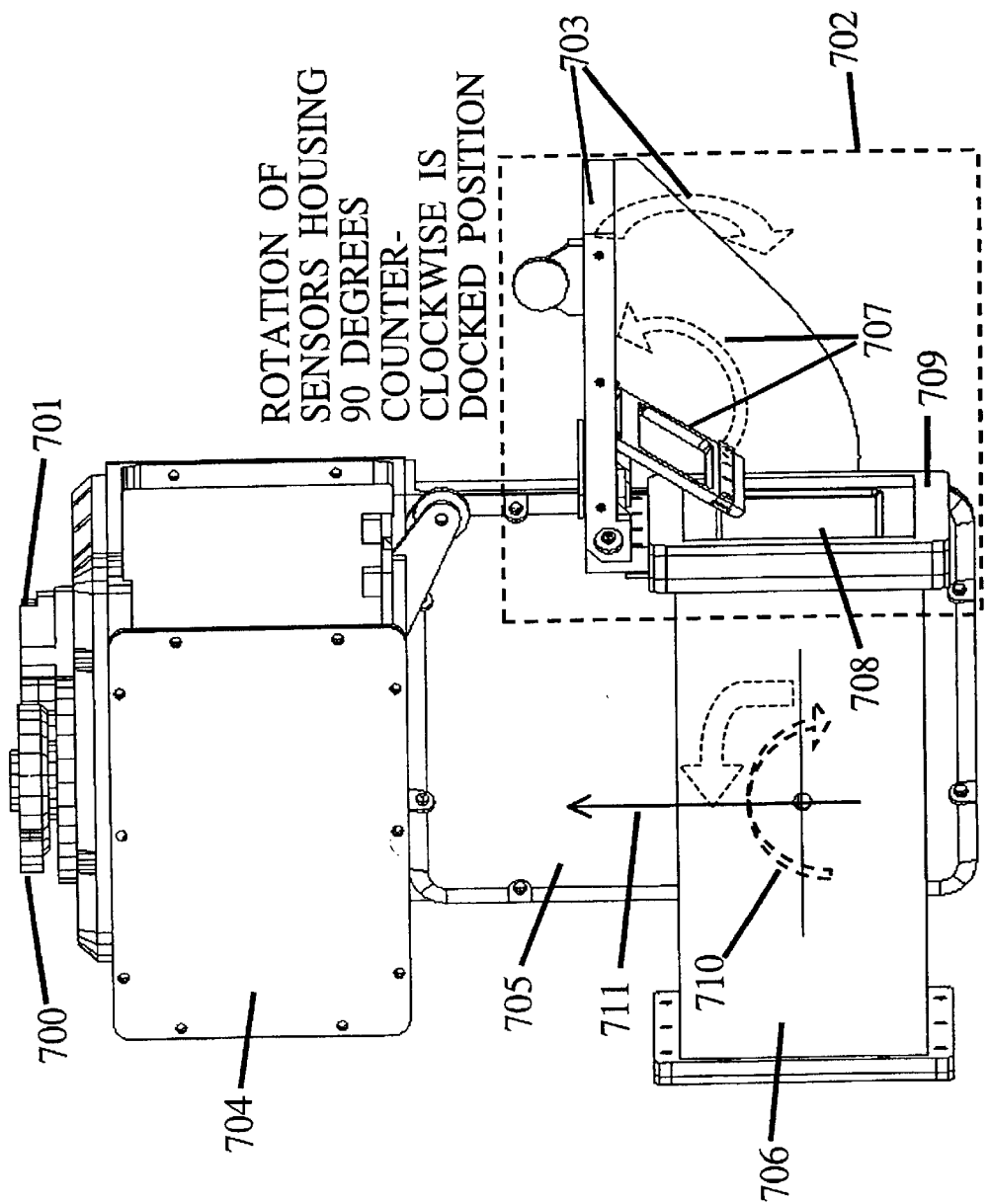
FIG. 7A is a left side plan view of the preferred embodiment of the GSU.

FIG. 7A is a left side plan view of the preferred embodiment of the GSU. The pan/azimuth axle 700 with a hollow wire-way and a hard stop 701 that resides at the top of the GSU to insure a single rotation without damage to the device and/or exiting cables. The azimuth drive assembly 704 contains electronics and azimuth rotation mechanisms and is contained within a rugged housing assembly. The elevation/tilt drive assembly 705 is also in a rugged housing and contains mechanisms to rotate the sensor housing assembly 706 approximately 100 degrees in the downward direction and approximately 90 degrees in the upward direction. Rotation through 300 degrees is possible with slight design variations if required by the application. The sensor housing assembly 706 is also within a rugged housing and contains a dust-proof sealing gasket 709 and a glass window 708 for viewing. The axis of movement 710 is shown about the elevation/tilt drive assembly 705. Non-optical sensors require a self-cleaning method to work in a "fixed/permanent" installation. The wiper/sealing assembly 702 will function to both seal out contamination/dust/grime and to wipe/clean said incidental deposits on the optical (transparent) window 708. A spring-loaded cover 703 will close 90 degrees against the dust-proof sealing gasket 709 when the wiper/sealing assembly 702 is in a docked position. A spring-loaded automatic wiper arm 707 can have its movement activated by cables or other linked mechanisms in lieu of a spring. The wiper-to-glass interface material can be cloth, rubber, or other application-specific material. The wiper/sealing assembly 702 is in a docked position 711 when fully upright. Further detail will be explained below in views of FIGS. 7B through 7J.

Figure 7B:
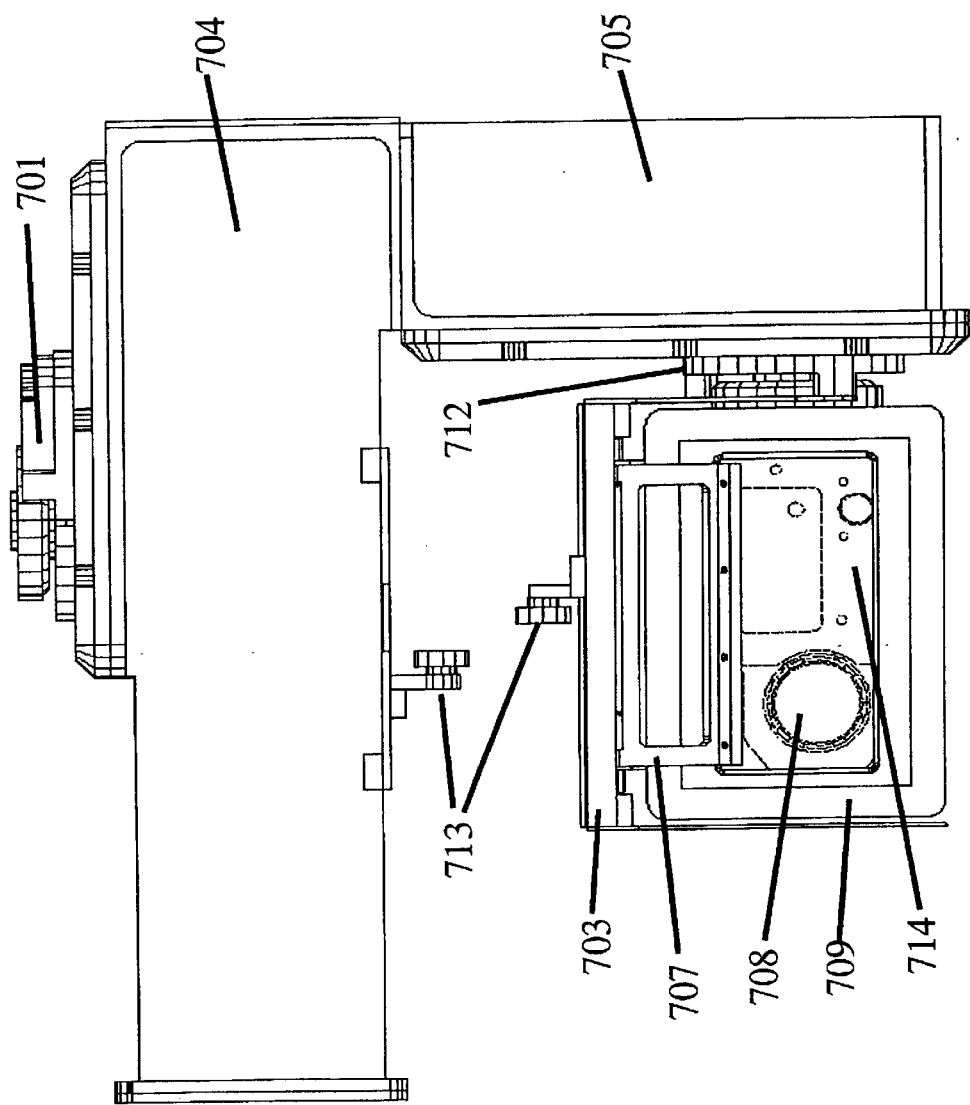
FIG. 7B is a front view plan of the preferred embodiment of the GSU.

FIG. 7B is a front view plan of the preferred embodiment of the GSU. Not shown in FIG. 7A are the tilt/elevation drive axle 712 with hard stops and hollow shaft for wire routing. Also not shown in FIG. 7A are the compression and guide rollers 713 for the window cover 703. Also not shown in FIG. 7A is a depiction of a video camera, laser rangefinder and other optical sensors 714 behind the optical (transparent) window 708.

Figure 7C:
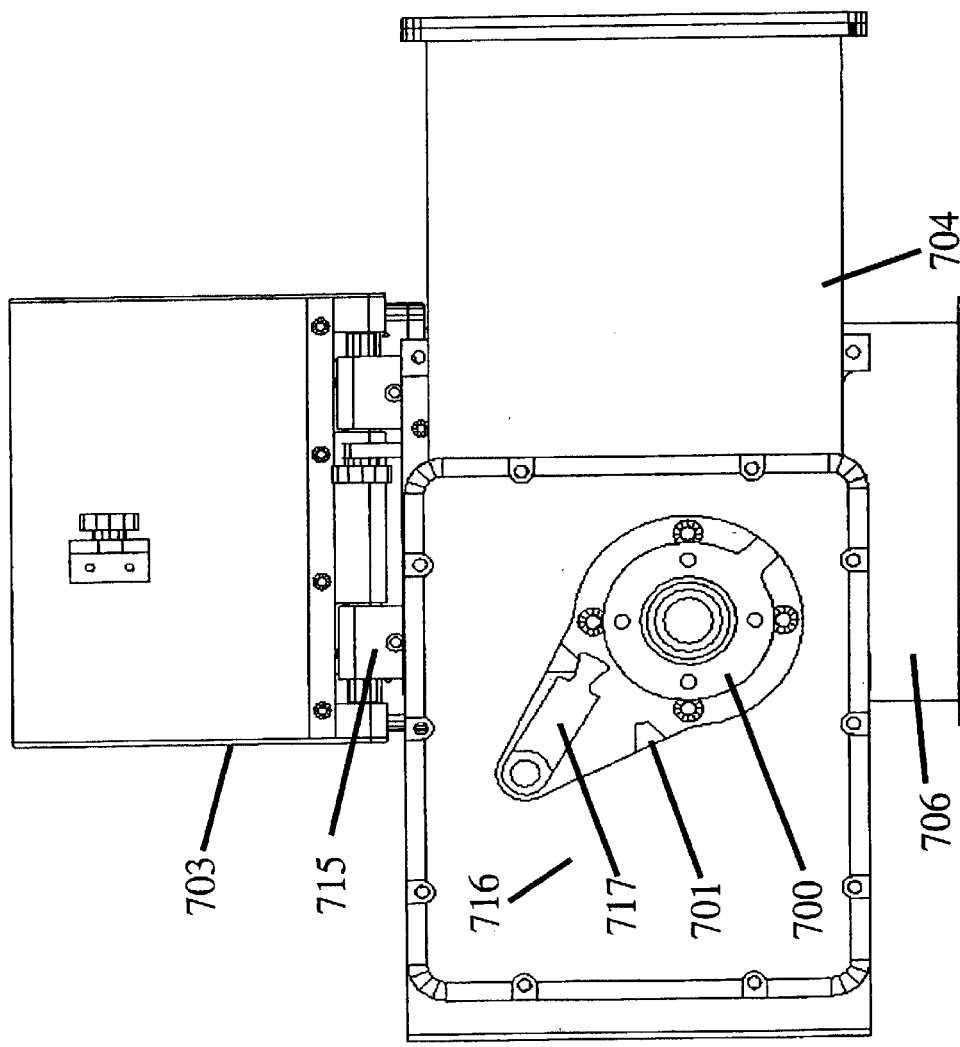
FIG. 7C is a top view plan of the preferred embodiment of the GSU.

FIG. 7C is a top view plan of the preferred embodiment of the GSU. Not previously shown in FIGS. 7A and 7B are the window cover hinge 715, the pan/azimuth base-plate 716, and the 360 degree toggle (ratchet) 717.

Figure 7D:
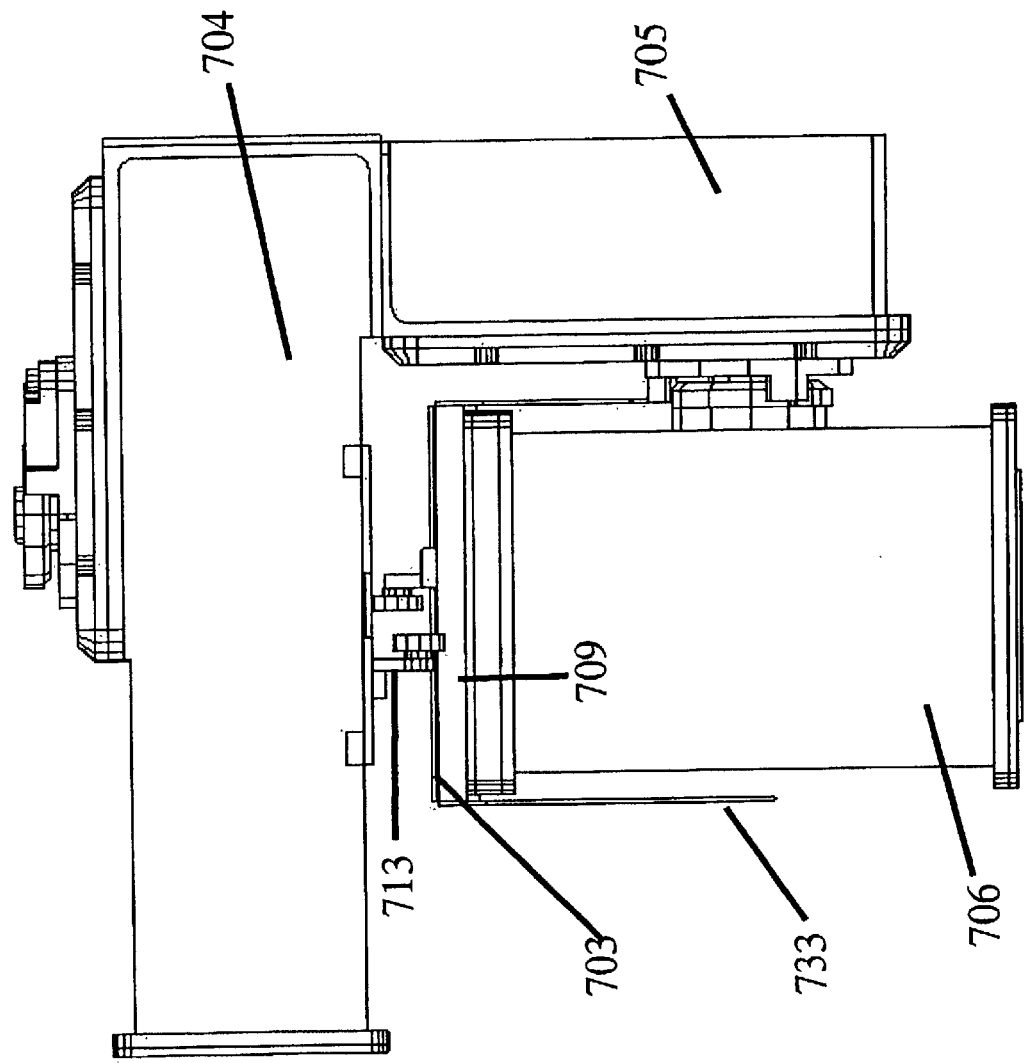
FIG. 7D is a front view plan of the preferred embodiment of the GSU in a docked position.

FIG. 7D is a front view plan of the preferred embodiment of the GSU in a "docked" position. Not previously shown is a view of the glass window cover integrated side shields 733. The sensor housing assembly 706 is shown in an upright "docked" position with the spring loaded cover 703 compressed by the guide rollers 713 against the dust-proof sealing gasket 709. When the sensor housing assembly 706 is rotated (deployed) downward, the spring-loaded automatic wiper arm (707 of FIG. 7A) springs the window cover hinge (715 of FIG. 7C) to open the cover.

Figure 7E:
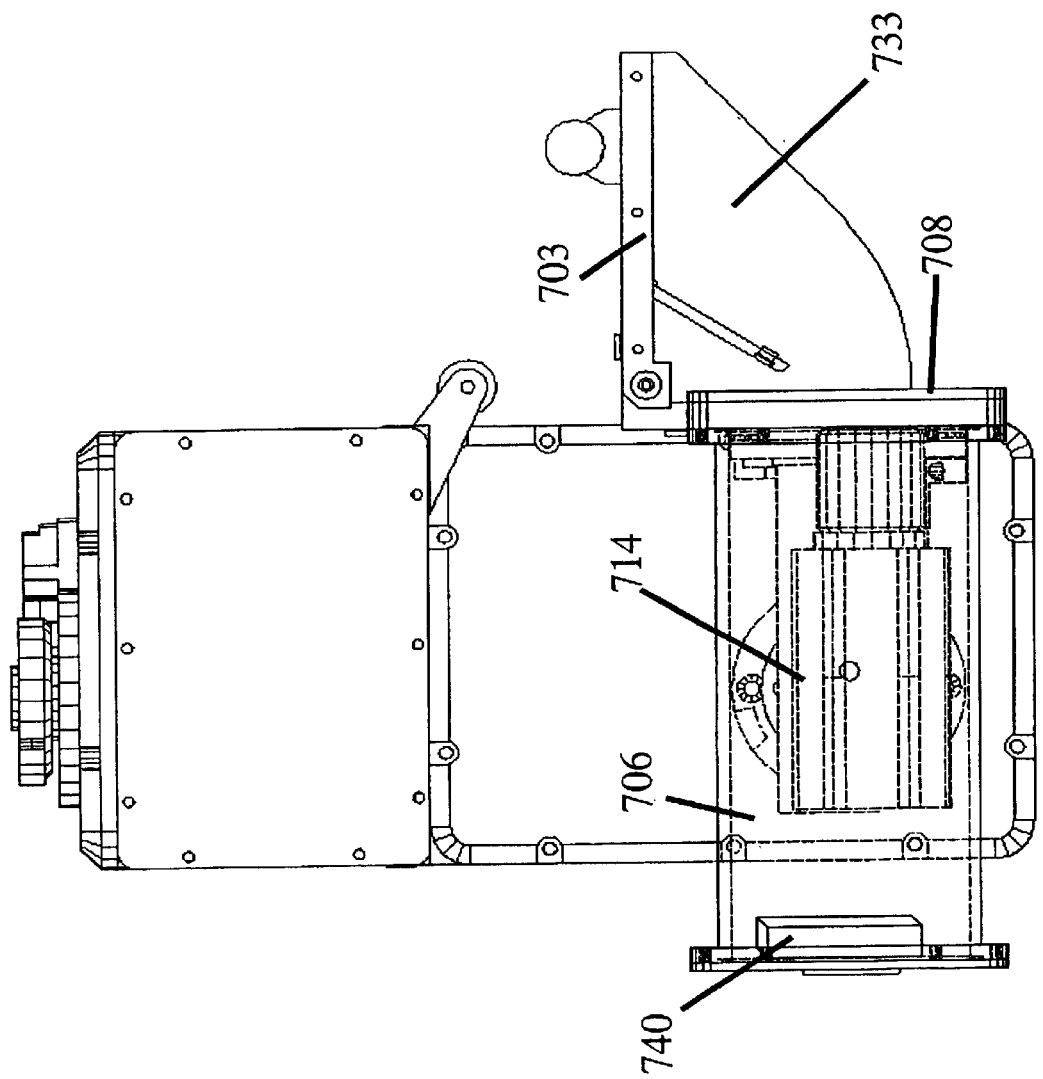
FIG. 7E is a left view plan of the preferred embodiment of the GSU showing sensors within the sensor housing (transparent).

FIG. 7E is a left view plan of the preferred embodiment of the GSU showing sensors 714 within the sensor housing (transparent) assembly 706. The rugged environment sensor housing (transparent) assembly 706 will contain the laser rangefinder, video camera and other optical or non-optical sensors. The electromechanical tilt sensor 740 is shown located in the sensor housing. It can also be mounted in the drive's housing. This device is required to maintain benchmark/ground-plane position accuracy of the SSU package. Benchmark or ground plane accuracy is necessary for any "surveying" system as all subsequent surveyed data points are referenced from this initial point. Portable surveying systems such as theodolites and total stations address this problem with a combination of manual and auto leveling at each initial tripod setup. If such a portable system is moved (i.e. bumped) sufficiently to mis-align the instrument during data acquisition, it must be re-leveled to prevent error. However, for permanent instruments, "leveling" requirements must be met totally automatically over the life of the instrument to compensate for the instrument's alignment changes over time. Misalignments will occur due to normal physical movement of the support structures from which the instrument (GSU) is suspended. Movement of the support structure may result from temperature-induced structural deflection, or structural creep due to gravity, wind loads, foundations settlements, etc. The tilt sensor 740 continuously monitors for any such position changes of the instrument from its original setup. The tilt sensor 740 also provides the angular data necessary for the precise mathematical correction of the instrument's acquired data (e.g. distances measured by the laser and the instrument's azimuth and elevation angles).

Figure 7F:
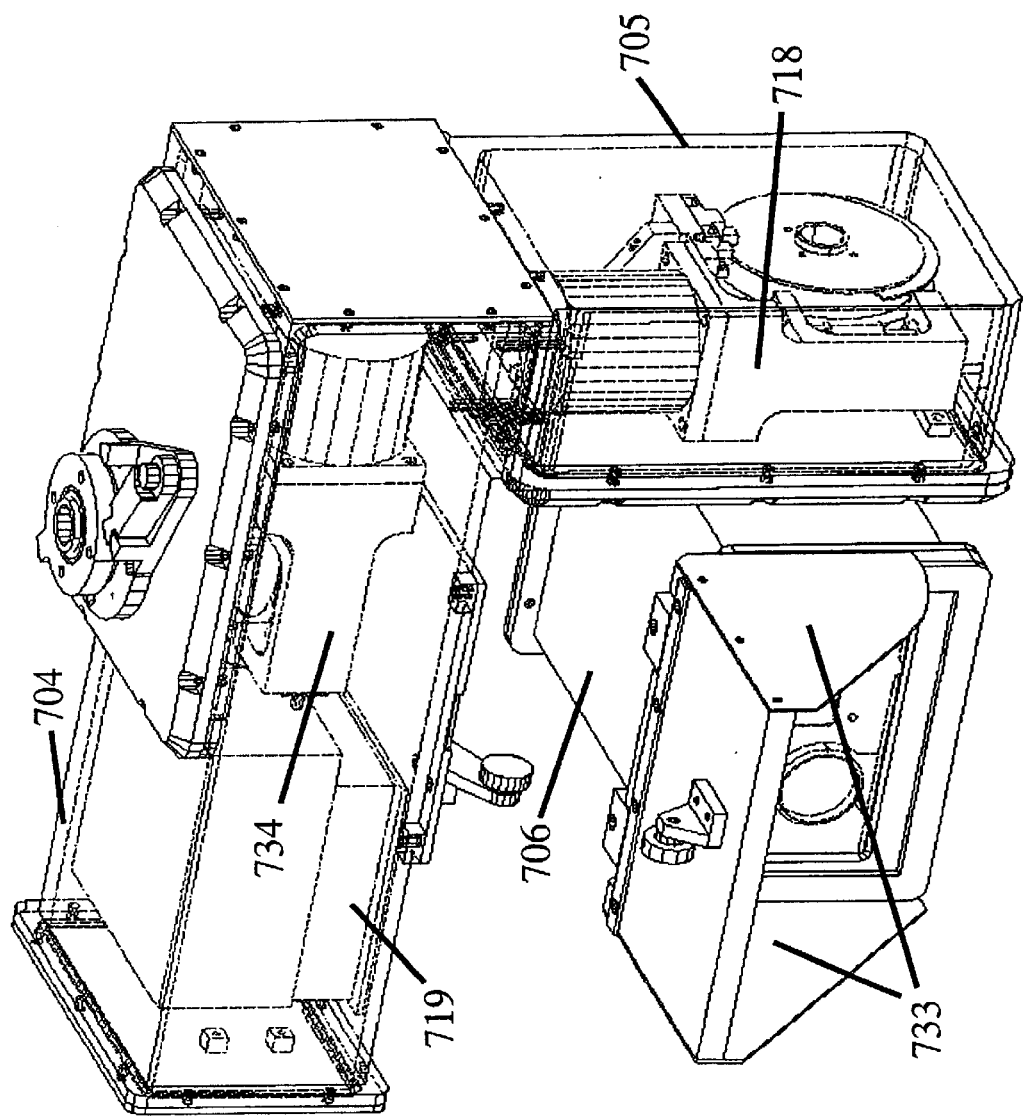
FIG. 7F is an isometric perspective view plan of the preferred embodiment of the GSU showing motorized gear trains (drive mechanisms).

FIG. 7F is an isometric perspective view of the GSU showing motorized gear trains (drive mechanisms). The pan/azimuth motorized drive assembly 734 and electronic boxes 719 are shown within the azimuth drive assembly 704. The electronic boxes will contain the on-board computer which controls all on-board commands, communications, data processing, control circuitry, power distribution and communications between the GSU and the host computer. The elevation/tilt motorized drive assembly 718 is shown housed within the elevation tilt motor drive assembly 705.

Figure 7G:
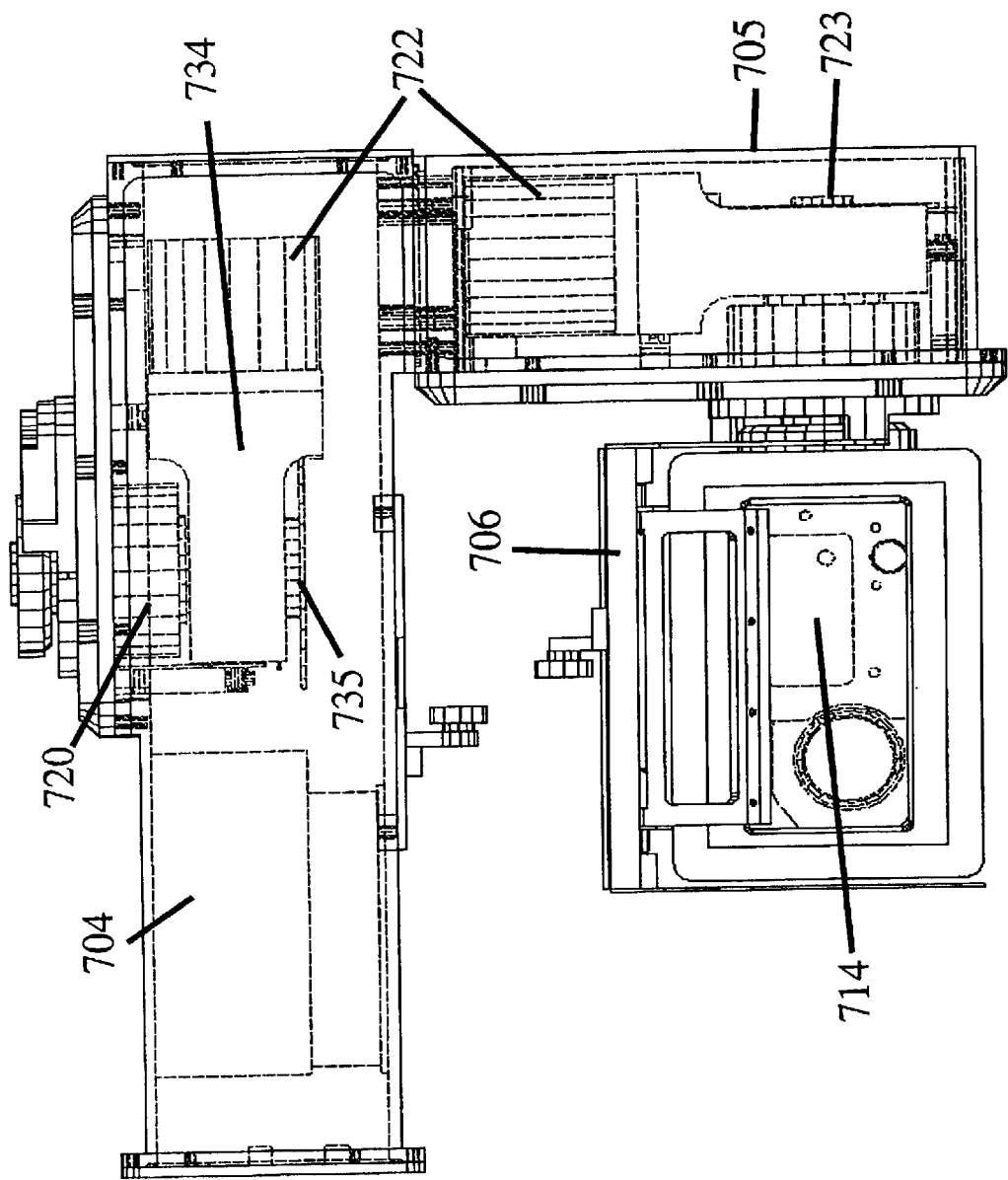
FIG. 7G is a front view plan of the preferred embodiment of the GSU showing motorized gear trains (drive mechanisms).

FIG. 7G is a front view plan of the preferred embodiment of the GSU showing motorized gear trains (drive mechanisms). Shown within the azimuth drive assembly 704 is the drive axle with gear wheel 735 which has optical soft stop disks attached, the roller bearing housing 720, the motor and worm gear mounting chassis 721 and the pan/tilt electric stepper motor 722. The pan/tilt electric stepper motor drive 722 is the same part as in the elevation tilt drive assembly 705 for cost optimization. Shown within the elevation tilt/drive assembly 705 are the pan/tilt electric stepper motor 722 and the hollow shaft 723 for feed-through of wires to sensors.

Figure 7H:
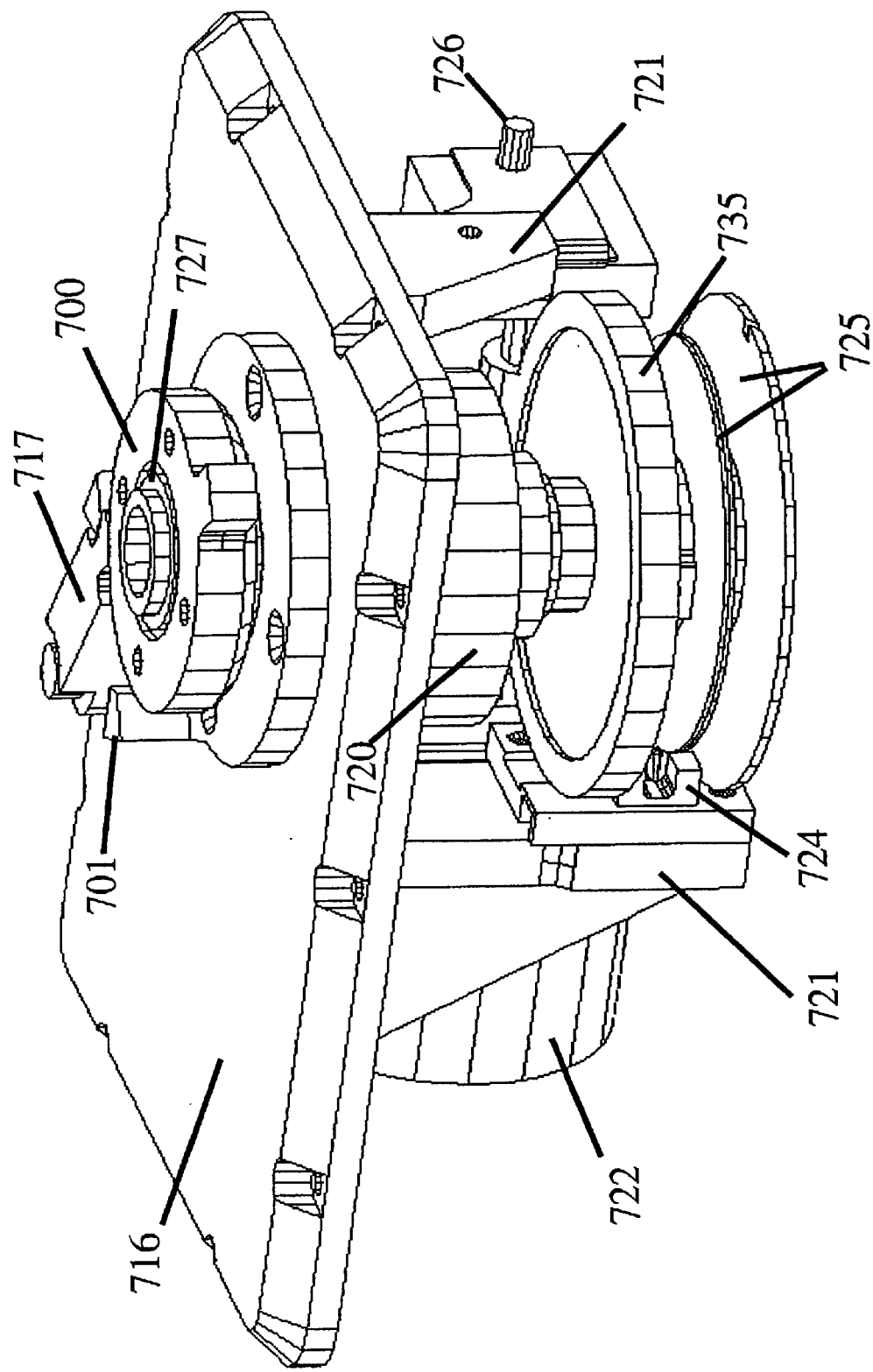
FIG. 7H is a perspective side view plan of the preferred embodiment of the GSU showing the azimuth drive/gear train assembly.

FIG. 7H is a perspective view plan of the preferred embodiment of the GSU showing the azimuth drive/gear train assembly. On the upper end of the pan/azimuth base-plate 716, is the 360 degree toggle (ratchet) 717, the pan/azimuth axle 700 the hard stop 701 and an O-ring slot 727. On the lower end of the pan/azimuth base-plate 716 is shown the drive axle gear wheel 735, the optical soft stop disks 725, the roller bearing housing 720, and the optical limit switches 724. The motor and worm gear mounting chassis 721 contains an anti-backlash spring pre-loaded mounting pin 726 to prevent damage.

Figure 7I:
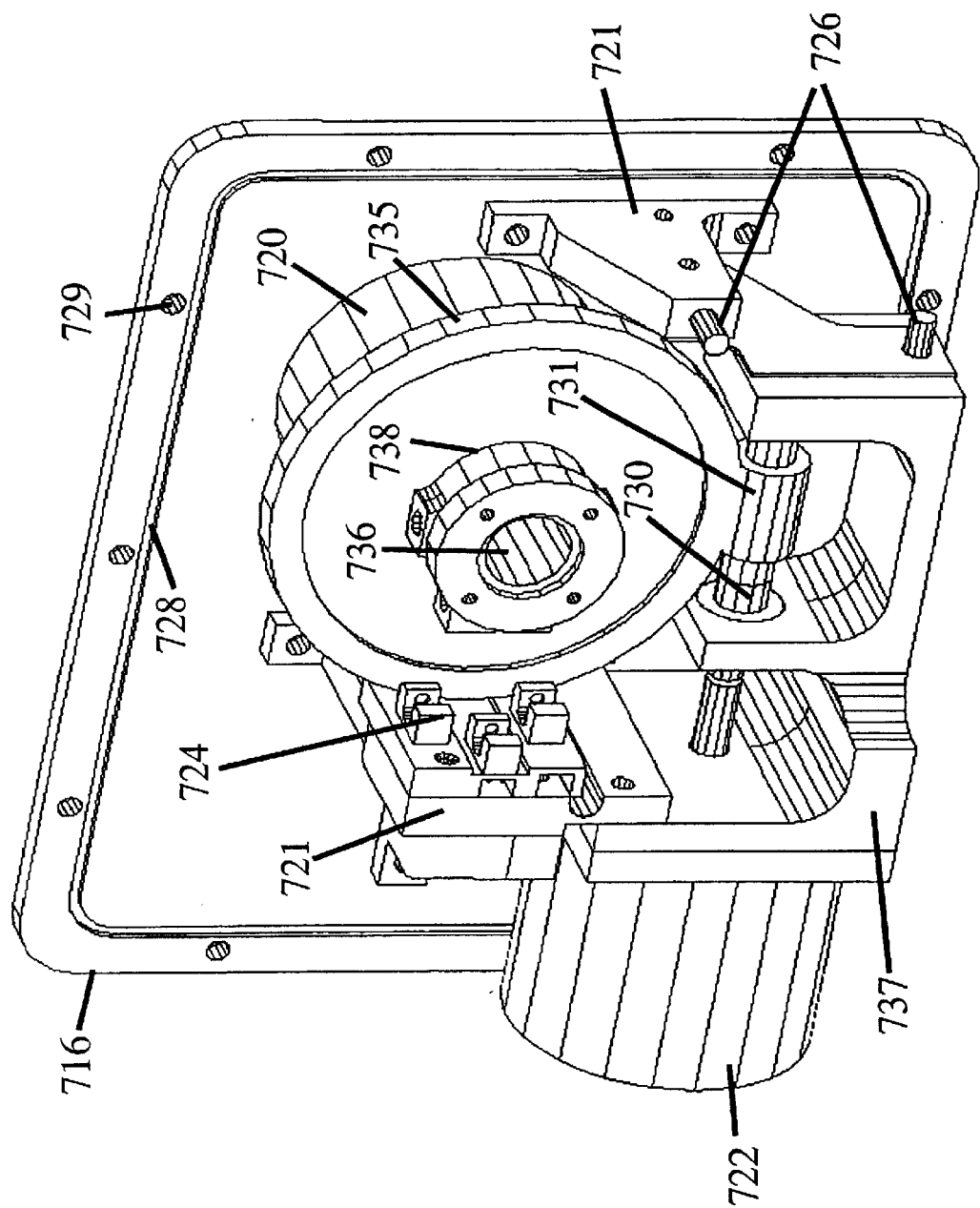
FIG. 7I is a perspective bottom view plan of the preferred embodiment of the GSU showing the azimuth drive/gear train.

FIG. 7I is a perspective bottom view plan of the preferred embodiment of the GSU showing the azimuth drive/gear train. Shown and not previously described are the O-ring seal 728 and fastener holes 729 for the base plate 716. The O-ring seal 728 is typical for every mating surface over the entire envelope of assemblies. Also shown and not previously described are the worm gear shaft 730 and the worm gear 731 for the pan/tilt electric stepper motor 722. The motor, worm gear, and worm gear shaft alignment base 737 keep all components of the drive assembly in alignment. The hollow shaft 736 which allows cabling through is shown along with the hollow shaft clamp 738.

Figure 7J:
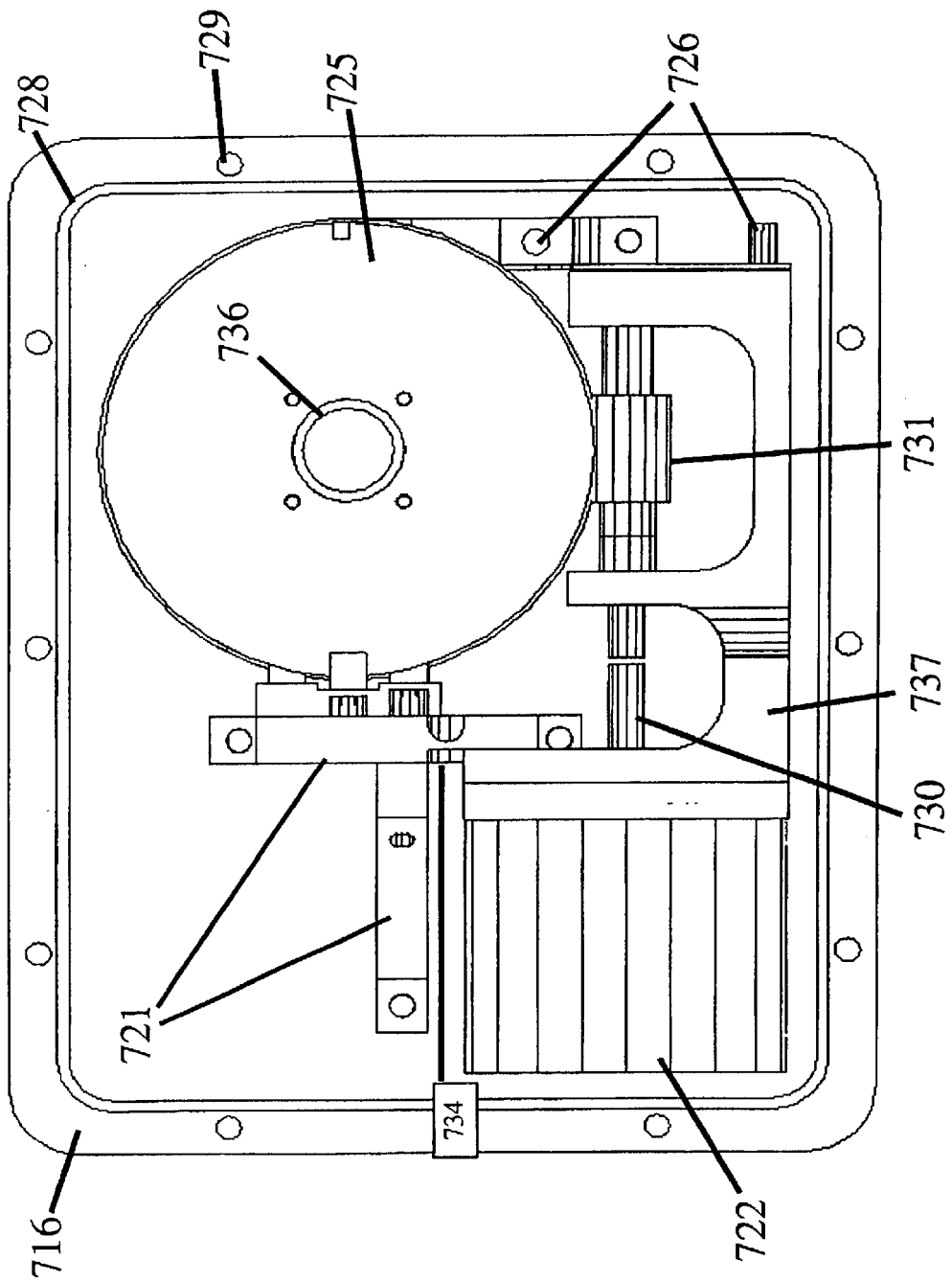
FIG. 7J is a bottom view of the preferred embodiment of the azimuth drive/gear train assembly.

FIG. 7J is a bottom view of the preferred embodiment of the azimuth drive/gear train assembly. Shown is the anti-backlash living hinge 733. All other components depicted have been previously referenced.

Figure 8A:
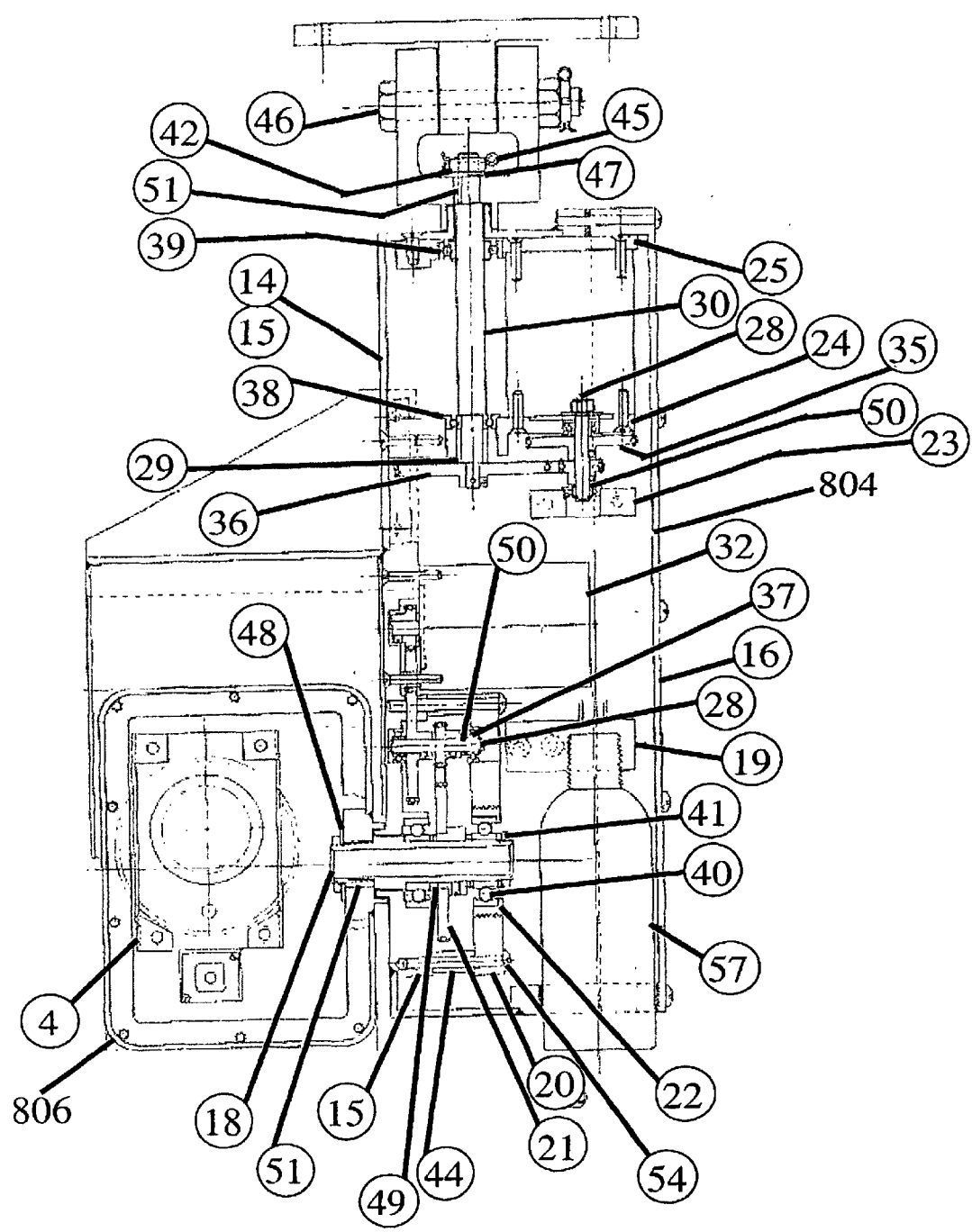
FIG. 8A is a front view plan of an alternate embodiment of the GSU of the present invention.
Figure 8B:
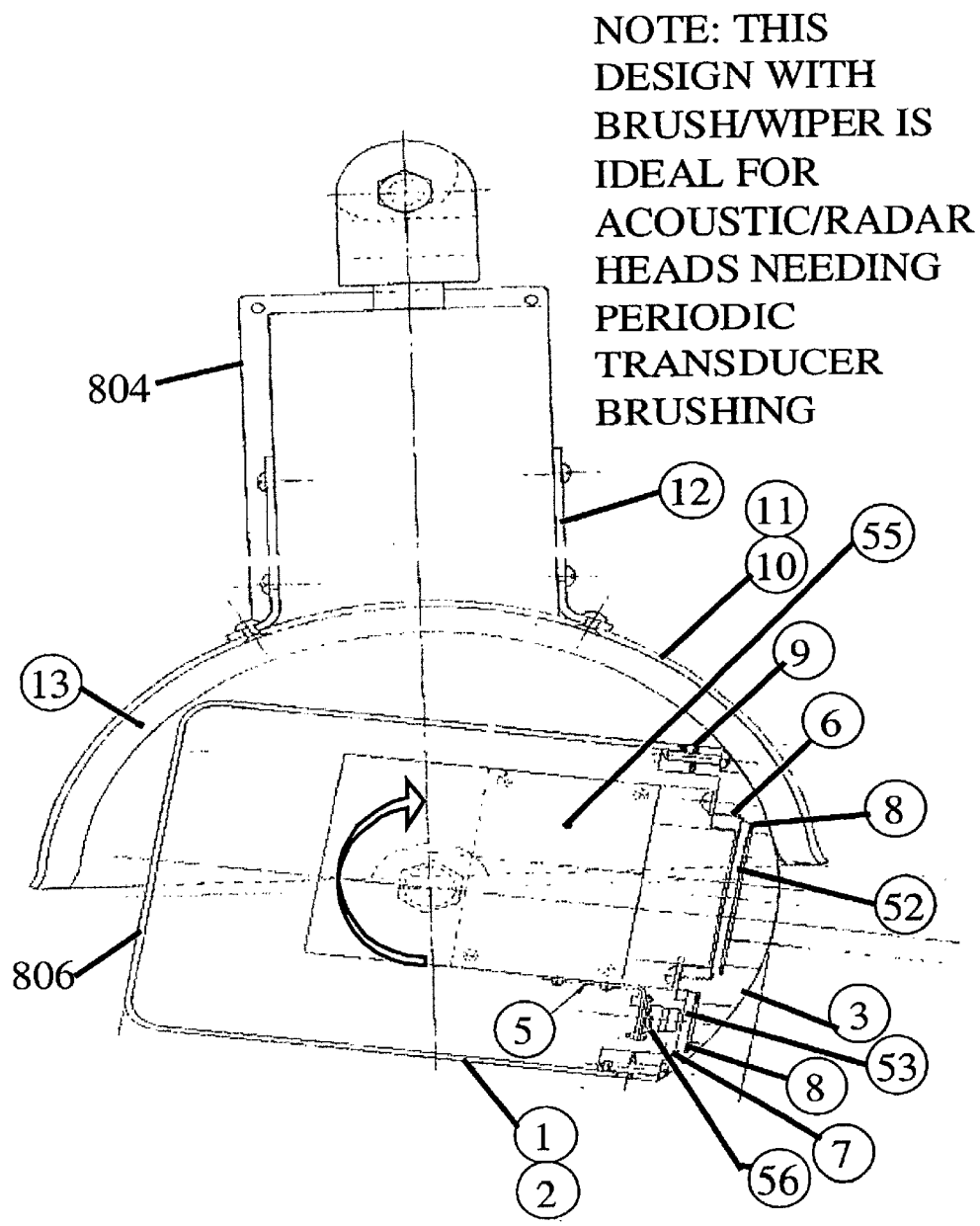
FIG. 8B is a left view plan of an alternate embodiment of the GSU of the present invention.
Figure 8C:
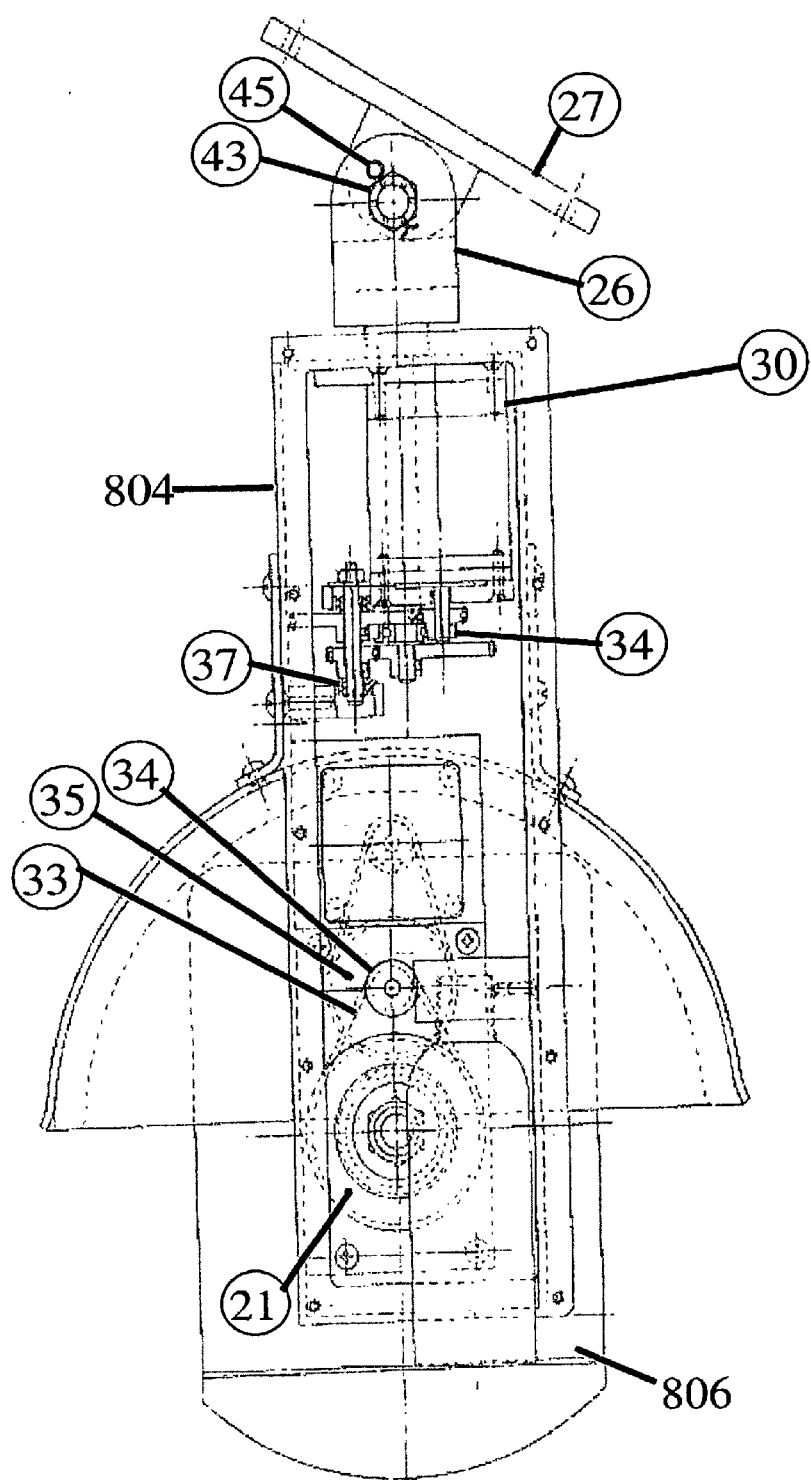
FIG. 8C is a right view plan of an alternate embodiment of the GSU of the present invention.

FIGS. 8A, 8B, 8C are drawings of an alternate embodiment of the GSU of the present invention. This alternate embodiment contains all of the basic function as the preferred embodiment as described above (FIGS. 7A–7J) and is primarily different in its packaging scheme. This alternate embodiment is less expensive to manufacture, and thus may be preferable in a less harsh application environment than the preferred embodiment. This alternate embodiment utilizes a brush for the sensor wiper motion and thus is somewhat sensitive to dust contamination. The design shown in FIGS. 8A, 8B, and 8C will protect the sensor housing face. For each set of environment design requirements, the sensor protection shall be slightly different. The present invention will resolve this. For instance, the glass shown on the drawing is recessed. However, it could be curved for accepting mechanical brushing as it docks and undocks. Also, the dock cover is shown as a stationary fixture, whereas it could be more active such as a pneumatic air cleaner or a spring-loaded brush/covering mechanism. The design shown will scan with nearly zero hysteresis (backlash) and will be for conditions/uses that can tolerate some backlash. The design of the alternate embodiment has sensors shown both on the azimuth and tilt axis. Depending on the sensor function, the locations can be interchangeable. For instance, the acoustical ranger (part 57 of FIG. 8A) shown on the GSU is in the vertical position fixed to only rotate with the azimuth direction. This specific sensor could also be included on the GSU sensor housing assembly 806 that also can tilt. The GSU has operable sensors shown behind the glass face. Other sensor(s) could be mounted in other positions. For example, the acoustical ranger could be installed with its operable transmit/receive direction oriented 180 degrees from that of the laser rangefinder.

FIG. 8A is a front view plan of an alternate embodiment of the present invention. The azimuth and elevation drive assembly 804 contains the same basic function as the previously described azimuth drive assembly (704 of FIGS. 7A–7J) and the tilt drive assembly (705 of FIGS. 7A–7J). The azimuth and elevation drive assembly 804 can be enlarged per design requirements to fit the required electronic components (printed circuit boards, etc.) and sensors. The primary sensor housing assembly 806 contains the same basic function as the previously described sensor housing assembly (706 of FIGS. 7A–7J). The acoustical ranger (part 57 of FIG. 8A) is shown mounted on the GSU azimuth and elevation drive assembly 804 in a vertically fixed position to allow rotation only in the azimuth direction. This specific sensor could also be included on the GSU sensor housing assembly 806, which is driven to tilt in the vertical direction.

FIG. 8B is a left view plan of an alternate embodiment of the present invention. The primary sensor housing assembly 806 is shown with a clockwise rotation.

FIG. 8C is a right view plan of an alternate embodiment of the present invention. The alternate embodiment uses drive belts 33 and pulleys 34 versus drive shafts (as in the preferred embodiment). The GSU is mounted with a roof mount 27 and a support arm 26.

FIGS. 9A, 9B, 9C is a GSU parts listing for the alternate embodiment of the present invention. The item numbers are listed in "ITEM NO." column (block 900). The part numbers are listed in "PART NO." column (block 901). The "NOMENCLATURE" column (block 902) describes the part name etc.

Figure 10:
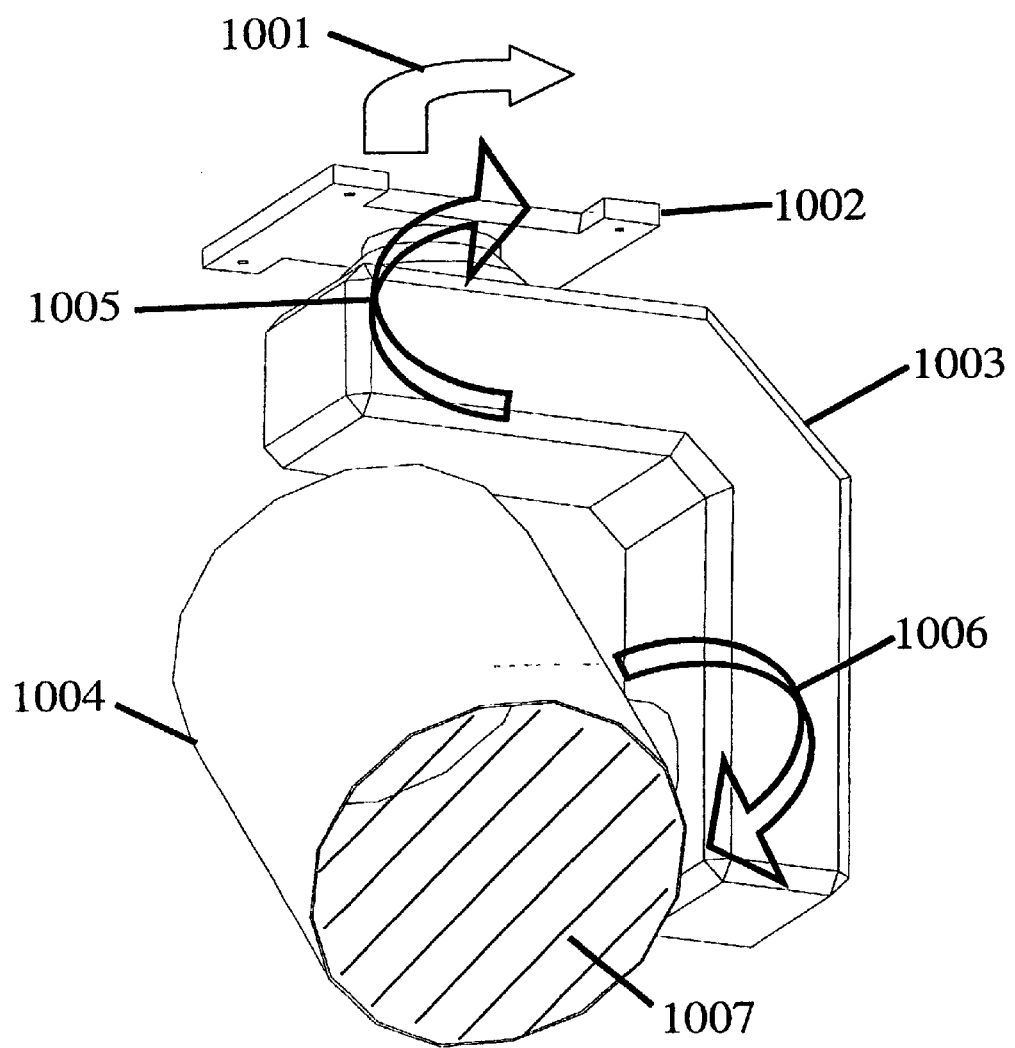
FIG. 10 is a schematic showing the two rotational axes of the GSU in an schematic of an alternate round sensor housing design.

FIG. 10 is a schematic showing the two rotational axes of the GSU in an alternate round sensor housing embodiment design. The command/control-in, power-in and data out to the host computer 1001 is on the data/power bus. The mounting plate 1002 affixes the unit. The rotation is controlled by the drive mechanism assembly 1003. The drive mechanism assembly 1003 rotates the upper assembly in a >360 degree azimuth 1005 about the mounting plate 1002. The drive mechanism assembly 1003 also drives the sensor can assembly 1004 in a >180 degree azimuth 1006 about itself. For window cleaning of the sensor glass lens 1007 a windshield wiper style mechanism can be used. The wiper (not shown) can be stationary and the glass lens 1007 can rotate in lieu of the wiper moving.

Figure 11:
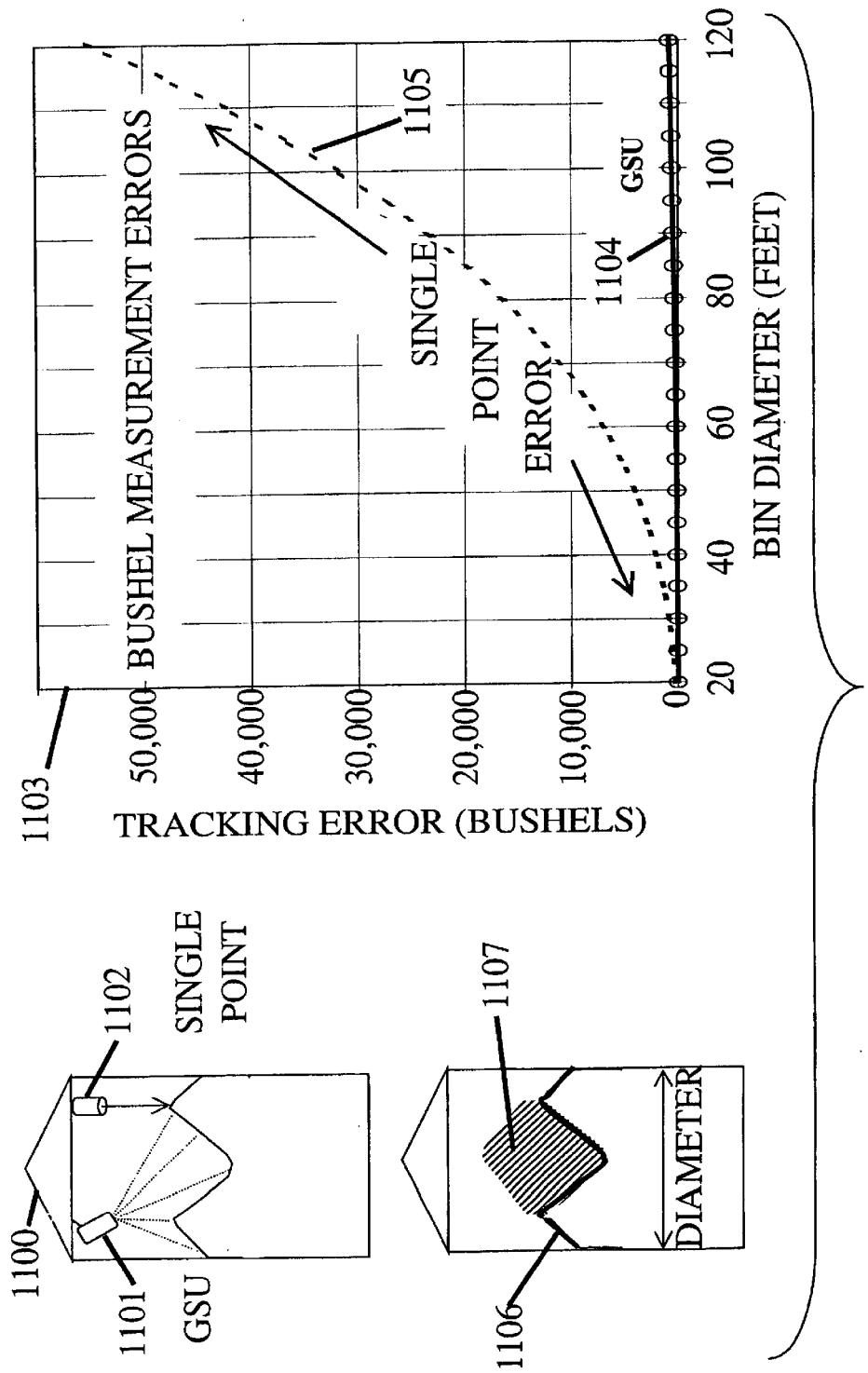
FIG. 11 is a schematic showing typical measurement error comparison of volume measurements between a GSU and a typical competitor single point measurement method.

FIG. 11 is a comparison of volume measurement error between a GSU and a competitive single point measurement method. A storage bin 1100 measured with a GSU 1101 is plotted on the bushel measurement error chart 1103. The GSU is highly accurate because it scans the entire surface of any shape with very small errors. The plot of GSU tracking error curve 1104 shows an error of approximately 150 bushels maximum over a bin diameter of up to 120 feet. On the other hand, a single point measurement system 1102 will generate large errors. As can be seen from the error curve 1105 of a single point measurement method, the total error can exceed 50,000 bushels for a 120-foot diameter bin. Thus, the GSU's ability to accurately scan an entire surface will result in high accuracy volume measurements. The grain/material volume calculated by a single point instrument 1102 would continue the upward slope to indicate a larger profile 1107 and thus calculate a larger than true volume. The true storage bin profile 1106 measured with a GSU 1101 results in a smaller, but true, volume. Thus, single point measurements can result in large errors as seen from the error curve 1105.

Figure 12A:
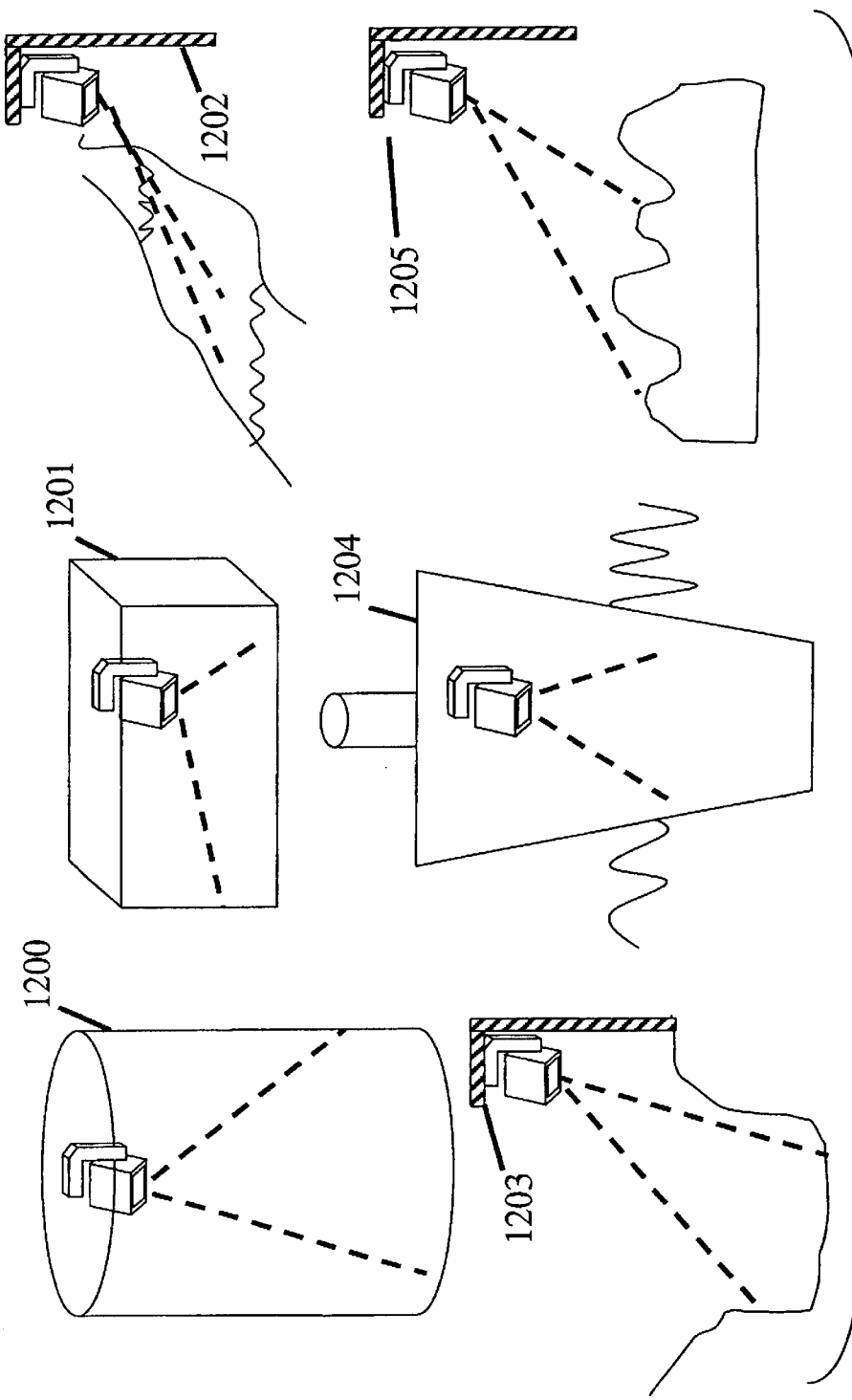
FIG. 12A is a schematic showing some of the potential installation locations for a GSU.

FIG. 12A is a schematic depicting some of the potential installation locations of a GSU. The GSU is a very flexible and adaptive unit. The GSU can be mounted in a silo 1200, in rectangular buildings or storage containers 1201, over rivers or other bodies of water 1202, over open pits or open mines 1203, in ship or barge storage bins 1204, or over land mass 1205 to monitor changes such as sand dune monitoring, dam building or monitoring, coal storage and usage etc.

Figure 12B:
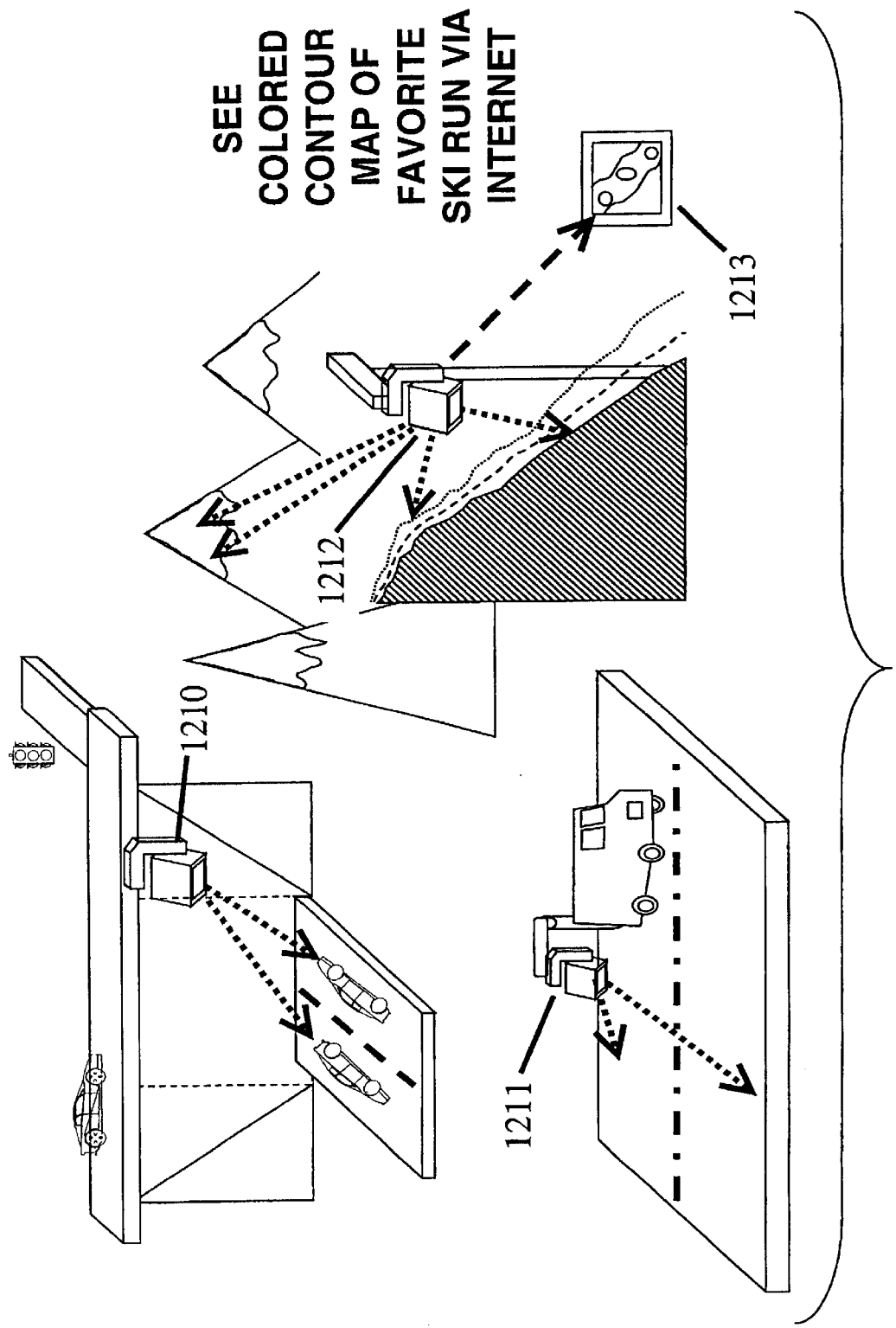
FIG. 12B is a schematic showing additional potential installation locations for a GSU.

FIG. 12B is a schematic showing additional potential installation locations for a GSU. The GSU can be used for commuter traffic jam monitoring 1210 with data links to systems within vehicles. It can be used for road surface monitoring 1211 during construction, reconstruction or movement of surfaces on potential slip faults etc. The GSU can also be used for monitoring snow accumulation 1212. Snow accumulation can be used for better avalanche management/control, resort snow making and grooming management and data can be linked to home computers 1213 whereas users can monitor ski conditions and see contours of accumulation on the ski slopes.

Figure 13:
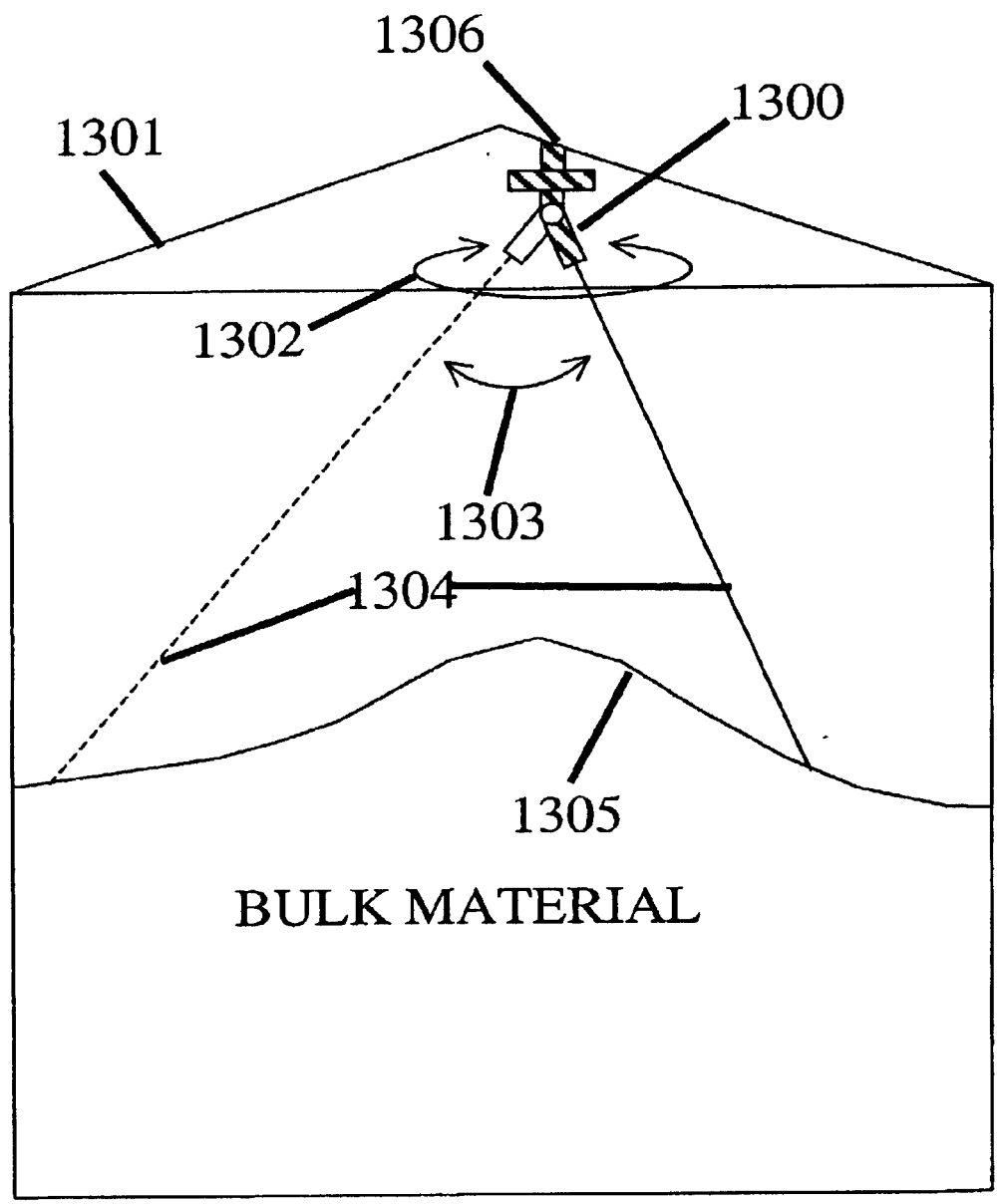
FIG. 13 is a schematic of a scanning laser rangefinder in a storage facility, the preferred embodiment.

FIG. 13 is a schematic of a scanning laser rangefinder. The rangefinder 1300 is shown mounted on the upper portion of a storage facility 1301. The scanning laser rangefinder 1300 can rotate about a >360 degree azimuth 1302 around the bulk material surface 1305 within the storage facility 1301. The scanning laser rangefinder can also rotate approximately 90 degrees in an upward/downward elevation 1303. Thus, laser beams 1304 can accurately digitize surface height, profile and volume. A cable data communications port 1306 can transmit and receive data. The laser rangefinders (time-off-light or phased-based design) are both existing art. The rangefinder sends out pulses 1304 of infrared or visible light to obtain reflections off a desired surface 1305. The instrument 1300 contains the laser rangefinder, control and processor electronics, rotation stage mounting, environmental enclosure and a cable-borne, RF, IR or point to point laser communication path.

By successively aiming the rangefinder at different points across the surface of the bulk material being measured, the surface profile is characterized. As previously explained, this information is used to convert to a standard volume measurement. Additionally, the same rangefinder can be used to measure and monitor the bulk material's physical container. This structural monitoring is used to ensure the container is not developing a potential failure (i.e. burst open, fall over, etc.).

Figure 13A:
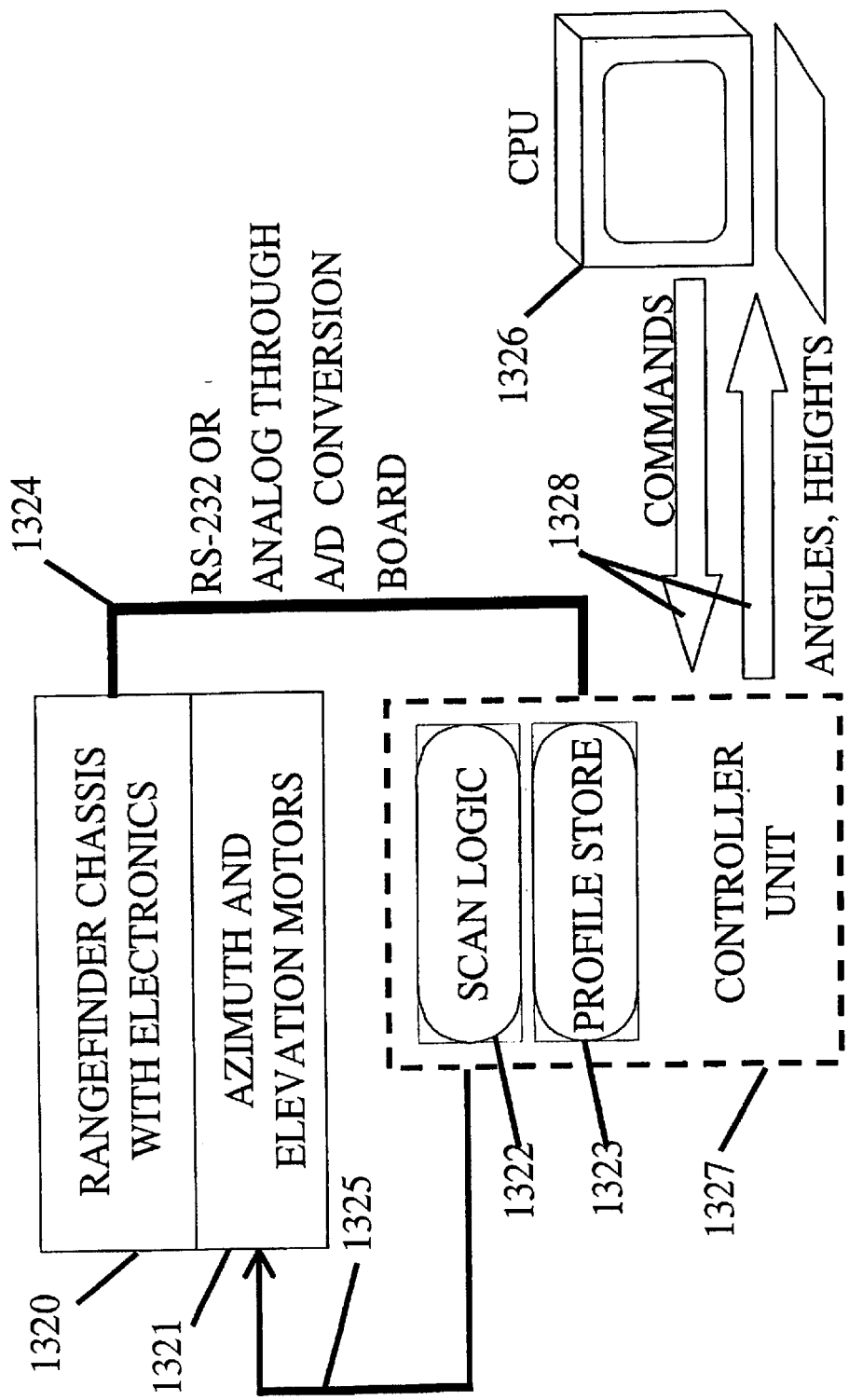
FIG. 13A is a scanning laser rangefinder flow diagram.

FIG. 13A is a scanning laser rangefinder flow diagram. The ranger chassis with electronics (block 1320) and the azimuth and elevation motors (block 1321) are electronically coupled to the control unit via hard wire (block 1325) and RS-232 or an analog A/D converter board (block 1324). The system control unit (block 1327) contains scan logic (block 1322) and profile storage (block 1323). The system control unit (block 1327) sends data to and receives commands from the CPU (block 1326) in a bi-directional mode over a parallel interface (block 1328). The CPU (block 1326) calculates all of the necessary volume measurements and is the data display interface to the user.

FIG. 13B is a volume measurement flow diagram. At the start (block 1350) of the process, the user is asked if it is a new bin (block 1351). If a new bin, a setup procedure is started (block 1352). Inputs to the bin physical parameters (block 1353) are inputted regarding sensor location, and physical bin dimensions. The sensor is initialized (block 1354), known ranges are verified (block 1355), and bin scan variables are saved (block 1356). The bin contents can now be measured (block 1357). If the user selects to measure a bin (block 1358), the bin to be measured is selected (block 1359). Bin variables (physical and scan data) are recalled from memory (block 1360), the sensor is initialized (block 1361), known ranges are verified (block 1362), scanning is performed, and data is saved (block 1363). Geometric operations are performed, volume is calculated (block 1364), and material type and moisture information is gathered (block 1365). Then total factored weight and volume are calculated (block 1365). Finally all data is saved (block 1366) for subsequent user use.

Figure 14:
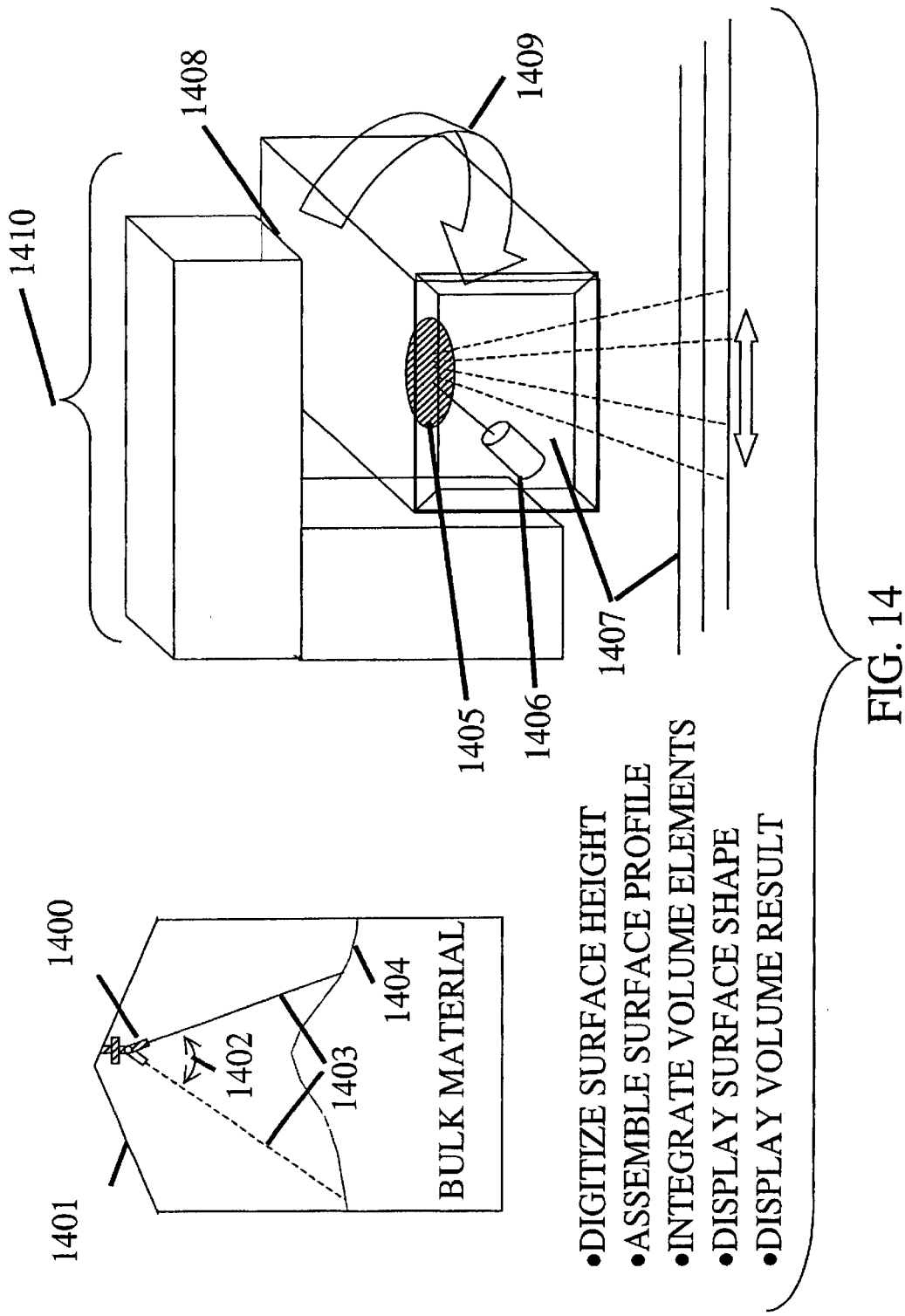
FIG. 14 is a schematic of a scanned mirror with laser rangefinder, an alternate embodiment of the present invention.

FIG. 14 is a schematic of a scanned mirror with laser rangefinder, an alternate embodiment. The instrument 1400 contains the laser rangefinder, control and processor electronics, rotation stage mounting, environmental enclosure and a cable-borne, RF, IR or point to point laser communication path. The storage facility 1401 and bulk material 1404 are depicted. A view of the laser scanning mirror housing 1410 shows the elements of this alternate embodiment. The optical cover and wiper 1408 reside under the horizontal leg of the housing. The rotating mirror 1405 rotates perpendicular to the housing "elevation" movement on a single axis. The laser rangefinder 1406 directs beams off of the rotating mirror 1405. The field of view 1407 is up to 180 degrees traversing across a full vertical cross section of the stored material, regardless of fill level. The rotation of the laser scanning mirror 1409 is 270 degrees insuring full surface coverage. The scanning mirror housing 1405 docks into its covered and dust wiped position when not in use.

Figure 15:
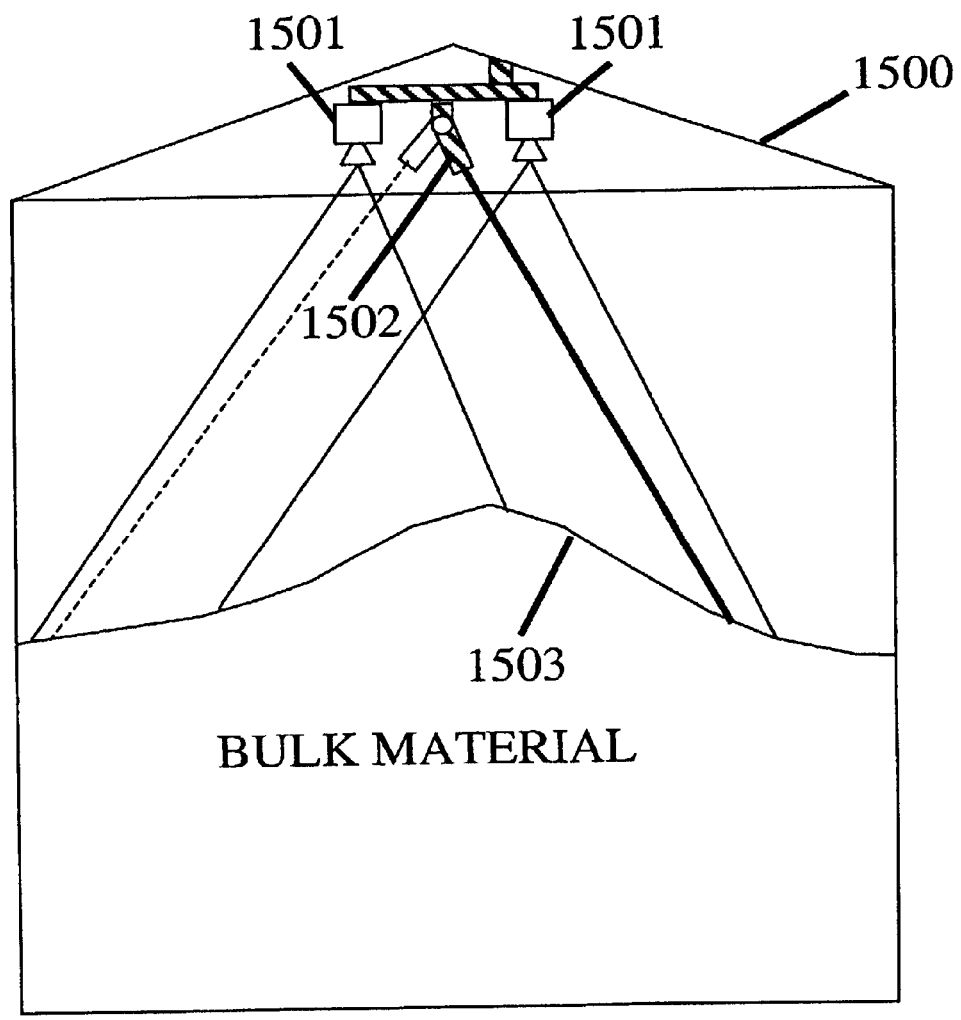
FIG. 15 is a schematic of a stereo camera and structured light for volume measurement, an alternate embodiment of the present invention.

FIG. 15 is of an alternate embodiment for volume measurement using stereo cameras 1501 and a source of structured light 1502. The instrument packages are environmentally enclosed. FIG. 15 depicts a storage container 1500 with bulk material 1503. Surface profiling is performed via use of the stereoscopic camera pair and a source of structured light (a fixed pattern of light extending across material surface or a steered beam spot) to measure distances to a succession of different points across the material surface. Information is transmitted out via cable-borne, RF, IR or laser point-to-point communications.

Figure 16:
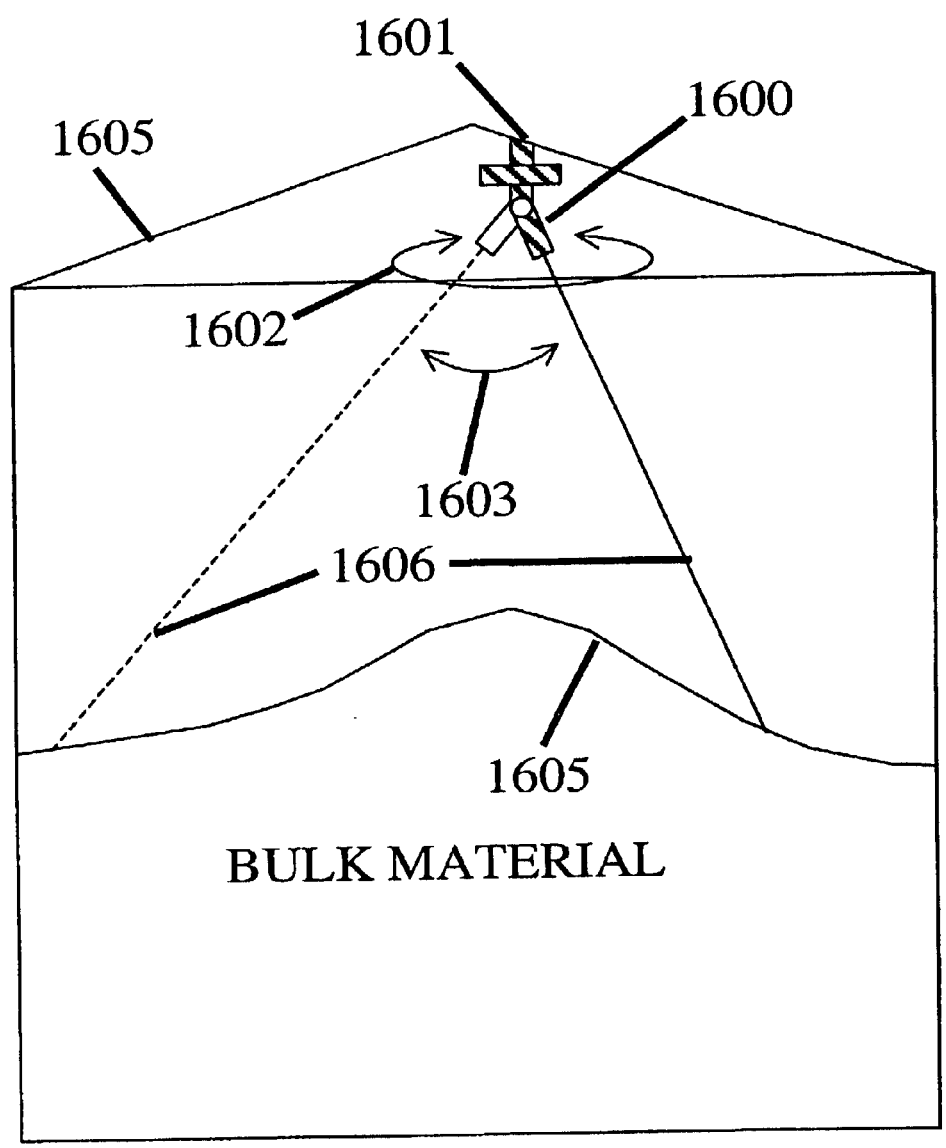
FIG. 16 is a schematic representation of an alternate embodiment of the present invention using a scanning ultrasonic rangefinder for volume measurement.

FIG. 16 is an alternate embodiment of the present invention using a scanning ultrasonic rangefinder for volume measurement. The ultrasonic rangefinder 1600 is shown mounted on the upper portion of a storage facility 1605. The ultrasonic rangefinder can rotate >360 degrees in azimuth 1602 above the bulk material surface 1604 within the storage facility 1605. The rangefinder can also rotate approximately 90 degrees in elevation 1603. Thus, ultrasonic beams 1606 can accurately digitize the surface height, profile and underlying volume. A cable data communications port 1601 can transmit and receive data via a cable-borne data communications port, RF (radio frequency) transmit/receive, IR (infrared) transmit/receive or a laser point to point transmit/receive communication. The ultrasonic rangefinder sends out pulses 1606 to obtain reflections off a desired surface 1604.

Figure 17:
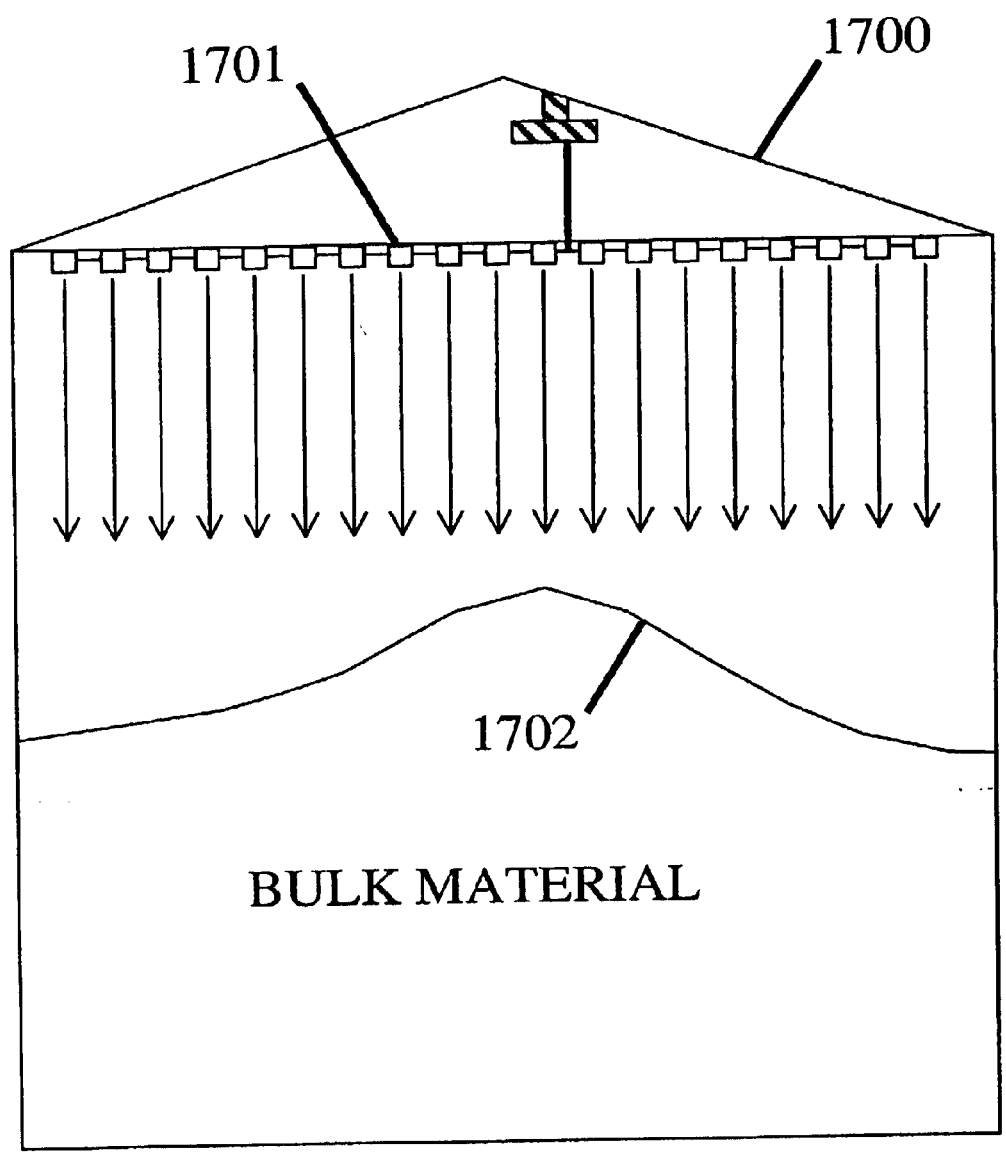
FIG. 17 is a schematic showing use of multi-ultrasonic single point rangefinders for volume measurement, an alternate embodiment of the present invention.

FIG. 17 is an alternate embodiment of the present invention using multiple ultrasonic single point rangefinders for volume measurement. The ultrasonic rangefinders 1701 are mounted in fixed positions within the storage facility 1700 and obtain reflections off the desired bulk material surface 1702. Data is transmitted as described in FIG. 16 above.

Figure 18:
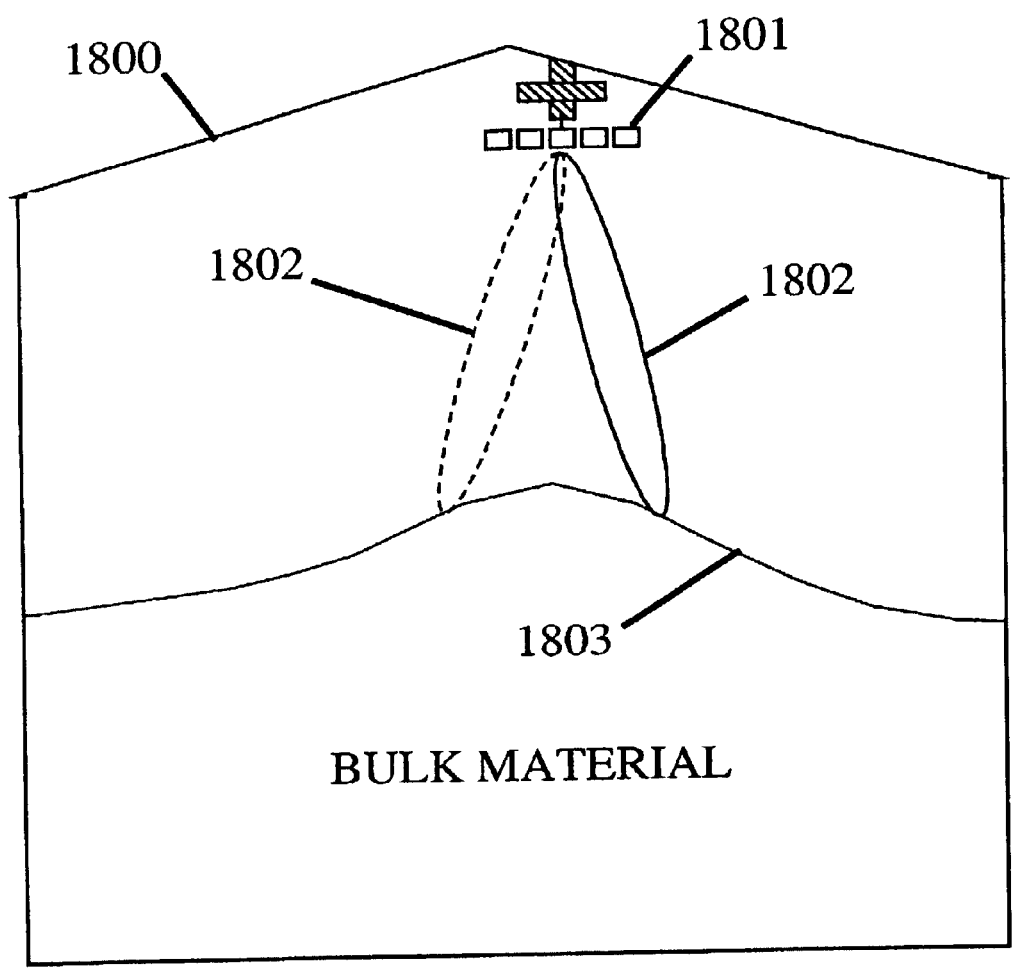
FIG. 18 is a schematic representation of an alternate embodiment of the present invention using an ultrasonic phased array rangefinder for volume measurement.

FIG. 18 is a schematic representation of an alternate embodiment using an ultrasonic phased array rangefinder 1801 for volume measurement. An array of transducers 1801 is mounted in a storage facility 1800. The control and processor electronics fire the transducers nearly simultaneously to form and steer a single, resultant probe beam 1802 across the bulk material 1803 to measure surface height, profile, and underlying volume. Data is transmitted as described in FIG. 16. Further explanations of this alternate embodiment are explained below in FIGS. 18A through 18K.

Figure 18A:
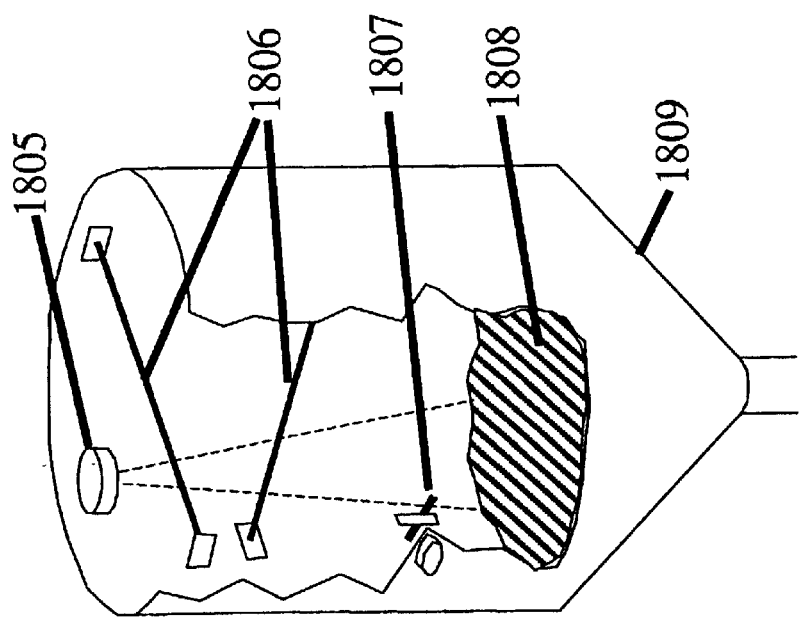
FIG. 18A is a schematic representation of a volume measurement sensor.

FIG. 18A is a schematic representation of a volume measurement sensor 1805 mounted atop a storage facility 1809. There are typically obstructions such as bracing 1806 or paddle level detectors 1807 that the measurement sensor 1805 must deal with appropriately. Historically, ultrasonic systems have used analog detectors to determine the time for an echo to return. Typical analog systems have difficulty differentiating between a false echo from a structural feature of the building and an echo from the surface of the grain.

Figure 18B:
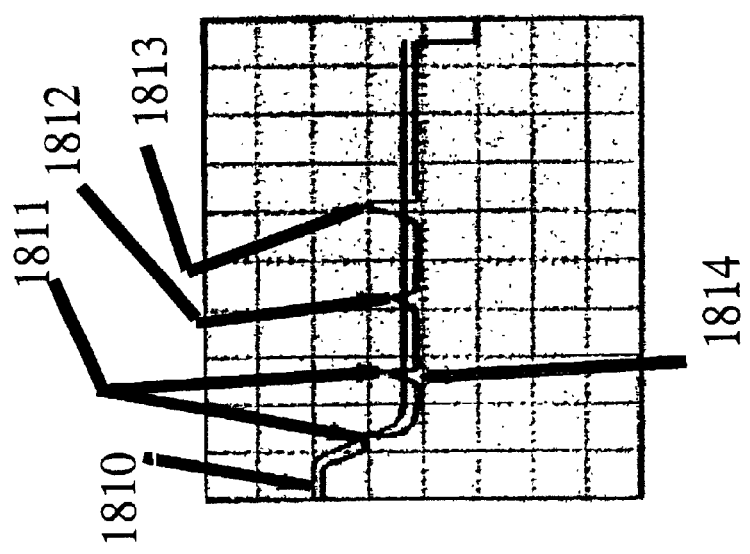
FIG. 18B is a schematic representation of typical analog signal processing.

FIG. 18B is a schematic representation of typical analog signal processing. As can be seen, a threshold level 1810 is monitored. Echo returns above the set threshold 1810 can result from obstructions such as bracing 1811 or paddle level detectors 1812 versus the desired material surface echo 1813. Thus, if the first echo to cross the threshold was from a built-in obstruction, the instrument would provide a false level indication 1814.

Figure 18C:
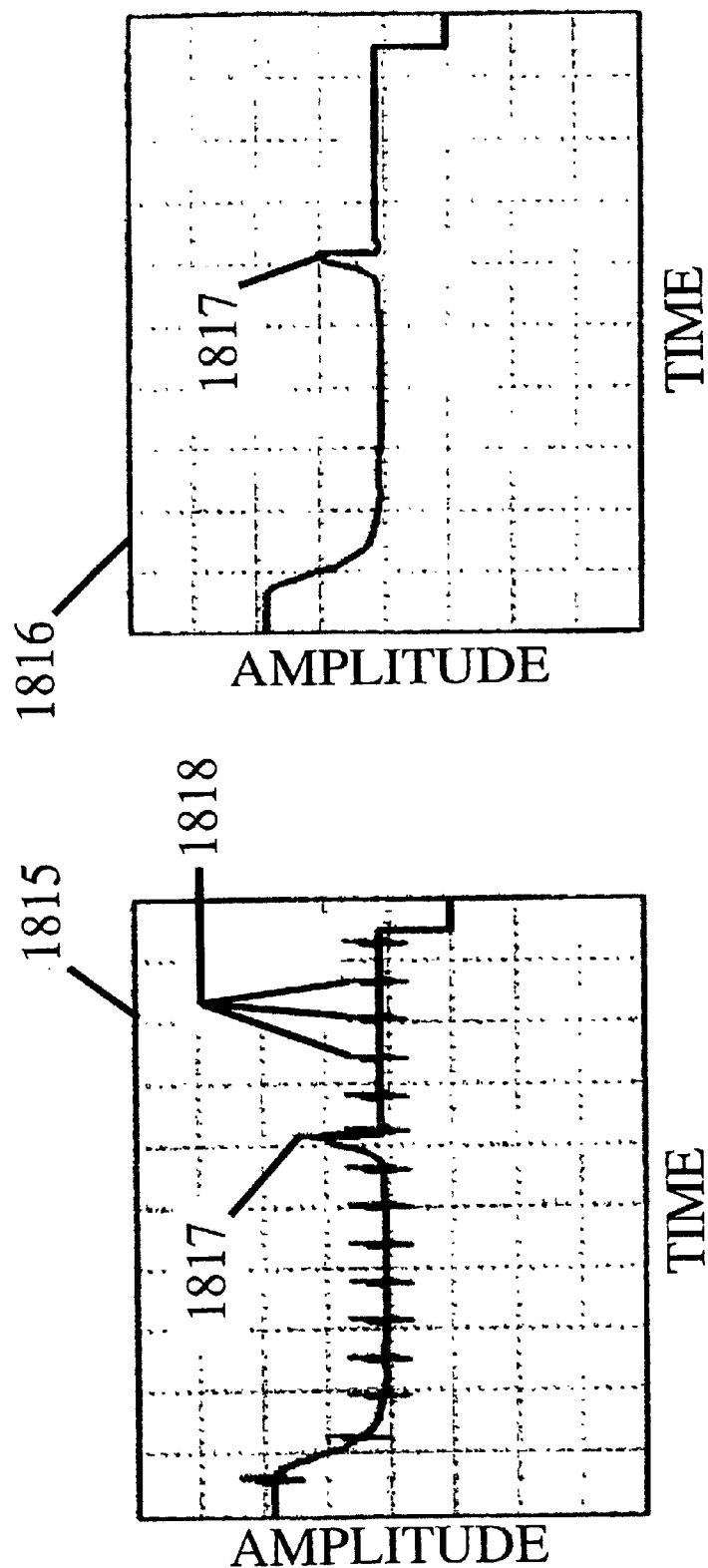
FIG. 18C is a schematic representation of non-digitized (non-filtered) analog signals versus filtered (digitized) signals.

FIG. 18C is a schematic representation of non-digitized (non-filtered) analog signals 1815 versus filtered (digitized) signals 1816. In this example the display of non-filtered signals 1815 depict noise from variable speed drives 1818 and an echo from the material surface 1817. The display after filtering 1816 shows the true echo of the material surface 1817. Thus digitizing the return signal and then processing the signal in software can remove most unwanted reflections so that only the desired return signal (echo) 1817 is used.

Figure 18D:
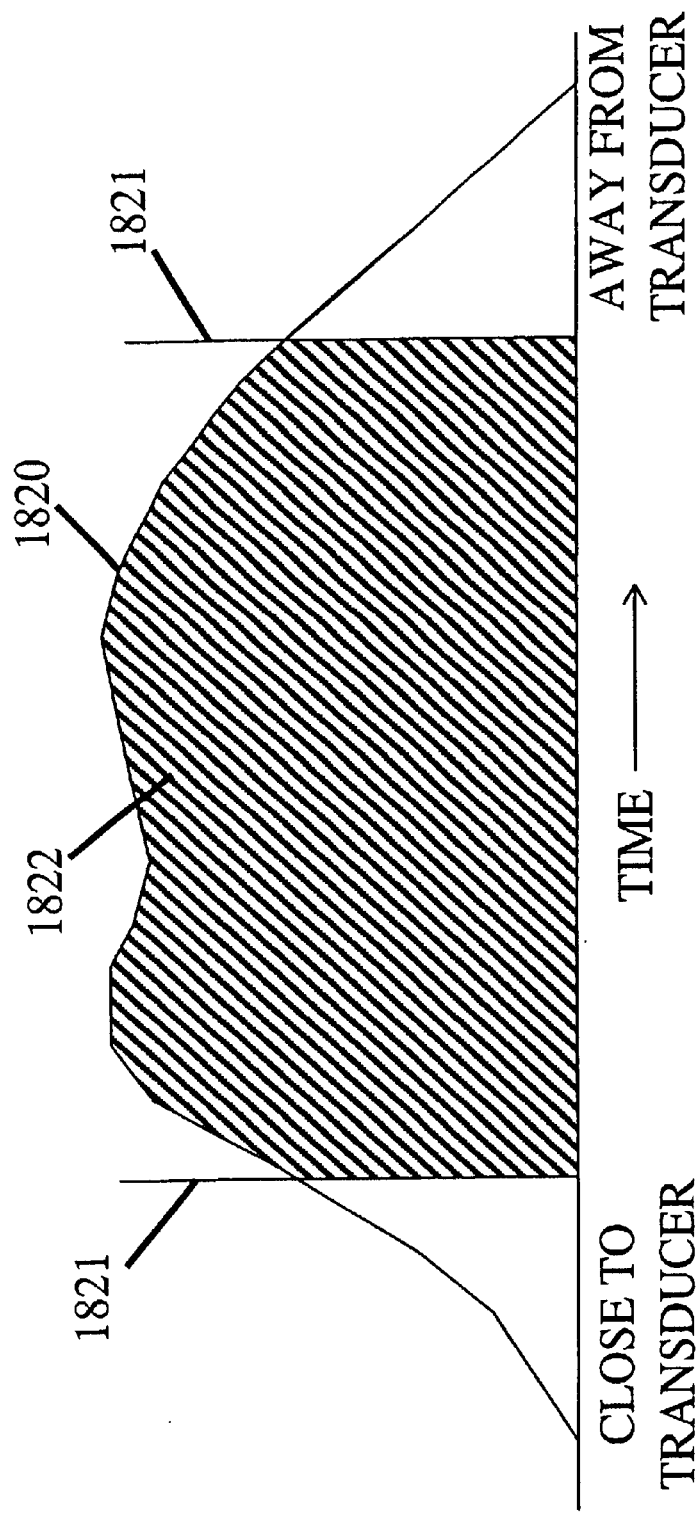
FIG. 18D is a schematic representation of utilizing the signal shape for analysis.

FIG. 18D is a schematic representation of utilizing the signal shape 1820 for analysis. In this example, rather than using only a single trigger point to time the reflected signal

1820, the shape of the return signal can be analyzed and the area under the curve 1822 integrated between trigger points 1821 to get a more accurate picture of the grain surface. A simple voltage trigger point shows the bin to be fuller than it was. Integrating returned signal strength as a function of time gives a more accurate measurement of the grain.

Figure 18E:
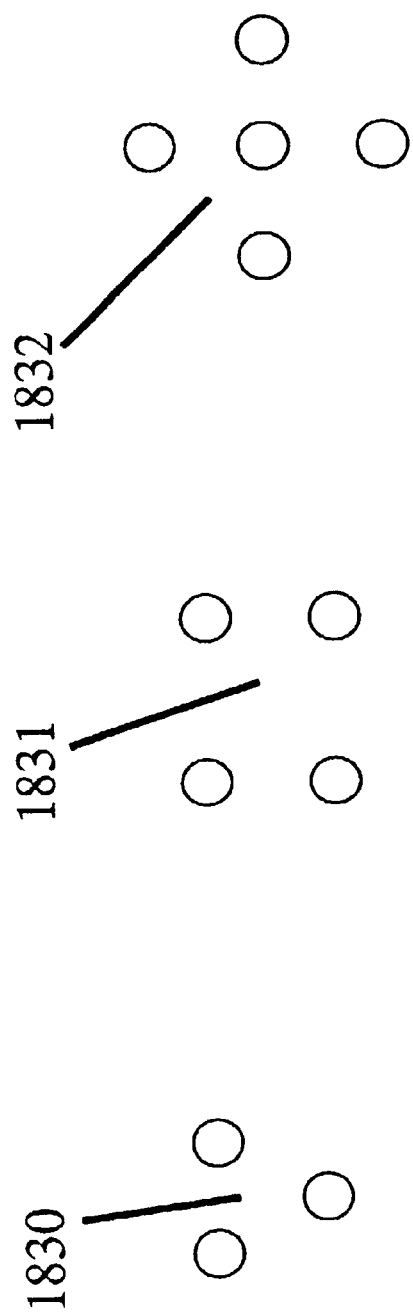
FIG. 18E is a schematic representation of some of the possible combinations of ultrasonic phased array (beam-forming) transducers.

FIG. 18E is a schematic representation of some of the possible combinations of ultrasonic phased array (beam-forming) transducers. Shown are a three element triangular combination (block 1830), a four element rectangular combination (block 1831) and a five element diamond combination (block 1832). The biggest benefit of digitizing the return signal is the ability to array individual ultrasonic transducers using a digital beam-forming technique. In this technique, ultrasonic transducers are installed in groups of three or more. A representative system schematic of this technique is described below in FIG. 18F.

Figure 18F:
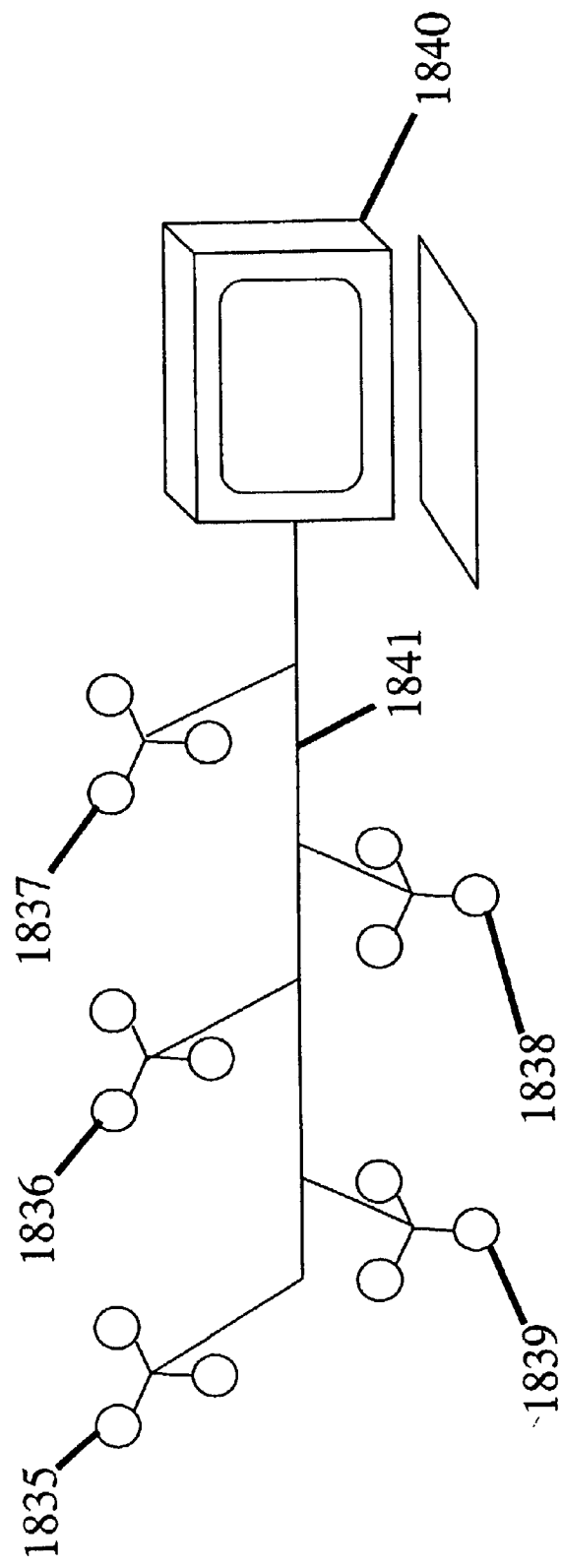
FIG. 18F is a schematic representation of a system configuration of five groups of three element ultrasonic phased arrays attached to a "beam-forming" computer.

FIG. 18F is a schematic representation of a system configuration of five groups of three-element ultrasonic phased arrays attached to a beam-forming computer 1840. In this example "array #1" 1835, each of the three transducers would digitize its own return signal and pass that data back to the central computer 1840. "Array #2" 1836, "array #3" 1837, "array #4" 1838 and "array #5 1839 would do likewise. Each array is attached to the beam-forming computer 1840 with a digital data stream 1841. Using just one data set from each transducer, the computer 1840 can combine the individual return signals in both amplitude and phase to produce a much narrower effective beam than the individual transducers can produce. In addition, by changing the phase relationship between the individual return signals, this narrow beam can then be steered across the entire surface of the grain. Although only five groups of three element transducers are shown, there can be many more. For example there can be "n" arrays of three elements each. Normally, only one array group is needed per container. The requirement for more than one array group is dependent on the size of the bulk container or bulk pile.

Figure 18G:
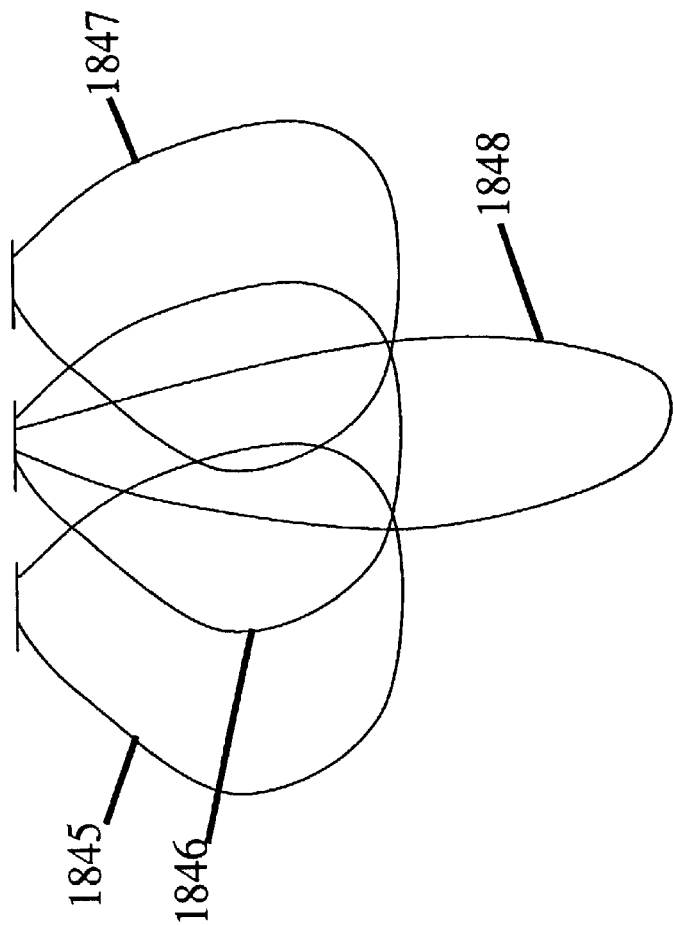
FIG. 18G is a schematic representation of the array effect of combination of individual beams to a single narrow beam.

FIG. 18G is a schematic representation of the array effect of combination of individual beams to a single narrow beam. In the example depicted, three individual beams 1845, 1846, 1847 are combined by the computer into one much narrower beam 1848 which greatly enhances total volume accuracy.

FIG. 18H is a schematic representation of narrow beam steering across the material surface. By changing the phase relationship between the individual return signals, the narrow beam can be steered across the material surface. Thus, by manipulating one set of digitized return signals through software, a large area of material can be measured with great accuracy. In the example depicted, the three individual beams as described in FIG. 18G above are combined into a single beam that is phase shifted and thus steered across the entire surface of the material to be measured. "Beam1" 1850 is a phase shifted relationship of the original three beams as shown in the formulation for "Beam1" 1855. Likewise, "Beam2" 1851 is a different phase shift as shown in formulation for Beam2 1856. "Beam3" 1852, "Beam4" 1853 and "Beam5" 1854 are further phase shifted as shown in the formulation for "Beam3" 1856, formulation for "Beam4" 1858 and finally the formulation for "Beam5" 1859 respectively. The result is a volume measurement with a high degree of accuracy.

Figure 18I:
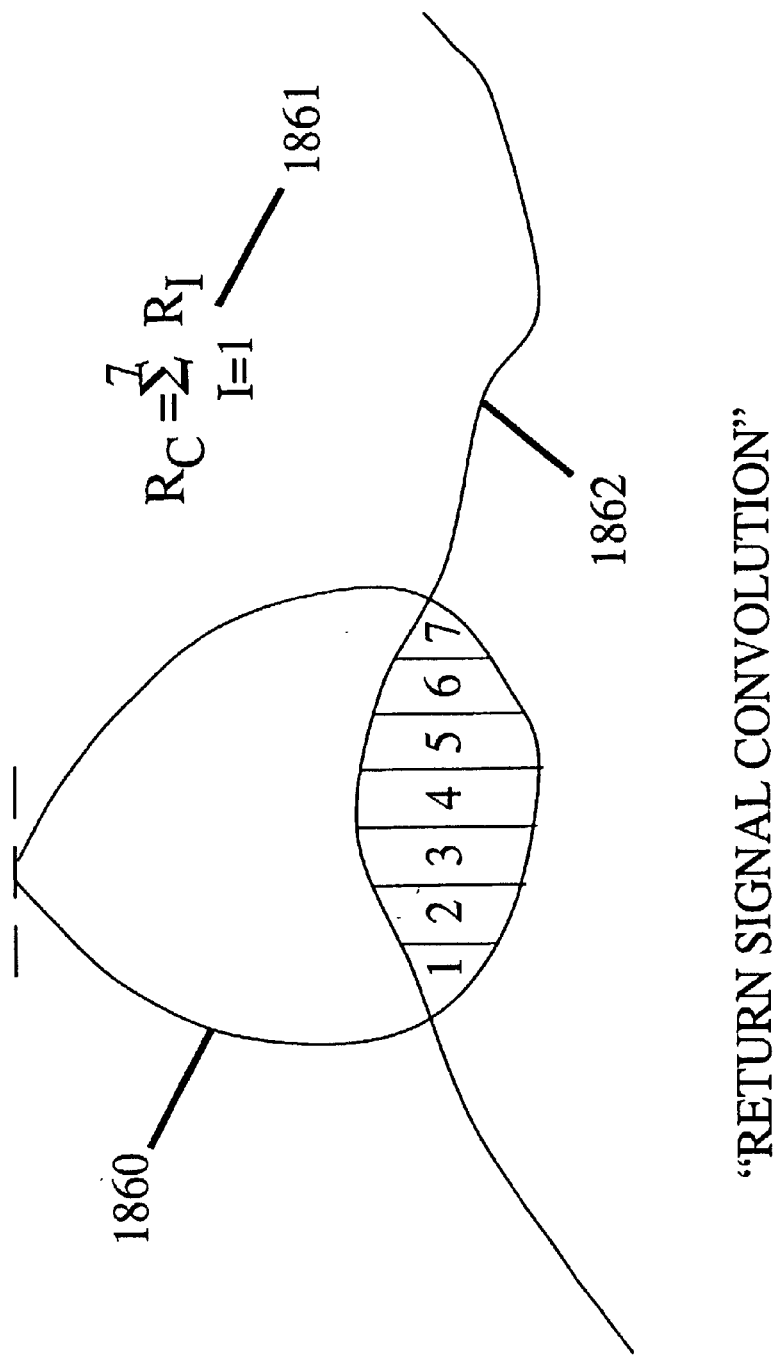
FIG. 18I is a schematic that shows the convolution or summation of a series of returned signals from the ultrasonic phased beam steering.

FIG. 18I is a graphical representation that shows the convolution or summation of a series of returned signals that form the ultrasonic phased beam steering. The returned beam 1860 from the material surface 1862 is represented by "$R_c$" 1861 which is a summation or convolution of seven returned signals. Thus, if the surface of the material is irregular, it is hard to resolve features on the surface that are smaller than the beam-width. A solution for this problem is described below in FIG. 18J.

Figure 18J:
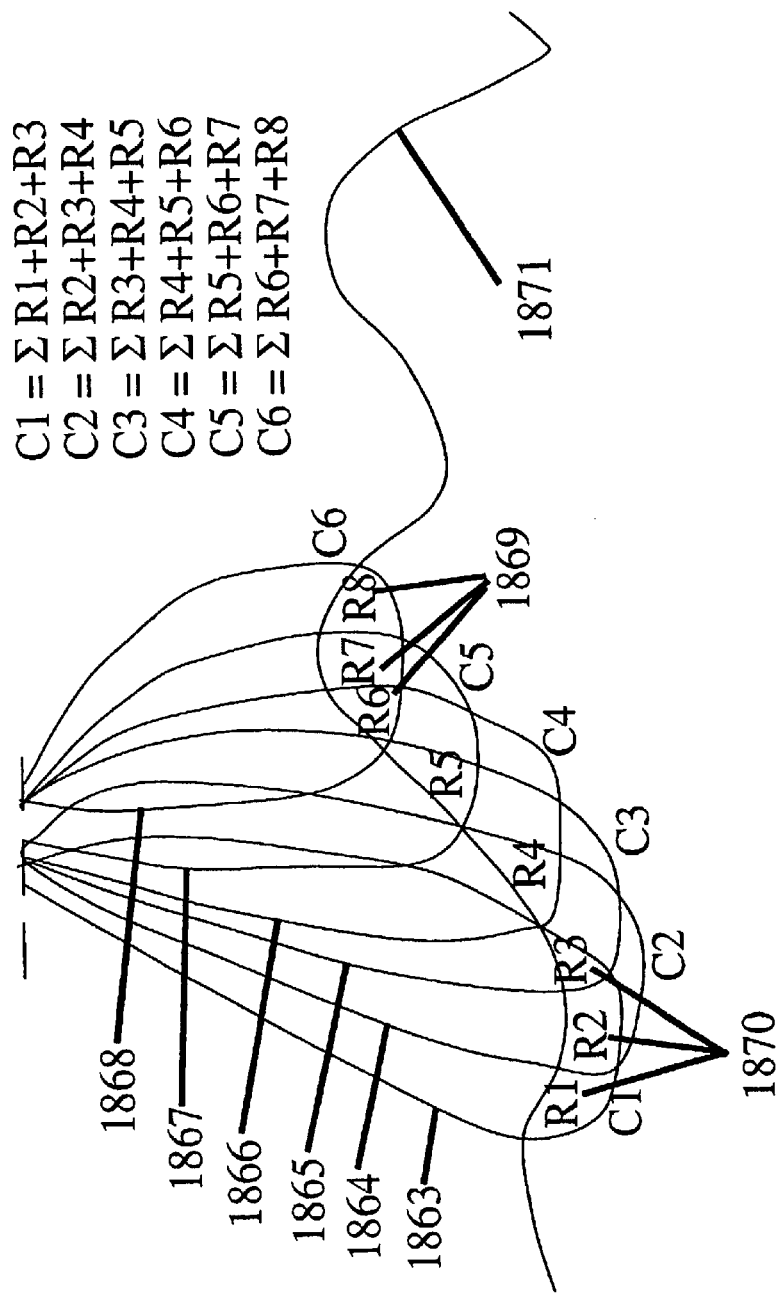
FIG. 18J is a graphical representation showing a beam deconvolution array.

FIG. 18J is a graphical representation showing a beam de-convolution array. By steering the beam from the ultrasonic transducer array in increments that are smaller than the beam-width, the returned signals from spots on the grain as small as the step size can be resolved. With some reasonable assumptions of the edge conditions, the beam deconvolution is a simple matter of solving a system of linear equations. "$C_n$" is the convoluted beam represented by C1 1863, C2 1864, C3 1865, C4 1866, C5 1867 and C6 1868. "$R_n$" represents the reflected signal from the material surface 1871. For example R1, R2, R3 1870 represents the reflected signal of the material surface area reflected back from the convoluted beam C1 1863 whereas R6, R7, R8 1869 represents the reflected signal of the material surface area reflected back from the convoluted beam C6 1868.

Figure 18K:
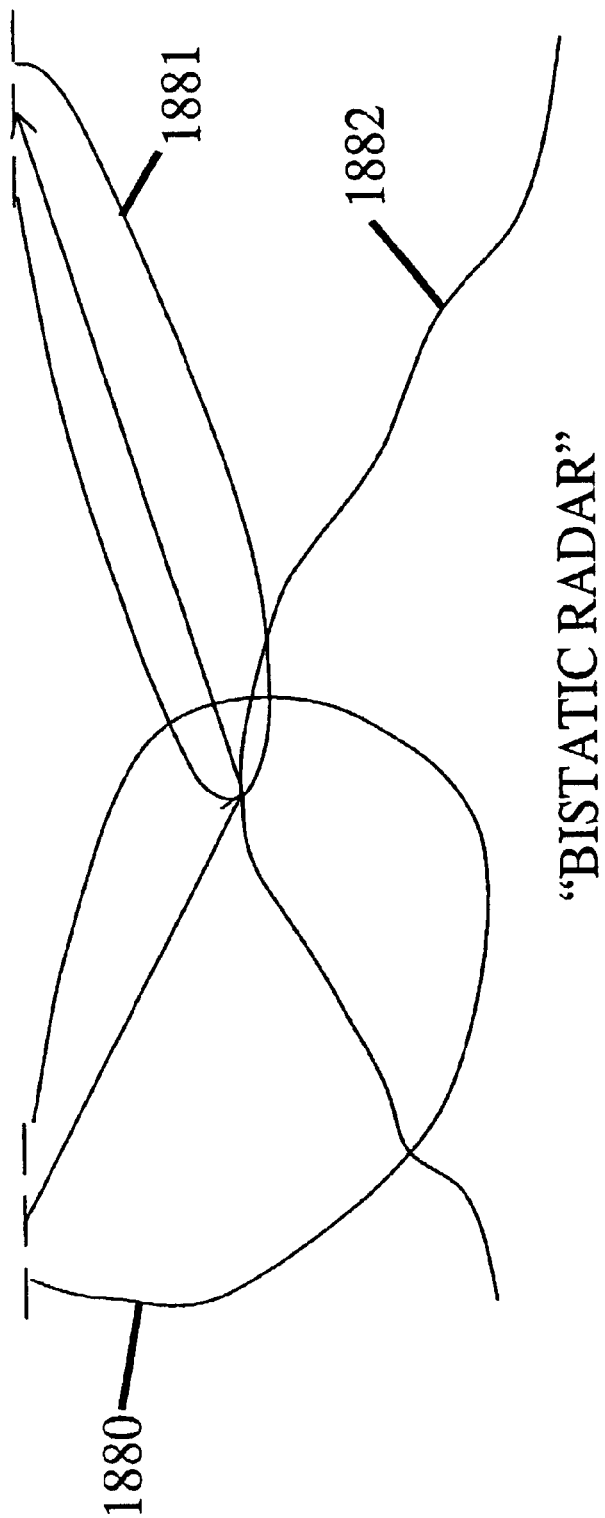
FIG. 18K is a graphical representation of a bi-static radar measurement.

FIG. 18K is a graphical representation of a bi-static radar measurement. Another benefit of digital beam-forming is the possibility of bi-static as well as mono-static radar measurements previously described. A group of transducers sends out transmit array signals 1880 to the material surface 1882 and a second group of transducers receives the signals for processing 1881. By recording the pulses from the adjacent group of transducers, the surface area and volume between the two groups can be analyzed. This technique can be used to increase accuracy in this inter-group region or allow wider spacing of the transducer groups using less hardware.

The alternate embodiment utilizing digital beam-forming was described above in FIGS. 18, 18A, 18B, 18C, 18D, 18E, 18F, 18G, 18H, 18I, 18J and 18K. The hardware for a digital beam-forming system is not complex. At each transducer, there will be an A/D (Analog to Digital) converter and a micro-controller, which are all rather inexpensive parts. There will be a central computer, data transfer wiring, and beam processing software. Thus, virtually all improvements to the system will involve software upgrades versus hardware changes in a storage facility. Other solutions that have not been covered in detail involve super-resolution techniques using grating lobes in a digitally created interference pattern, optical image enhancement techniques, RCS algorithms, and other algorithms for the fields of optics, electromagnetics, and mathematics. This wealth of possible improvements demonstrates that digital data processing is a system that is not only inexpensive to install but also inexpensive to upgrade and maintain.

Figure 19:
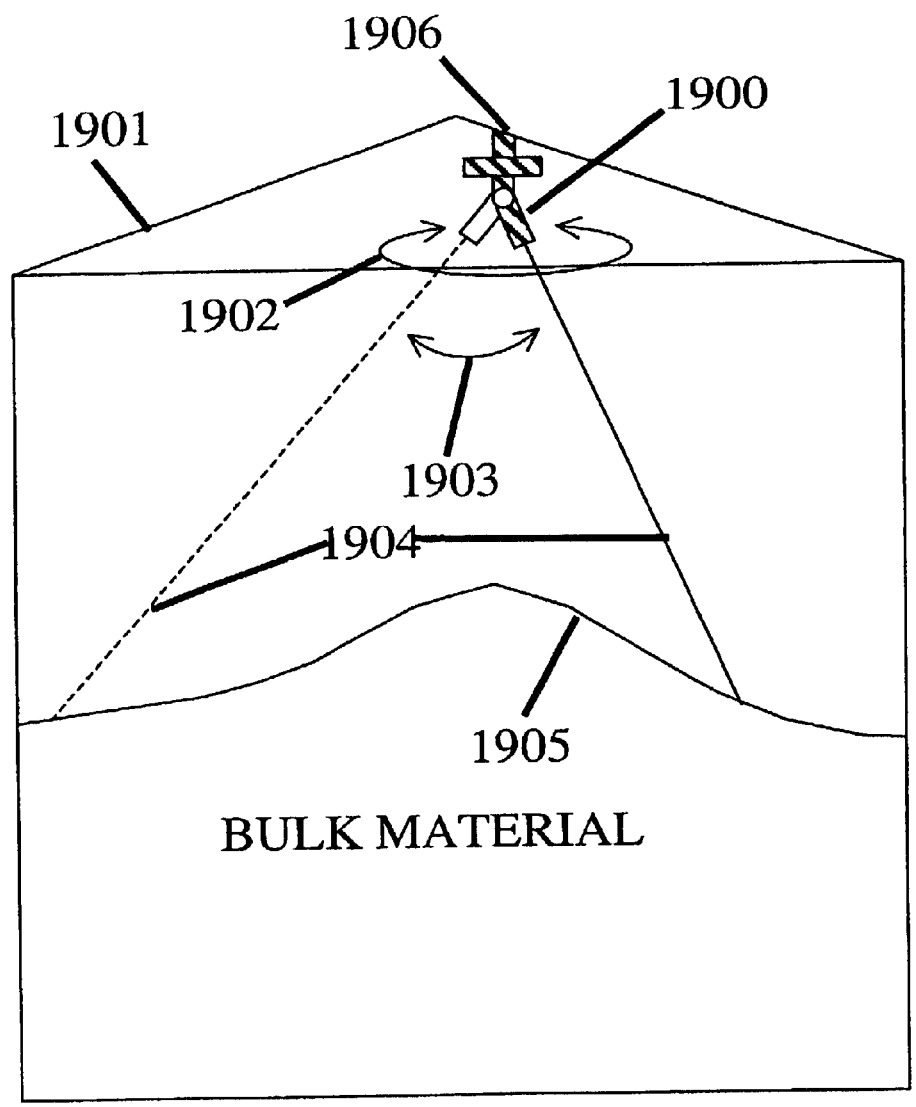
FIG. 19 is a schematic of an alternate embodiment of the present invention depicting a scanning radar rangefinder in a storage facility.

FIG. 19 is a schematic of an alternate embodiment of the present invention depicting a scanning radar rangefinder 1900 in a storage facility 1901. The scanning radar rangefinder 1900 is shown mounted on the upper portion of a storage facility 1901. The scanning radar rangefinder 1900 can rotate >360 degree in azimuth 1902 above the bulk material surface 1905 within the storage facility 1901. The scanning radar rangefinder can also rotate approximately 90 degrees in elevation 1903. Thus, radar signals 1904 can accurately digitize the surface height, profile and underlying volume. A cable data communications port 1906 can transmit and receive data via a cable-borne data communications port, RF (radio frequency) transmit/receive, IR (infrared) transmit/receive or a laser point to point transmit/receive communication. The radar rangefinder is known in existing art. The scanning radar rangefinder 1900 sends out pulses 1904 and obtains reflections off a desired surface 1905. The instrument 1900 contains the radar rangefinder, control and processor electronics, rotation stage mounting, environmental enclosure and a cable-borne, RF, IR or point to point laser communication path.

Figure 20:
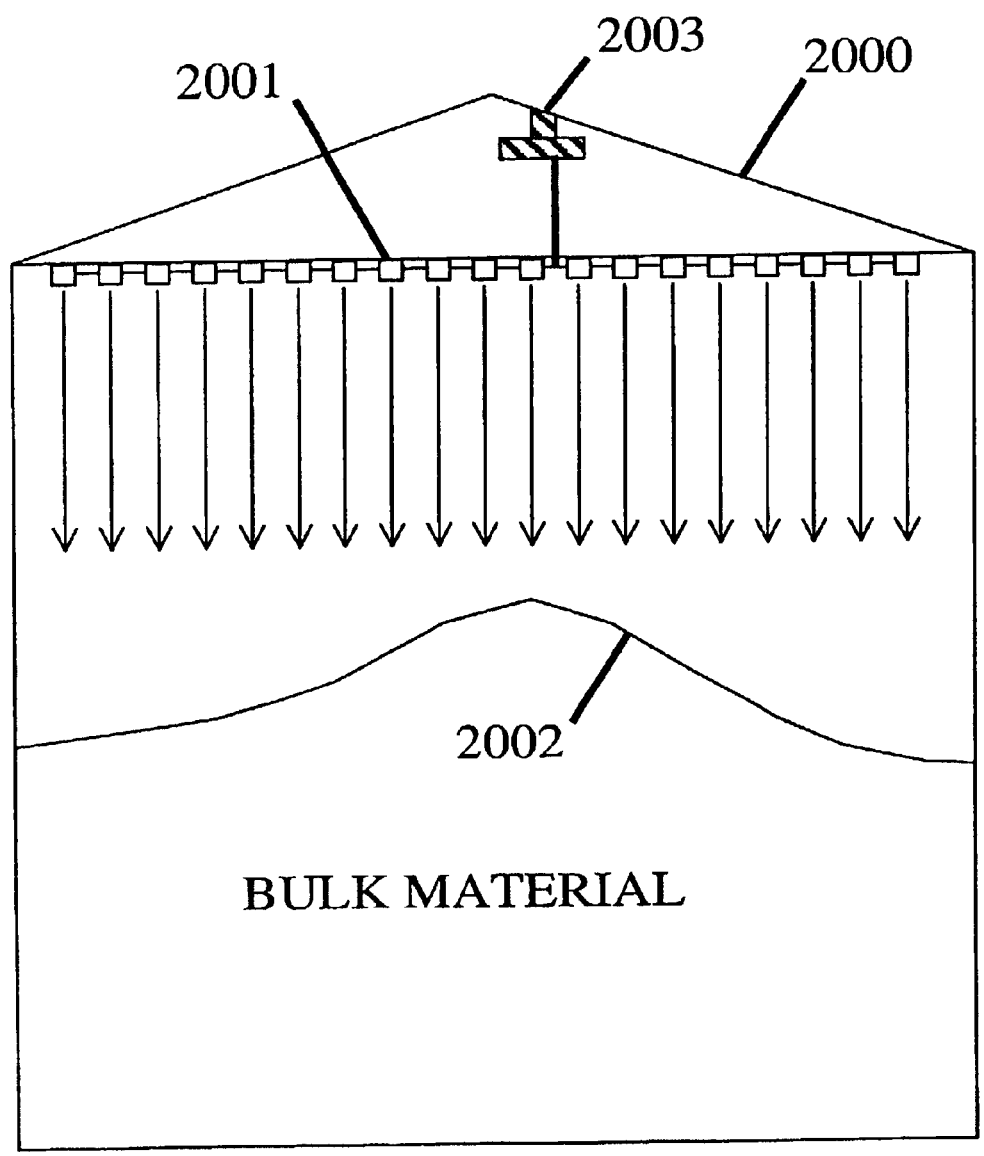
FIG. 20 is a schematic of an alternate embodiment of the present invention using multiple radar single point rangefinders for volume measurement.

FIG. 20 is an alternate embodiment of the present invention using multiple radar single point rangefinders for volume measurement. The radar rangefinders 2000 are mounted in fixed positions within the storage facility 2000 and obtain reflections off the desired bulk material surface 2002. A cable data communications port 2003 can transmit and receive data via a cable born data communications port, RF (radio frequency) transmit/receive, IR (infrared) transmit/receive or a laser point to point transmit/receive communication port.

Figure 21:
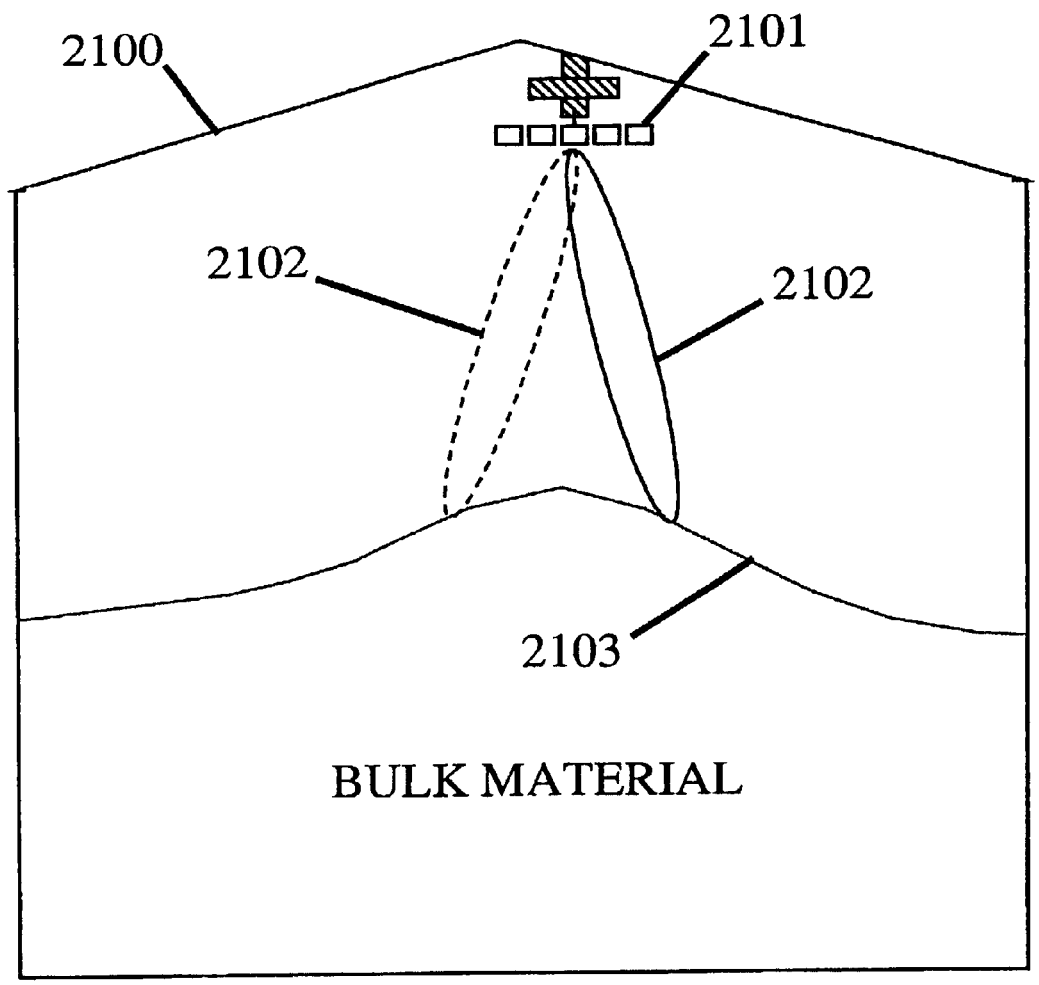
FIG. 21 is a schematic representation of an alternate embodiment of the present invention using a radar phased array (beam-forming) rangefinder for volume measurement.

FIG. 21 is a schematic representation of an alternate embodiment of the present invention using a radar phased array (beam-forming) rangefinder for volume measurement. A phased array of transducers 2101 is mounted in a storage facility 2100. The control and processor electronics fire the radar rangefinders nearly simultaneously to form and steer a single probe beam 2102 to measure the bulk material 2103 surface profile and underlying volume. Data is transmitted as described above in FIG. 20. This technique is functionally implemented (enabled) via the detailed discussions covered by FIGS. 18A–18K regarding beam-forming.

Figure 22:
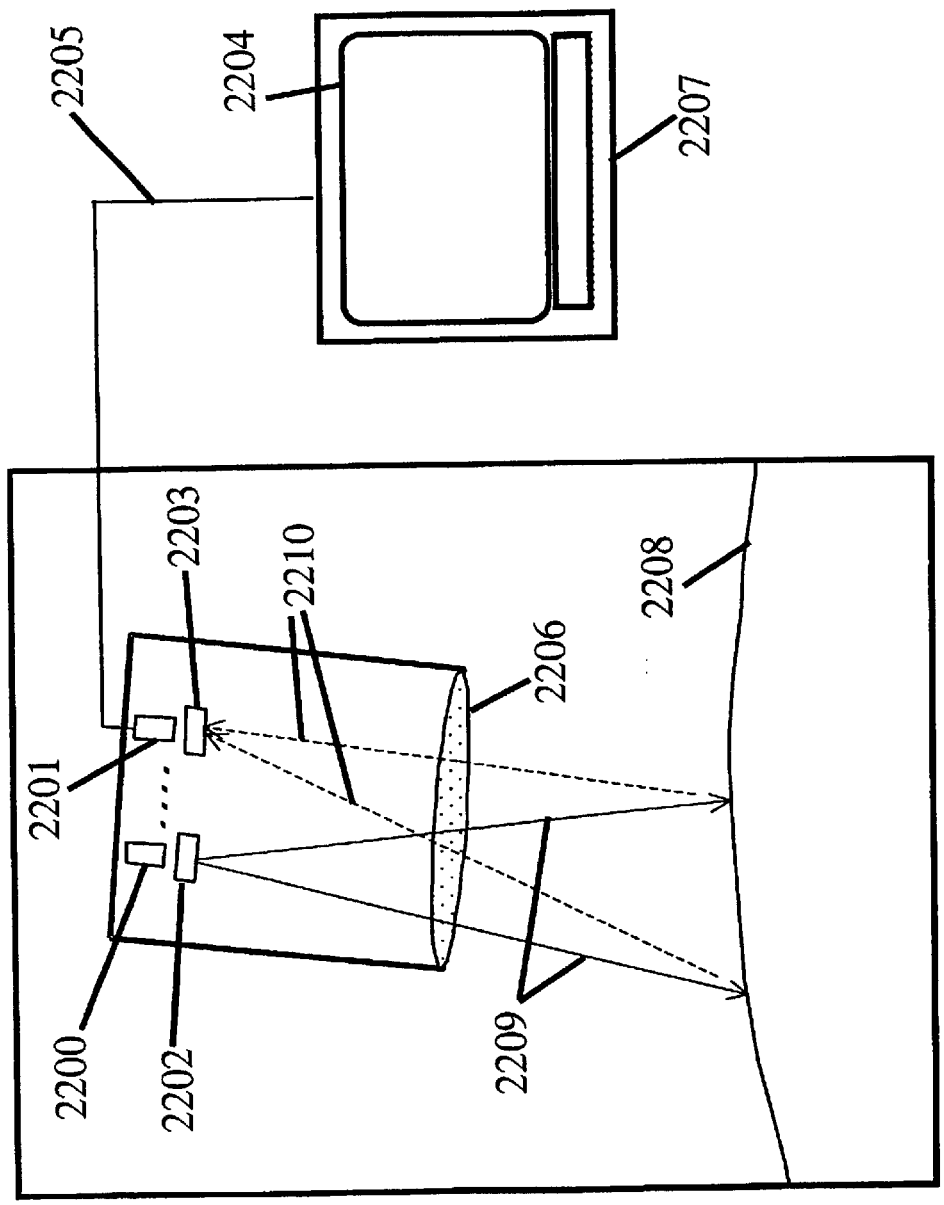
FIG. 22 is a schematic representation of an interference (Moire) based volume measurement instrument in an integrated package, an alternate embodiment of the present invention.

FIG. 22 is a schematic representation of an interference (Moire) based volume measurement instrument in an integrated package, an alternate embodiment of the present invention. The Moire interferometric method will use a light projector 2200 coupled with a pattern mask 2202 to project a varying light pattern 2209 onto the grain/material surface 2208. A video camera 2201 coupled with a pattern filter 2203 similar to the pattern mask 2202 will image the grain/material surface 2208. The resultant interference pattern (as shown in the video monitor 2204) will be analyzed by a machine vision system 2207 to locate each interference line 2210. Each interference line 2210 represents a constant distance contour, and via computer analysis, can be used to generate a surface contour (profile). The surface contour is then used to calculate the total volume of the bulk material/grain in the bin. An additional lens 2206, can be placed at the package output window if required.

Figure 22A:
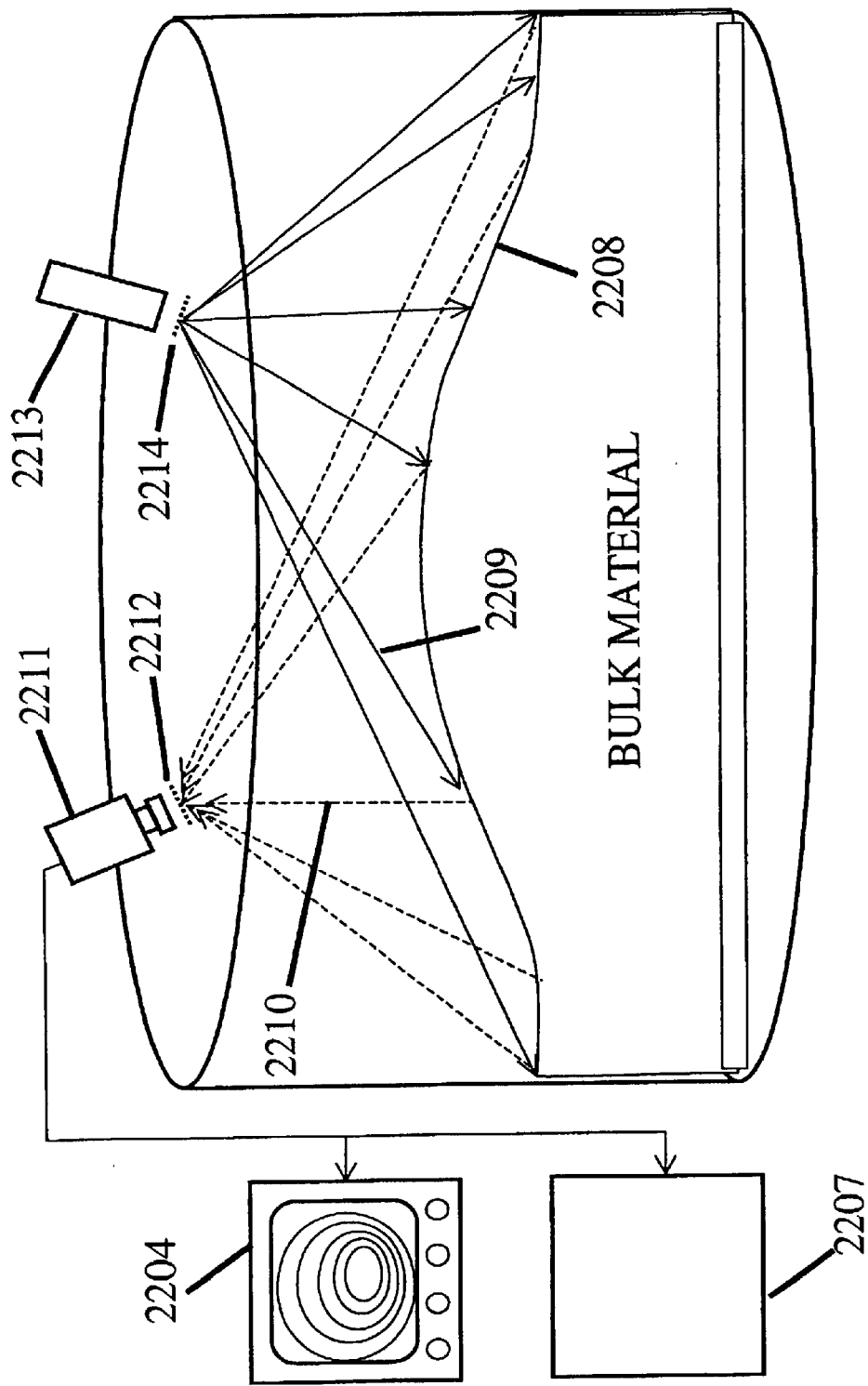
FIG. 22A is a schematic representation of an interference (Moire) based volume measurement system with instruments separately packaged. This is an alternate embodiment of the present invention.

FIG. 22A is a schematic representation of an interference (Moire) based volume measurement system with instruments separately packaged. This is an alternate embodiment of the present invention. In this configuration the light projector 2213 and the pattern mask (filter) 2214 are integrated into one package whereas the camera 2211 and pattern filter 2212 are integrated into a separate package. All elements function as described above in FIG. 22.

Figure 23:
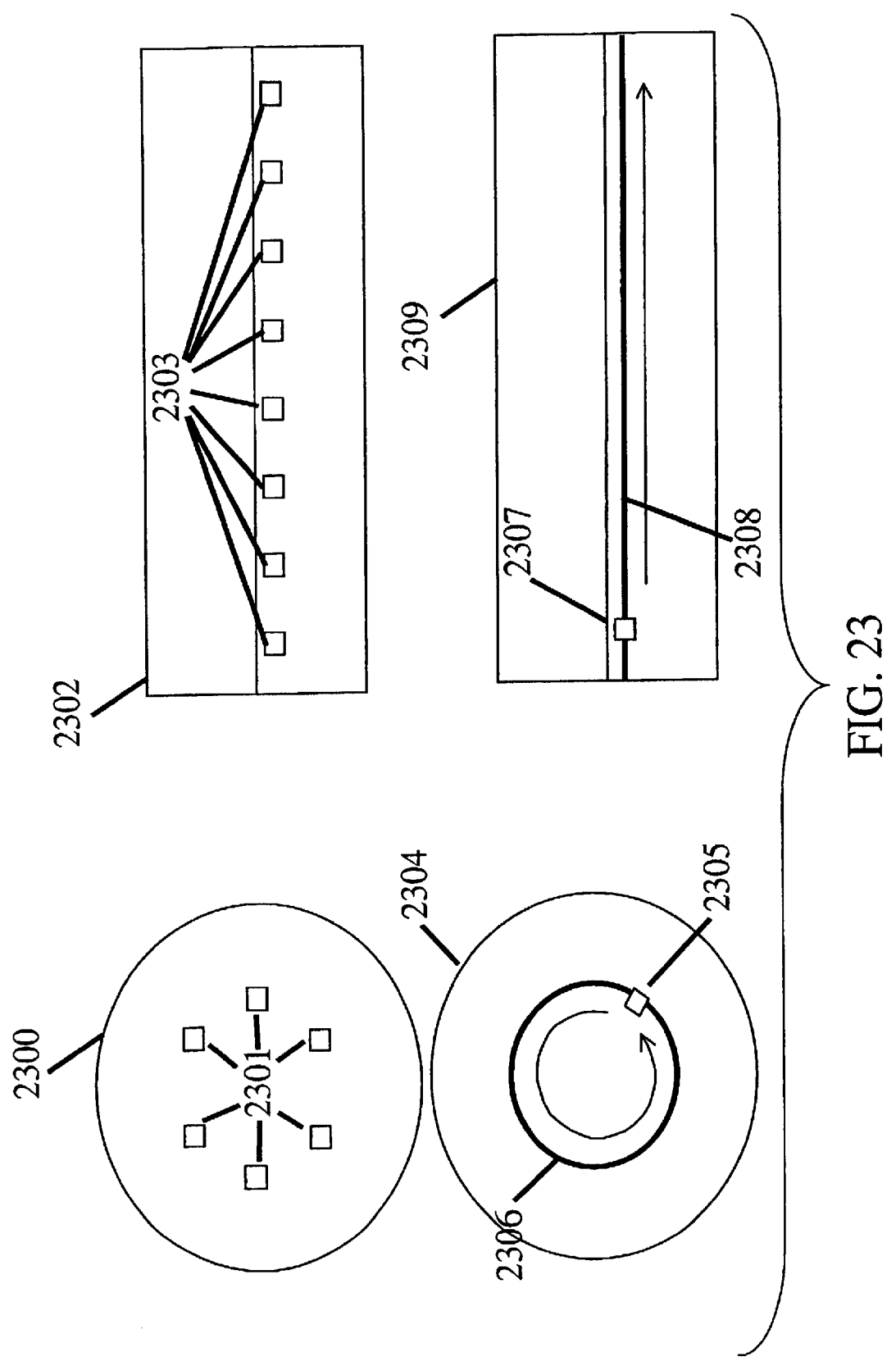
FIG. 23 is a schematic of alternative installation configurations for volume measurement instrumentation packages.

FIG. 23 is a schematic of alternative installation configurations for volume measurement instrumentation packages. Typical multi-sensor installation alternatives are shown with six sensors 2301 mounted in a circular configuration within an oval container 2300 and eight sensors 2303 mounted in-line within a rectangular container 2302. Also shown are potential single instrument installations. A single instrument 2305 mounted to move counterclockwise about a rail 2306 in circular path within an oval storage container 2304 is shown. Also shown is a single instrument 2307 mounted to move in a linear direction along a rail 2308 within a rectangular storage facility 2309.

Figure 24:
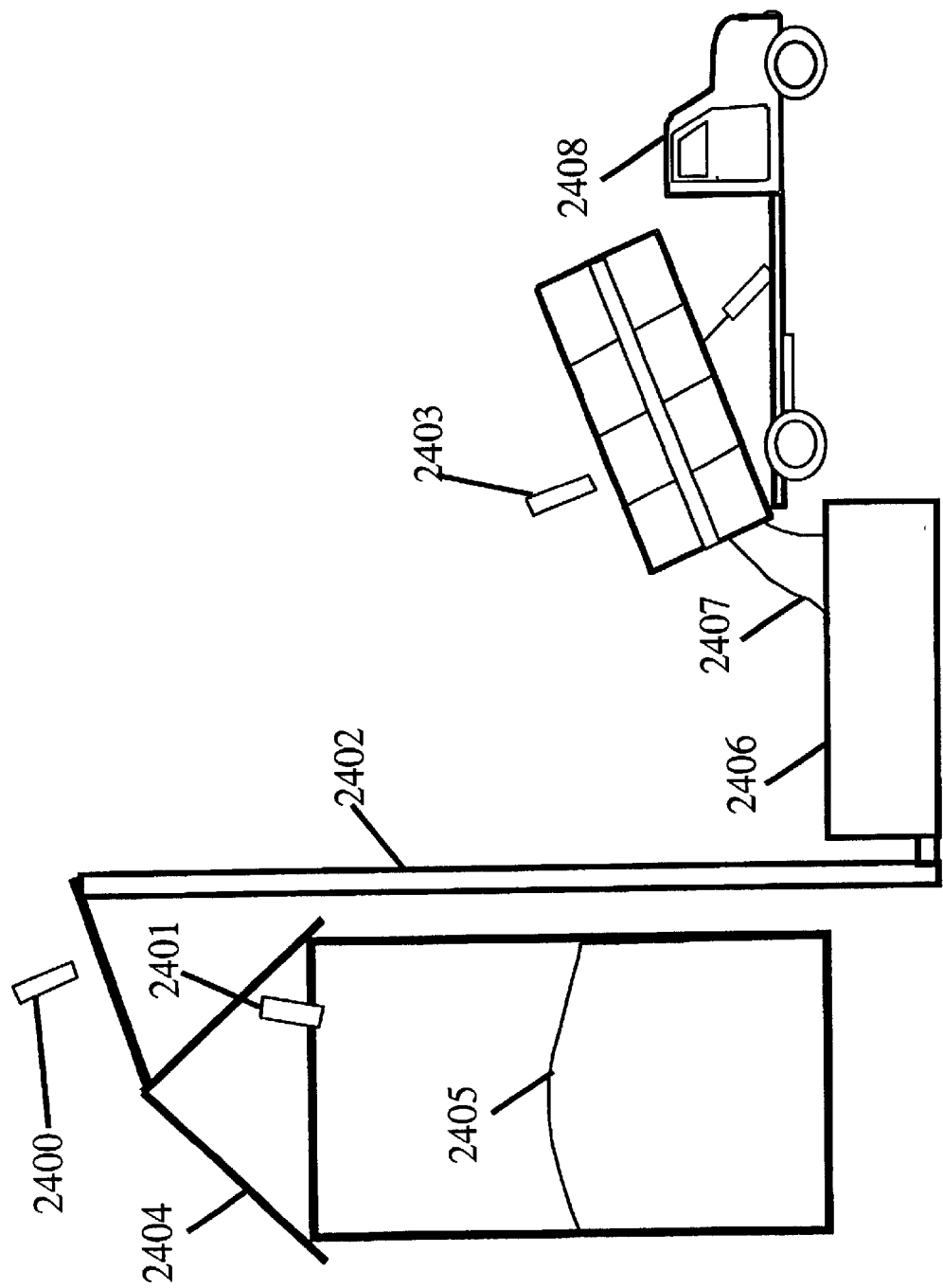
FIG. 24 is a schematic of a grain/material recognition system.

FIG. 24 is a schematic of a grain/material recognition system "ISU". Incoming grain or bulk material is transported to a storage facility 2404 by truck 2408 or other means (rail, barge, ship, etc.). A handheld or fixed recognition instrument 2403 can be utilized prior to unloading of the grain/material. In the example shown, grain/material 2407 is unloaded into a grain/material transfer pit 2406 and transported up an elevator 2402. A material recognition sensor is mounted at the exit of the elevator chute 2400. Another material recognition sensor 2401 is mounted within the storage facility 2404 to monitor facility grain/material content 2405. Alternative to the shown location 2403, the ISU can be installed in the pit location 2406. The pit location 2406 is the preferred installation spot when the ISU is the instrument version providing full flow quantitative and qualitative sample data. Where the initial ISU is intended for material type and sub-type discrimination, the wider spectrum version provides near 100% sampling of constituent data such as moisture content, foreign material, protein, starch, oils, etc. when applied to cereal grains. As well, other similar constituent data is provided for other bulk materials.

Figure 24A:
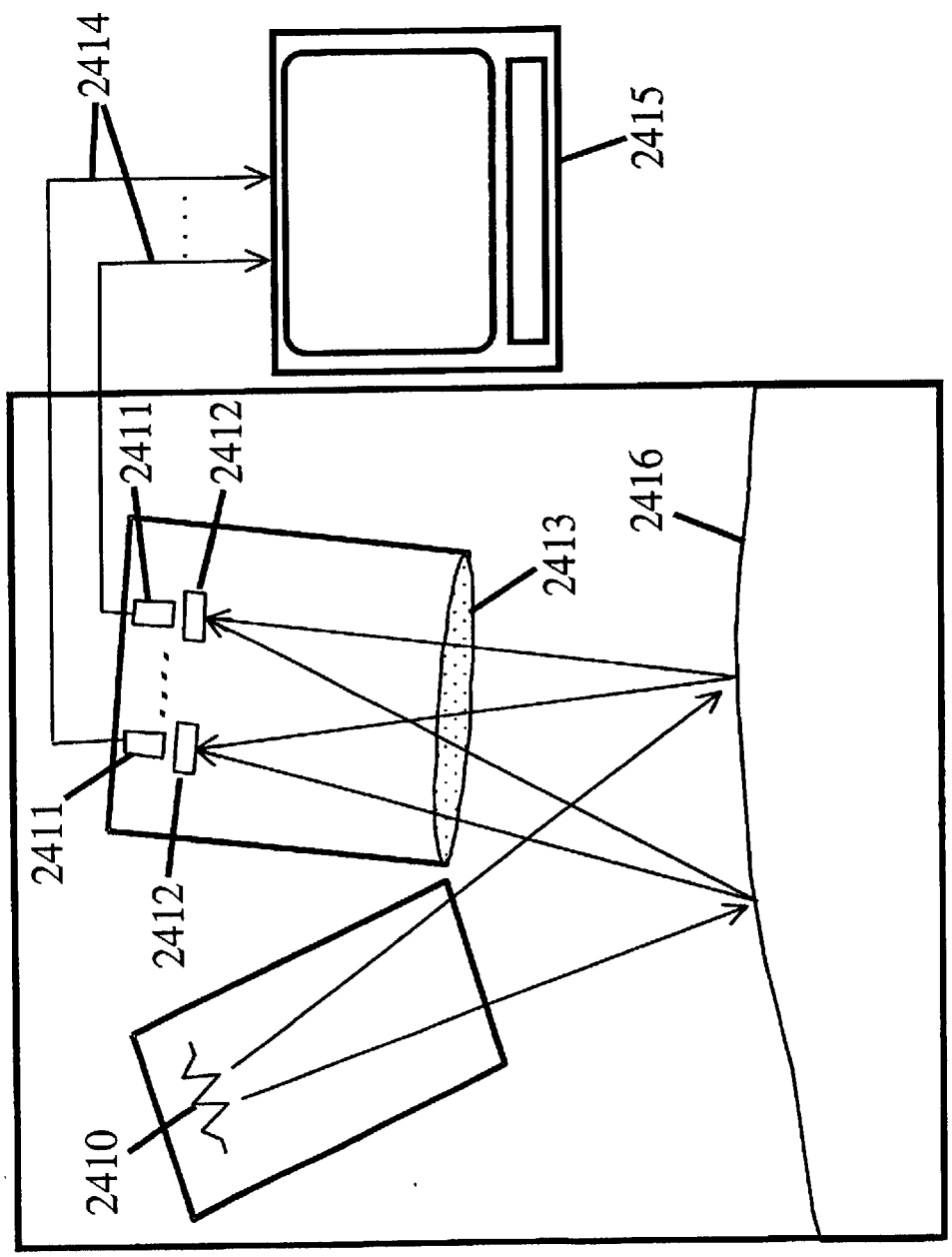
FIG. 24A is a schematic representation of a bulk material recognition system.

FIG. 24A is a schematic representation of a bulk material recognition system. A light source 2410 provides a known spectral illuminance across the bulk grain/material to be classified. Light reflects off of the grain/material through a lens 2413 (if necessary) and through a series of optical bandpass filters 2412 each coupled to a photometer 2411. Each photometric sensor is coupled 2414 to a computer 2415 which receives successive signal samples from each photometer 2411. An algorithm is then utilized to determine the stored material 2416 type.

Figure 24B:
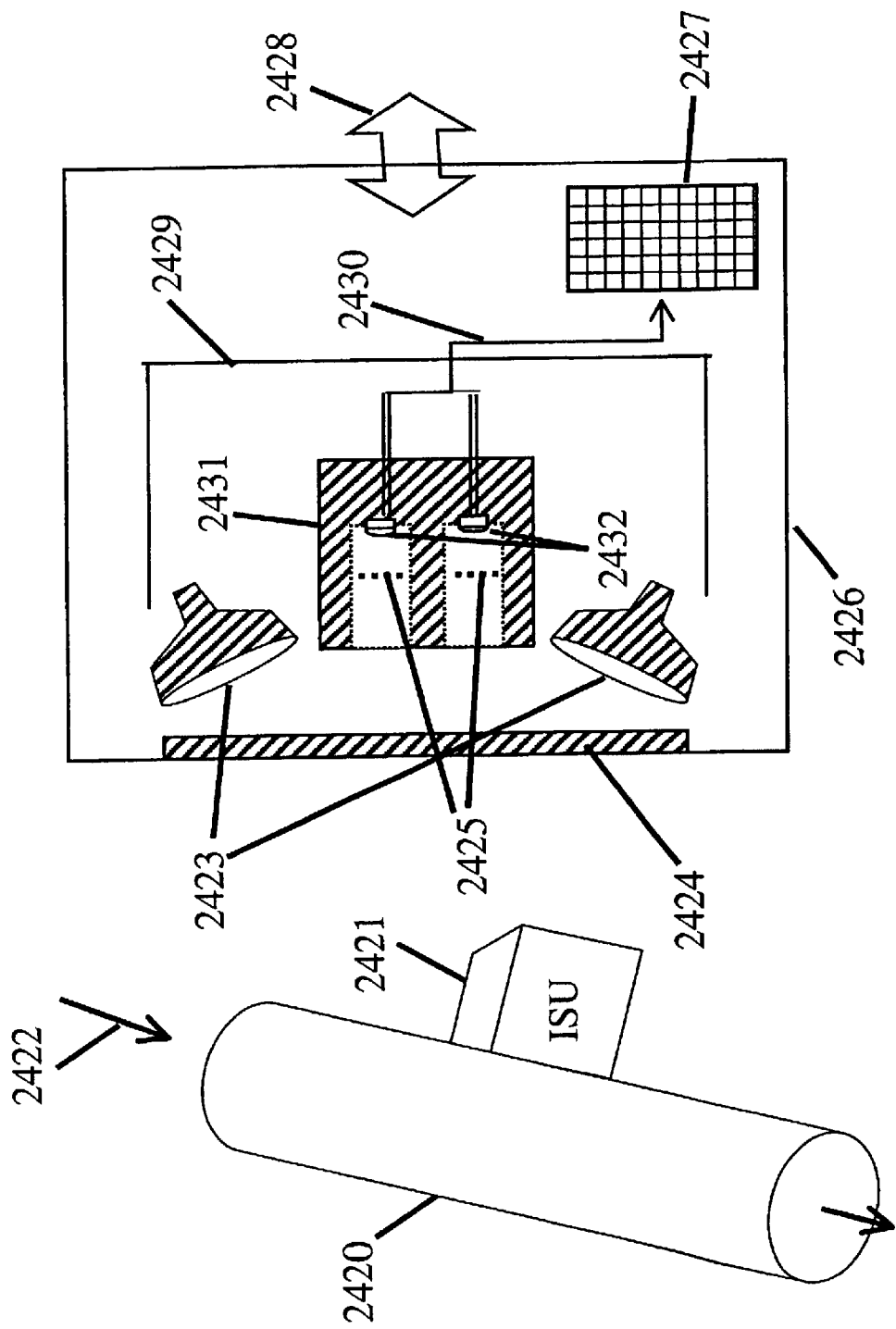
FIG. 24B is a schematic representation of an ISU (In-Flow Sensor Unit).

FIG. 24B is a schematic representation of an ISU 2421 (In-Flow Sensor Unit). Bulk material 2422 enters a chute 2420 and an ISU 2421 is attached to the chute 2420. A sectional view 2426 shows the various components of the ISU which is packaged in a NEC Class II Div I compliant (NEMA 9 or otherwise) environmental enclosure. A glass window 2424 can be standard glass with chute conformal shape if installed above the flow. If under the chute 2420, sapphire, diamond deposition or other scratchproof material may be used. The ISU contains light sources 2423, narrow band spectral filters 2425, photo diodes 2432, input power for the lamps 2429, a printed circuit control board 2427 and a low voltage, power and data input cable 2428. There may be three or more photo diodes 2432 depending on the number of materials to discriminate. The ISU sensor 2421 may equally be embodied by an on-board commercial spectrometer in lieu of the components shown.

Figure 24C:
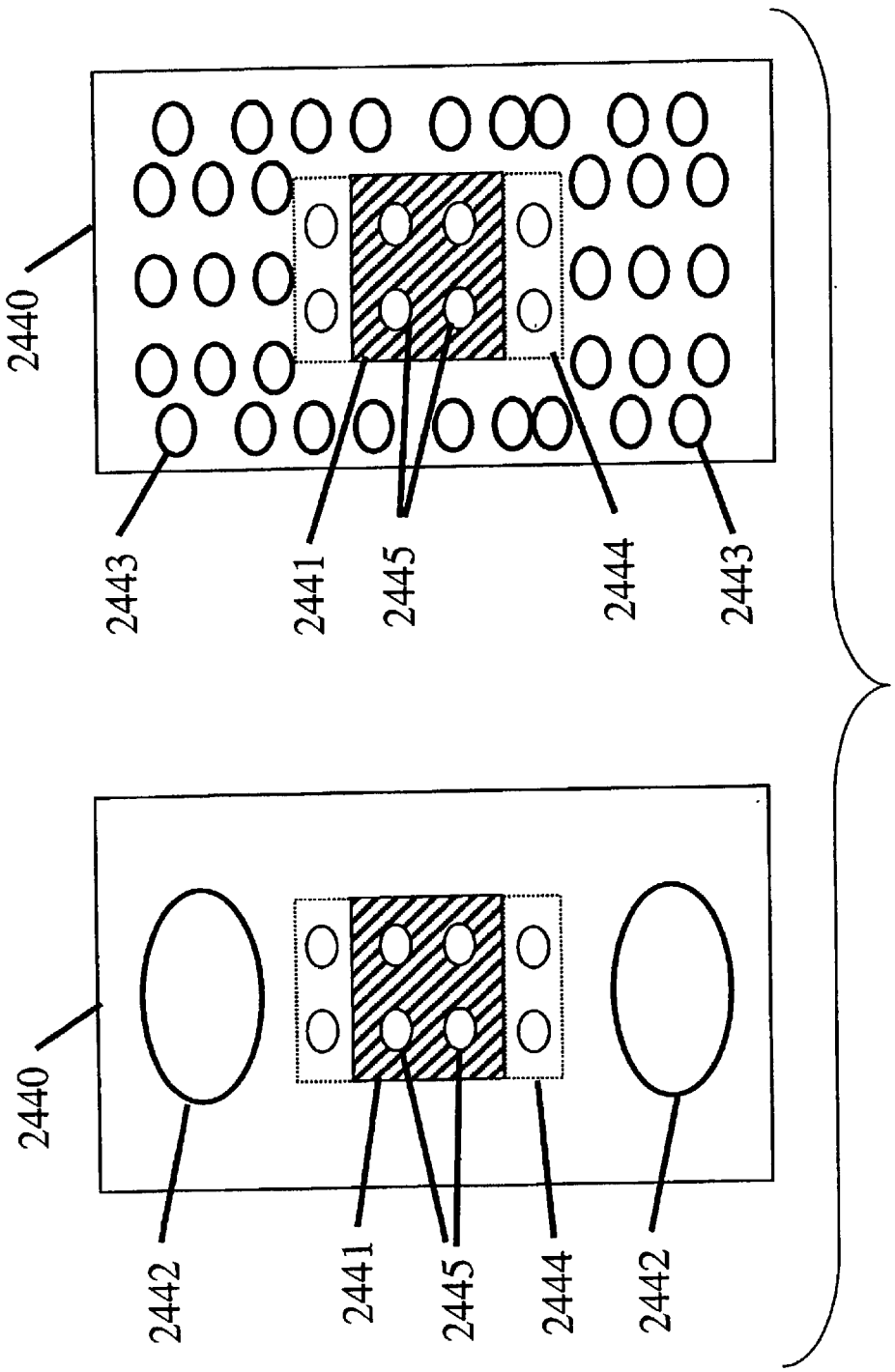
FIG. 24C is a schematic representation of the face view of the ISU.

FIG. 24C is a schematic representation of the face view of the ISU. Two alternate layouts are shown. The ISU is housed in an environmentally secure enclosure 2440. Light sources may be halogen or incandescent 2442 or may consist of many multispectral light emitting diode (LED) arrayed sources 2443 mounted on a single printed circuit board. Photodiodes and filters 2445 are typically centrally mounted. Narrow band optical filters match spectral wavelength of the LEDs. The photo diodes and optical filters 2445 are mounted within an optical housing 2441. Optional locations for the photo diodes and optical filters are shown 2444.

Figure 24D:
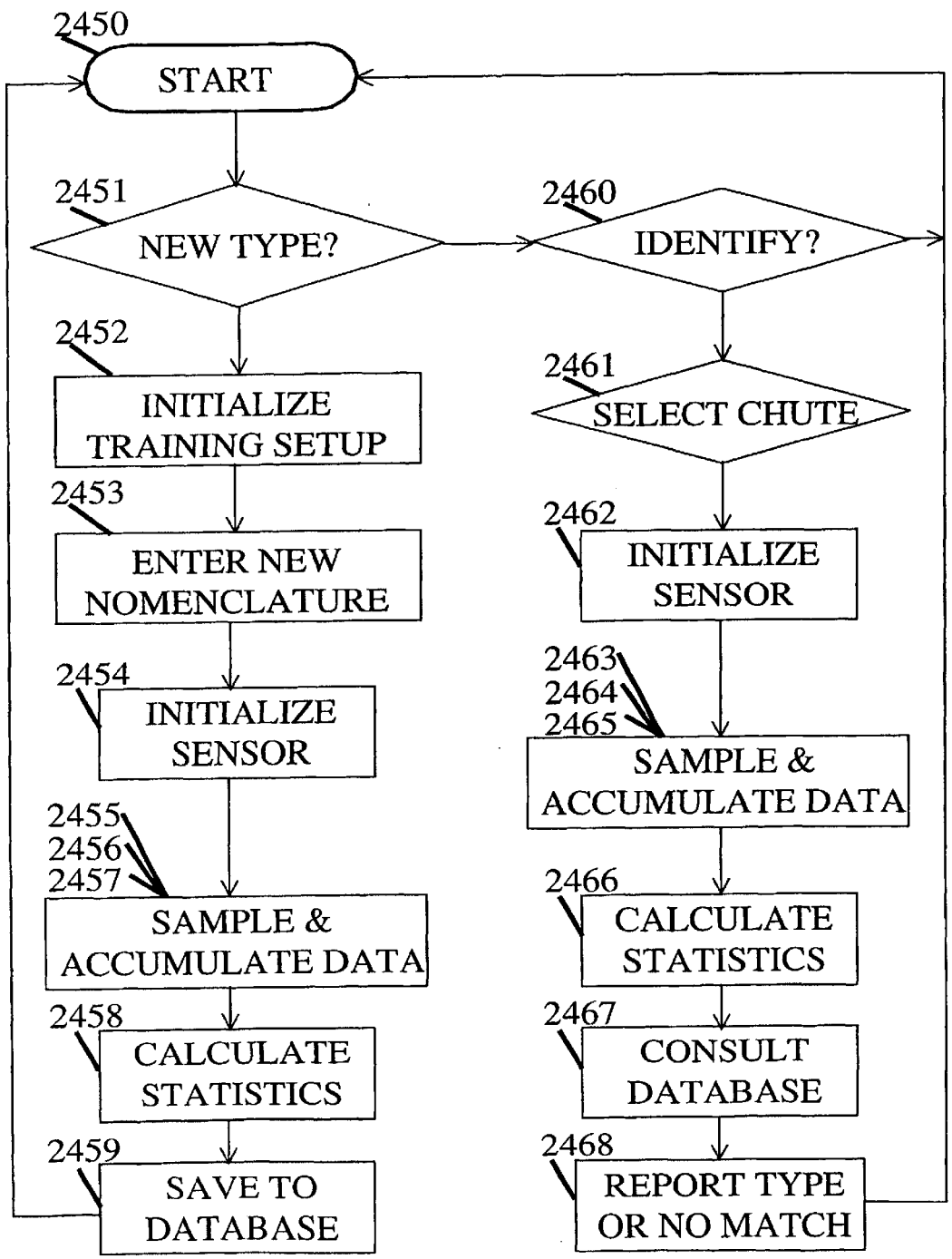
FIG. 24D is a flow chart representing the steps in ISU bulk material recognition.

FIG. 24D is a flow chart representing the steps in ISU bulk material recognition. At the process start (block 2450), the user is asked if there is a new type material (block 2451), if "yes" the user is asked to initialize training setup (block 2452), enter the new type nomenclature (block 2453), initial the ISU sensor (block 2454), and start the sampling (block 2455). The system will accumulate the data (block 2456), stop sampling (block 2457), calculate appropriate statistics (block 2458), save the data to a database (block 2459), and return to start (block 2450). If there is not a new material type (block 2451), the system will ask if identification is wanted (block 2460), if not the system will return to the start position (block 2450). If identification is requested (block 2460), a chute is selected (block 2461), the system initializes the sensor (block 2462), starts sampling (block 2463), accumulates data (block 2464), stops sampling (block 2465), calculates statistics (block 2466), compares to the database (block 2467), and finally reports the type identification or reports a "no match" (block 2468). The system then returns to the start position (block 2450).

Figure 24E:
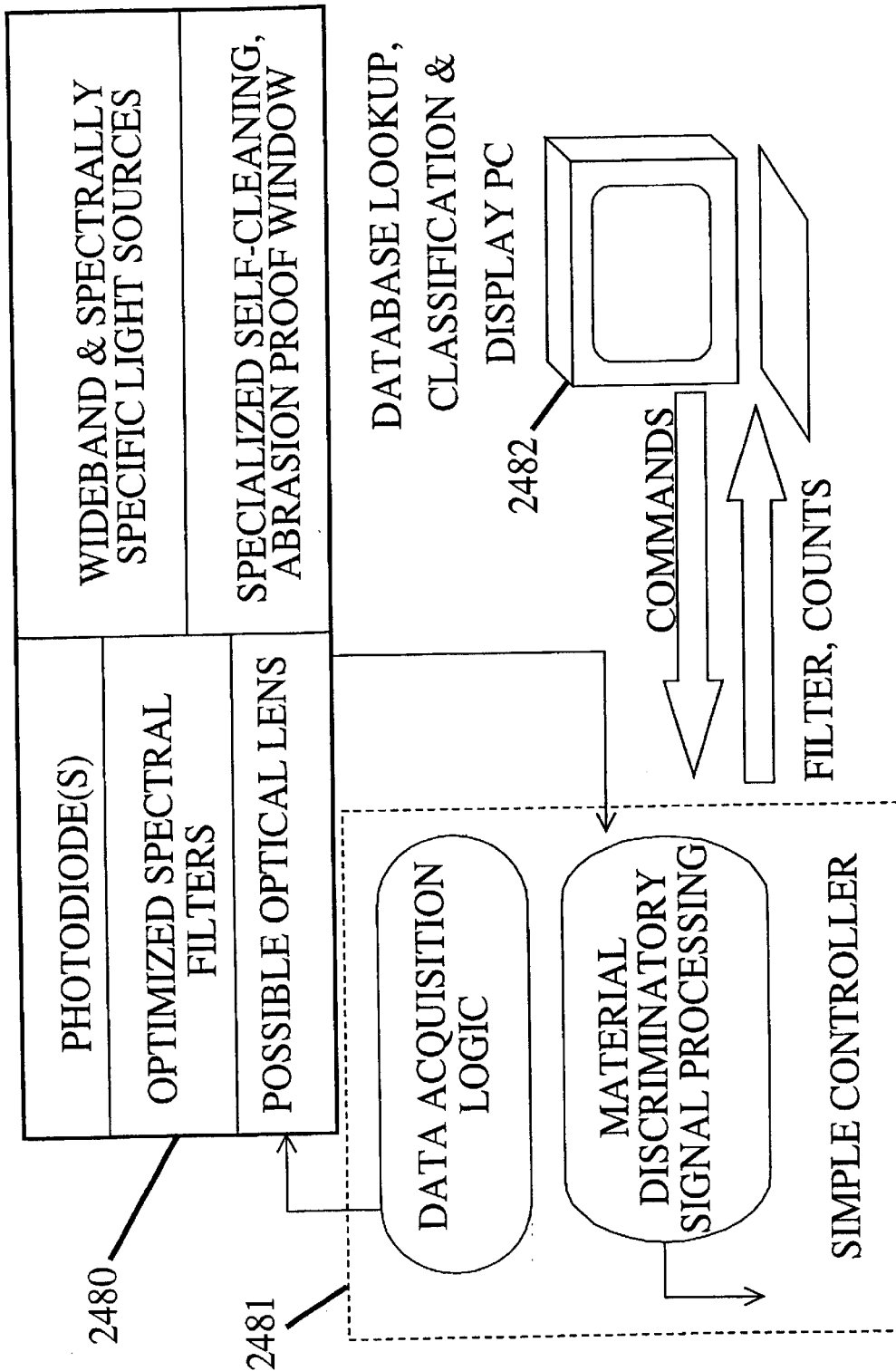
FIG. 24E is an ISU flow diagram.

FIG. 24E is an ISU flow diagram. The ISU (block 2480) contains the photodiodes, optimized spectral filters, possible optical lens, light source and self-cleaning and abrasion-proof glass covering. The ISU controller (block 2481) contains data acquisition logic and material discriminatory signal processing logic. The ISU controller (block 2481) also communicates with the Processing Controller (block 2482) or Central Processing Unit. The Processing Controller (block 2482) acts as the user interface, performs data base lookup, performs algorithmic calculations, and displays appropriate classification and identification information.

Figure 25:
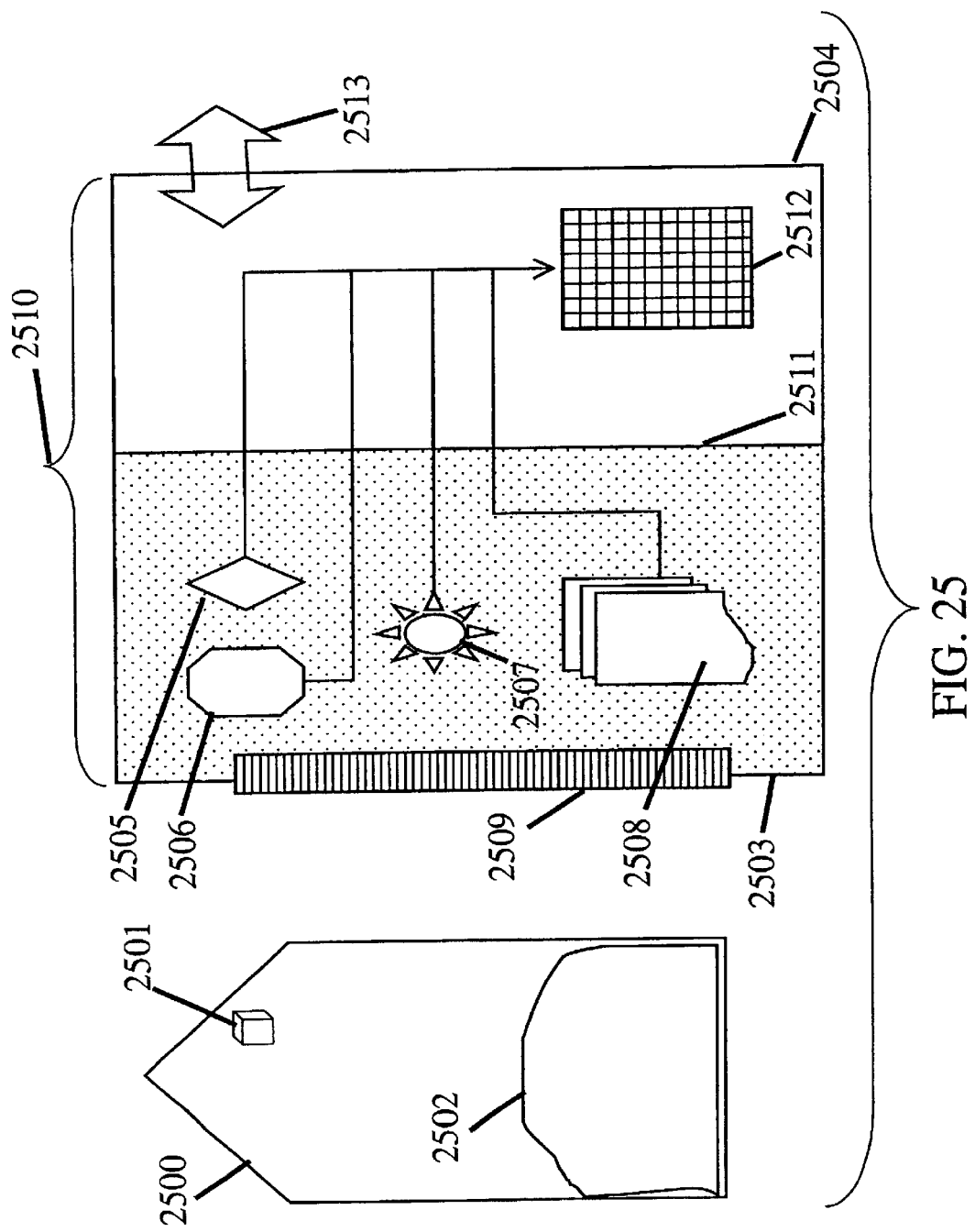
FIG. 25 is a schematic representation of an ESU (Environmental Sensor Unit).

FIG. 25 is a schematic representation of an ESU (Environmental Sensor Unit). The ESU can be packaged separately or in combination with the SSU gimbal. The ESU 2501 is attached to the top of a storage bin 2500 which contains bulk material 2502. A sectional view 2510 shows the various components of the ESU, which is packaged in a NEC Class II Div I compliant (NEMA 9 or otherwise) environmental enclosure. The enclosure 2510 consists of an unsealed housing 2503 and a sealed housing 2504. The unsealed side of the housing 2503 has a vented wall 2509 for headspace air access, a humidistat 2505, a thermostat 2506, conventional gas detectors 2507 and electronic nose hardware 2508. The electronic nose hardware 2508 consists of co-ductivity types (metal oxide, conducting polymer, etc.) or Piezo-electric types (quartz crystal micro-balance, surface acoustic wave etc.) or capacitive charge coupled (MOSFET, etc.) or other semiconductor-based sensors of an Enose nature. The sealed side of the housing 2504 contains a printed circuit board 2512 for signal processing and a low voltage, power and data input cable 2513. In this embodiment of the present invention, the elevation/tilt axis of the GSU can be used to seal and deploy the intake vented face 2509 as well as to clean the intake filters with the mechanical wiping motion as described in FIG. 7A above. This embodiment of the present invention offers advantage that sealing and cleaning the filter will extend the life of the filters by minimizing clogging from airborne dust/dirt deposits and will extend the life of all detectors 2505, 2606, 2507, 2508 because they will only have periodic and controlled exposure to the ambient air in the bulk storage container. Furthermore, when packaged in combination with the GSU, the GSU's dust measurement algorithm will ensure the filter face will not be unnecessarily exposed to heavy dust. The GSU algorithm will open the system, get a range to a known point, compare the known distance to measured distance, and close. If the measured distance is less than the known distance, then it will be concluded that the air is filled with too much dust.

Figure 25A:
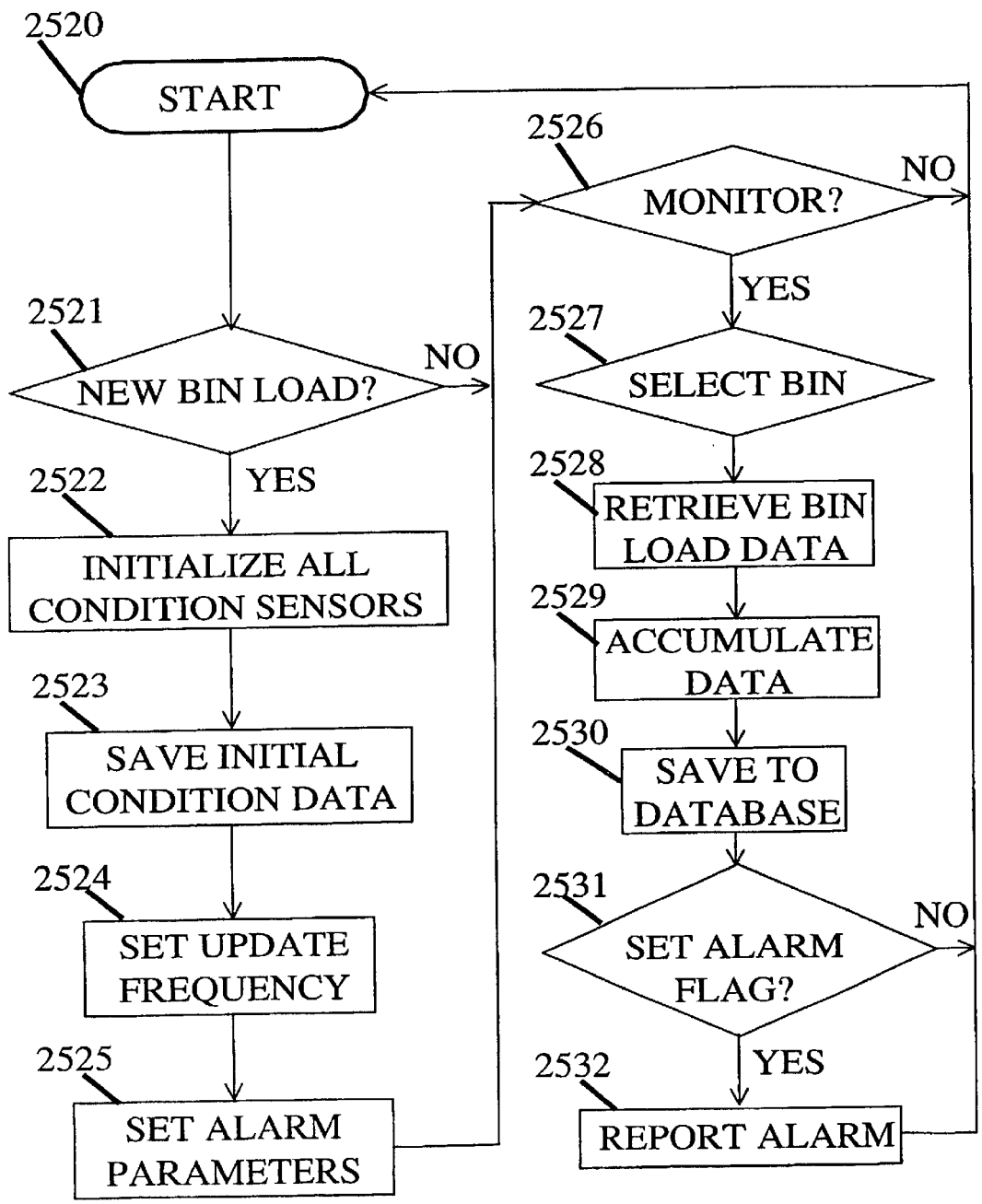
FIG. 25A is a flow chart representing the steps in ESU bulk material condition monitoring.

FIG. 25A is a flow chart representing the steps in ESU bulk material condition monitoring. At the process start (block 2520), the user is asked if there is a new bin load (block 2521). If "no", the user is asked if the bin material is to be monitored (block 2526). If there is a new bin load (block 2521), all condition sensors are initialized (block 2522), initial condition data is saved (block 2523), the update frequency is set (block 2524), and finally, alarm parameters are set (block 2525). The user is then asked if the bin should be monitored (block 2526). If "No", a return to start (block 2520) is completed. If "Yes", the user selects the bin to be monitored (block 2527), bin load data is retrieved (block 2528), sensor data is accumulated (block 2529), and data is saved to a database (block 2530). Data is checked to determine if an alarm flag should be set (block 2531). If an alarm should be set, it is reported to the control unit (block 2532). If no alarm is to be set, a return to start (block 2520) is completed.

Figure 26:
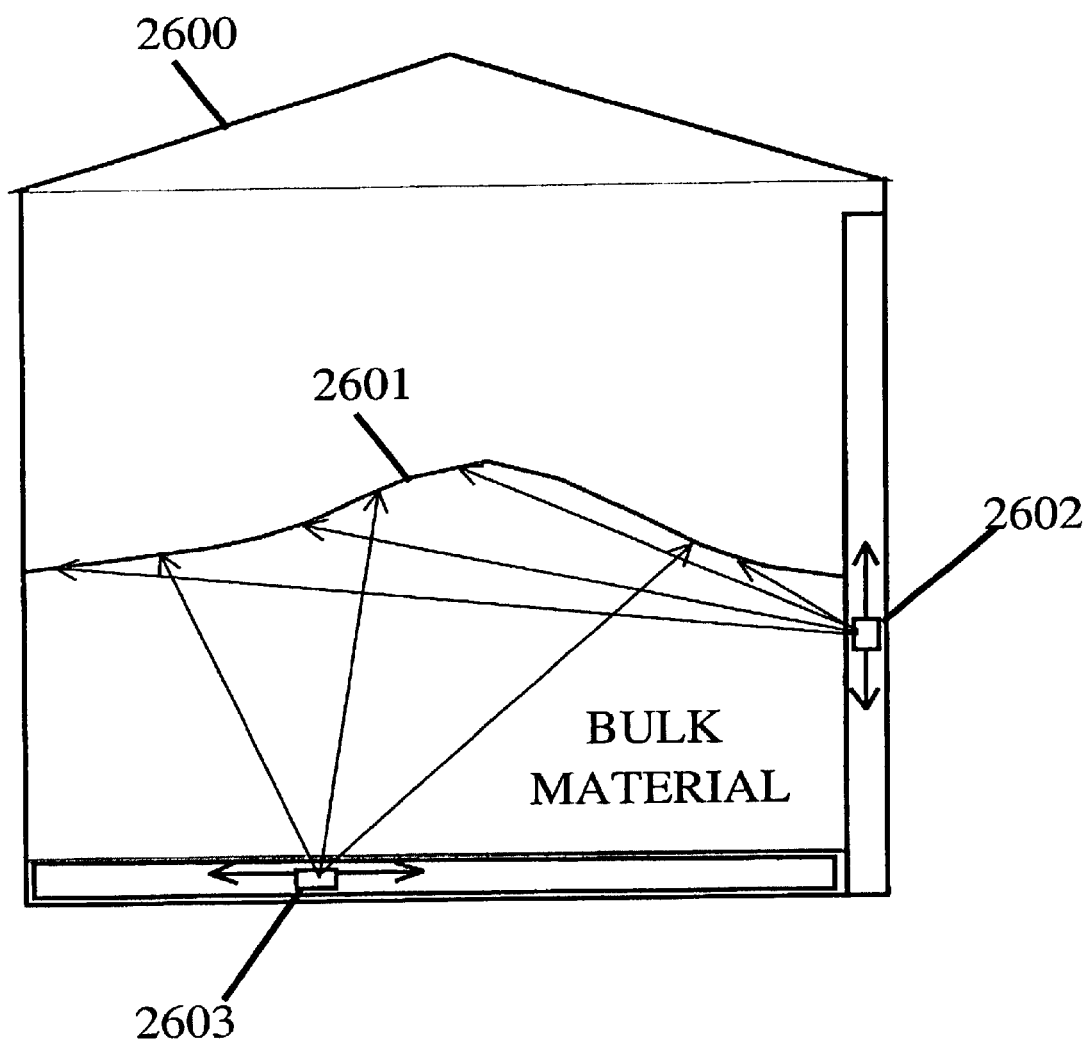
FIG. 26 is a schematic representation of horizontal and vertical combined grain (bulk material) penetrating radar.

FIG. 26 is a schematic representation of horizontal and vertical combined grain (bulk material) penetrating radar. The emitter and receiver penetrating radar instruments 2602-2603 are within the storage facility 2600 and are located underneath and along the material to be measured 2601. The instruments are embedded, movable and contain the control and processor electronics and synthetic aperture image processing electronics. A cable data communications port (not shown) can transmit and receive data via a cable-borne data communications port, RF (radio frequency) transmit/receive, IR (infrared) or other optical communication method.

Figure 26A:
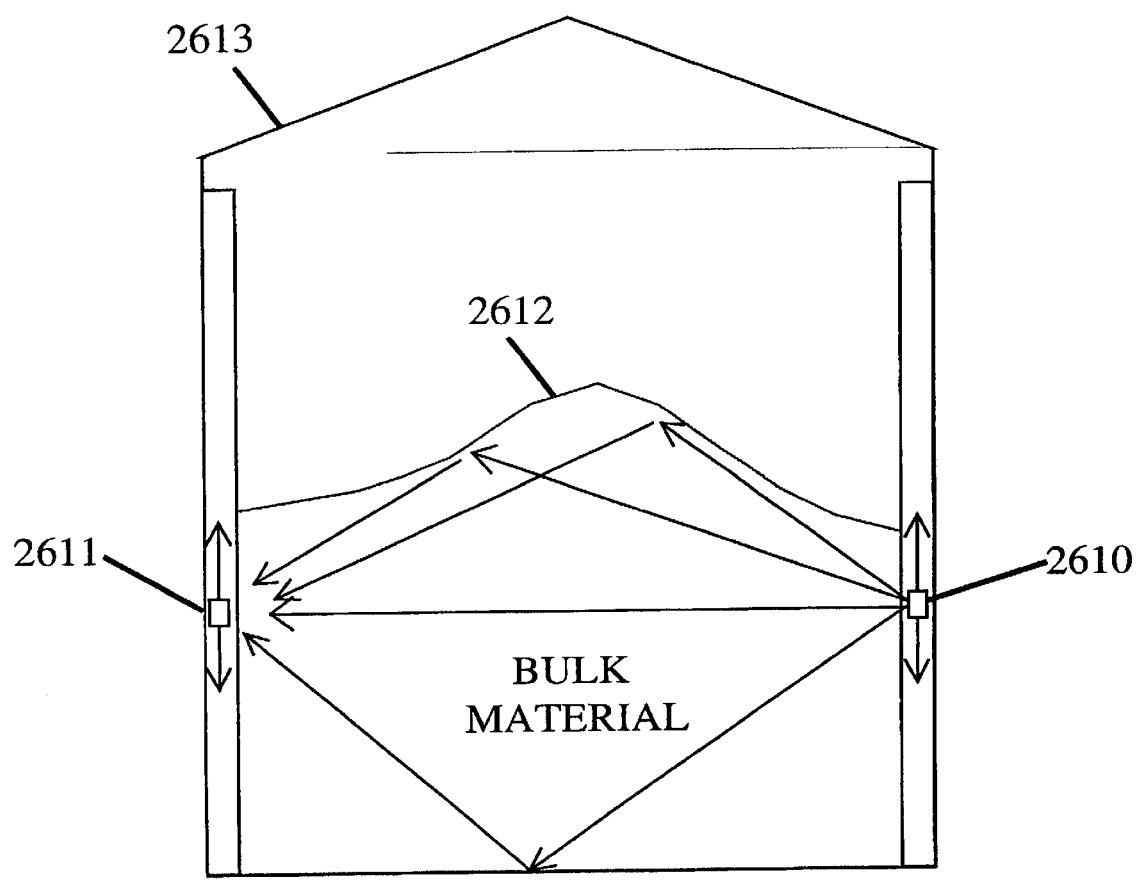
FIG. 26A is a schematic representation of two movable vertically mounted combined grain (bulk material) penetrating radar units.

FIG. 26A is a schematic representation of two movable, vertically mounted combined grain (bulk material) penetrating radar units. In this alternate embodiment of the present invention, one instrument acts as the emitter 2610 and the other as the receiver 2611. The embedded instruments can measure the bulk material 2612 within the storage facility 2613. Electronics and communication is as described in FIG. 26 above.

Figure 26B:
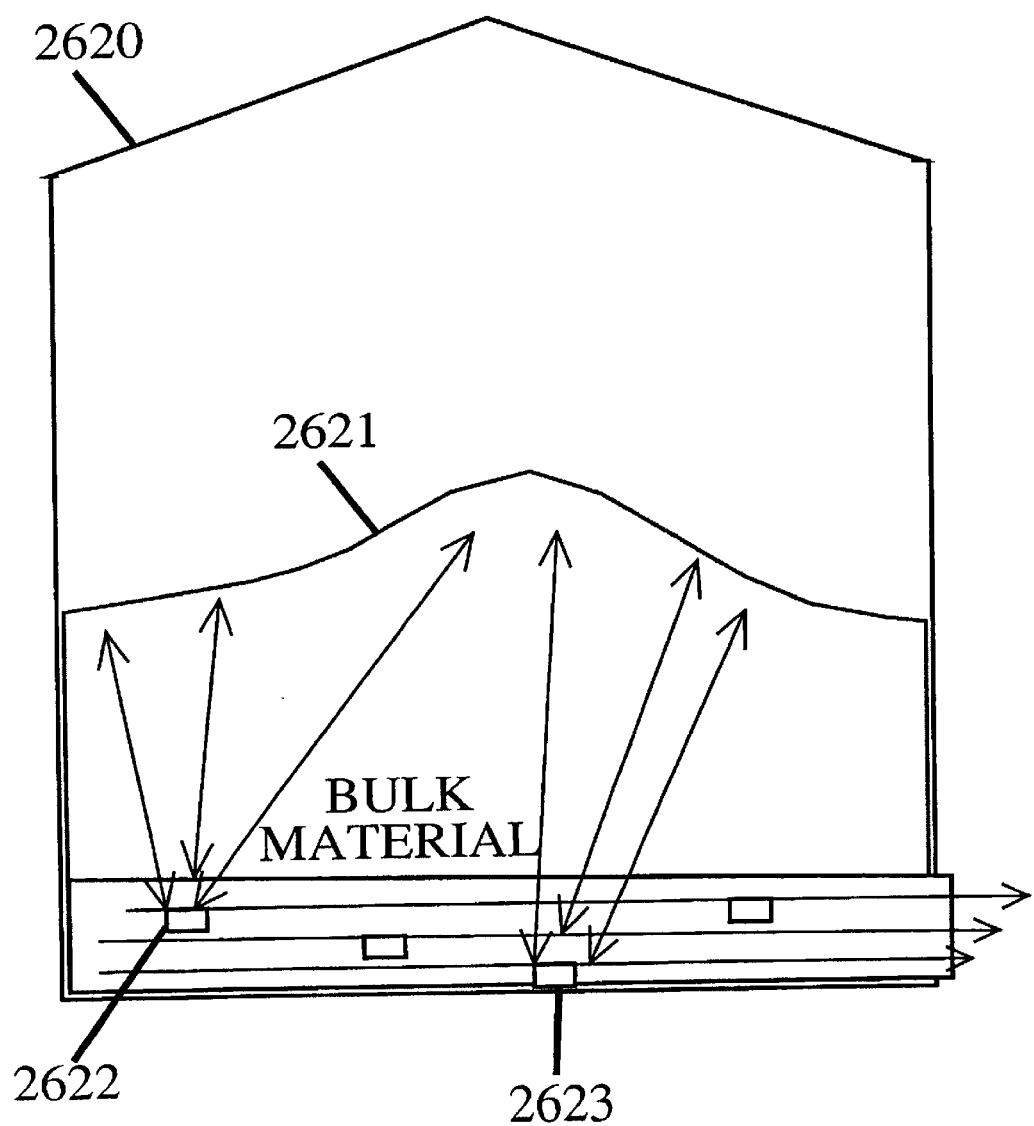
FIG. 26B is a schematic representation of an alternate grain (bulk material) penetrating radar via wire bundled arrays.

FIG. 26B is a schematic representation of an alternate grain (bulk material) penetrating radar via wire bundled arrays. Wire bundles 2622,2623 are in conduit or as electrical cord configurations with evenly spaced antennae in emitter and receiver nodal arrays for measurement of bulk material 2621 with a storage facility 2620. In this configuration a pulsed wave can be created in a similar fashion as a mobile transceiver array but with the advantage of no moving parts. The instruments are embedded, movable and contain the control and processor electronics and synthetic aperture image processing electronics. A cable data communications port (not shown) can transmit and receive data via a cable-borne data communications port, RF (radio frequency) transmit/receive, IR (infrared) or other optical communication method.

Figure 26C:
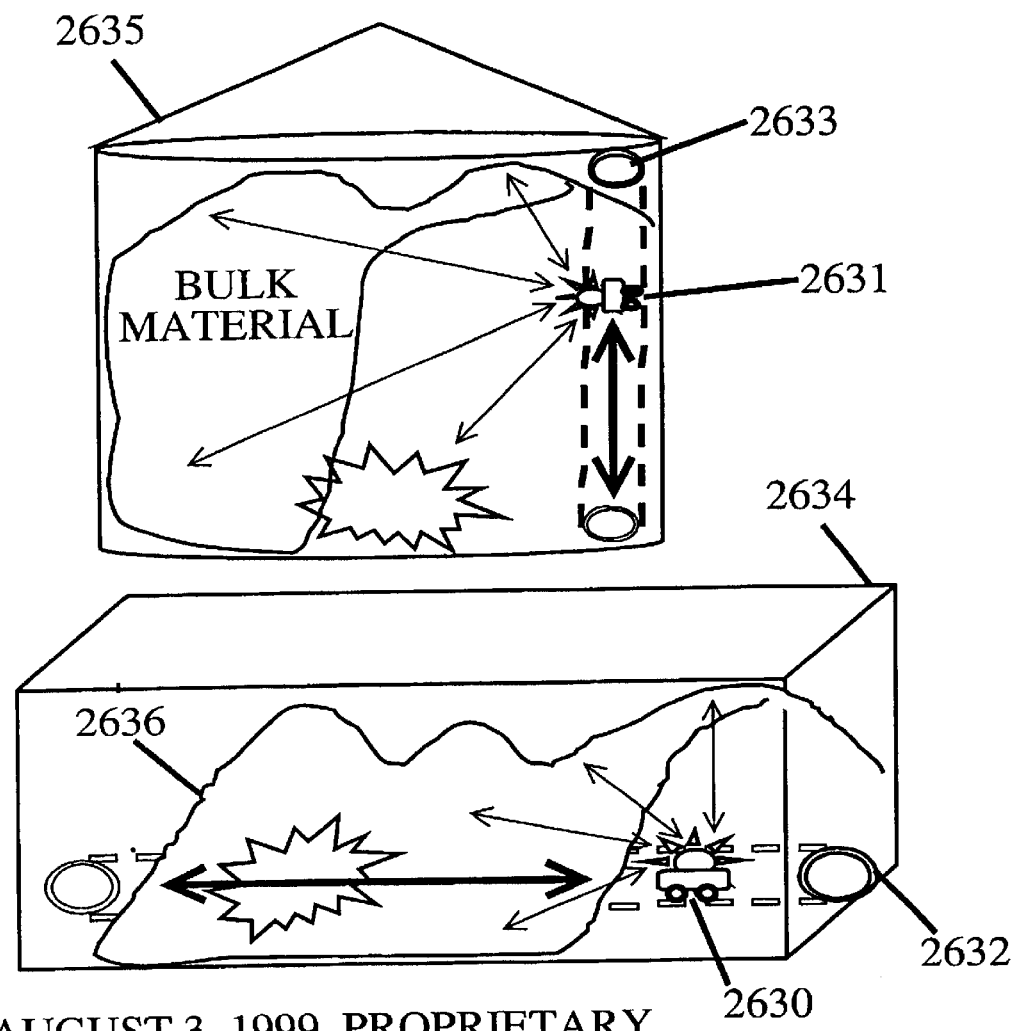
FIG. 26C is a schematic representation of a grain penetrating radar installation.

FIG. 26C is a schematic representation of a grain penetrating radar (GPR) installation. Movable radar antenna array 2630, 2631 are shown mounted in a cylindrical storage facility 2635 and a rectangular storage facility 2634 for measuring bulk material/grain 2634. The GPR 2630, 2631 is movable within a housing 2632, 2633. The GPR measures grain/air boundary surface discontinuity for a full surface plot and engulfment awareness (volume and safety). The RF dielectric signature throughout the material mass is collected for recognition. The RF dielectric property changes throughout the material mass will pinpoint targeting of quality problems (conditioning). The instrumentation will detect general density and density anomalies such as voids for quantity, quality and engulfinent hazards (volume, condition, safety). A combination of the above provides bulk material weight. The instrumentation will also provide insect detection and control.

Figure 27:
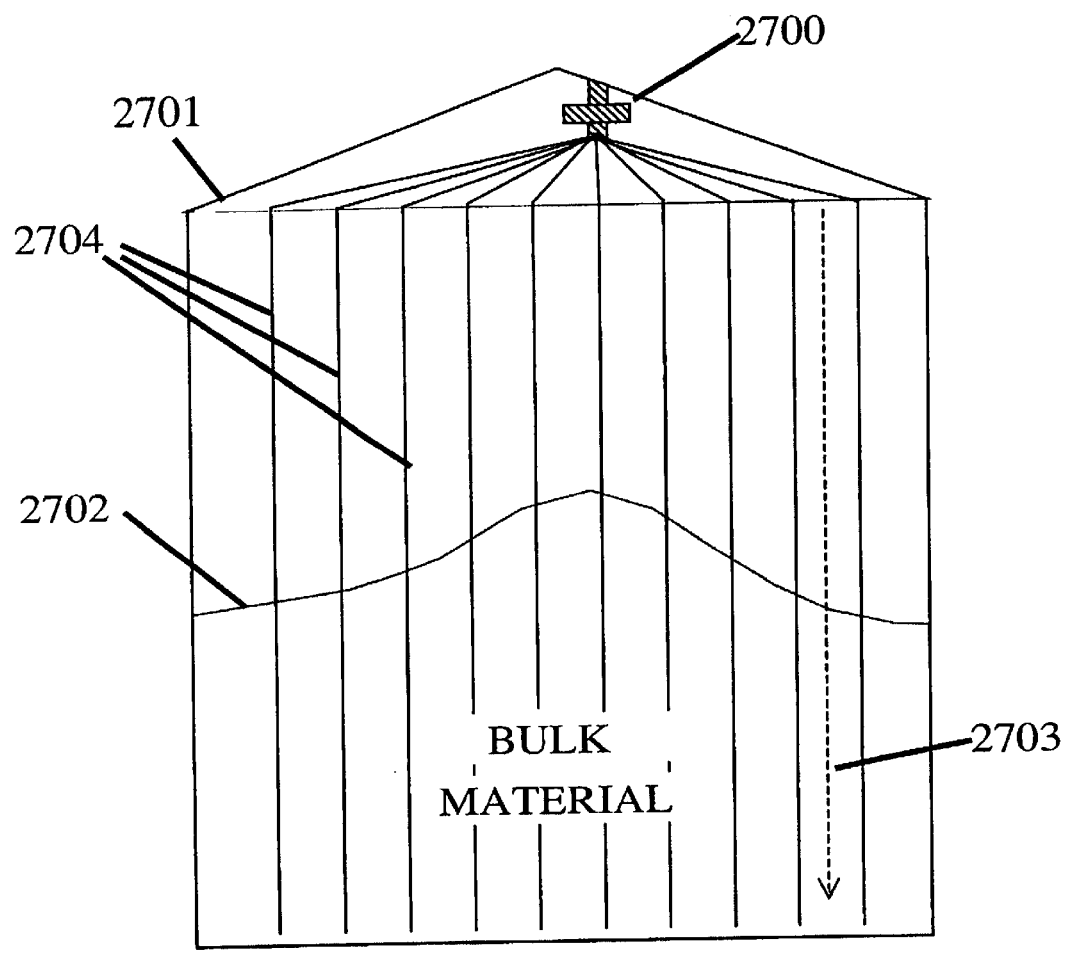
FIG. 27 is a schematic representation of a multi-point time domain reflectometry installation.

FIG. 27 is a schematic representation of a multi-point time domain reflectometry 2700 installation, an alternate embodiment of the present invention. Existing cable shields, twin lead or coax cables 2704 can be utilized to measure bulk material 2702 within a storage facility 2701. A RF signal 2703 is sent along successive conductor pairs. The grain to air boundary at the top of the leads as well as at the base provides a full surface profile (volume and safety). The average grain boundary between the lead pairs can provide additional accuracy for measurement. The dielectric signature throughout the grain/bulk material is obtained for type identification (recognition) and dielectric monitoring is performed to detect changes such as heating, etc. for condition monitoring. The density is measured for volume calculation and detection of quality characteristics such as compaction, caking, and voids, etc. Moisture measurements can be made at full depth to monitor quality. A combination of the above measurements will yield the total weight of the grain/material. Insect detection and possible control is also provided.

Figure 28:
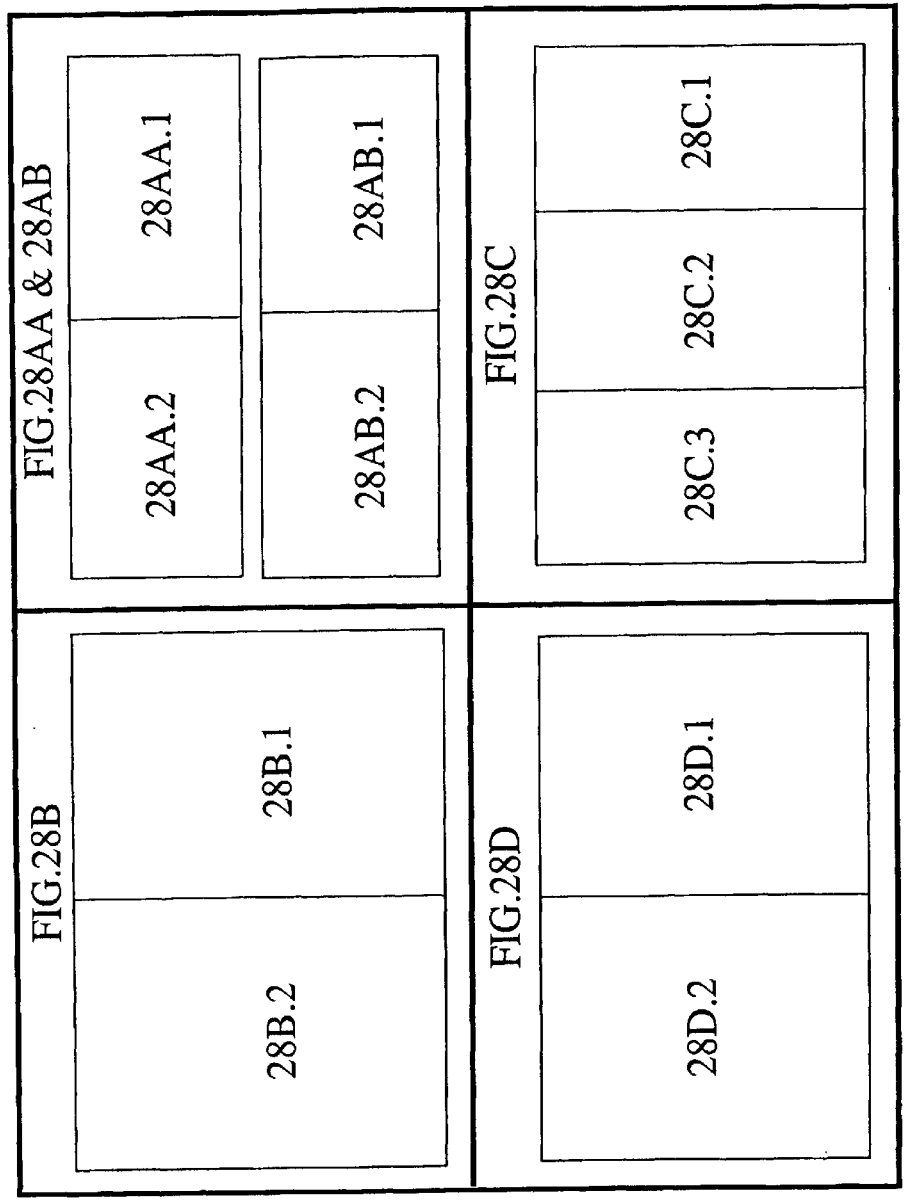
FIG. 28 is a modular representation of a typical installation configuration.

FIG. 28 is a modular representation of a typical installation configuration. The ISU 2801 and the ESU 2802 are serially connected via a category 5 LAN cable 2805 with 8 wires. The LAN cable 2805 can accommodate up to one hundred maximum additional units, which can be serially attached within a facility as required. The LAN cable 2805 enters the roof 2821 via a dust-proof electrical conduit box 2818. The roof 2821 contains a support bracket 2819 to hold the weight (20–25 lbs.) of the SSU 2803 (note: all references to the SSU-Scanning Sensor Unit-are equal to the GSU). A waterproof electrical conduit box 2820 interconnects all cables vial a captive 25 pin D-connector 2813. The SSU 2803 is hung via a sturdy metal vertical mounting bracket 2806. A nine wire cable 2812 is contained within the vertical mounting bracket 2806. A quick-disconnect 9 pin D-connector 2811 allows the SSU 2803 to be physically removed when necessary. The SSU circuit board 2808 contains all control electronics and is connected via cable 2809 to the 9 pin D-connector 2811. The azimuth gimbal 2810 allows rotation of the SSU 2803. A conduit 2814 carries cables from the conduit box 2820 to the junction box 2804. The waterproof junction box 2804 is shown mounted external to the facility. The junction box carries 117V A/C power in, communicates to/from other downstream junction boxes via conduit 2816 as necessary and communicates to the host computer and internet via category 5 cable within conduit 2817.

Figure 28A:
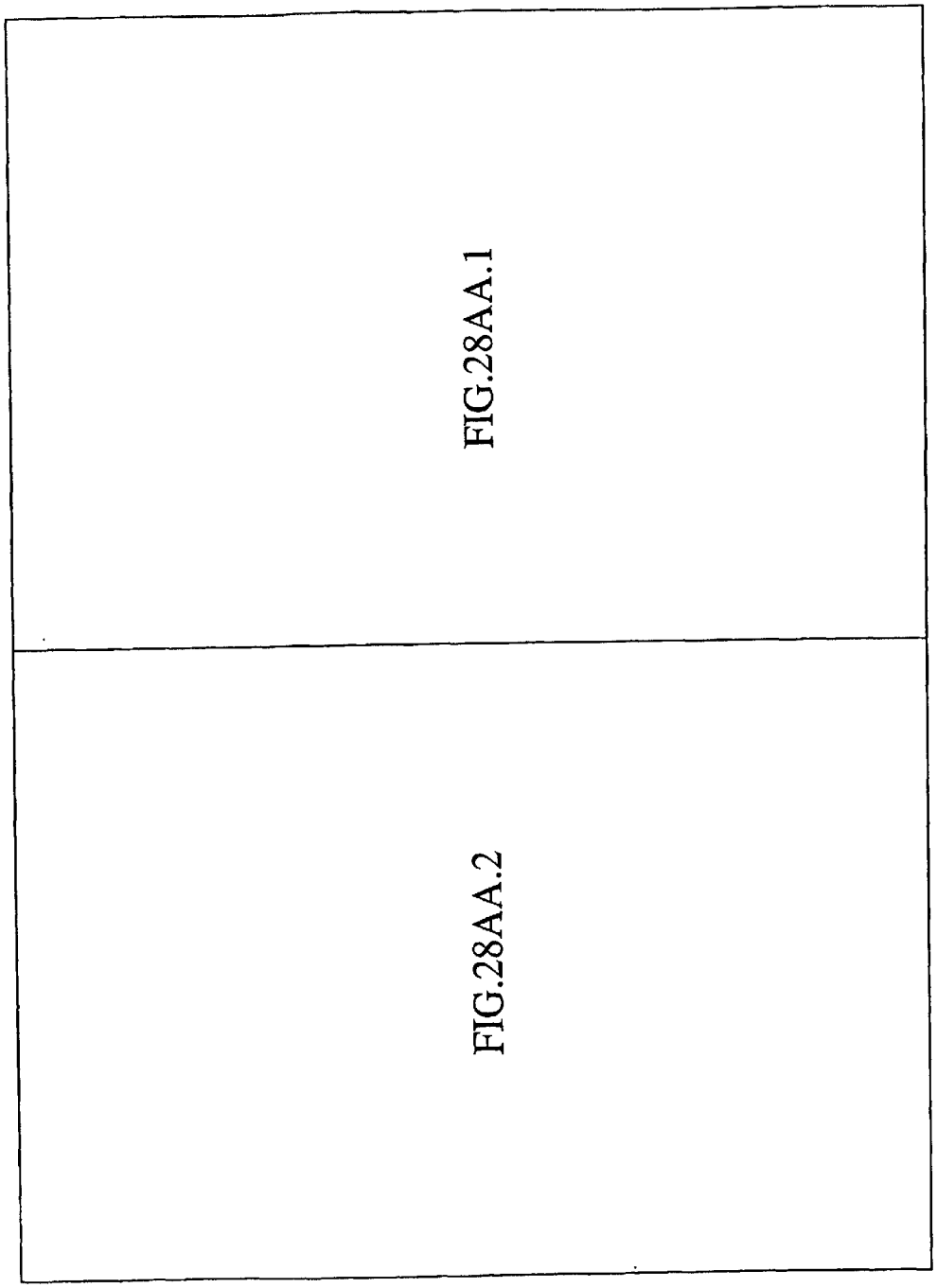
FIG. 28AA, 28AB are schematics of the internal electronics and sensors within a GSU (SSU).
Figure 28A:
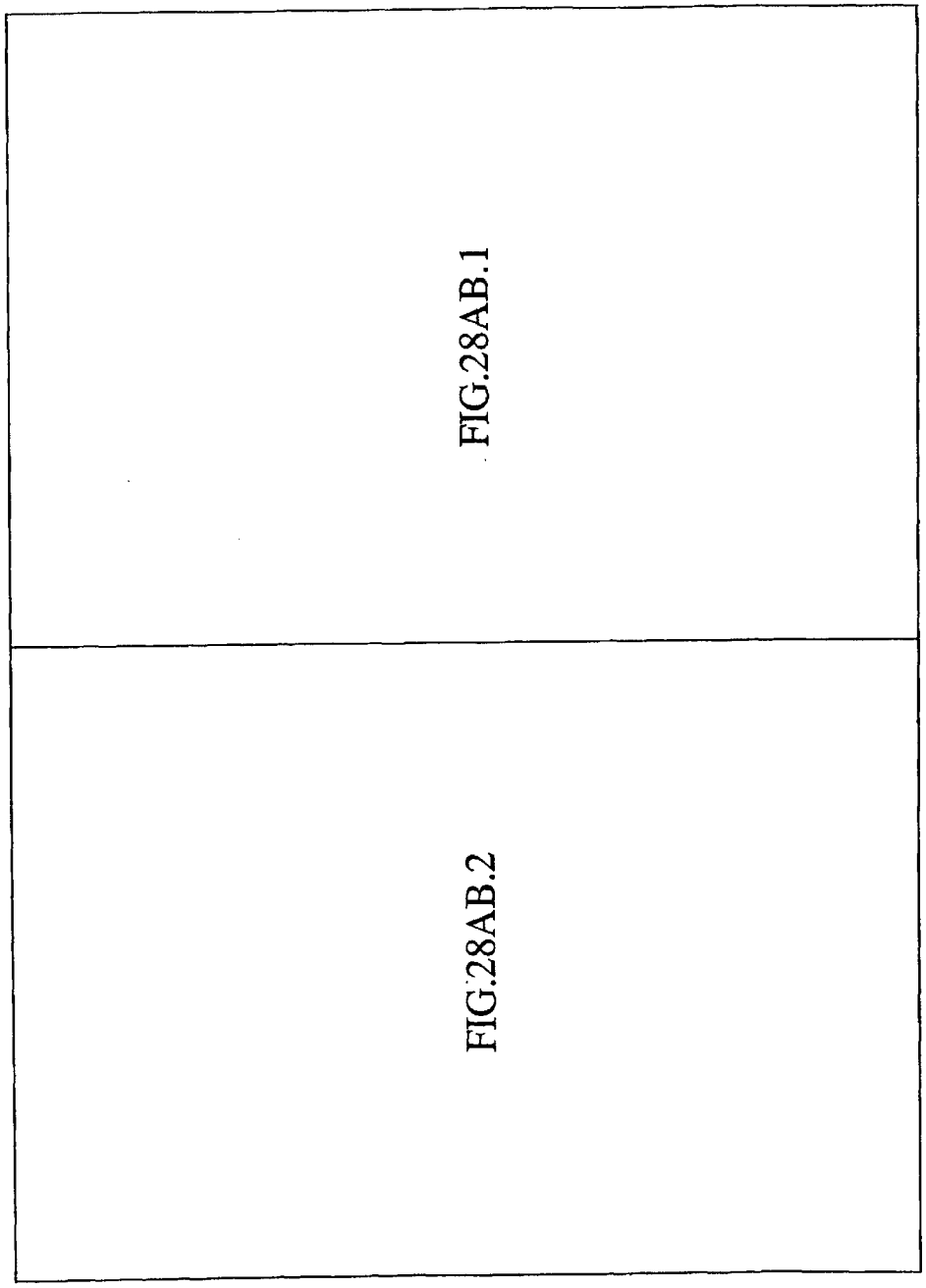

FIGS. 28AA, 28AB are a schematics of the internal electronics and sensors within a GSU (SSU). The SSU 2803 can rotate in elevation and contains a tilt sensor 2830, video camera 2831 and laser rangefinder 2832 which are electronically connected to the SSU circuit board 2808. The upper portion 2841 of the SSU contains a circuit board 2808 and stepper motors 2833, 2834. The SSU circuit board 2808 contains the motor drivers 2835, micro-controller 2836, optical switches 2837, the RS232 interface 2838, UARTS 2839 and cable connections 2840. Electronic stepper motors 2833, 2834 drive the SSU in elevation and azimuth respectively.

Figure 28B:
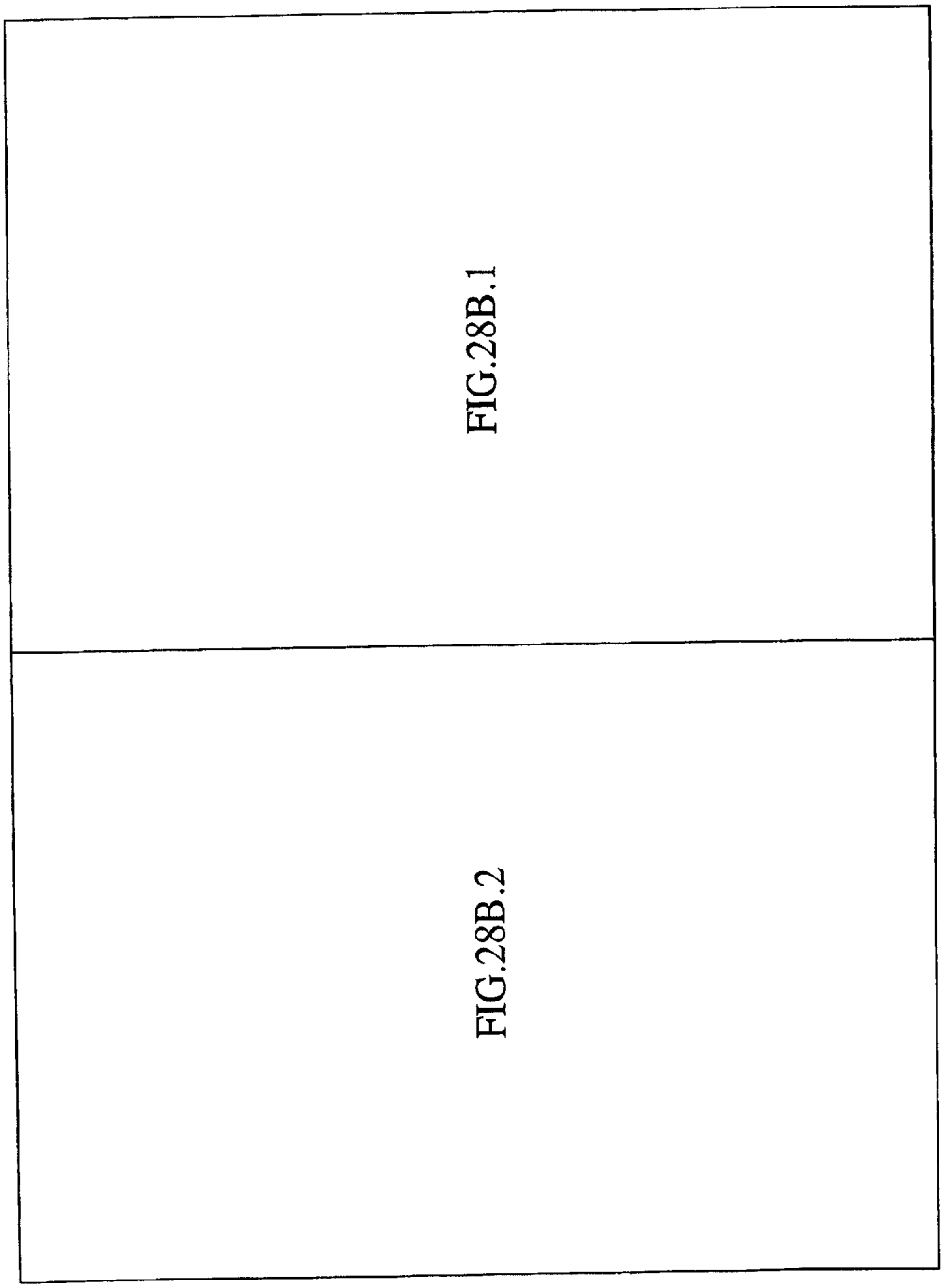
FIG. 28B is a schematic of the internal electronics and sensors within the ESU and ISU.

FIG. 28B is a schematic of the internal electronics and sensors within the ESU 2802 and the ISU 2801. The ISU 2801 contains a lamp source 2850, the spectrum-analyzer 2851 and the ISU printed circuit board 2852 with control and interface electronics. The ESU 2802 contains a temperature sensor 2854, and gas detectors for $CO_2$ 2855, ammonia 2856, and phosphine 2857 (note: other gas detectors can be added/substituted) and also a relative humidity sensor 2858. The ESU printed circuit board 2853 contains all control and communication electronics.

Figures 28C, 28C.1, 28C.2, 28C.3:
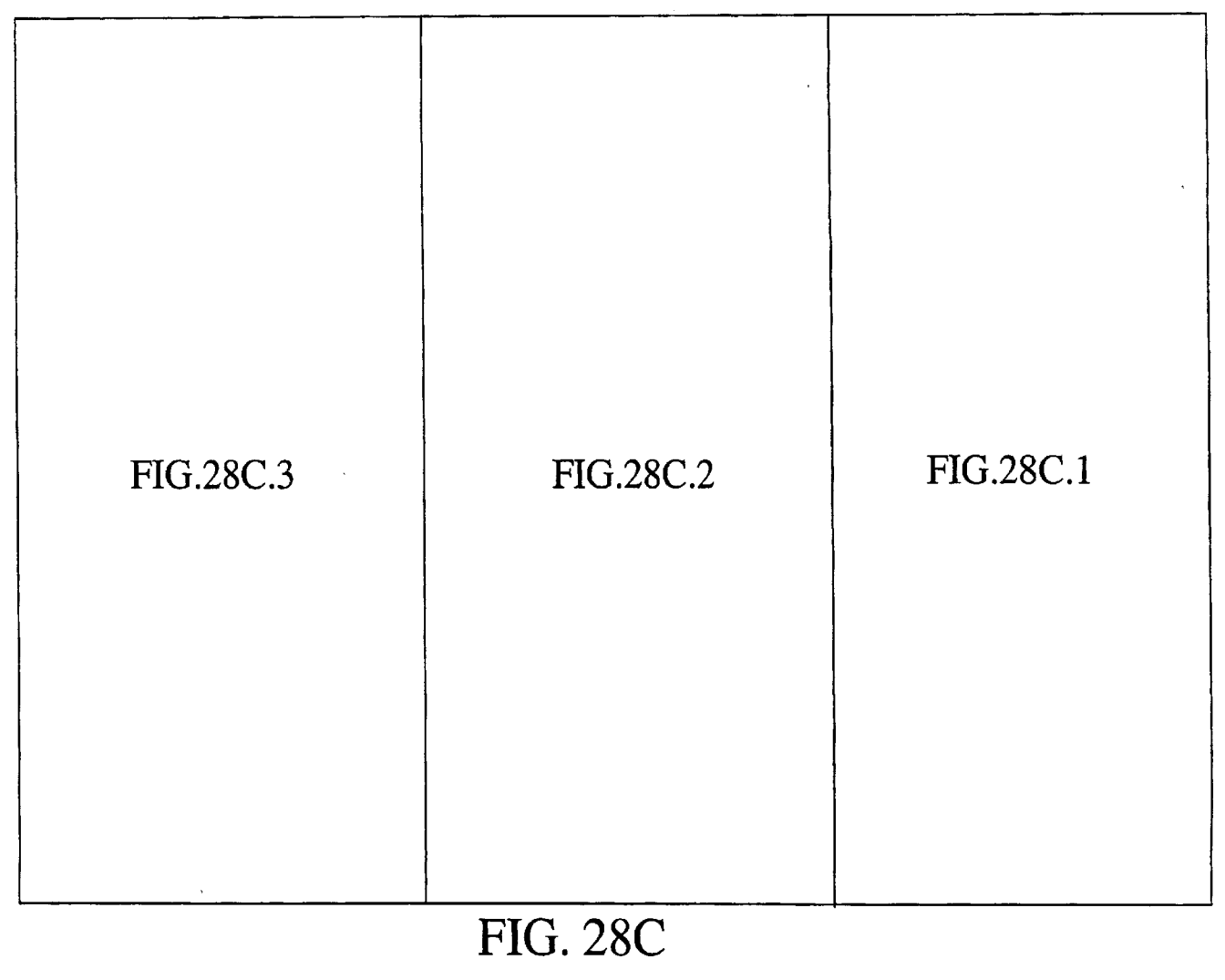

FIG. 28C is a schematic of the internal electronics and power for the junction box 2804. The junction box contains noise and voltage spike transient suppressors 2862, an AC to DC converter board 2860, and an optional buffer board 2861 to interface with other junction boxes via output cable 2816 for video multiplexing and control reporting. In the illustration of FIG. 28C, the buffer board 2861 contains video multiplexers and components for installations with multiple cameras and long runs. For smaller installations the buffer board 2861 will have passive wiring. If no other junction boxes are required, the buffer board is passively wired and the interface is directly to the host computer via output cable 2817. All cables to junction box interfaces are waterproof interfaces.

FIG. 28D is a schematic of the host computer and interface to the junction box. The interface cable 2817 is connected via a terminal box 2875 near the computer. The video interface 2870 is connected to the monitor 2872. The user interface 2874 consists of a keyboard and mouse. A printer 2873 is needed for report and screen capture printing. The minimum computer 2871 requirements are a 300 MHz Pentium II processor with at lease 128 MB RAM, 10 GB HD, and a control area network (CAN) interface board.

FIG. 29 is a schematic of the universal AIP instrument board. Shown are the SSU circuit board 2808, the ISU printed circuit board 2852, and the ESU printed circuit board 2853. The base unpopulated circuit board is one part number and universal for SSU, ISU, ESU usage. The components are unique to the SSU 2803, the ISU 2801 and the ESU 2802 which require different assemblies and thus have different part numbers when assembled.

Figure 29A:
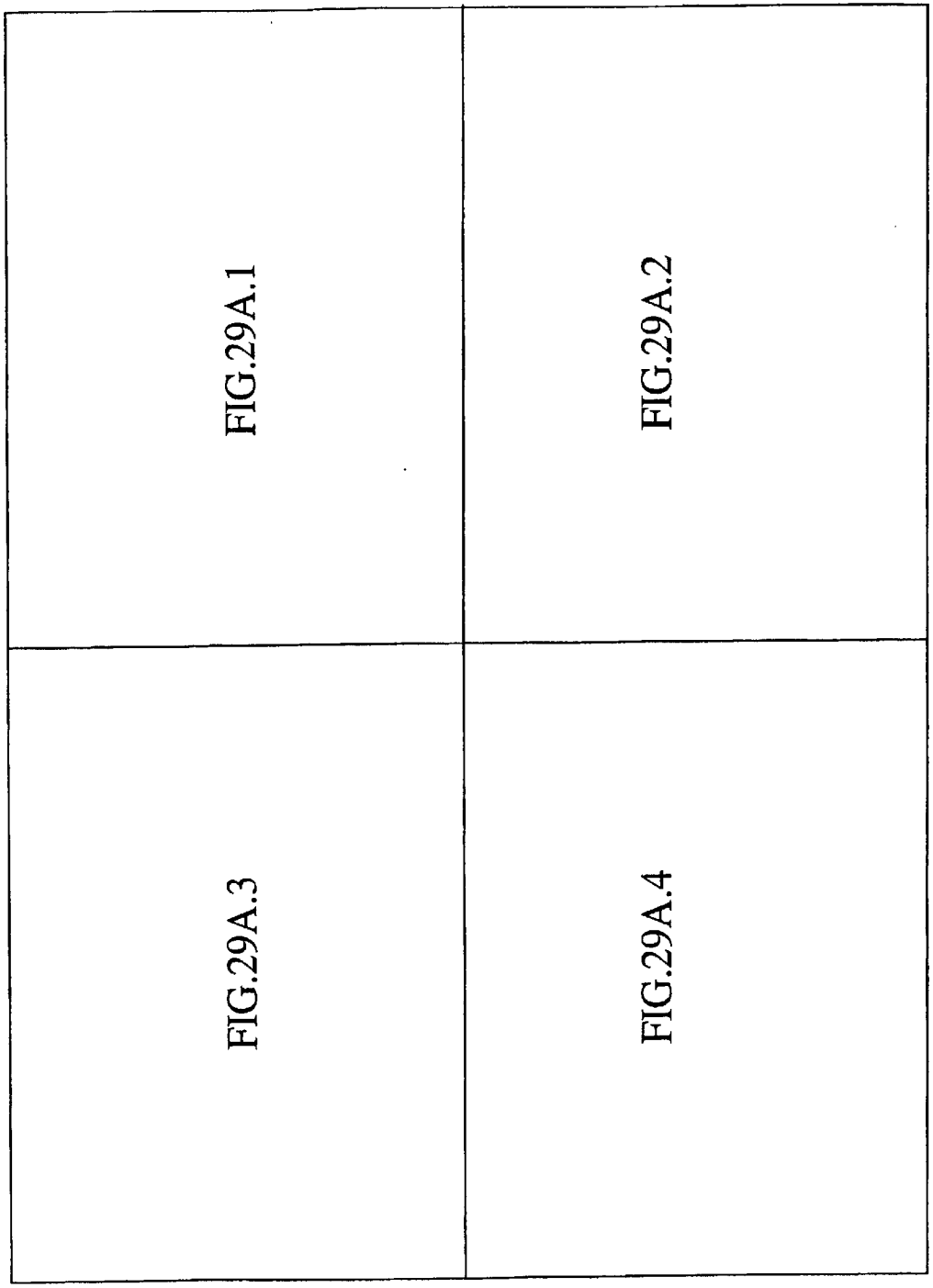
FIG. 29A is an electrical schematic of the universal AIP board connections when wired as in a SSU configuration.

FIG. 29A is an electrical schematic of the universal AIP board connections when wired as in a SSU configuration 2808. Shown are cable connections to the elevation stepper motor 2833 and the azimuth stepper motor 2834. Also shown is the connection 2902 which goes to the nine wire cable 2812 (See FIG. 28) that is contained within the vertical mounting bracket 2806 (See FIG. 28). Also shown is a 20-pin connector 2901 which allows communication to the SSU 2803 (See FIG. 28).

Figures 29B, 29B.1, 29B.2, 29B.3, 29B.4:
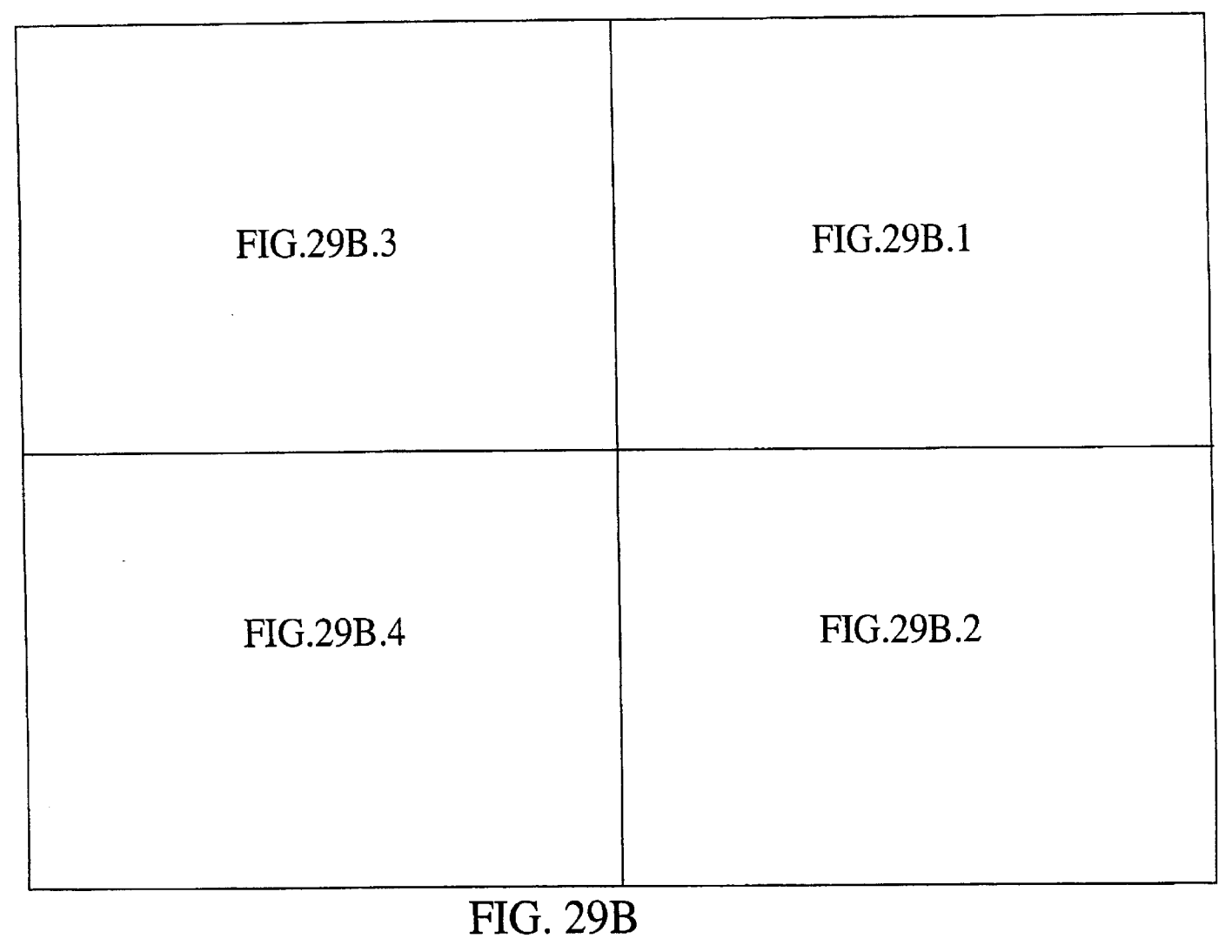

FIG. 29B is an electrical schematic of the SSU elevation/tilt section wiring. The 20 wire input cable 2901 supplies communications to and from the SSU circuit board 2808 (FIGS. 28, 29A). The 20 wire cable 2901 must contain stranded 28 gage flex cable as the wires flex approximately 180 degrees in elevation. The 20 wire cable 2901 connects the SSU tilt sensor 2830, video camera 2831 and laser rangefinder 2832 to the SSU circuit board 2808.

Figure 29C:
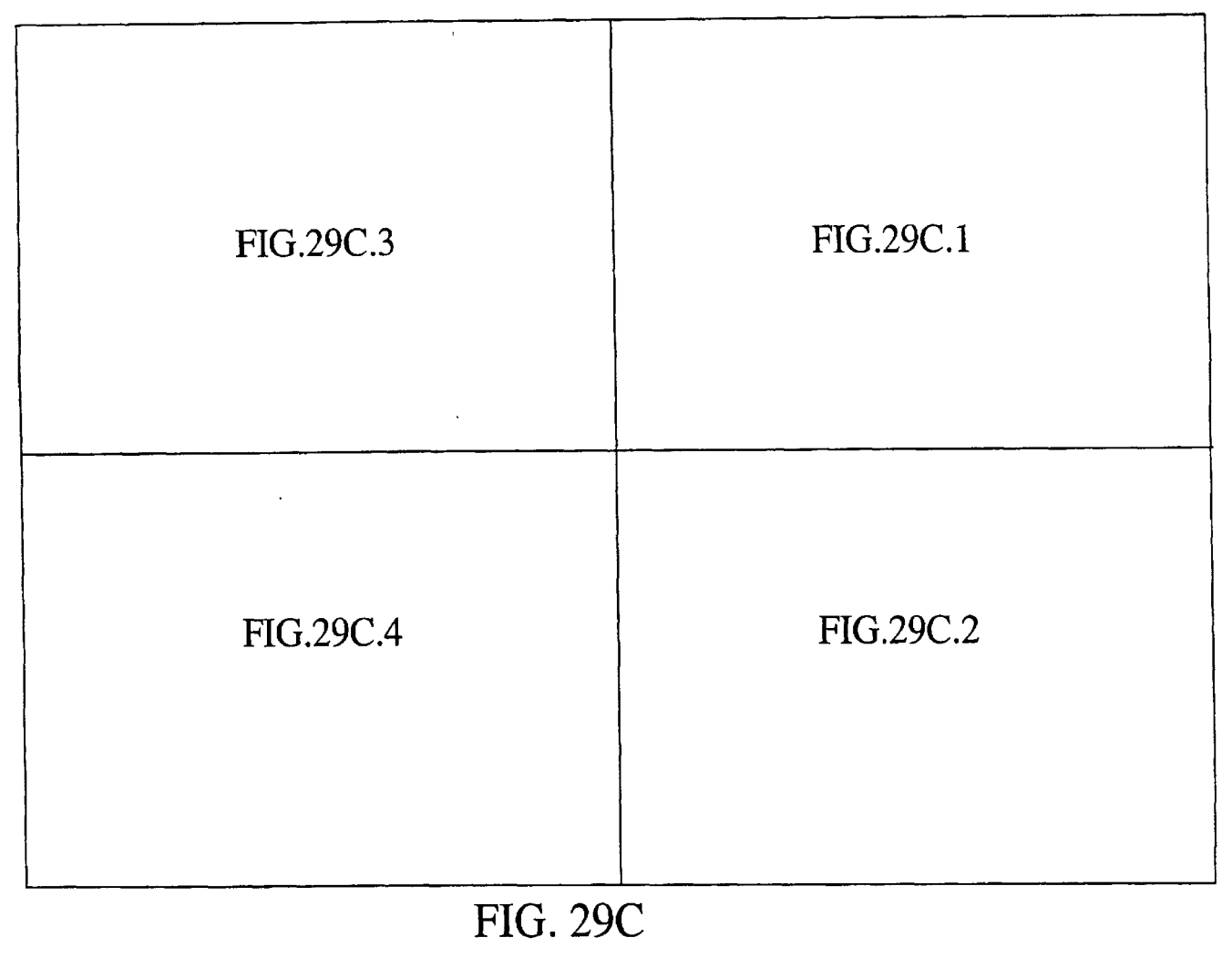

FIG. 29C is an electrical schematic of the main power and data junction box wiring. A small electrical conduit box 2903 located in the SSU top assembly integrates connection wiring between the SSU, downstream ESUs and ISUs, and the junction box. The input cable 2906 must be flex cable as the azimuth can rotate 360 degrees. In the illustration of FIG. 28C, the buffer board 2861 contains video multiplexers and components for installations with multiple cameras and long runs. The buffer board 2905 is identical to the buffer board 2861 (FIG. 28C) shown with a more detailed wiring schematic. A passive wiring board 2904 (for smaller installations) is also shown. The passive board 2904 will substitute for the buffer board 2905 in small installations.

FIG. 29D is an electrical schematic of the host computer connection through a small conduit box 2875 (FIG. 28D). The input cable 2817 (FIG. 28D) to the conduit box 2875 is a category 5 cable within conduit. A dongle box 2910 (a supplier/user hardware protection key) is supplied to the user application system. Also (as seen in FIG. 28D) shown in FIG. 29D are the video interface 2870, the system monitor 2872, the user interface 2874 (keyboard and mouse) and a printer 2873. The user may select video camera within the facility for display on the video monitor 2870.

FIG. 30 is a schematic layout of the "Universal" ESU/ISU/SSU" printed circuit board 3000. The base unpopulated circuit board 3000 is one part number and universal for SSU, ISU, and ESU usage. When components are added for the SSU, ISU or ESU, the populated board will have different assembly part numbers. Shown are all of the input/output connectors. There are two 12-pin (J2, J3), two 14-pin (J4, J5), and two 20-pin (J1, J6) connectors on the board.

FIGS. 30A, 30B, 30C, 30D are schematic component layouts of the "Universal" ESU/ISU/SSU printed circuit board.

Figure 30A:
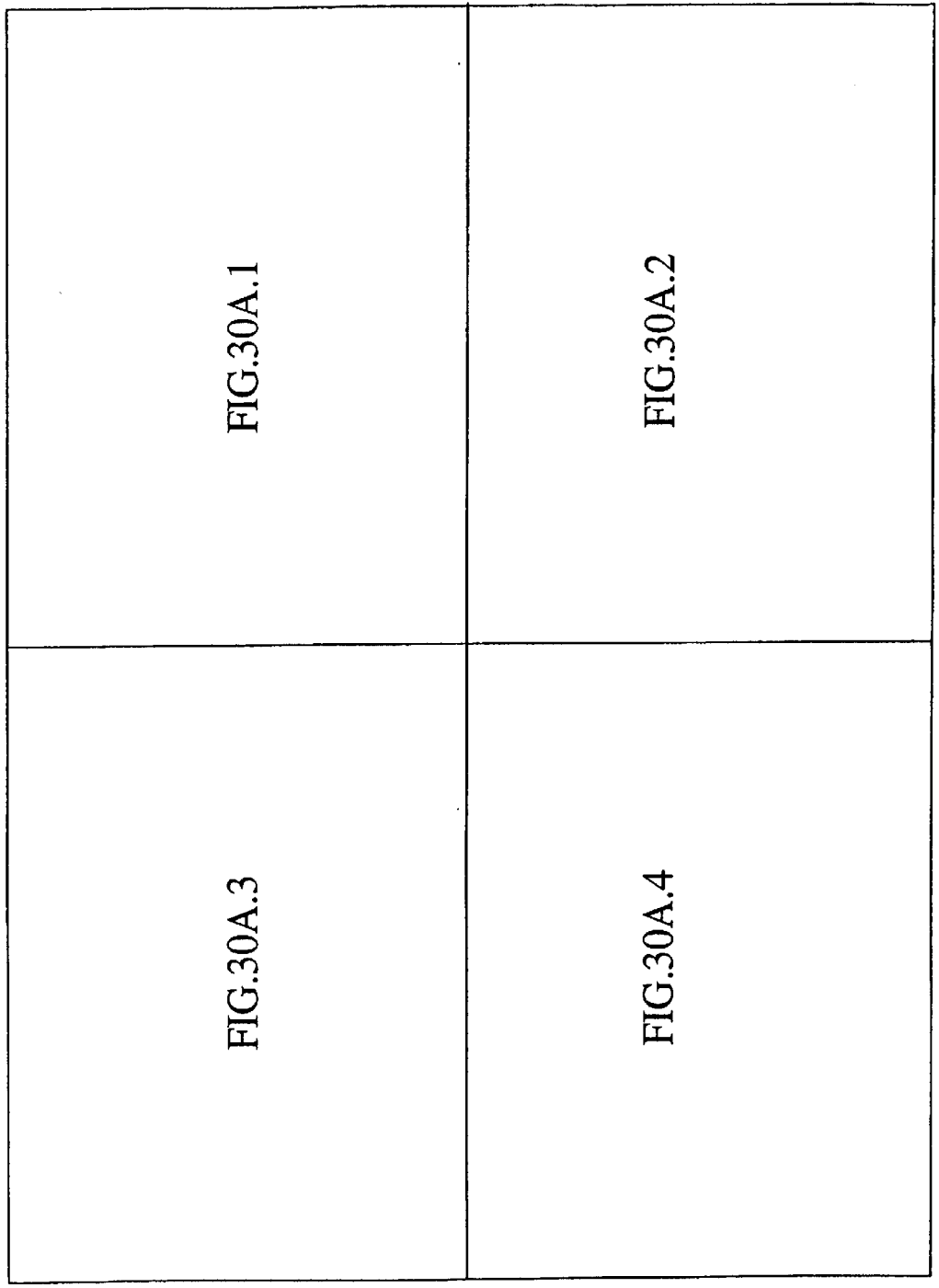

FIG. 30A represents the upper left quadrant of the board 3000 and shows an insert schematic of the "Universal" ESU/ISU/SSU" printed circuit board 3000. Wiring 3021 is shown to a 12-pin connector J3 for ESU connectivity. Wiring 3022 is also shown to the second 12-pin connector J2 for ISU connectivity. The micro-controller 3010 is shown. The micro-controller 3010 is type 18C452 which contains an analog to digital converter, 32 kB of EPROM, 1.5 k RAM, etc. internal to the module. Also shown are a 12 volt regulators 3011, and two 5 volt regulators 3012, 3013. A bank of digital power switches 3014 is shown which extend to FIG. 30B below.

Figure 30B:
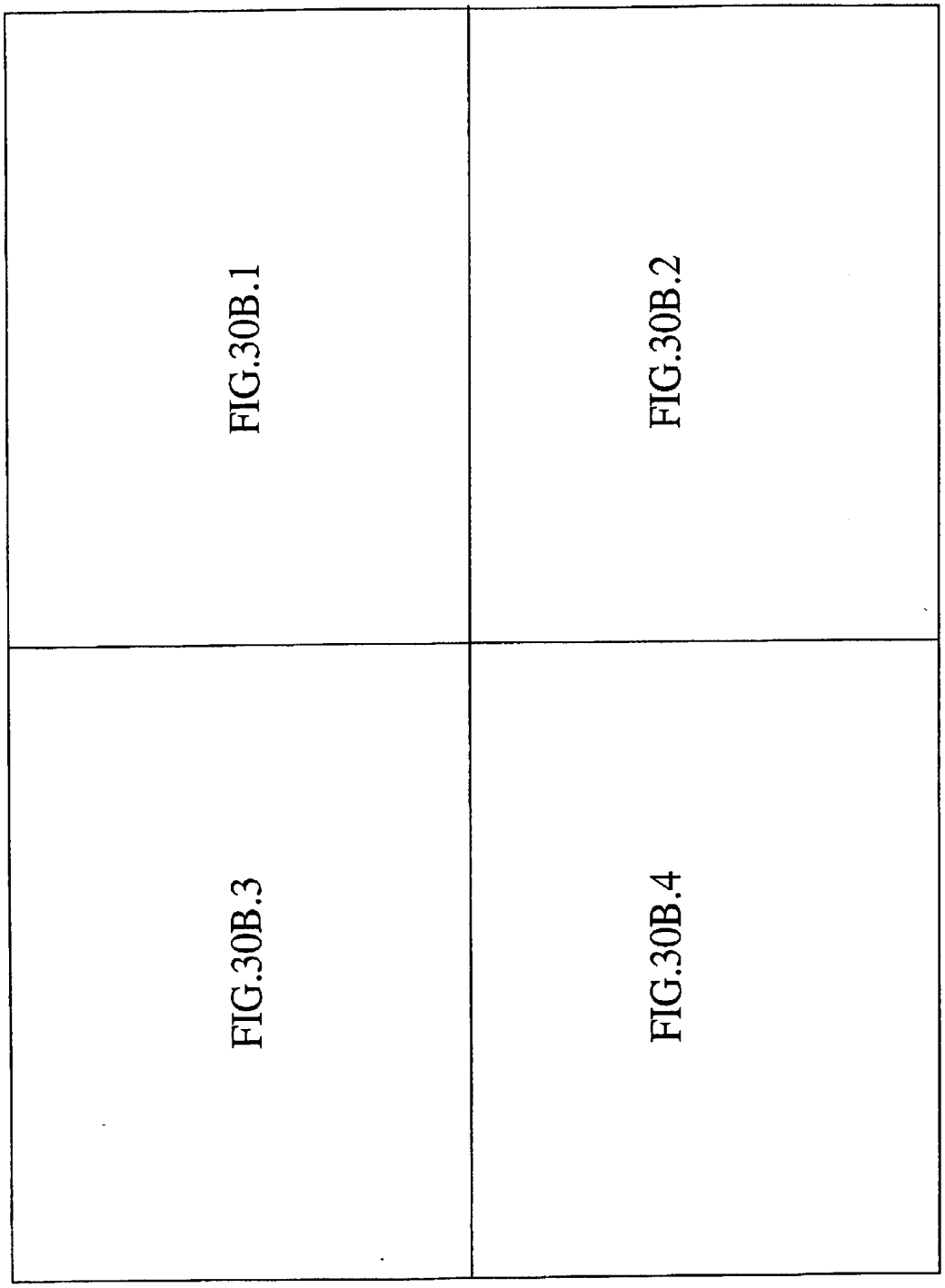

FIG. 30B represents the lower left quadrant of the "Universal" ESU/ISU/SSU" printed circuit board 3000. Shown are connector J2 3022, a partial 5V regulator 3013, the bottom extension of the digital power switches 3014, the SSU gimbal interface and drivers 3015 which connect to a 20-pin connector J6, ground jumpers 3016 and a contingency area 3017 for future engineering change activity.

Figures 30C, 30C.3:
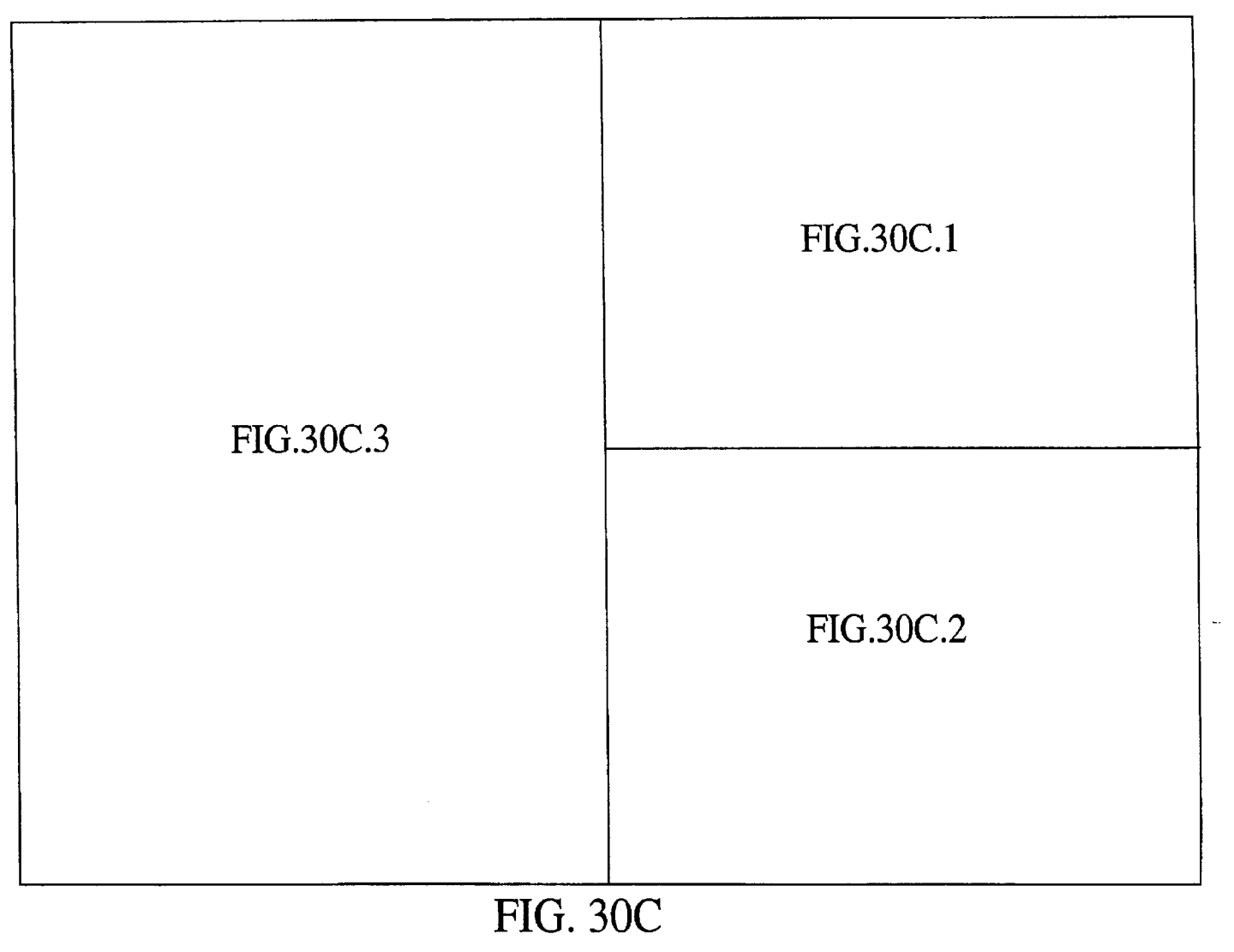

FIG. 30C represents the lower right quadrant of the "Universal" ESU/ISU/SSU" printed circuit board 3000. Shown is the contingency area 3017 (FIG. 30B), extension of the digital power switches 3014 (FIGS. 30A, 30B), a RS232 level shifter 3015, and the lower portion of the power input and control area network regulators 3020 which connect to a 20-pin connector J1.

Figures 30D, 30D.1, 30D.2, 30D.3, 30D.4:
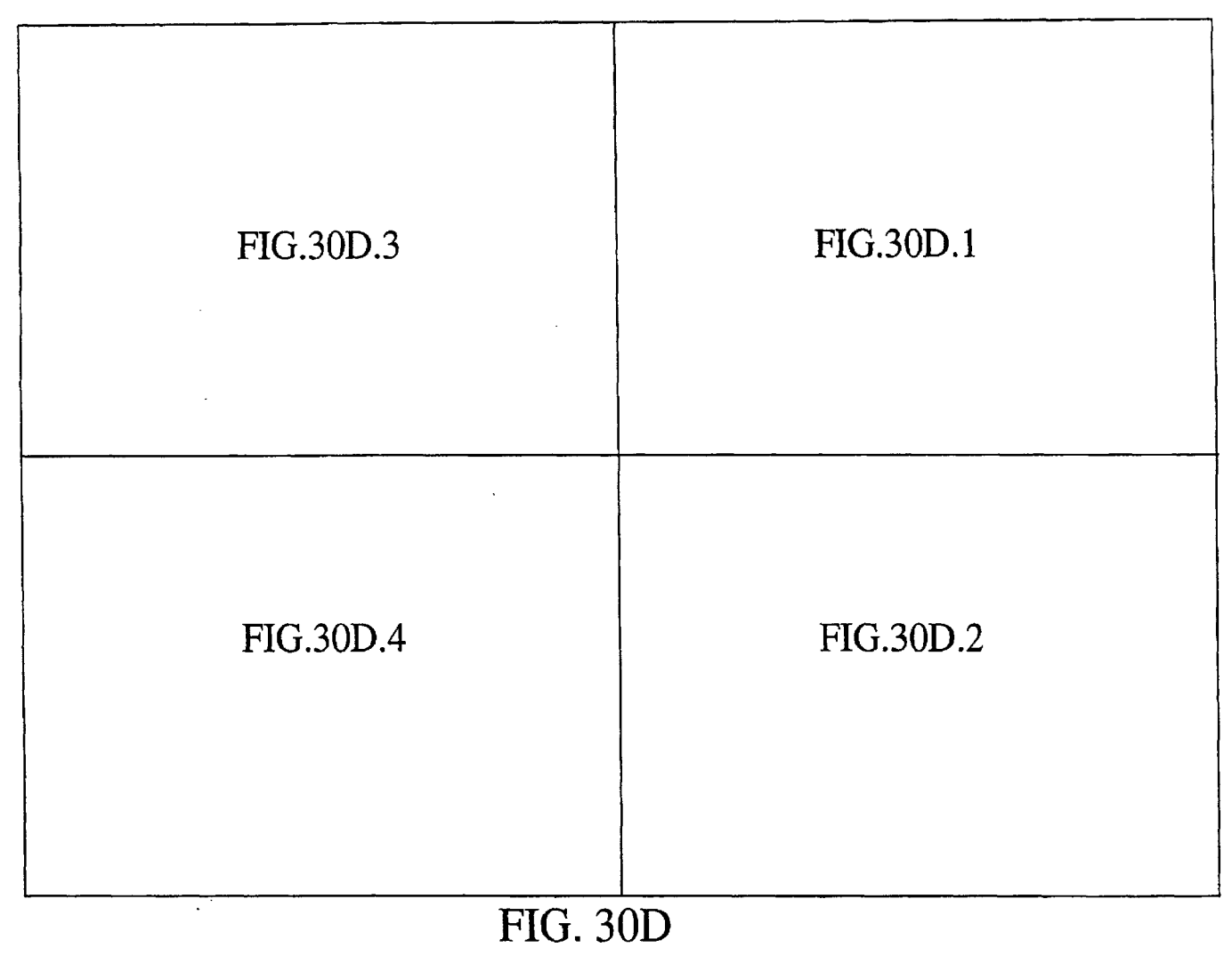

FIG. 30D represents the upper right quadrant of the "Universal" ESU/ISU/SSU" printed circuit board 3000. Shown is a portion of the micro-controller 3010, a 1 kB EEPROM, and a portion of the digital power switches 3014 (FIGS. 30A, 30B), and the upper portion of the power input and control area network regulators 3020 (FIG. 30C). Also shown is the azimuth and elevation motor drivers 3019 which connect to J4 and J5 14-pin connectors.

Figure 31:
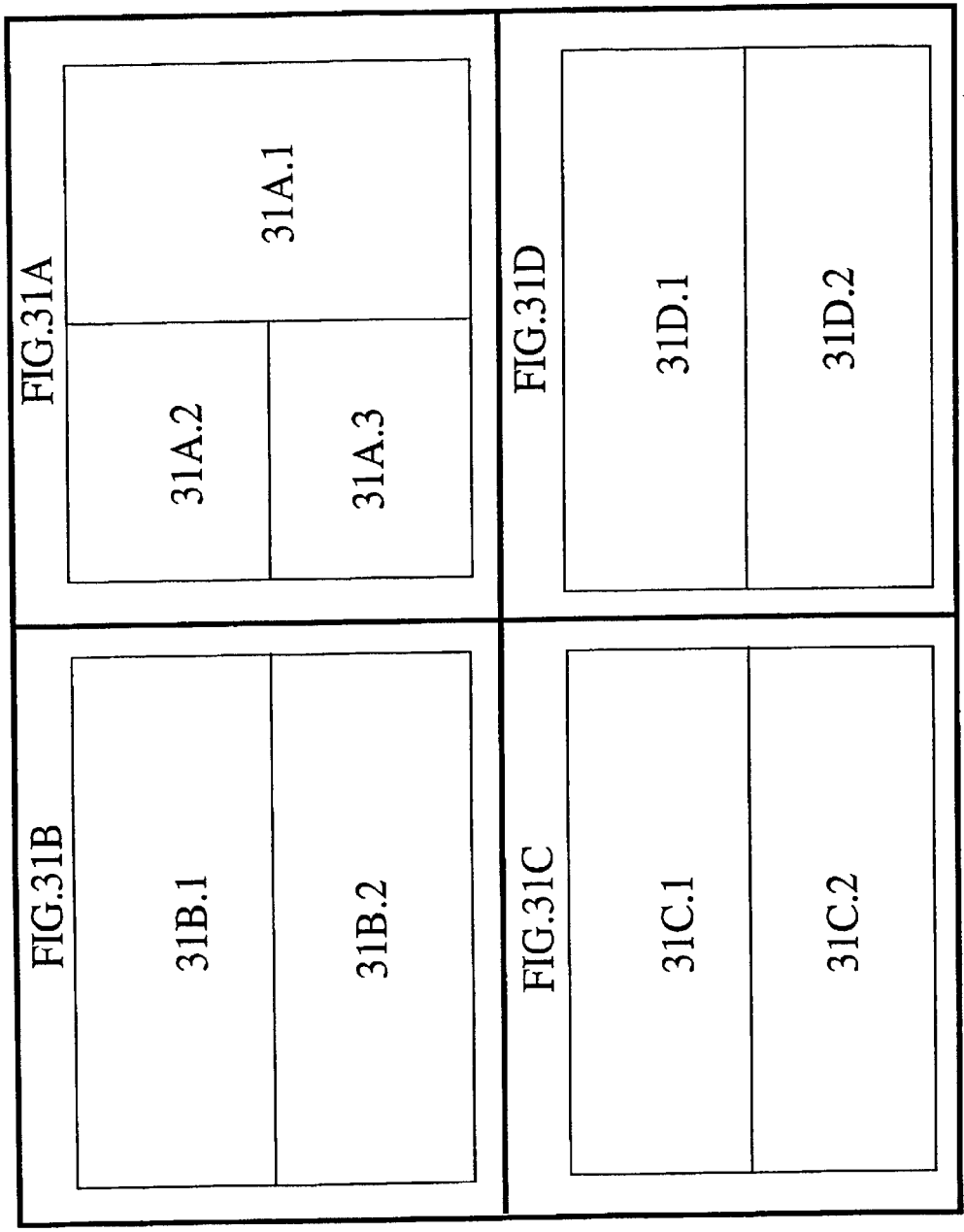
FIG. 31, 31E are schematics of the CAN (Controller Area Network) repeater and video multiplex printed circuit board within the junction box.
Figure 31B:
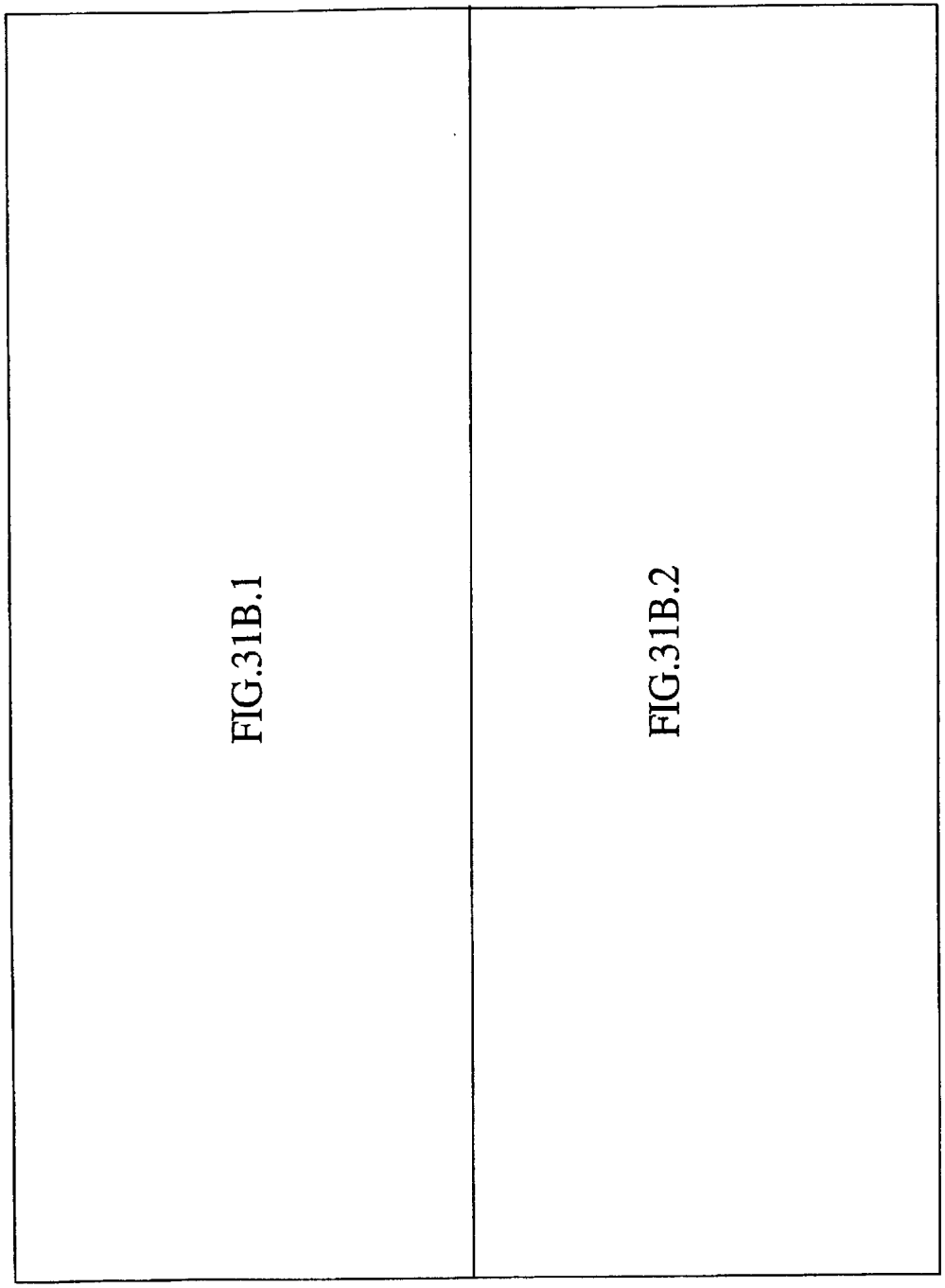
Figure 31C:
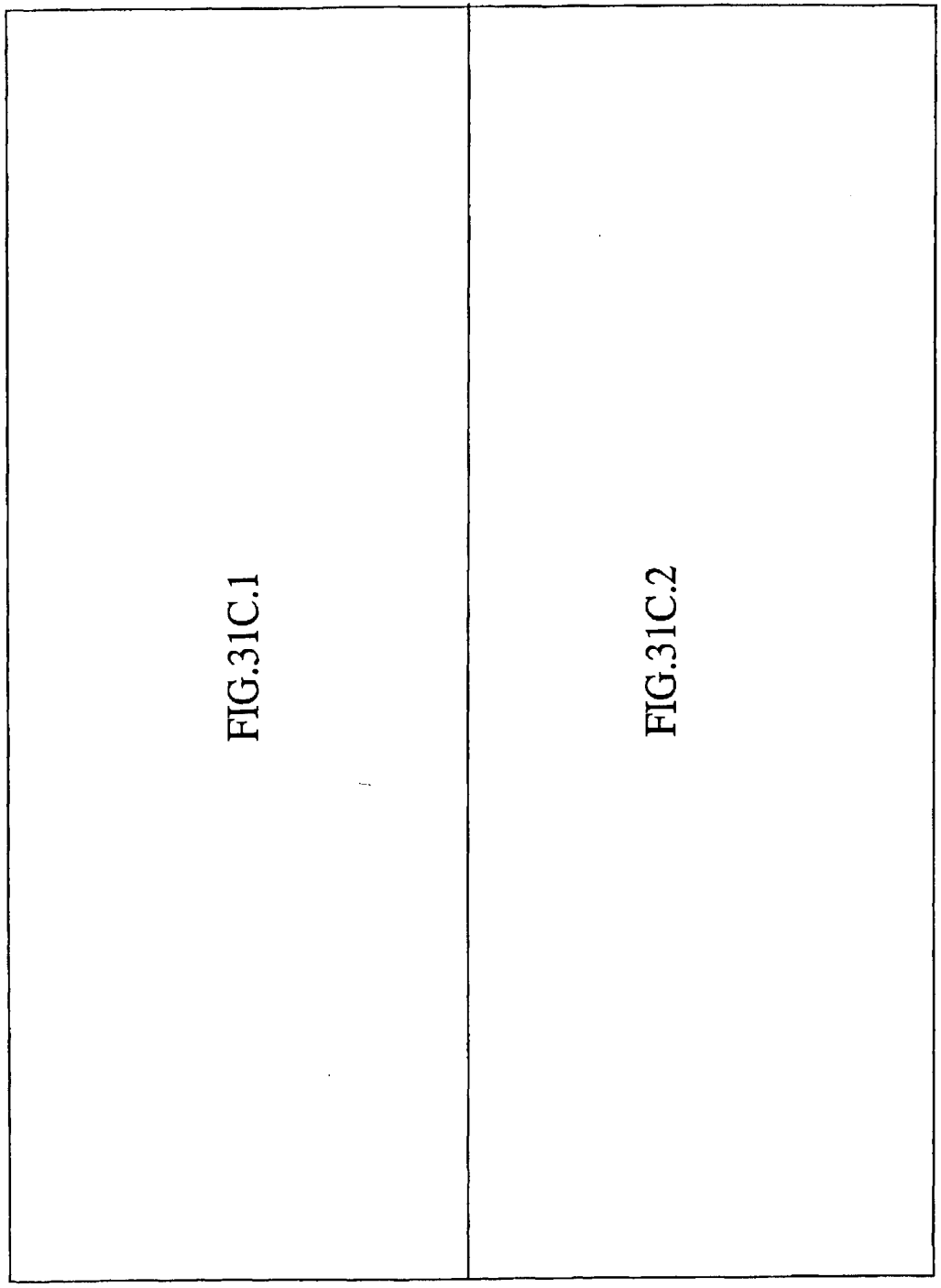
Figure 31D:
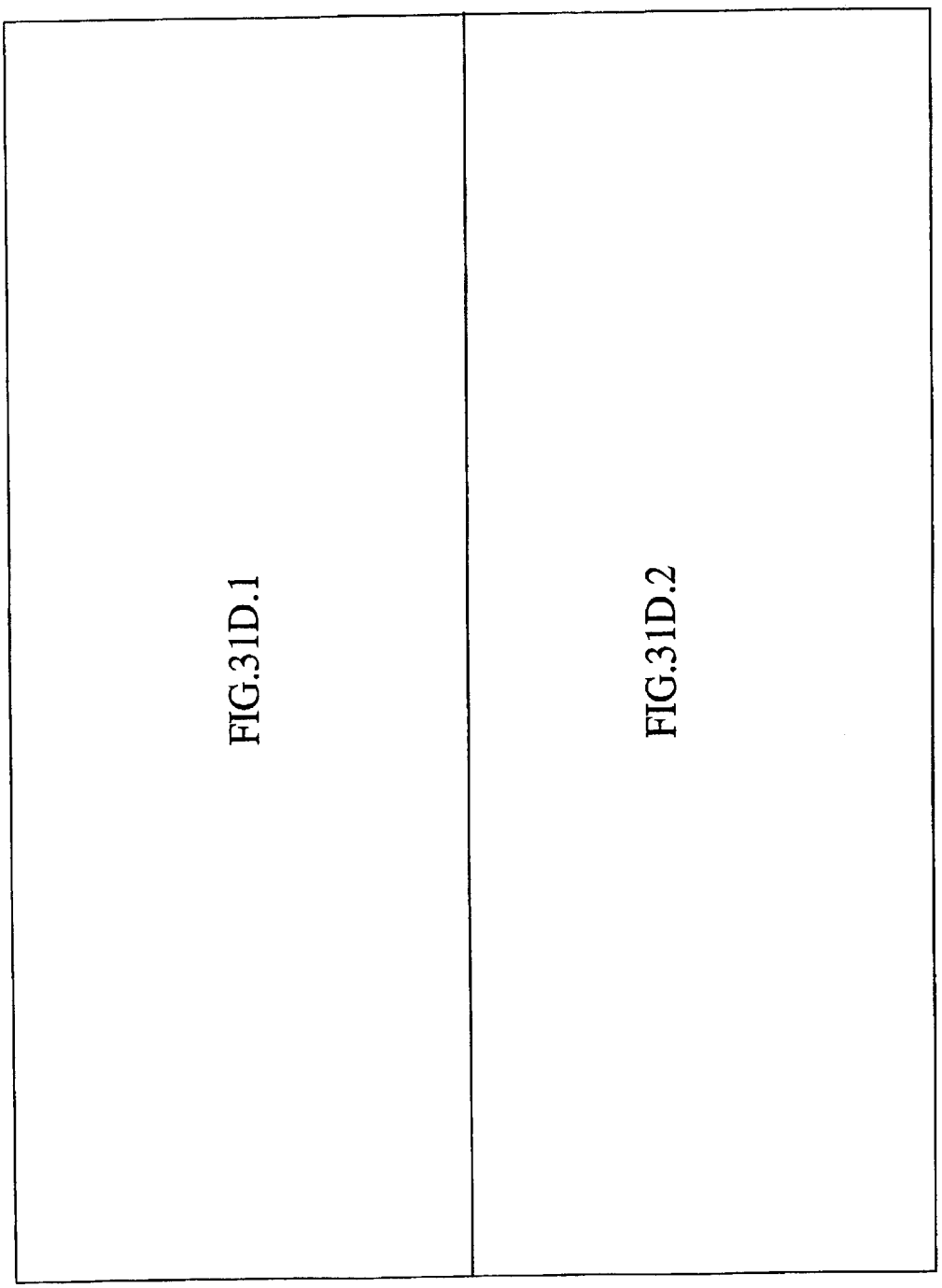
Figure 31E:
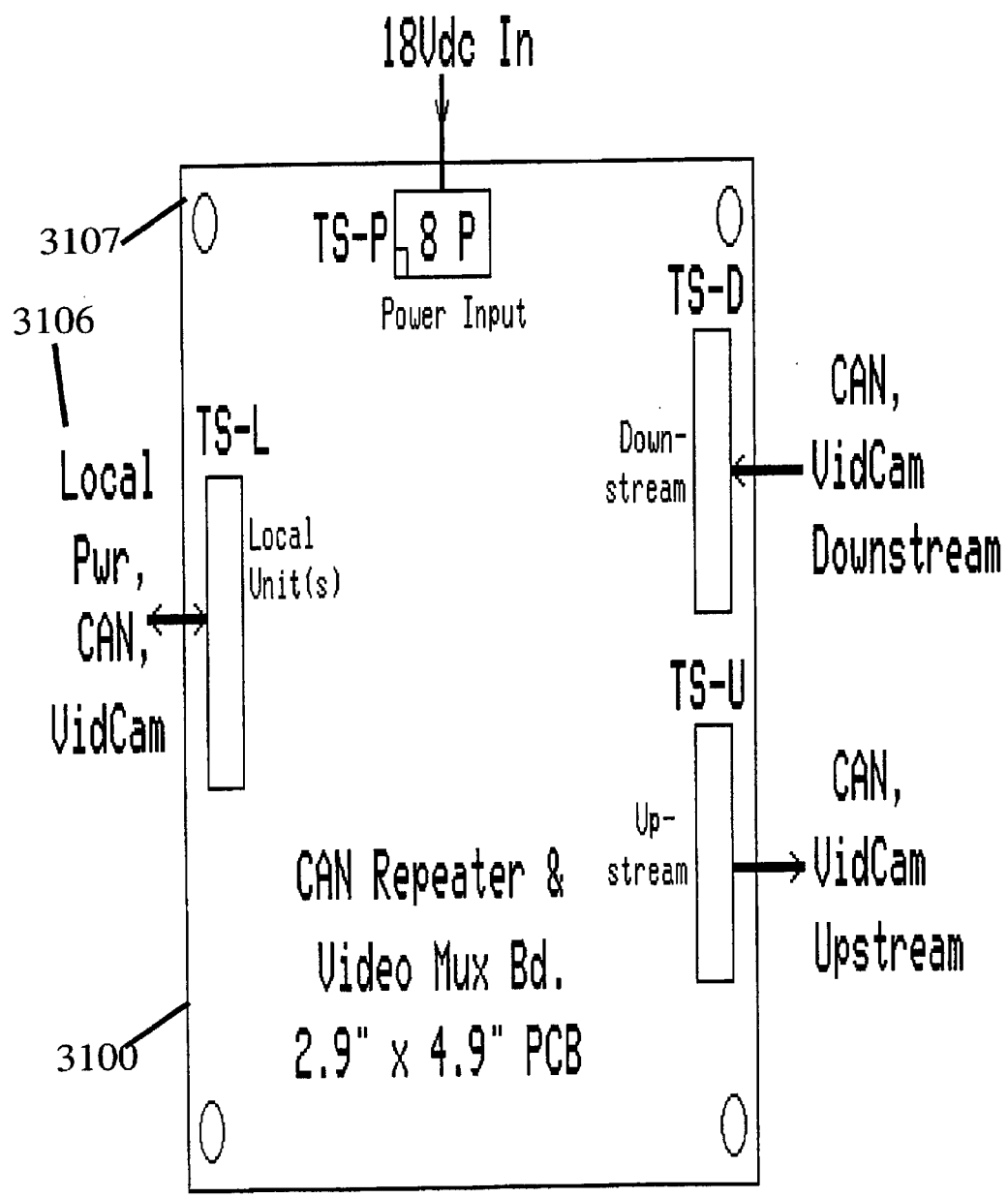

FIG. 31 is a schematic of the CAN (Controller Area Network) repeater and video multiplex printed circuit board 3100 within the junction box, see FIG. 31E for a layout diagram of the CAN repeater and video multiplex printed circuit board 3100. This is the same board (shown with I/O connectors only) as the board 2861 of FIG. 28C. The board has four connectors. TS-P is for power input, TS-D is for interfacing to downstream CAN and video cameras whereas TS-U is for interfacing to upstream CAN and video cameras. TS-L is for interfacing to local power, CAN and video cameras.

FIGS. 31A, 31B, 31C, 31D are schematic component layouts of each quadrant of the CAN repeater and video multiplexer circuit board 3100.

FIG. 31A is a schematic of the upper left quadrant of the CAN repeater and video multiplexer circuit board 3100. It shows an insert of the board 3100. Shown is a 5V regulator 3102 which receives input from P connector 3101. Transient arrestors 3109 act to filter voltage spikes. Video multiplexer/buffer 3103 connects to upstream and downstream video cameras (the upper portion is shown). It also interfaces to the L connector 3104. The CAN upstream control circuitry 3105 (left portion shown) contains a micro-controller 3110 with on-board memory (left portion shown). Also shown is a portion of the downstream CAN control circuitry 3108.

FIG. 31B is a schematic of the lower left quadrant of the CAN repeater and video multiplexer circuit board 3100 and shows a portion of the Video multiplexer/buffer 3103 (FIG. 31A) and a portion of the downstream CAN control circuitry 3108 (FIG. 31A).

FIG. 31C is a schematic of the lower right quadrant of the CAN repeater and video multiplexer circuit board 3100. Shown is the lower section of the downstream CAN control circuitry 3108 which contains a micro-controller 3113, a 1 kB EEPROM 3107, a CAN controller 3116 and a CAN transceiver 3115. Also shown is a contingency area 3106 for future engineering changes.

FIG. 31D is a schematic of the upper right quadrant of the CAN repeater and video multiplexer circuit board 3100. Shown is the upper section of the downstream CAN control circuitry 3108 (See FIG. 31C). Also shown is the major portion of the CAN upstream control circuitry 3105 (right portion shown) which contains a micro-controller 3110 with on-board memory (right portion shown), a 1 kB EEPROM 3114, a CAN controller 3111 and a CAN transceiver 3112.

FIGS. 32A, 32B, 32C, 32D, 32E, 32F, 32G, 32H, 32I, 32J, 32K are parts listings for an AIP for an alternate embodiment of the present invention.

FIG. 32A details the CU items.

FIGS. 32B, 32C detail the GSU items.

FIGS. 32D, 32E detail the ISU items.

FIG. 32F details the ESU items.

FIGS. 32G, 32H, 32I detail the general purpose embedded microcomputer, the RS-232 Serial Protocol Module, the multiple output DC power supply and the stepper motor drive.

FIGS. 32J, 32K detail an alternate embedded micro-controller, on-board analog to digital converters and the on-board serial interface.

FIGS. 32L, 32M, 32N are a minimum performance specification for the laser rangefinder in an alternate embodiment of the present invention. Detailed are the physical, electrical, laser, performance and quality requirements.

Although the present invention has been described with reference to preferred embodiments, numerous modifications and variations can be made and still the result will come within the scope of the invention. No limitation with respect to the specific embodiments disclosed herein is intended or should be inferred.

What is claimed is:

1. An automated instrumentation package (AIP) for bulk materials monitoring, the AIP comprising:

a bulk material surface profile scanner;

an avalanche warning sub-system connected to the bulk material surface profile scanner; and wherein the surface profile scanner further comprises a volume computation sub-system.

2. The AIP of claim 1, wherein the volume computation sub-system further comprises a quantity sub-system based on a density data input.

3. The AIP of claim 1, wherein the bulk material profile scanner further comprises a laser range finder.

4. The AIP of claim 1 further comprising an electronic data sub-system and a remote central processing unit.

5. An automated instrumentation package (AIP) for bulk materials monitoring, the AIP comprising:

a bulk material surface profile scanner:

an avalanche warning sub-system connected to the bulk material surface profile scanner; and a video camera.

6. An automated instrumentation package (AIP) for bulk materials monitoring, the AIP comprising:
a bulk material surface profile scanner;
an avalanche warning sub-system connected to the bulk material surface profile scanner; and
a spectral recognition sensor to enable identification of bulk material type.

7. The AIP of claim 6, wherein the spectral recognition sensor further comprises a moisture content sub-system.

8. The AIP of claim 7, wherein the spectral recognition sensor further comprises a qualitative and quantitative sub-system for detection of at least one of the following variables; protein, starch, sugar, and oil content of the bulk material.

9. The AIP of claim 6, wherein the spectral recognition sensor further comprises a dynamic flow measurement sub-system.

10. The AIP of claim 9, wherein the dynamic flow measurement sub-system further comprises a bulk material input routing sub-system based on machine vision identification of incoming bulk materials.

11. The AIP of claim 6, wherein the spectral recognition sensor further comprises a pattern matching sub-system to distinguish among the spectral characteristics of a plurality of bulk materials.

12. An automated instrumentation package (AIP) for bulk materials monitoring, the AIP comprising:
a bulk material surface profile scanner;
an avalanche warning sub-system connected to the bulk material surface profile scanner; and
an environmental gas monitoring system to monitor dust, temperature, humidity, dew point and out-gassing.

13. The AIP of claim 12, wherein the environmental gas monitoring system further comprises an early warning sub-system to detect an out-gas that denotes a problem.

14. The AIP of claim 12, wherein the environmental gas monitoring system further comprises a human safety alarm sub-system.

15. The AIP of claim 14 further comprising a central processing unit and stored table data to classify gas types detected into normal and abnormal classifications.

16. An automated instrumentation package (AIP) for bulk materials monitoring, the AIP comprising:
a bulk material surface profile scanner;
an avalanche warning sub-system connected to the bulk material surface profile scanner; and
a bulk material penetrating scanner having a density calculating sub-system to determine at least one of the following variables; voids, insects, mold growth, moisture content and volume.

17. The AIP of claim 16, wherein the bulk material penetrating scanner further comprises a ground penetrating radar (GPR).

18. An automated instrumentation package (AIP) for bulk materials monitoring, the AIP comprising:
a bulk material surface profile scanner;
an avalanche warning sub-system connected to the bulk material surface profile scanner; and
an acoustical single point ranger to prevent overfilling.

19. An automated instrumentation package (AIP) for bulk materials monitoring, the AIP comprising:
a bulk material surface profile scanner;
an avalanche warning sub-system connected to the bulk material surface profile scanner; and
a dust ignition proof enclosure comprising a two axis gimbal mount for motion control of the automated instrument package.

20. The AIP of claim 19, wherein the dust-ignition proof enclosure has an instrument lens cleaning apparatus.

* * * * *